(12) United States Patent
Kobayashi et al.

(10) Patent No.: US 10,611,964 B2
(45) Date of Patent: *Apr. 7, 2020

(54) POLYMERIZABLE COMPOUND, POLYMERIZABLE COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Masahide Kobayashi, Chiba (JP); Yasuyuki Gotoh, Tokyo (JP); Mayumi Goto, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 285 days.

This patent is subject to a terminal disclaimer.

(21) Appl. No.: 14/786,555

(22) PCT Filed: Mar. 13, 2014

(86) PCT No.: PCT/JP2014/056748
§ 371 (c)(1),
(2) Date: Oct. 23, 2015

(87) PCT Pub. No.: WO2014/174929
PCT Pub. Date: Oct. 30, 2014

(65) Prior Publication Data
US 2016/0075950 A1    Mar. 17, 2016

(30) Foreign Application Priority Data

Apr. 25, 2013 (JP) .................................. 2013-092150

(51) Int. Cl.
| | | |
|---|---|---|
| *G02F 1/1333* | (2006.01) | |
| *C09K 19/54* | (2006.01) | |
| *C08F 20/30* | (2006.01) | |
| *C08F 20/26* | (2006.01) | |
| *C08F 218/12* | (2006.01) | |
| *C09K 19/04* | (2006.01) | |
| *C08K 5/00* | (2006.01) | |
| *C07C 43/215* | (2006.01) | |
| *C07C 69/533* | (2006.01) | |
| *C07C 69/65* | (2006.01) | |

(Continued)

(52) U.S. Cl.
CPC .......... *C09K 19/544* (2013.01); *C07C 43/215* (2013.01); *C07C 69/533* (2013.01);
(Continued)

(58) Field of Classification Search
CPC .............. C09K 19/544; C09K 19/0403; C09K 2019/0448; C09K 2019/122;
(Continued)

(56) References Cited

U.S. PATENT DOCUMENTS 8,568,839 B2 * 10/2013 Takeuchi ........... C09K 19/2007
                                                            252/299.61
8,968,597 B2 *  3/2015 Furusato ................ C09K 19/56
                                                             252/299.6
(Continued)

FOREIGN PATENT DOCUMENTS

DE         4434976         4/1996
EP         2906662         8/2015
(Continued)

OTHER PUBLICATIONS

Nobuhiro Kawatsuki, et al. "Synthesis, characterization and photoreaction of side-chain liquid-crystalline polymers and copolymers comprising alkenyloxy-biphenyl mesogen", Macromolecular Chemistry and Physics, Sep. 1997, vol. 198, No. 9, p. 2853-2866.
"International Search Report (Form PCT/ISA/210)", dated May 27, 2014, with English translation thereof, pp. 1-5.
"Office Action of China Counterpart Application" with English translation thereof, dated Nov. 1, 2016, p. 1-p. 28.
(Continued)

Primary Examiner — Geraldina Visconti
(74) Attorney, Agent, or Firm — JCIPRNET

(57) ABSTRACT

A polymerizable compound has a high polymerizability, a high conversion ratio and a high solubility in a liquid crystal composition. A polymerizable composition contains the compound. A liquid crystal composite is prepared from the composition. A liquid crystal display device includes the liquid crystal composite. The polymerizable compound is formed in which the polymerizable compound has at least two polymerizable groups in which at least one polymerizable group is acryloyloxy or methacryloyloxy, and at least one remaining polymerizable group is a polymerizable group selected from the group of groups represented by formulas (P-1), (P-2) and (P-3).

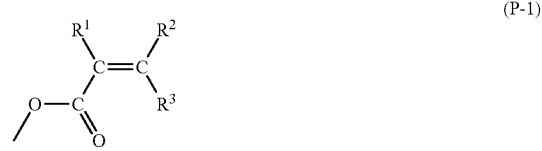

(P-1)

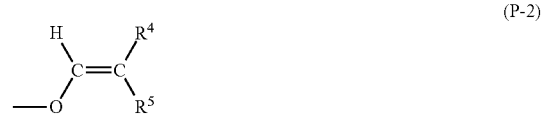

(P-2)

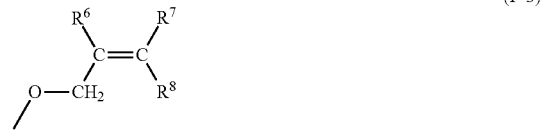

(P-3)

In formulas (P-1) to (P-3), $R^1$ to $R^8$ are independently hydrogen, fluorine, methyl, ethyl or trifluoromethyl.

17 Claims, No Drawings

(51) Int. Cl.
    *C07C 69/73*    (2006.01)
    *C07C 69/78*    (2006.01)
    *C09K 19/12*    (2006.01)

(52) U.S. Cl.
    CPC .............. *C07C 69/65* (2013.01); *C07C 69/73* (2013.01); *C07C 69/78* (2013.01); *C08F 20/26* (2013.01); *C08F 20/30* (2013.01); *C08F 218/12* (2013.01); *C08K 5/0008* (2013.01); *C09K 19/0403* (2013.01); *C09K 2019/0448* (2013.01); *C09K 2019/122* (2013.01); *C09K 2019/123* (2013.01); *C09K 2019/546* (2013.01)

(58) Field of Classification Search
    CPC ........ C09K 2019/123; C09K 2019/546; G02F 1/1333; C07C 43/215; C07C 69/533; C07C 69/65; C07C 69/73; C07C 69/78; C08F 20/26; C08F 20/30; C08F 218/12; C08F 5/0008
    USPC .................................................. 252/299.01
    See application file for complete search history.

(56) References Cited

U.S. PATENT DOCUMENTS

| | | | | |
|---|---|---|---|---|
| 9,139,672 | B2* | 9/2015 | Fujita | C08F 20/20 |
| 9,315,728 | B2* | 4/2016 | Hirai | C09K 19/32 |
| 9,617,477 | B2* | 4/2017 | Goto | C09K 19/12 |
| 9,714,210 | B2* | 7/2017 | Furusato | C07C 69/54 |
| 2010/0078593 | A1 | 4/2010 | Takeuchi et al. | |
| 2010/0143612 | A1 | 6/2010 | Hirai | |
| 2011/0147657 | A1 | 6/2011 | Hirai et al. | |
| 2016/0083330 | A1* | 3/2016 | Furusato | C08F 20/30 252/299.4 |

FOREIGN PATENT DOCUMENTS

| | | |
|---|---|---|
| JP | 2008100982 | 5/2008 |
| JP | 2008-164925 | 7/2008 |
| JP | 2010-83947 | 4/2010 |
| JP | 2010-134073 | 6/2010 |
| JP | 2012-018215 | 1/2012 |
| JP | 2013-014538 | 1/2013 |
| WO | 2011/124522 | 10/2011 |
| WO | 2013/054682 | 4/2013 |

OTHER PUBLICATIONS

"Search Report of Europe Counterpart Application", dated Dec. 9, 2016, p. 1-p. 12.
"Office Action of Japan Counterpart Application," dated Mar. 14, 2018, with English translation thereof, p. 1-p. 10.
"Office Action of Taiwan Counterpart Application," dated Mar. 14, 2018, with English translation thereof, p. 1-p. 10.
"Office Action of China Counterpart Application" dated Jul. 3, 2018, with English translation thereof, p. 1-p. 26.
"Office Action of China Counterpart Application", dated Apr. 2, 2019, with English translation thereof, p. 1-p. 22.
"Office Action of Taiwan Counterpart Application," with English translation thereof, dated Sep. 12, 2017, p. 1-p. 14.
"Office Action of China Counterpart Application," with English translation thereof, dated Aug. 21, 2017, p. 1-p. 22.

* cited by examiner

POLYMERIZABLE COMPOUND, POLYMERIZABLE COMPOSITION AND LIQUID CRYSTAL DISPLAY DEVICE

CROSS-REFERENCE TO RELATED APPLICATION

This application is a 371 application of International PCT application serial no. PCT/JP2014/056748, filed on Mar. 13, 2014, which claims the priority benefit of Japan application no. 2013-092150, filed on Apr. 25, 2013. The entirety of each of the above-mentioned patent applications is hereby incorporated by reference herein and made a part of this specification.

TECHNICAL FIELD

The invention relates to a polymerizable compound, a polymerizable composition containing the polymerizable compound and a liquid crystal composition, a liquid crystal composite prepared from the polymerizable composition, and a liquid crystal display device.

BACKGROUND ART

A liquid crystal display device utilizes optical anisotropy, dielectric anisotropy or the like of liquid crystal molecules in a liquid crystal composition. A classification based on an operating mode for liquid crystal molecules includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a fringe field switching (FFS) mode, a vertical alignment (VA) mode and so forth.

The liquid crystal display device having a mode in combination of a polymer with a liquid crystal composition is known. The mode is a polymer sustained alignment (PSA) mode or a polymer stabilized (PS) mode, for example. In the liquid crystal display device having the mode, the liquid crystal composition to which the polymerizable compound is added is injected into the display device. The polymerizable compound is polymerized by irradiating the compound with ultraviolet light in a state of applying voltage between electrodes to form the polymer in the liquid crystal composition. According to the method, the liquid crystal display device is obtained in which a response time is shortened and image persistence is improved.

The above method can be applied to the liquid crystal display devices having various operating modes, and the modes such as a PS-TN mode, a PS-IPS mode, a PS-FFS mode, a PSA-VA mode and a PSA-OCB are known. The polymerizable compound used in the device having such a mode is considered to have a high capability for aligning liquid crystal molecules, but solubility thereof in the liquid crystal composition is far from high. An attempt for improving the solubility in the liquid crystal composition has been made so far, but if the solubility in the liquid crystal composition is improved, polymerizability tends to decrease. Therefore, desire has been expressed for development of the polymerizable compound having a suitable balance between the solubility and the polymerizability.

CITATION LIST

Patent Literature

Patent literature No. 1: JP 2012-18215 A.
Patent literature No. 2: JP 2013-14538 A.

SUMMARY OF INVENTION

Technical Problem

The invention provides a polymerizable compound having a high polymerizability, a high conversion ratio and a high solubility in a liquid crystal composition. The invention further provides a liquid crystal composite satisfying at least one of physical properties such as a high maximum temperature of a nematic phase, a low minimum temperature of the nematic phase, a small viscosity, a suitable optical anisotropy, a large dielectric anisotropy, a suitable elastic constant, a large specific resistance and a suitable pretilt angle. The invention provides a liquid crystal composite having a suitable balance regarding at least two of the physical properties. The invention also provides a liquid crystal display device having a wide temperature range in which the device can be used, a short response time, a large voltage holding ratio, a low threshold voltage, a large contrast ratio and a long service life.

Solution to Problem

The invention concerns a polymerizable compound having at least two polymerizable groups in which at least one polymerizable group is acryloyloxy or methacryloyloxy, and at least one remaining polymerizable group is a polymerizable group selected from the group of groups represented by formulas (P-1), (P-2) and (P-3), a polymerizable composition containing the polymerizable compound and a liquid crystal composition, a liquid crystal composite prepared from the polymerizable composition and a liquid crystal display device including the liquid crystal composite.

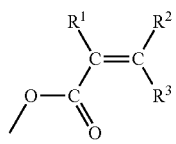
(P-1)

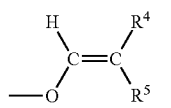
(P-2)

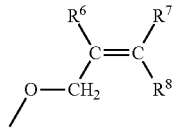
(P-3)

wherein, in formulas (P-1) to (P-3), $R^1$, $R^2$, $R^3$, $R^4$, $R^5$, $R^6$, $R^7$ and $R^8$ are independently hydrogen, fluorine, alkyl having 1 to 5 carbons, or alkyl having 1 to 5 carbons in which at least one of hydrogen is replaced by halogen; when $R^1$ is hydrogen or methyl, at least one of $R^2$ and $R^3$ is fluorine, alkyl having 1 to 5 carbons, or alkyl having 1 to 5 carbons in which at least one of hydrogen is replaced by halogen; at least one of $R^4$ and $R^5$ is fluorine, alkyl having 1 to 5 carbons, or alkyl having 1 to 5 carbons in which at least one of hydrogen is replaced by halogen; and at least one of $R^6$, $R^7$ and $R^8$ is fluorine, alkyl having 1 to 5 carbons, or alkyl having 1 to 5 carbons in which at least one of hydrogen is replaced by halogen.

Advantageous Effects of Invention

A first advantage of the invention is that a polymerizable compound has a high polymerizability, a high conversion ratio, a high solubility in a liquid crystal composition. A second advantage is that a liquid crystal composite satisfies at least one of physical properties such as a high maximum temperature of a nematic phase, a low minimum temperature of the nematic phase, a small viscosity, a suitable optical anisotropy, a large dielectric anisotropy, a suitable elastic constant, a large specific resistance and a suitable pretilt. The advantage is that the liquid crystal composition has a suitable balance regarding at least two of the physical properties. A third advantage is that a liquid crystal display device has a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a non-polymerizable compound having a liquid crystal phase such as a nematic phase and a smectic phase, and also a non-polymerizable compound having no liquid crystal phase but being added for the purpose of adjusting physical properties of the liquid crystal composition, such as a maximum temperature, a minimum temperature, viscosity and dielectric anisotropy. The compound has a six-membered ring such as 1,4-cyclohexylene and 1,4-phenylene, and a rod like molecular structure. The liquid crystal composition is a mixture of the liquid crystal compounds. A polymerizable compound is added to the composition for the purpose of forming a polymer. A polymerizable composition is a mixture containing the polymerizable compound, and the mixture containing the polymerizable compound, the liquid crystal composition and an additive, for example. A liquid crystal composite is a composite produced by polymerization of the polymerizable composition. A Liquid crystal display device is a generic term for a liquid crystal display panel and a liquid crystal display module. A maximum temperature of the nematic phase is a transition temperature between the nematic phase and an isotropic phase in the liquid crystal composition, the polymerizable composition or the liquid crystal composite, and may be occasionally abbreviated as "maximum temperature." A minimum temperature of the nematic phase may be occasionally abbreviated as "minimum temperature." Polymerizability means a degree of easiness when a reactant is polymerized. A conversion ratio is a weight ratio of a reactant consumed by a chemical reaction based on the total reactant.

The liquid crystal composition is prepared by mixing the liquid crystal compounds. A ratio (content) of the liquid crystal compound is expressed in terms of weight percent (% by weight) based on the weight of the liquid crystal composition. An additive such as an optically active compound, an antioxidant, an ultraviolet light absorber, a light stabilizer, a heat stabilizer, an antifoaming agent, a polymerization initiator and a polymerization inhibitor is added to the liquid crystal composition, when necessary. A ratio (content) of the additive is expressed in terms of weight percent (% by weight) based on the weight of the liquid crystal composition in a manner similar to the ratio of the liquid crystal compound. Weight parts per million (ppm) may be occasionally used. A ratio of the polymerization initiator and the polymerization inhibitor is exceptionally expressed based on the weight of the polymerizable compound.

A compound represented by formula (1) may be occasionally abbreviated as "compound (1)." The abbreviation also applies to a compound represented by formula (2) or the like. Compound (1) means one compound or two or more compounds represented by formula (1). In formulas (1) to (8), a symbol such as $A^1$, $B^1$ and $C^1$ surrounded by a circle or a hexagonal shape corresponds to ring $A^1$, ring $B^1$, ring $C^1$ or the like, respectively. In formula (1), an oblique line crossing the circle represents that a bonding position on the ring can be arbitrarily selected for a $P^1$—$S^1$ group. A same rule further applies to a $P^2$—$S^2$ group or the like. A same rule further applies to an oblique line crossing a six-membered ring in formula (1-1) or the like. In formula (1), a subscript such as a1 represents the number of bonding groups. When a1 is 2, two $P^1$—$S^1$ groups exist on ring $A^1$. Two groups represented by two $P^1$—$S^1$ groups may be identical or different. A same rule also applies to a case where a1 is larger than 2. A same rule also applies to other groups. A symbol of $R^{11}$ is used in a plurality of formulas such as formula (2) and formula (3). In the compounds, two terminal groups represented by two of arbitrary $R^{11}$ may be identical or different. In formula (8), when i is 2, two of symbol $D^1$ exists in one formula. In the compound, two rings represented by two of symbol $D^1$ may be identical or different. A same rule also applies to a symbol such as $Z^{17}$.

An expression "at least one of 'A' may be replaced by 'B'" represents that a position of 'A' when the number of 'A' is 1 is arbitrary, and the positions thereof can be selected without restriction when the number of 'A' is 2 or more. An expression "at least one of A may be replaced by B, C or D" represents the case where at least one of A is replaced by B, the case where at least one of A is replaced by C, and the case where at least one of A is replaced by D, and also the case where a plurality of A are replaced by at least two of B, C and D. For example, alkyl in which at least one of —CH$_2$— (or —CH$_2$CH$_2$—) may be replaced by —O— (or —CH=CH—) includes alkyl, alkenyl, alkoxy, alkoxyalkyl, alkoxyalkenyl and alkenyloxyalkyl. In addition, the case where replacement of two of successive —CH$_2$— by —O— results in forming —O—O— is not preferred. In the alkyl or the like, the case where replacement of —CH$_2$— of a methyl part (—CH$_2$—H) by —O— results in forming —O—H is not preferred, either.

Then, 2-fluoro-1,4-phenylene means two divalent groups described below. In a chemical formula, fluorine may be leftward (L) or rightward (R). A same rule also applies to an asymmetrical divalent ring such as tetrahydropyran-2,5-diyl.

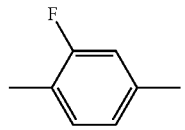

(L)

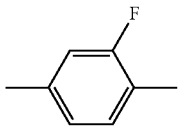

(R)

The invention includes a content described in items as described below.

Item 1. A polymerizable compound having at least two polymerizable groups in which at least one polymerizable group is acryloyloxy or methacryloyloxy, and at least one remaining polymerizable group is a polymerizable group selected from the group of groups represented by formulas (P-1), (P-2) and (P-3):

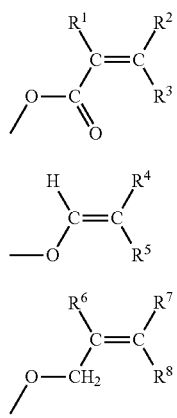

(P-1)

(P-2)

(P-3)

wherein, in formulas (P-1) to (P-3), $R^1$, $R^2$, $R^3$, $R^4$, $R^5$, $R^6$, $R^7$ and $R^8$ are independently hydrogen, fluorine, alkyl having 1 to 5 carbons, or alkyl having 1 to 5 carbons in which at least one of hydrogen is replaced by halogen; when $R^1$ is hydrogen or methyl, at least one of $R^2$ and $R^3$ is fluorine, alkyl having 1 to 5 carbons, or alkyl having 1 to 5 carbons in which at least one of hydrogen is replaced by halogen; at least one of $R^4$ and $R^5$ is fluorine, alkyl having 1 to 5 carbons, or alkyl having 1 to 5 carbons in which at least one of hydrogen is replaced by halogen; and at least one of $R^6$, $R^7$ and $R^8$ is fluorine, alkyl having 1 to 5 carbons, or alkyl having 1 to 5 carbons in which at least one of hydrogen is replaced by halogen.

Item 2. The polymerizable compound according to item 1, having at least two polymerizable groups in which at least one polymerizable group is acryloyloxy or methacryloyloxy, and at least one remaining polymerizable group is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy.

Item 3. The polymerizable compound according to item 1, represented by formula (1):

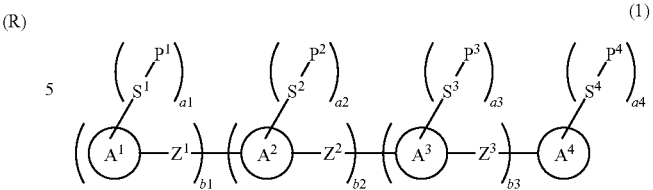

(1)

wherein, in formula (1),
at least one of $P^1$, $P^2$, $P^3$ and $P^4$ is acryloyloxy or methacryloyloxy, and at least one remainder is a polymerizable group selected from the group of groups represented by formulas (P-1), (P-2) and (P-3);

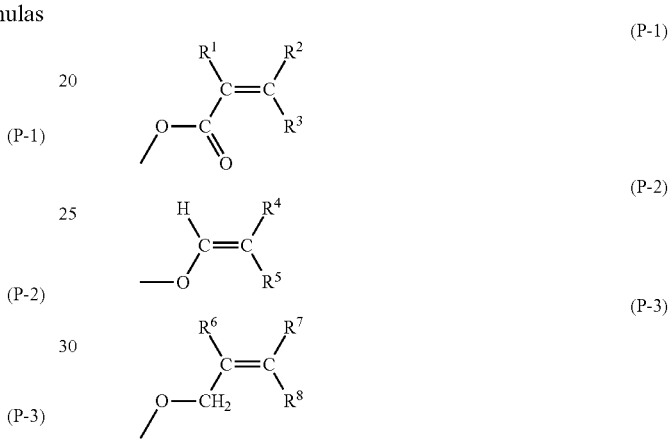

(P-1)

(P-2)

(P-3)

wherein, in formulas (P-1) to (P-3), $R^1$, $R^2$, $R^3$, $R^4$, $R^5$, $R^6$, $R^7$ and $R^8$ are independently hydrogen, fluorine, alkyl having 1 to 3 carbons, or alkyl having 1 to 3 carbons in which at least one of hydrogen is replaced by halogen; when $R^1$ is hydrogen or methyl, at least one of $R^2$ and $R^3$ is fluorine, alkyl having 1 to 3 carbons, or alkyl having 1 to 3 carbons in which at least one of hydrogen is replaced by halogen; at least one of $R^4$ and $R^5$ is fluorine, alkyl having 1 to 3 carbons, or alkyl having 1 to 3 carbons in which at least one of hydrogen is replaced by halogen; and at least one of $R^6$, $R^7$ and $R^8$ is fluorine, alkyl having 1 to 3 carbons, or alkyl having 1 to 3 carbons in which at least one of hydrogen is replaced by halogen;

$S^1$, $S^2$, $S^3$ and $S^4$ are independently a single bond or alkylene having 1 to 10 carbons, and in the alkylene, at least one of —$CH_2$— may be replaced by —O—, —COO—, —OCO— or —OCOO—, at least one of —$CH_2$—$CH_2$— may be replaced by —CH=CH— or —C≡C—, and at least one of hydrogen may be replaced by fluorine or chlorine;

a1, a2, a3 and a4 are independently 0, 1, 2, 3 or 4, and a sum of a1, a2, a3 and a4 is an integer from 2 to 10;

ring $A^1$ and ring $A^4$ are independently phenyl, pyrimidyl, pyridyl, naphthyl, cyclohexyl, cyclohexenyl, tetrahydropyranyl or 1,3-dioxanyl, and in the rings, at least one of hydrogen may be replaced by halogen, alkyl having 1 to 12 carbons, or alkyl having 1 to 12 carbons in which at least one of hydrogen is replaced by halogen;

ring $A^2$ and ring $A^3$ are independently 1,4-phenylene, pyrimidine-2,5-diyl, pyridine-2,5-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2, 6-diyl, naphthalene-2,7-diyl, 1,4-cyclohexylene, 1,4-cyclohexenylene, tetrahydropyran-2,5-diyl or 1,3-dioxane-2,5-diyl, and in the rings, at least one of hydrogen may be replaced by halogen, alkyl having 1 to 12 carbons, or alkyl having 1 to 12 carbons in which at least one of hydrogen may be replaced by halogen;

$Z^1$, $Z^2$ and $Z^3$ are independently a single bond or alkylene having 1 to 10 carbons, and in the alkylene, at least one of —$CH_2$— may be replaced by —O—, —CO—, —COO— or —OCO—, at least one of —$CH_2$—$CH_2$— may be replaced by —CH=CH—, —C($CH_3$)=CH—, —CH=C($CH_3$)— or —C($CH_3$)=C($CH_3$)—, and at least one of hydrogen may be replaced by fluorine or chlorine; and b1, b2 and b3 are independently 0 or 1.

Item 4. The polymerizable compound according to item 1, wherein, in formula (1) described in item 3, at least one of $P^1$, $P^2$, $P^3$ and $P^4$ is acryloyloxy or methacryloyloxy, and at least one remainder is 2-butenoyloxy, 2-methyl-2-butenoyloxy, 2-methylenebutanoyloxy, 2-methyl-1-ropenyloxy, 2,2-difluorovinyloxy, 2-butenyloxy or 2-methyl-2-propenyloxy;

$S^1$, $S^2$, $S^3$ and $S^4$ are independently a single bond or alkylene having 1 to 10 carbons, and in the alkylene, at least one of —$CH_2$— may be replaced by —O—, —COO—, —OCO— or —OCOO—, at least one of —$CH_2$—$CH_2$— may be replaced by —CH=CH— or —C≡C—, and at least one of hydrogen may be replaced by fluorine or chlorine;

a1, a2, a3 and a4 are independently 0, 1, 2 or 3, and a sum of a1, a2, a3 and a4 is an integer from 2 to 6;

ring $A^1$ and ring $A^4$ are independently phenyl, pyrimidyl, pyridyl or naphthyl, and in the rings, at least one of hydrogen may be replaced by halogen, alkyl having 1 to 12 carbons, or alkyl having 1 to 12 carbons in which at least one of hydrogen is replaced by halogen;

ring $A^2$ and ring $A^3$ are independently 1,4-phenylene, pyrimidine-2,5-diyl, pyridine-2,5-diyl, naphthalene-1,4-diyl, naphthalene-1,5-diyl, naphthalene-2,6-diyl, 1,4-cyclohexylene, tetrahydropyran-2,5-diyl or 1,3-dioxane-2,5-diyl, and in the rings, at least one of hydrogen may be replaced by fluorine, chlorine, alkyl having 1 to 5 carbons, alkoxy having 1 to 5 carbons, or alkyl having 1 to 5 carbons or alkoxy having 1 to 5 carbons in which at least one of hydrogen is replaced by halogen;

$Z^1$, $Z^2$ and $Z^3$ are independently a single bond, alkylene having 1 to 5 carbons, —CO—, —COO—, —OCO—, —CH=CH—, —CH=CH—COO—, —OCO—CH=CH—, —C($CH_3$)=CH—COO—, —OCO—CH=C($CH_3$)—, —CH=C($CH_3$)—COO—, —OCO—($CH_3$)C=CH—, —C($CH_3$)=C($CH_3$)—COO—, —OCO—C($CH_3$)=C($CH_3$)—, —CO—CH=CH—, —CH=CH—CO—, —C($CH_3$)=C($CH_3$)—, —CH=CH—$CH_2$O—, —OCH_2—CH=CH—, —CH=CH—OCH_2— or —$CH_2$O—CH=CH—; and b1, b2 and b3 are independently 0 or 1.

Item 5. The polymerizable compound according to item 1, represented by formula (1-1):

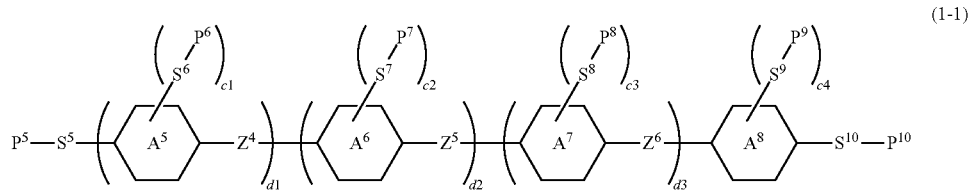

(1-1)

wherein, in formula (1-1), at least one of $P^5$, $P^6$, $P^7$, $P^8$, $P^9$ and $P^{10}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

$S^5$, $S^6$, $S^7$, $S^8$, $S^9$ and $S^{10}$ are independently a single bond or alkylene having 1 to 5 carbons, and in the alkylene, at least one of —$CH_2$— may be replaced by —O—, —COO— or —OCO—, and at least one of —$CH_2$—$CH_2$— may be replaced by —CH=CH—;

c1, c2, c3 and c4 are independently 0, 1 or 2, and a sum of c1, c2, c3 and c4 is an integer from 0 to 5;

ring $A^5$, ring $A^6$, ring $A^7$ and ring $A^8$ are independently 1,4-phenylene, pyrimidine-2,5-diyl, pyridine-2,5-diyl, naphthalene-1,4-diyl, naphthalene-1,5-diyl, naphthalene-2,6-diyl, 1,4-cyclohexylene, tetrahydropyran-2,5-diyl or 1,3-dioxane-2,5-diyl, and in the rings, at least one of hydrogen may be replaced by fluorine, chlorine, alkyl having 1 to 5 carbons, alkoxy having 1 to 5 carbons, or alkyl having 1 to 5 carbons or alkoxy having 1 to 5 carbons in which at least one of hydrogen is replaced by halogen;

$Z^4$, $Z^5$ and $Z^6$ are independently a single bond, alkylene having 1 to 5 carbons, —CO—, —OCO—, —OCO—, —CH=CH—, —CH=CH—OCO—, —OCO—CH=OH—, —C($CH_3$)=CH—OCO—, —OCO—CH=C($CH_3$)—, —CH=C($CH_3$)—OCO—, —OCO—($CH_3$)C=CH—, —C($CH_3$)=C($CH_3$)—OCO—, —OCO—C($CH_3$)=C($CH_3$)—, —CO—CH=CH—, —CH=CH—CO—, —($CH_3$)C=C($CH_3$)—, —CH=OH—$CH_2$O—, —OCH_2—CH=CH—, —CH=CH—OCH_2— or —$CH_2$O—CH=CH—; and d1, d2 and d3 are independently 0 or 1.

Item 6. The polymerizable compound according to item 5, wherein, in formula (1-1) in item 5, $P^5$ and $P^{10}$ are independently acryloyloxy or methacryloyloxy, at least one of $P^6$, $P^7$, $P^8$ and $P^9$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy:

$S^5$, $S^6$, $S^7$, $S^8$, $S^9$ and $S^{10}$ are a single bond; c1, c2, c3 and c4 are independently 0 or 1, and a sum of c1, c2, c3 and c4 is 1, 2 or 3; ring $A^5$, ring $A^6$, ring $A^7$ and ring $A^8$ are independently 1,4-phenylene, and at least one of hydrogen may be replaced by fluorine, chlorine, alkyl having 1 to 5 carbons, alkoxy having 1 to 5 carbons, or alkyl having 1 to 5 carbons or alkoxy having 1 to 5 carbons in which at least one of hydrogen is replaced by halogen; $Z^4$, $Z^5$ and $Z^6$ are a single bond; and d1, d2 are d3 are independently 0 or 1, and a sum of d1, d2 and d3 is 1, 2 or 3.

Item 7. The polymerizable compound according to item 1, represented by any one of formulas (1-1-1) to (1-1-3):

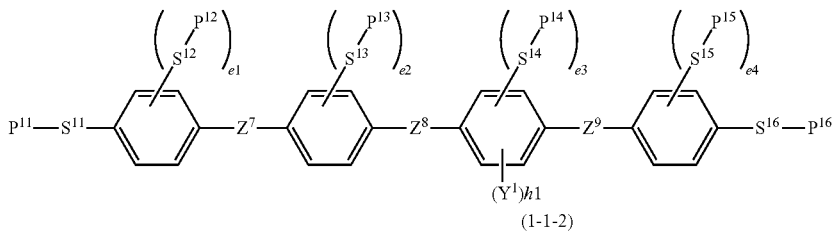
(1-1-1)

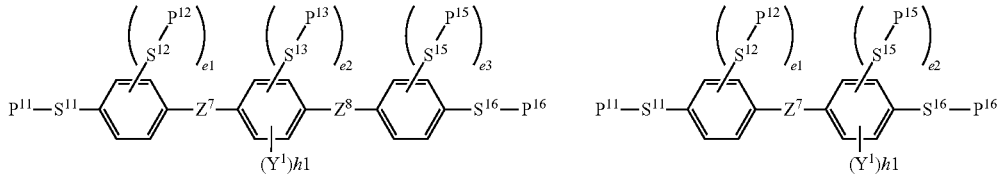
(1-1-2) (1-1-3)

wherein, in formula (1-1-1),
at least one of $P^{11}$, $P^{12}$, $P^{13}$, $P^{14}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-1-2),
at least one of $P^{11}$, $P^{12}$, $P^{13}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-1-3),
at least one of $P^{11}$, $P^{12}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; and in formulas (1-1-1) to (1-1-3),
$S^{11}$, $S^{12}$, $S^{13}$, $S^{14}$, $S^{15}$ and $S^{16}$ are independently a single bond, —CH$_2$—, —CH$_2$O—, —OCH$_2$—, —COO—, —OCO—, —CH═CH—, —C≡C—, —CH$_2$CH$_2$O—, —OCH$_2$CH$_2$—, —CH═CH—O— or —O—CH═CH—;
e1, e2, e3 and e4 are independently 0, 1 or 2;
$Z^7$, $Z^8$ and $Z^9$ are independently a single bond, —CO—, —COO—, —CH═CH—, —CH═CH—COO—, —C(CH$_3$)═CH—OCO—, —CH═C(CH$_3$)—OCO—, —C(CH$_3$)═C(CH$_3$)—OCO—, —COCH═CH—, —C(CH$_3$)═C(CH$_3$)—, —CH═CH—CH$_2$O— or —CH═CH—OCH$_2$—;

h1 is 0, 1 or 2; and
$Y^1$ is halogen, alkyl having 1 to 5 carbons, alkoxy having 1 to 5 carbons, alkyl having 1 to 5 carbons in which at least one of hydrogen is replaced by halogen or alkoxy having 1 to 5 carbons in which at least one of hydrogen is replaced by halogen.

Item 8. The polymerizable compound according to item 1, represented by any one of formulas (1-2) to (1-4):

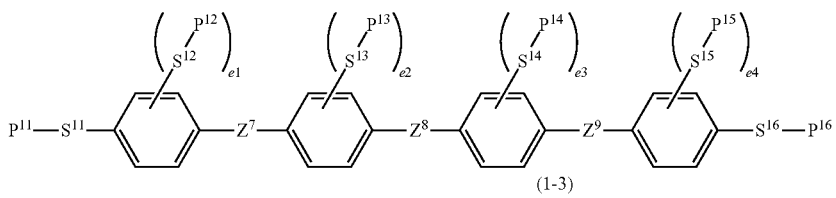
(1-2)

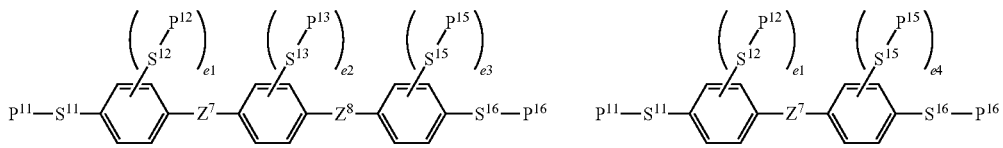
(1-3) (1-4)

wherein, in formula (1-2),
at least one of $P^{11}$, $P^{12}$, $P^{13}$, $P^{14}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-3),
at least one of $P^{11}$, $P^{12}$, $P^{13}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-4),
at least one of $P^{11}$, $P^{12}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; and in formulas (1-2) to (1-4), $S^{11}$, $S^{12}$, $S^{13}$, $S^{14}$, $S^{15}$ and $S^{16}$ are independently a single bond, —CH$_2$—, —CH$_2$O—, —OCH$_2$—, —COO—, —OCO—, —CH=CH—, —C≡C—, —CH$_2$CH$_2$O—, —OCH$_2$CH$_2$—, —CH=CH—O— or —O—CH=CH—;

e1, e2, e3 and e4 are independently 0, 1 or 2; and $Z^7$, $Z^8$ and $Z^9$ are independently a single bond, —CO—, —COO—, —CH=CH—, —CH=CH—COO—, —C(CH$_3$)=CH—OCO—, —CH=C(CH$_3$)—OCO—, —C(CH$_3$)=C(CH$_3$)—OCO—, —COCH=CH—, —C(CH$_3$)=C(CH$_3$)—, —CH=CH—CH$_2$O— or —CH=CH—OCH$_2$—.

Item 9. The polymerizable compound according to item 8: wherein, in formulas (1-2) to (1-4) described in item 8, $P^{11}$ and $P^{16}$ are independently acryloyloxy or methacryloyloxy, at least one of $P^{12}$, $P^{13}$, $P^{14}$ and $P^{15}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; $S^{11}$, $S^{12}$$S^{13}$, $S^{14}$, $S^{15}$ and $S^{16}$ are a single bond; e1, e2, e3 and e4 are independently 0, 1 or 2, and a sum of e1, e2, e3 and e4 is 1, 2, 3 or 4; and $Z^7$, $Z^8$ and $Z^9$ are a single bond.

Item 10. The polymerizable compound according to item 1, represented by formula (1-1-4) or (1-1-5):

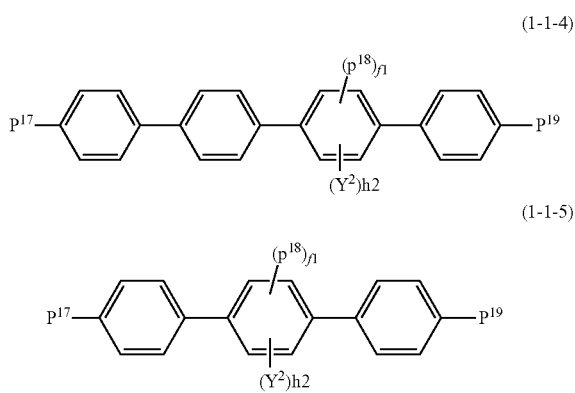

wherein, in formulas (1-1-4) and (1-1-5), at least one of $P^{17}$, $P^{18}$ and $P^{19}$ is acryloyloxy or methacryloyloxy, and at least one remainder is a polymerizable group selected from the group of

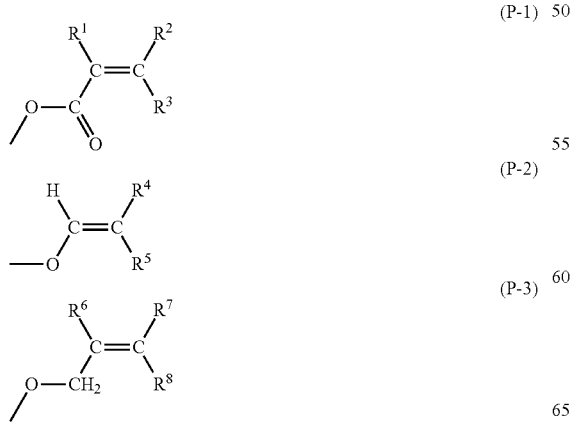

groups represented by formulas (P-1), (P-2) and (P-3):

wherein, in formulas (P-1) to (P-3), $R^1$, $R^2$, $R^3$, $R^4$, $R^5$, $R^6$, $R^7$ and $R^8$ are independently hydrogen, fluorine, methyl, ethyl or trifluoromethyl;

in formula (P-1), when $R^1$ is hydrogen or methyl, at least one of $R^2$ and $R^3$ is fluorine, methyl, ethyl or trifluoromethyl;

in formula (P-2), at least one of $R^4$ and $R^5$ is fluorine, methyl, ethyl or trifluoromethyl; and in formula (P-3), at least one of $R^6$, $R^7$ and $R^8$ is fluorine, methyl, ethyl or trifluoromethyl;

f1 and h2 are independently 1 or 2; and $Y^2$ is halogen, alkyl having 1 to 5 carbons, alkoxy having 1 to 5 carbons, alkyl having 1 to 5 carbons in which at least one of hydrogen is replaced by halogen or alkoxy having 1 to 5 carbons in which at least one of hydrogen is replaced by halogen.

Item 11. The polymerizable compound according to item 1, represented by formulas (1-5) to (1-6):

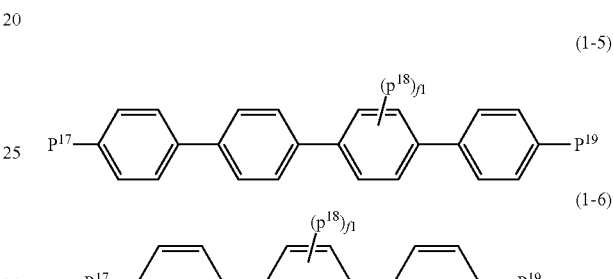

wherein, in formulas (1-5) and (1-6), at least one of $P^{17}$, $P^{18}$ and $P^{19}$ is acryloyloxy or methacryloyloxy, and at least one remainder is a polymerizable group selected from the group of groups represented by formulas (P-1), (P-2) and (P-3):

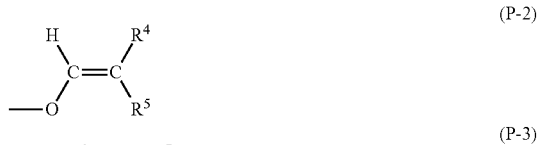

wherein, in formulas (P-1) to (P-3), $R^1$, $R^2$, $R^3$, $R^4$, $R^5$, $R^6$, $R^7$ and $R^8$ are independently hydrogen, fluorine, methyl, ethyl or trifluoromethyl;

in formula (P-1), when $R^1$ is hydrogen or methyl, at least one of $R^2$ and $R^3$ is fluorine, methyl, ethyl or trifluoromethyl;

in formula (P-2), at least one of $R^4$ and $R^5$ is fluorine, methyl, ethyl or trifluoromethyl; and in formula (P-3), at least one of $R^6$, $R^7$ and $R^8$ is fluorine, methyl, ethyl or trifluoromethyl; and f1 is 1 or 2.

Item 12. The polymerizable compound according to item 11, wherein, in formulas (1-5) and (1-6) described in item 11, at least one of $P^{17}$, $P^{18}$ and $P^{19}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; and f1 is 1 or 2.

Item 13. A polymerizable composition, containing at least one compound according to any one of items 1 to 12.

Item 14. The polymerizable composition according to item 13, further containing at least one compound selected from of the group of compounds represented by formulas (2) to (4):

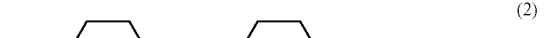

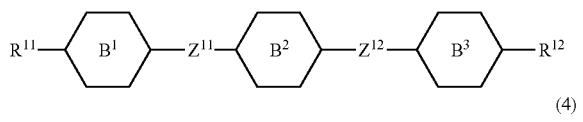

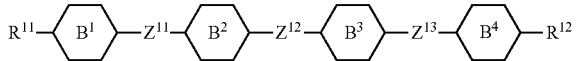

wherein, in formulas (2) to (4), $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 15. The polymerizable composition according to item 13 or 14, further containing at least one compound selected from the group of compounds represented by formulas (5) to (7):

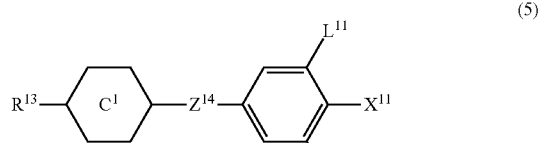

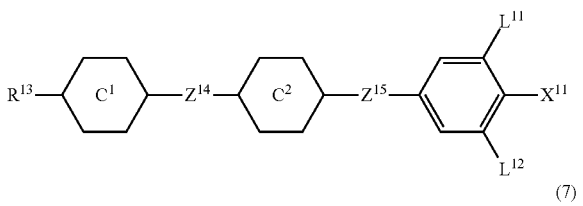

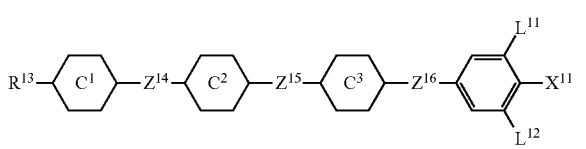

wherein, in formulas (5) to (7), $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 16. The polymerizable composition according to any one of items 13 to 15, further containing at least one compound selected from the group of compounds represented by formula (8):

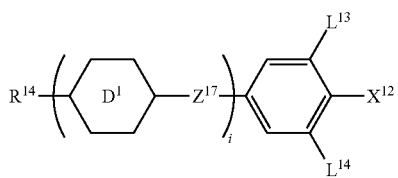

wherein, in formula (8), $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{12}$ is —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 17. A liquid crystal composite, produced by polymerization of the polymerizable composition according to any one of items 13 to 16.

Item 18. An optical anisotropic body, produced by polymerization of the polymerizable composition according to any one of items 13 to 16.

Item 19. A liquid crystal display device, including the polymerizable composition according to any one of items 13 to 16 or the liquid crystal composite according to item 17.

Item 20. Use of at least one selected from the compound according to any one of items 1 to 12, the polymerizable composition according to any one of items 13 to 16 and the liquid crystal composite according to item 17 in a liquid crystal display device.

The invention also includes the following items: (a) the polymerizable composition, further containing at least one of additives such as the optically active compound, the antioxidant, the ultraviolet light absorber, the heat stabilizer, the antifoaming agent, the polymerization initiator and the polymerization inhibitor; (b) the polymerizable composition, further containing a polymerizable compound different from the compound represented by formula (1); (c) an AM device, including the polymerizable composition; (d) a device, including the polymerizable composition and having a PS-TN mode, a PS-IPS mode, a PS-FFS mode, a PSA-VA mode or a PSA-OCB mode; (e) a transmissive device, including the polymerizable composition; (f) use of the polymerizable composition as a composition having the nematic phase; and (g) use as an optically active composition by adding the optically active compound to the composition.

The invention also includes the following items: (h) a polymerizable composition, having a positive dielectric anisotropy, and containing at least one compound selected from the group of compounds represented by formula (1); (i) a polymerizable composition, containing at least one compound selected from the group of compounds represented by formula (1), at least one compound selected from the group of compounds represented by formulas (2) to (4) and at least one compound selected from the group of compounds represented by formulas (5) to (7); (j) a polymerizable composition, containing at least one compound selected from the group of compounds represented by formula (1), at least one compound selected from the group of compounds represented by formulas (2) to (4) and at least one compound selected from the group of compounds represented by formula (8); (k) a polymerizable composition, containing at least one compound selected from the group of compounds represented by formula (1), at least one compound selected from the group of compounds represented by formulas (2) to (4), at least one compound selected from the group of compounds represented by formulas (5) to (7) and at least one compound selected from the group of compounds represented by formula (8); (l) the polymerizable composition, further containing a liquid crystal compound having 2,3-difluorophenylene and a negative dielectric anisotropy; (m) a liquid crystal composite, produced by polymerization of the polymerizable composition; and (n) use of the polymerizable composition or the liquid crystal composite in a liquid crystal display device having a PSA mode.

1. Polymerizable Compound

The polymerizable compound of the invention will be first described and then description will be made in the order of a synthetic method, the polymerizable composition, the liquid crystal composite and the liquid crystal display device. The polymerizable compound has at least two polymerizable groups in which at least one polymerizable group is acryloyloxy (—OCO—CH=CH$_2$) or methacryloyloxy (—OCO—C(CH$_3$)=CH$_2$), and at least one remaining polymerizable group is a polymerizable group selected from the group of groups represented by formulas (P-1), (P-2) and (P-3).

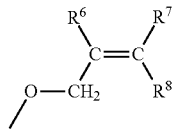

(P-1)

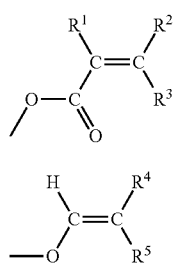

(P-2)

(P-3)

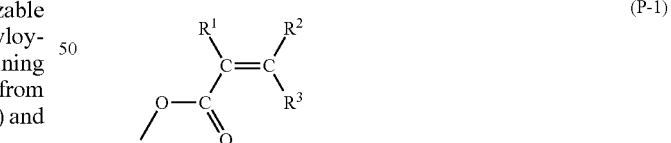

In formulas (P-1) to (P-3), R$^1$, R$^2$, R$^3$, R$^4$, R$^5$, R$^6$, R$^7$ and R$^8$ are independently hydrogen, fluorine, alkyl having 1 to 5 carbons or alkyl having 1 to 5 carbons in which at least one of hydrogen is replaced by halogen. However, the groups are different from acryloyloxy and methacryloyloxy.

A typical example of the polymerizable compound according to the invention is the compound represented by formula (1) below. First, compound (1) has a feature of having the rod like molecular structure. A commercially available liquid crystal composition used for the liquid crystal display device is a mixture of liquid crystal compounds each having the rod like molecular structure. Molecular structure of both are similar. Accordingly, compound (1) has a high solubility in the liquid crystal composition. Second, compound (1) has a feature of having a group having a high polymerizability and a group having a low polymerizability. The former is acryloyloxy or methacryloyloxy. The latter is 2-butenoyloxy or the like. Compound (1) has at least two kinds of polymerizable groups. Accordingly, molecular symmetry thereof decreases, and therefore the solubility in the liquid crystal composition is expected to be improved.

(1)

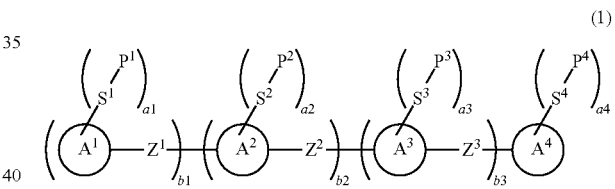

In formula (1), at least one of P$^1$, P$^2$, P$^3$ and P$^4$ is acryloyloxy or methacryloyloxy, and at least one remainder is a polymerizable group selected from the group of groups represented by formulas (P-1), (P-2) and (P-3).

(P-1)

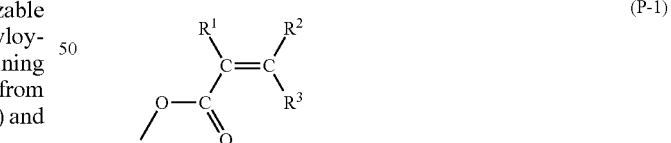

(P-2)

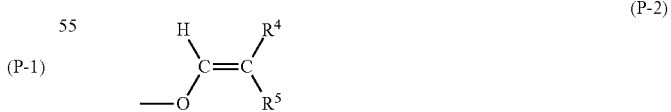

(P-3)

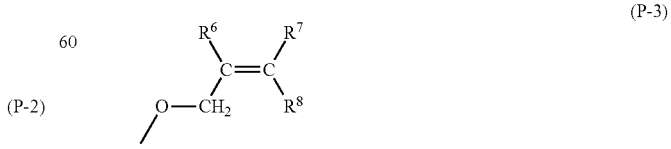

In formulas (P-1) to (P-3), R$^1$, R$^2$, R$^3$, R$^4$, R$^5$, R$^6$, R$^7$ and R$^8$ are independently hydrogen, fluorine, alkyl having 1 to 5 carbons, or alkyl having 1 to 5 carbons in which at least one of hydrogen is replaced by halogen; when $R^1$ is hydrogen or methyl, at least one of $R^2$ and $R^3$ is fluorine, alkyl having 1 to 5 carbons, or alkyl having 1 to 5 carbons in which at least one of hydrogen is replaced by halogen; at least one of $R^4$ and $R^5$ is fluorine, alkyl having 1 to 5 carbons, or alkyl having 1 to 5 carbons in which at least one of hydrogen is replaced by halogen; and at least one of $R^6$, $R^7$ and $R^8$ is fluorine, alkyl having 1 to 5 carbons, or alkyl having 1 to 5 carbons in which at least one of hydrogen is replaced by halogen. An expression "at least one of $P^1$, $P^2$, $P^3$ and $P^4$" means "at least one from $P^1$, $P^2$, $P^3$ and $P^4$ existing in one compound, and when a plurality exists, at least one from all thereof." A same rule applies to an expression "at least one" for others.

Preferred examples of groups (P-1) to (P-3) include 2-butenoyloxy (—OCO—CH=CH—CH$_3$), 2-methyl-2-butenoyloxy (—OCO—C(CH$_3$)=CH—CH$_3$), 2-methylenebutanoyloxy (—OCO—C(=CH$_2$)—CH$_2$—CH$_3$), 2-methyl-1-propenyloxy (—O—CH=O(CH$_3$)$_2$), 2,2-difluorovinyloxy (—O—CH=CF$_2$), 2-butenyloxy (—O—CH$_2$—CH=CH—CH$_3$) and 2-methyl-2-propenyloxy (—O—CH$_2$—C(CH$_3$)=CH$_2$). Further preferred examples of groups (P-1) to (P-3) include 2-butenyloxy, 2-methyl-2-butenyloxy or 2-methylenebutanoyloxy. Moreover, still further preferred examples of groups (P-1) to (P-3) include 2-methyl-1-propenyloxy, 2,2-difluorovinyloxy, 2-butenyloxy or 2-methyl-2-propenyloxy.

In formula (1), $S^1$, $S^2$, $S^3$ and $S^4$ are independently a single bond or alkylene having 1 to 10 carbons, and in the alkylene, at least one of —CH$_2$— may be replaced by —O—, —OCO—, —OCO— or —OCO—, at least one of —CH$_2$—CH$_2$— may be replaced by —CH=CH— or —C≡C—, and at least one of hydrogen may be replaced by fluorine or chlorine.

Preferred examples of $S^1$, $S^2$, $S^3$ or $S^4$ include a single bond, —CH$_2$—, —CH$_2$O—, —OCH$_2$—, —OCO—, —OCO—, —CH$_2$CH$_2$—, —CH=CH—, —C≡C—, —(CH$_2$)$_3$—, —CH$_2$CH$_2$O—, —OCH$_2$CH$_2$—, —CH=CH—O—, —O—CH=CH—, —C≡C—O—, —O—C≡C—, —(CH$_2$)$_4$—, —(CH$_2$)$_3$—O—, —O—(CH$_2$)$_3$, —(CH$_2$)$_4$O— or —O(CH$_2$)$_4$—. Further preferred examples include a single bond, —CH$_2$—, —CH$_2$O—, —OCH$_2$—, —COO—, —OCO—, —CH=CH—, —C≡C—, —CH$_2$CH$_2$O—, —OCH$_2$CH$_2$—, —CH=CH—O— or —O—CH=CH—. Particularly preferred examples include a single bond, —CH$_2$—, —CH=CH—, —CH=CH—O—, —O—CH=CH—, —CH$_2$CH$_2$O— or —OCH$_2$CH$_2$—. A most preferred example includes a single bond. A configuration of a double bond of —CH=CH— may be a cis or trans form. The trans form is preferred to the cis form.

In formula (1), a1, a2, a3 and a4 are independently 0, 1, 2, 3 or 4, and a sum of a1, a2, a3 and a4 is an integer from 2 to 10. A preferred example of a1, a2, a3 or a4 is 0, 1, 2 or 3, and a further preferred example is 0, 1 or 2.

In formula (1), ring $A^1$ and ring $A^4$ are independently phenyl, pyrimidyl, pyridyl, naphthyl, cyclohexyl, cyclohexenyl, tetrahydropyranyl or 1,3-dioxanyl, and in the rings, at least one of hydrogen may be replaced by halogen, alkyl having 1 to 12 carbons, or alkyl having 1 to 12 carbons in which at least one of hydrogen is replaced by halogen.

Ring $A^2$ and ring $A^3$ are independently 1,4-phenylene, pyrimidine-2,5-diyl, pyridine-2,5-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, 1,4-cyclohexylene, 1,4-cyclohexenylene, tetrahydropyran-2,5-diyl or 1,3-dioxane-2,5-diyl, and in the rings, at least one of hydrogen may be replaced by halogen, alkyl having 1 to 12 carbons, or alkyl having 1 to 12 carbons in which at least one of hydrogen is replaced by halogen.

Preferred examples of ring $A^1$, ring $A^2$, ring $A^3$ or ring $A^4$ include 1,4-phenylene, pyrimidine-2,5-diyl, pyridine-2,5-diyl, naphthalene-1,4-diyl, naphthalene-1,5-diyl, naphthalene-1,6-diyl, naphthalene-2,6-diyl, 1,4-cyclohexylene, tetrahydropyran-2,5-diyl or 1,3-dioxane-2,5-diyl, and in the rings, at least one or two of hydrogen may be replaced by fluorine, chlorine, alkyl having 1 to 3 carbons, or alkyl having 1 to 3 carbons in which at least one of hydrogen is replaced by halogen. Preferred examples of alkyl in which at least one of hydrogen is replaced by halogen as described above include —CH$_2$F, —CHF$_2$, —CF$_3$, —CClF$_2$, —CH$_2$CF$_3$, —CF$_2$CF$_3$ and —CH$_2$H$_2$CF$_3$.

Preferred examples of ring $A^1$, ring $A^2$, ring $A^3$ or ring $A^4$ include 1,4-phenylene, 2-fluoro-1,4-phenylene, 2,3-difluoro-1,4-phenylene, 2,5-difluoro-1,4-phenylene, 2,6-difluoro-1,4-phenylene, 2-chloro-1,4-phenylene, 2-chloro-3-fluoro-1,4-phenylene, 2-methyl-1,4-phenylene, 2-ethyl-1,4-phenylene, 2-difluoromethyl-1,4-phenylene, 2-trifluoromethyl-1,4-phenylene, pyrimidine-2,5-diyl or pyridine-2,5-diyl. Further preferred examples include naphthalene-1,4-diyl, naphthalene-1,5-diyl, naphthalene-1,6-diyl or naphthalene-2,6-diyl. Particularly preferred examples include 1,4-phenylene, naphthalene-1,4-diyl, naphthalene-1,5-diyl or naphthalene-2,6-diyl. A most preferred example is 1,4-phenylene.

In formula (1), $Z^1$, $Z^2$ and $Z^3$ are independently a single bond or alkylene having 1 to 10 carbons, and in the alkylene, at least one of —CH$_2$— may be replaced by —O—, —CO—, —OCO—, —OCO—, at least one of —CH$_2$—CH$_2$— may be replaced by —CH=CH—, —C(CH$_2$)=CH—, —CH=C(CH$_3$)— or —C(CH$_3$)=O(CH$_3$)—, and at least one of hydrogen may be replaced by fluorine or chlorine.

Preferred $Z^1$, $Z^2$ or $Z^3$ includes a single bond, alkylene having 1 to 5 carbons, —CO—, —COO—, —OCO—, —CH=CH—, —CH=CH—OCO—, —OCO—CH=CH—, —C(CH$_3$)=CH—OCO—, —OCO—CH=C(CH$_3$)—, —CH=C(CH$_3$)—OCO—, —OCO—(CH$_3$)C=CH—, —C(CH$_3$)=C(CH$_3$)—, —COO—, —OCO—C(CH$_3$)=C(CH$_3$)—, —CO—C(CH$_3$)—, —CH=CH—CO—, —C(CH$_3$)=C(CH$_3$)—, —CH=CH—CH$_2$O—, —OCH$_2$—CH=CH—, —CH=CH—OCH$_2$— or —CH$_2$O—CH=CH—. Further preferred $Z^1$, $Z^2$ or $Z^3$ includes a single bond, —OCO—, —OCO— or —CH=CH—. A most Preferred $Z^1$, $Z^2$ or $Z^3$ includes a single bond. When the bonding group has —CH=CH—, a configuration thereof may be a cis or trans form. A preferred configuration is a trans form.

In formula (1), b1, b2 and b3 are independently 0 or 1. A sum of b1, b2 and b3 is 0, 1, 2 or 3. A preferred example of the sum is 1, 2 or 3. A further preferred example of the sum is 2 or 3. A most preferred example the sum is 2.

In compound (1), preferred examples of polymerizable group P, linking group S, ring A and bonding group Z are as described above. The examples apply also to subordinate formulas of compound (1). With referring to the preferred examples described above, a polymerizable compound having objective physical properties can be obtained by suitably selecting a combination of polymerizable groups ($P^1$ to $P^4$), linking groups ($S^1$ to $S^4$), rings ($A^1$ to $A^4$) and bonding groups ($Z^1$ to $Z^3$). In addition, a case where an element of $S^1$ to be bonded with $P^1$ is oxygen is not preferred because a divalent group such as —COO—C— and —O—O— is formed. A same rule also applies to a bond between P² and S², or the like. Compound (1) may contain an isotope such as ²H (deuterium) and ¹³C in an amount larger than an amount of natural abundance because no significant difference is in the physical properties of the compound.

Preferred examples of compound (1) include compound (1-1). Further preferred examples include compounds (1-2) to (1-4) and compounds (1-1-1) to (1-1-3). Particularly preferred examples include compounds (1-2-a) to (1-2-m), compounds (1-3-a) to (1-3-o), compounds (1-4-a) to (1-4-g), compounds (1-1-1-a) to (1-1-1-f), compounds (1-1-2-a) to (1-1-2-g) and compounds (1-1-3-a) to (1-1-3-g).

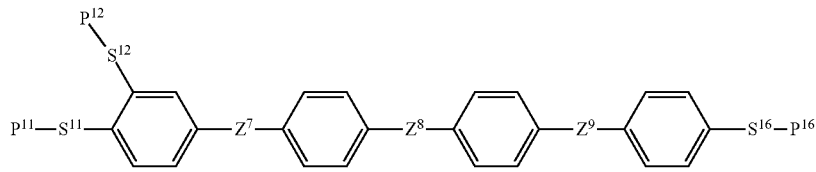
(1-2-a)

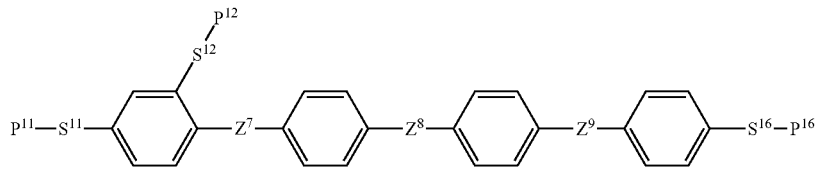
(1-2-b)

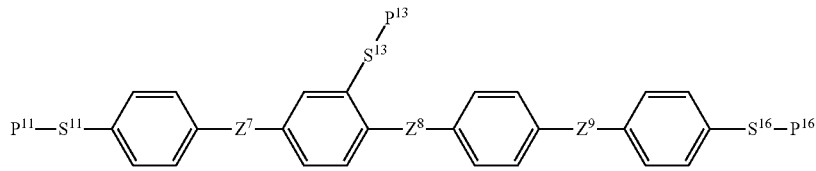
(1-2-c)

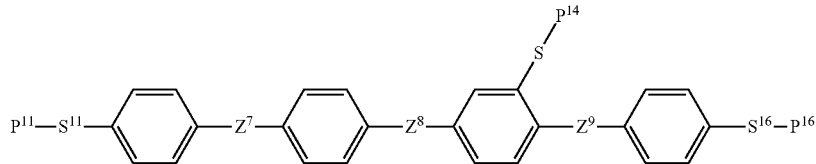
(1-2-d)

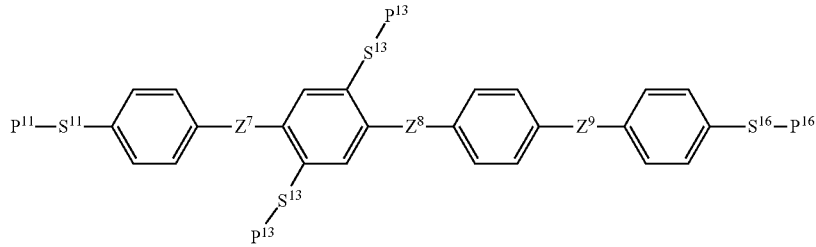
(1-2-e)

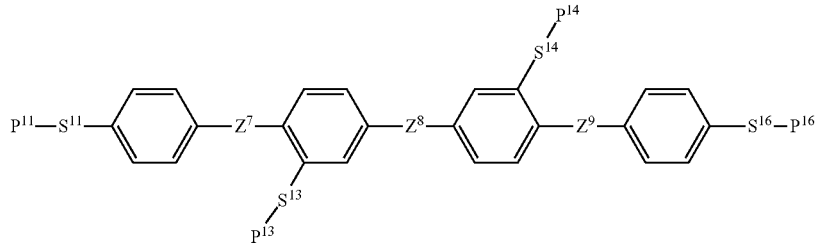
(1-2-f)

-continued
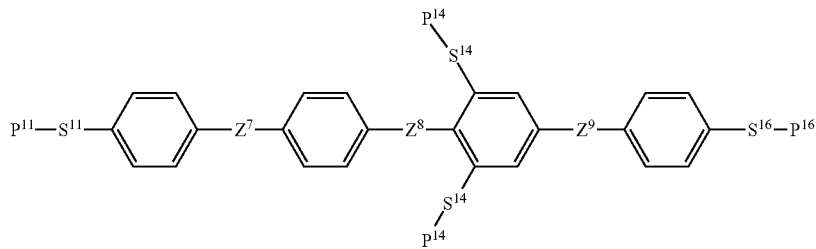
(1-2-g)
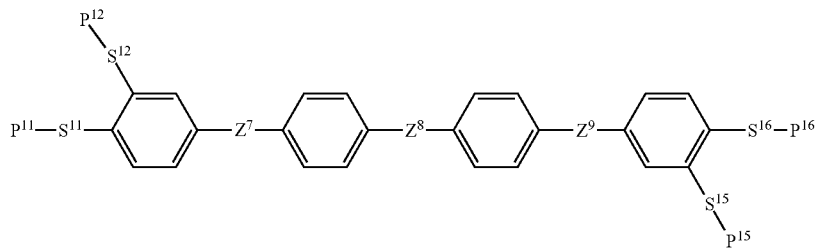
(1-2-h)
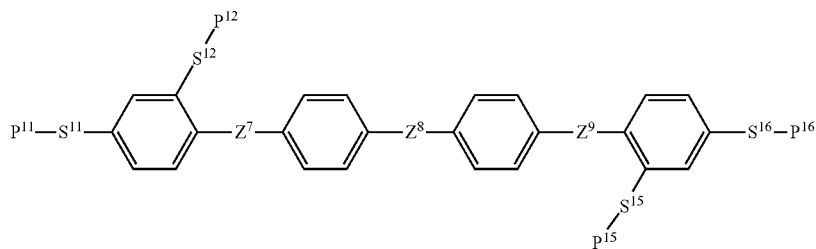
(1-2-i)
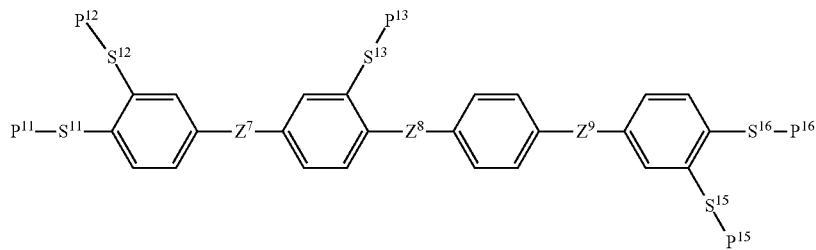
(1-2-j)
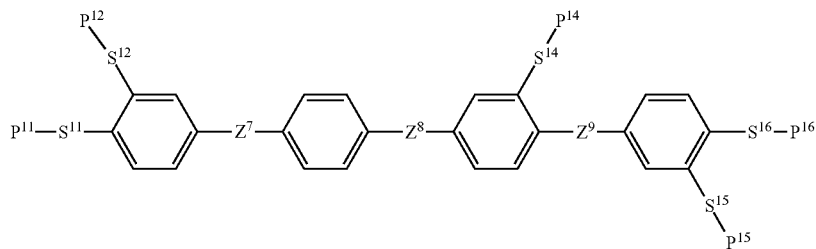
(1-2-k)
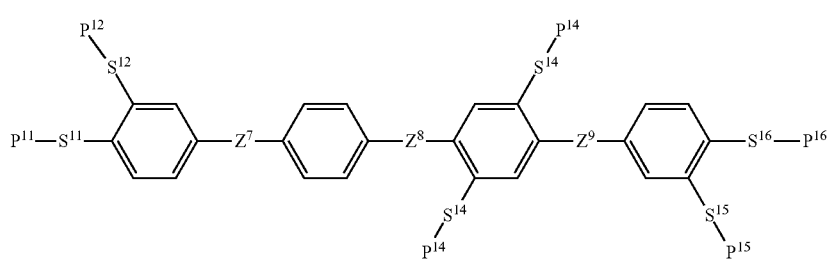
(1-2-l)

-continued
(1-2-m)
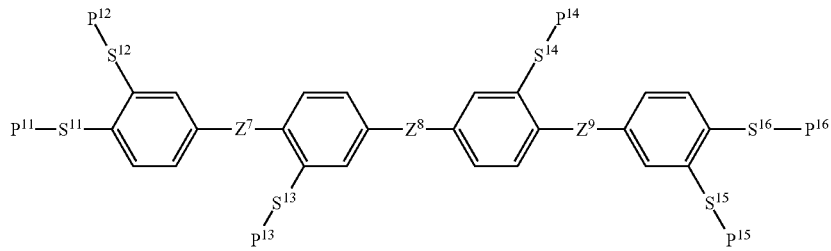
(1-3-a) (1-3-b)
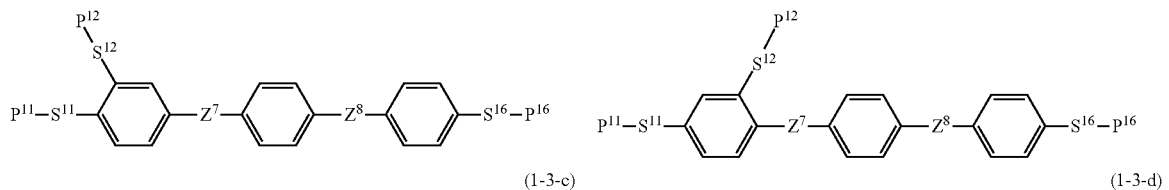
(1-3-c) (1-3-d)
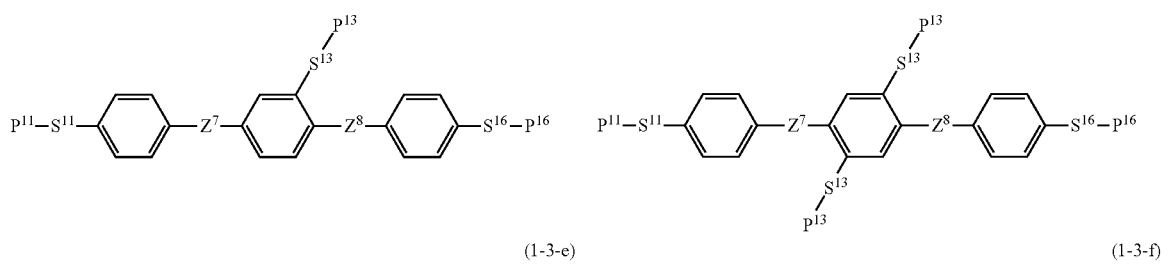
(1-3-e) (1-3-f)
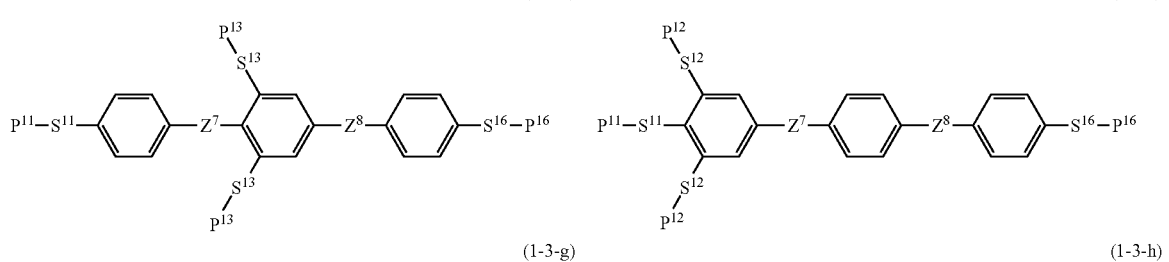
(1-3-g) (1-3-h)
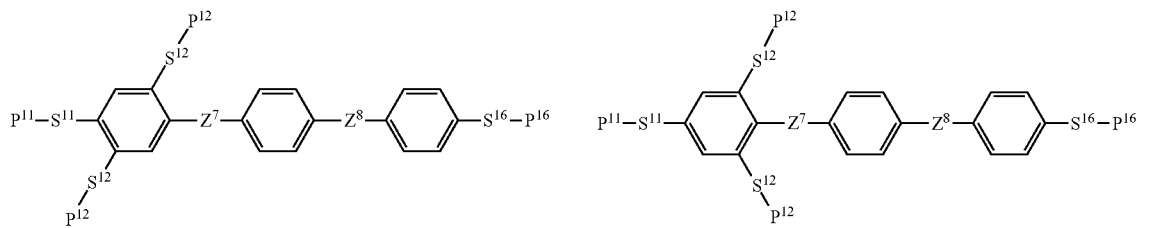
(1-3-i) (1-3-j)
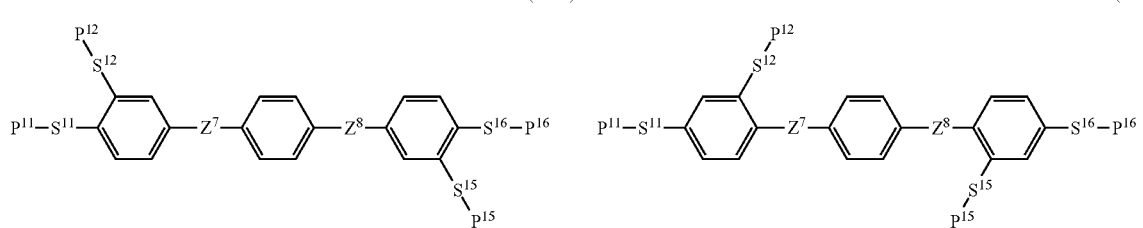

-continued
(1-3-k)
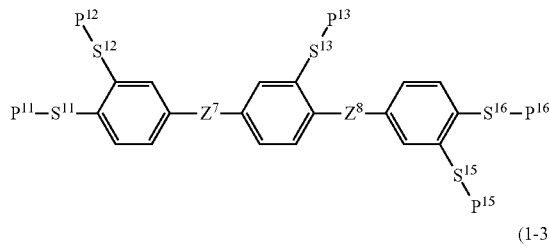
(1-3-l)
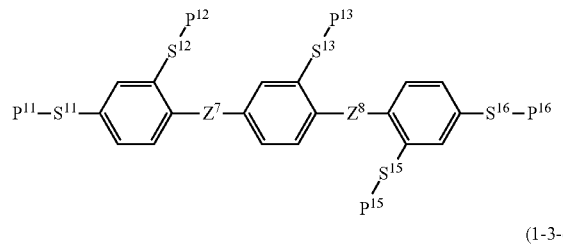
(1-3-m)
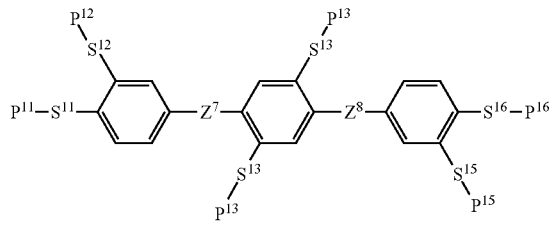
(1-3-o)
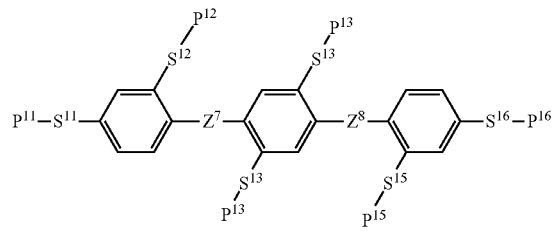
(1-4-a)
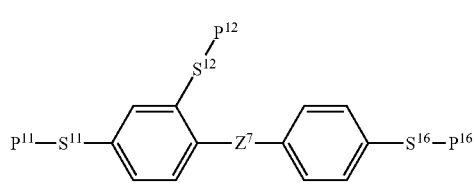
(1-4-b)
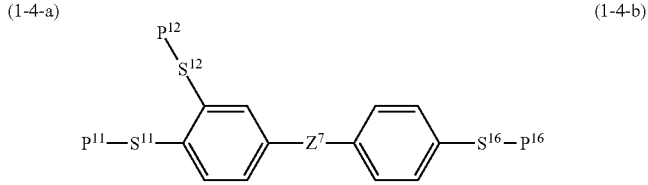
(1-4-c)
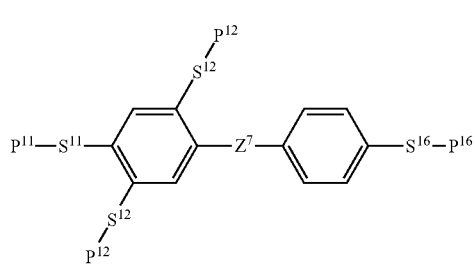
(1-4-d)
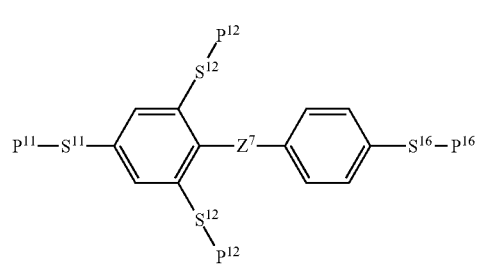
(1-4-e)
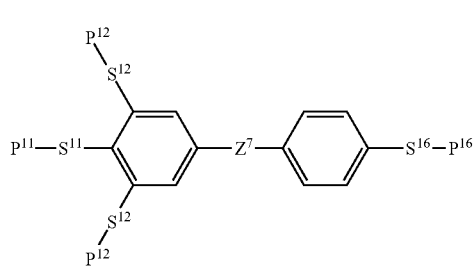
(1-4-f)
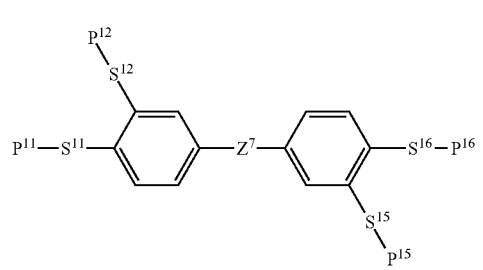
(1-4-g)
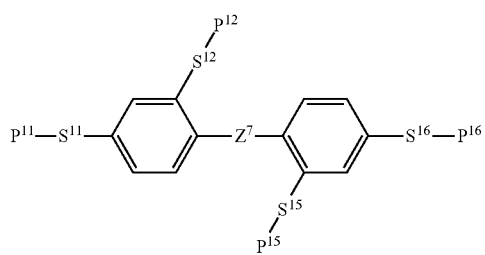

(1-1-1-a)
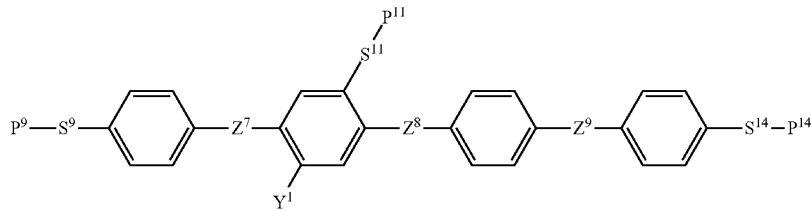
(1-1-1-b)
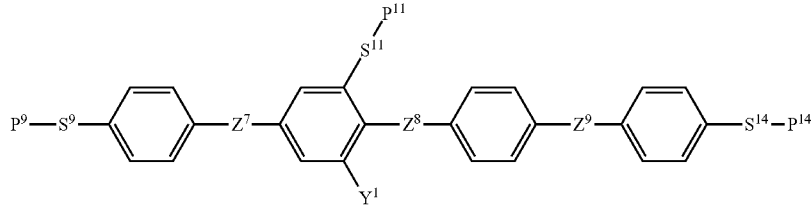
(1-1-1-c)
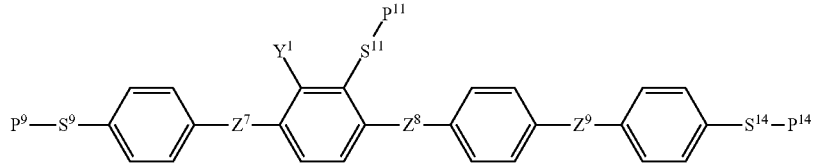
(1-1-1-d)
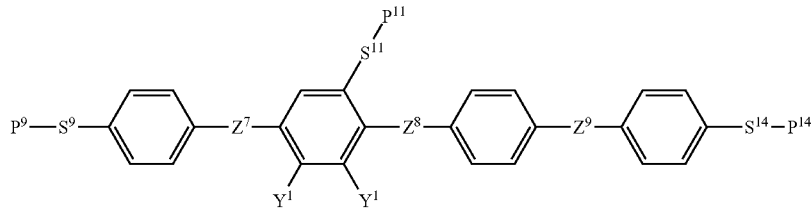
(1-1-1-e)
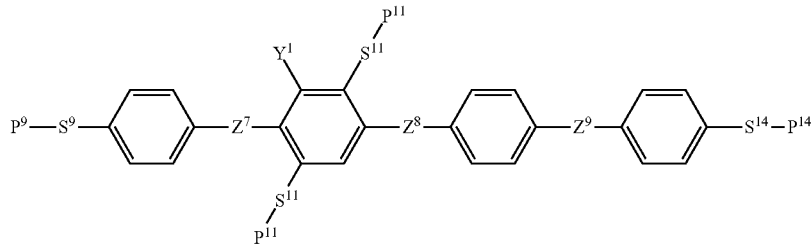
(1-1-1-f)
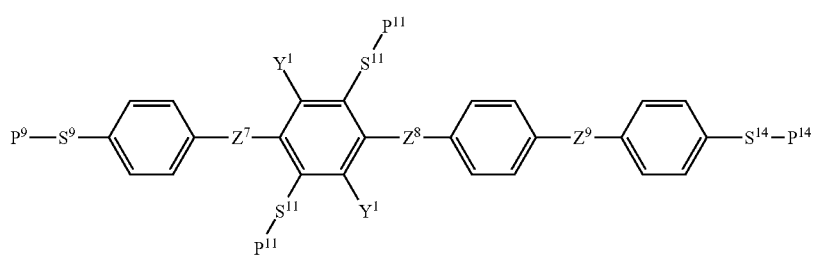
(1-1-2-a)
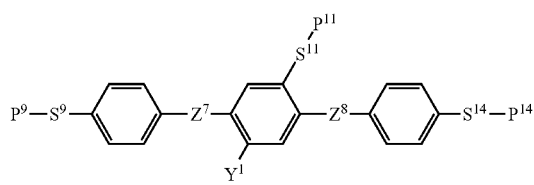
(1-1-2-b)
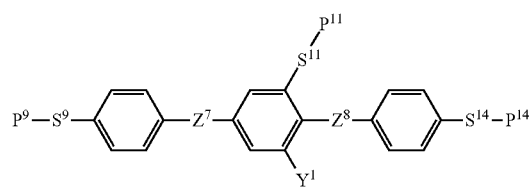

-continued
(1-1-2-c)
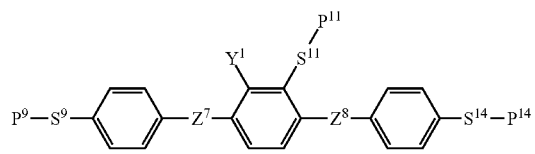
(1-1-2-d)
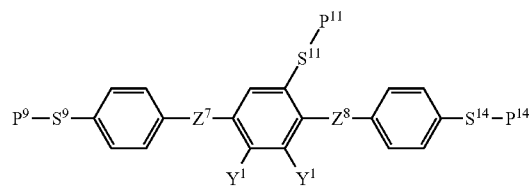
(1-1-2-e)
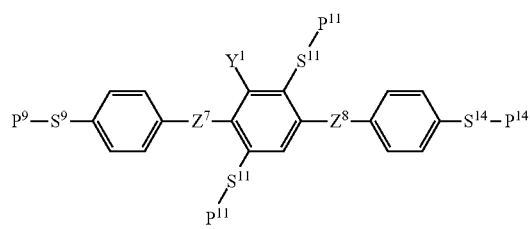
(1-1-2-f)
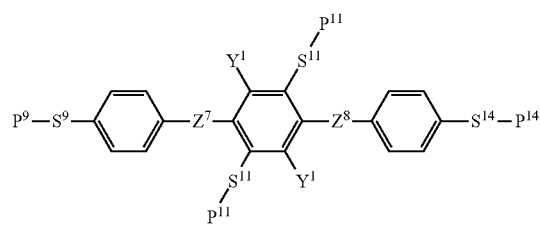
(1-1-2-g)
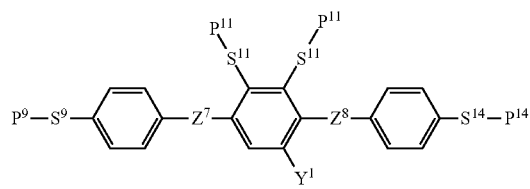
(1-1-3-a)
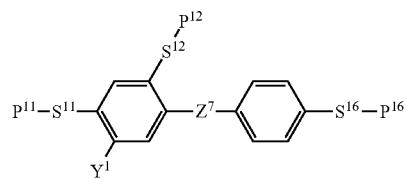
(1-1-3-b)
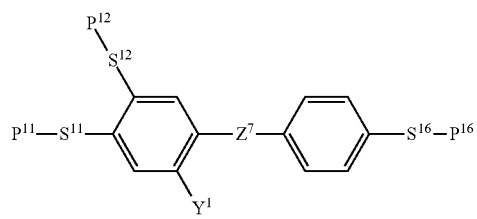
(1-1-3-c)
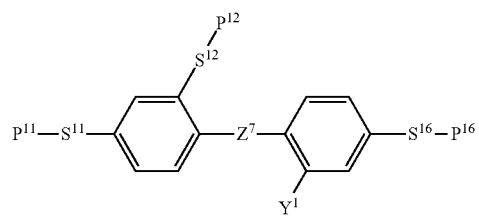
(1-1-3-d)
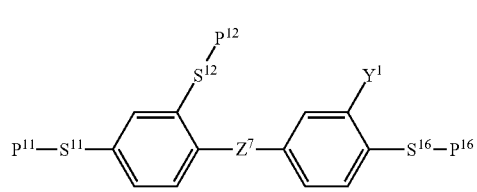
(1-1-3-e)
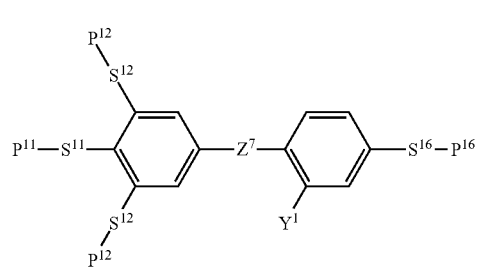
(1-1-3-f)
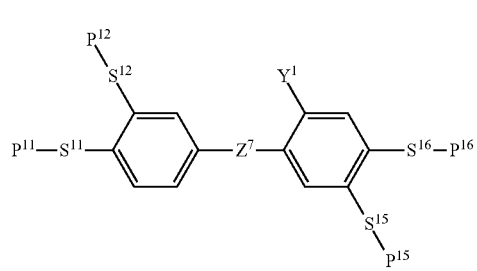
(1-1-3-g)
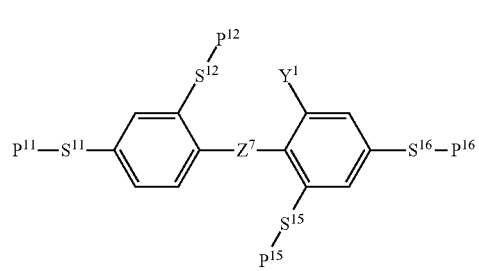

In compounds (1-2-a) to (1-2-m), compounds (1-3-a) to (1-3-c), compounds (1-4-a) to (1-4-g), compounds (1-1-1-a) to (1-1-1-f), compounds (1-1-2-a) to (1-1-2-g) and compounds (1-1-3-a) to (1-1-3-g), at least one of $P^{11}$, $P^{12}$, $P^{13}$, $P^{14}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

$S^{11}$, $S^{12}$, $S^{13}$, $S^{14}$, $S^{15}$ and $S^{16}$ are independently a single bond, —CH$_2$O—, —OCH$_2$—, —COO—, —OCO—, —CH=CH—, —C≡C—, —CH$_2$CH$_2$O—, —OCH$_2$CH$_2$—, —CH=CH—O— or —O—CH=CH—; and $Z^7$, $Z^8$ and $Z^9$ are independently a single bond, —CO—, —COO—, —CH=CH—, —CH=CH—COO—, —C(CH$_3$)=CH—OCO—, —CH=C(CH$_3$)—OCO—, —C(CH$_3$)=C(CH$_3$)—OCO—, —COCH=CH—, —C(CH$_3$)=C(CH$_3$)—, —CH=CH—CH$_2$O— or —CH=CH—OCH$_2$—.

An expression "at least one of $P^{11}$, $P^{12}$, $P^{13}$, $P^{14}$, $P^{15}$ and $P^{16}$" means "at least one selected from $P^{11}$ to $P^{16}$ existing in one compound." In compounds (1-2-a) to (1-2-j), compounds (1-3-a) to (1-3-o), compounds (1-4-a) to (1-4-g), compounds (1-1-1-a) to (1-1-1-f), compounds (1-1-2-a) to (1-1-2-g) and compounds (1-1-3-a) to (1-1-3-g), $P^{11}$ and $P^{16}$ are preferably acryloyloxy or methacryloyloxy, and $P^{11}$ and $P^{16}$ are further preferably methacryloyloxy. Further, $S^{11}$ and $S^{16}$ are preferably a single bond, and $Z^7$, $Z^8$ and $Z^9$ are preferably a single bond. In the compounds, preferred examples include compound (1-2-c), compound (1-2-d), compound (1-2-e), compound (1-2-h), compound (1-3-c), compound (1-3-d), compound (1-3-i), compound (1-3-k), compound (1-3-m) and compound (1-4-f). Further preferred examples include compound (1-3-c) and compound (1-3-d).

Moreover, in compounds (1-1-1-a) to (1-1-1-f), compounds (1-1-2-a) to (1-1-2-g) and compounds (1-1-3-a) to (1-1-3-g), even in a case where $Y^1$ is halogen, at least one of $P^9$, $P^{11}$ and $P^{14}$ is an acryloyloxy group and the other is a methacryloyloxy group, (improvement in the solubility in the liquid crystal composition is expected due to a decrease in symmetry of molecules), and such a case is preferred.

Particularly preferred examples of compound (1) include compounds (1-7-1) to (1-7-5) having a divalent group derived from naphthalene.

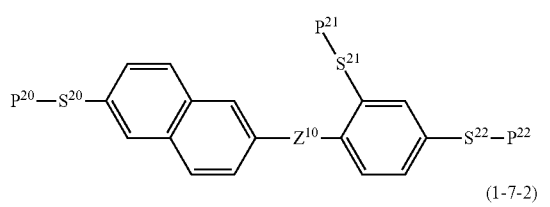

(1-7-1)

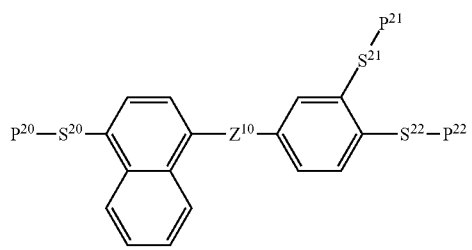

(1-7-2)

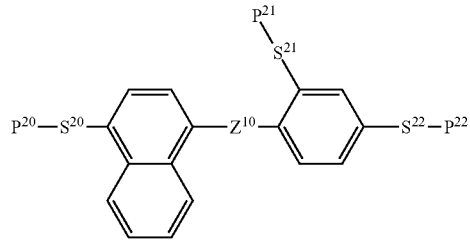

(1-7-3)

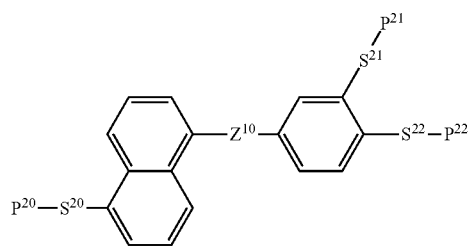

(1-7-4)

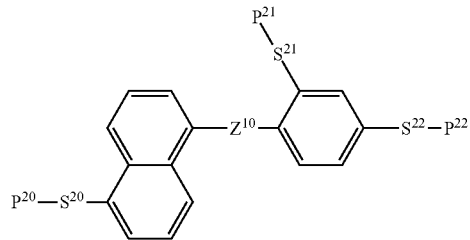

(1-7-5)

In compounds (1-7-1) to (1-7-5), at least one of $P^{20}$, $P^{21}$ and $P^{22}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

$S^{20}$, $S^{21}$ and $S^{22}$ are independently a single bond, —CH$_2$O—, —OCH$_2$—, —OCO—, —OCO—, —CH=CH—, —C≡C—, —CH$_2$CH$_2$O—, —OCH$_2$CH$_2$—, —CH=CH—O— or —O—CH=OH—; and $Z^{10}$ is a single bond, —CO—, —OCO—, —CH=CH—, —CH=CH—OCO—, —C(CH$_3$)=CH—OCO—, —CH=C(CH$_3$)—OCO—, —C(CH$_3$)=C(CH$_3$)—OCO—, —COCH=OH—, —C(CH$_3$)=C(CH$_3$)—, —CH=CH—CH$_2$O— or —CH=CH—OCH$_2$—.

In compounds (1-7-1) to (1-7-5), $P^{20}$ and $P^{22}$ are preferably acryloyloxy or methacryloyloxy. $S^{20}$ and $S^{22}$ are preferably a single bond.

Moreover, in compounds (1-7-1) to (1-7-5), even in a case where $Y^1$ halogen, at least one of $P^9$, $P^{11}$ and $P^{14}$ is acryloyloxy group and the other is methacryloyloxy group, (improvement in the solubility in the liquid crystal composition is expected due to a decrease in symmetry of molecules), an such a case is preferred.

2. Synthetic Method

The synthetic method of compound (1) will be described. Compound (1) can be synthesized by suitably combining methods in synthetic organic chemistry. Methods for introducing an objective terminal group, ring and bonding group into a starting material are described in books such as Houben-Wyle, Methoden der Organischen Chemie (Georg- Thieme Verlag, Stuttgart), Organic Syntheses (John Wily & Sons, Inc.), Organic Reactions (John Wily & Sons Inc.), Comprehensive Organic Synthesis (Pergamon Press) and New Experimental Chemistry Course (Shin Jikken Kagaku Koza in Japanese) (Maruzen Co., Ltd.).

2-1. Formation of bonding group Z

An example of a method of forming bonding groups $Z^1$ to $Z^3$ in compound (1) is as described in a scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to compound (1I) correspond to compound (1). In formation of ester, a synthetic method of a compound having —COO— is described. A compound having —OCO— can also be prepared by the synthetic method. Any other unsymmetrical bonding group can also be formed in a similar manner.

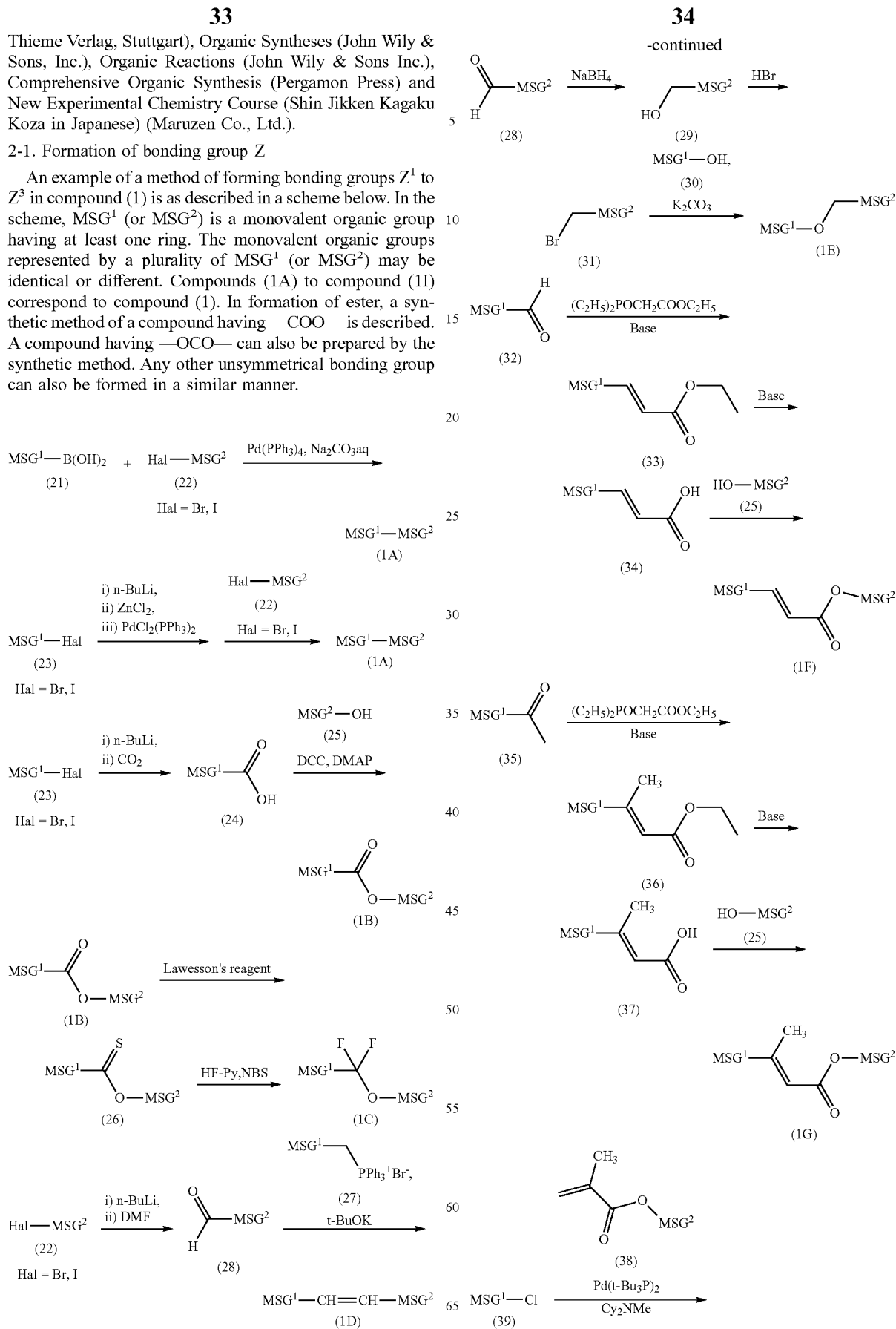

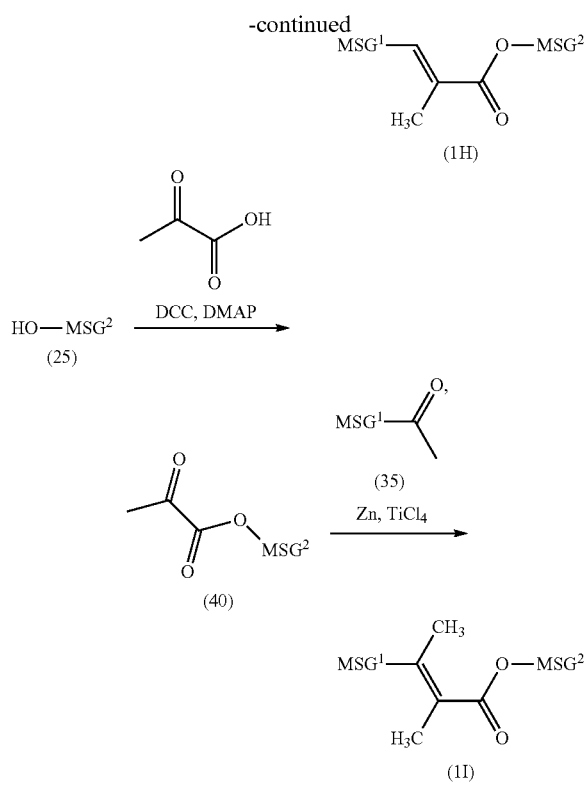

(1) Formation of a Single Bond

Compound (1A) is prepared by allowing aryl boronic acid (21) to react, in the presence of an aqueous carbonate solution and a catalyst such as tetrakis(triphenylphosphine) palladium, with compound (22) prepared according to a known method. Compound (1A) is also prepared by allowing compound (23) prepared according to a known method to react with n-butyllithium, and subsequently with zinc chloride, and further by allowing the resulting material to react with compound (22) in the presence of a catalyst such as dichlorobis(triphenylphosphine)palladium.

(2) Formation of —OCO—

Carboxylic acid (24) is obtained by allowing compound (23) to react with n-butyllithium and subsequently with carbon dioxide. Compound (1B) is prepared by performing dehydrating condensation of compound (24) and phenol (25) prepared according to a known method in the presence of 1,3-dicyclohexylcarbodiimide (DCC) and DMAP (N,N-dimethyl-4-aminopyridine).

(3) Formation of —CF$_2$O—

Compound (26) is obtained by treating compound (1B) with a thiation reagent such as Lawesson's reagent. Compound (1C) is prepared by fluorinating compound (26) with a hydrogen fluoride-pyridine complex and N-bromosuccinimide (NBS). Refer to M. Kuroboshi et al., Chem. Lett., 1992, 827. Compound (1C) can also be prepared by fluorinating compound (26) with (diethylamino)sulfurtrifluoride (DAST). Refer to W. H. Bunnelle et al., J. Org. Chem. 1990, 55, 768. The bonding group can also be prepared according to the method described in Peer. Kirsch et al., Angew. Chem. Int. Ed. 2001, 40, 1480.

(4) Formation of —CH═CH—

Aldehyde (28) is obtained by treating compound (22) with n-butyllithium, and subsequently allowing the resulting material to react with formamide such as N,N-dimethylformamide (DMF). Compound (1D) is prepared by allowing phosphorus ylide produced by treating phosphonium salt (27) prepared according to a known method with a base such as potassium tert-butoxide to react with aldehyde (28). A cis isomer may be generated depending on reaction conditions, and the cis isomer is isomerized to a trans isomer according to a known method, when necessary.

(5) Formation of —CH$_2$O—

Compound (29) is obtained by reducing compound (28) with a reducing agent such as sodium borohydride. Compound (31) is obtained by halogenating the obtained compound with hydrobromic acid or the like. Compound (1E) is prepared by allowing compound (31) to react with compound (30) in the presence of potassium carbonate or the like.

(6) Formation of —CH═CH—OCO—

Phosphorus ylide is prepared by allowing a base such as sodium hydride to react with diethylphosphoethyl acetate, the phosphorus ylide is allowed to react with aldehyde (32), and thus ester (33) is obtained. Carboxylic acid (34) is obtained by hydrolyzing ester (33) in the presence of abase such as sodium hydroxide. Compound (1F) is prepared by performing dehydrating condensation of the compound and compound (25).

(7) Formation of —C(CH$_3$)═CH—OCO—

Phosphorus ylide is prepared by allowing a base such as sodium hydride to react with diethylphosphoethyl acetate, and the phosphorus ylide is allowed to react with methyl ketone (35), and thus ester (36) is obtained. Next, carboxylic acid (37) is obtained by hydrolyzing the ester (36) in the presence of abase such as sodium hydroxide, and subsequently compound (1G) is prepared by performing dehydrating condensation of the acid and compound (25).

(8) Formation of —CH═C(CH$_3$)—OCO—

Compound (1H) is prepared by allowing compound (38) prepared according to a known method to react with compound (39) prepared according to a known method, in the presence of a base such as N,N-dicyclohexylmethylamine (Cy$_2$NMe) and a catalyst such as bis(tri-tert-butylphosphine) palladium.

(9) Formation of —C(CH$_3$)═C(CH$_3$)—OCO—

Compound (40) is obtained by dehydrating condensation of compound (25) and pyruvic acid. Compound (1I) is prepared by allowing compound (40) to react with compound (35) in the presence of zinc and titanium tetrachloride.

2-2. Formation of Linking Group S

In a compound in which the polymerizable group is —OCO-(M$^1$)C═CH(M$^2$), a synthetic method of linking group S will be described. A compound in which a polymerizable group is vinyloxy (P-2) subjected to replacement or allyloxy (P-3) subjected to replacement will be described in section 6.

(1) Single Bond

An example of a method of preparing compound (1) in which the connecting group is a single bond is as described in a scheme below. In the scheme, MSG$^1$ is a monovalent organic group having at least one ring. Compounds (1J) to (1M) correspond to compound (1).

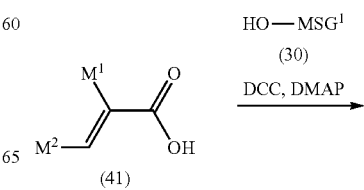

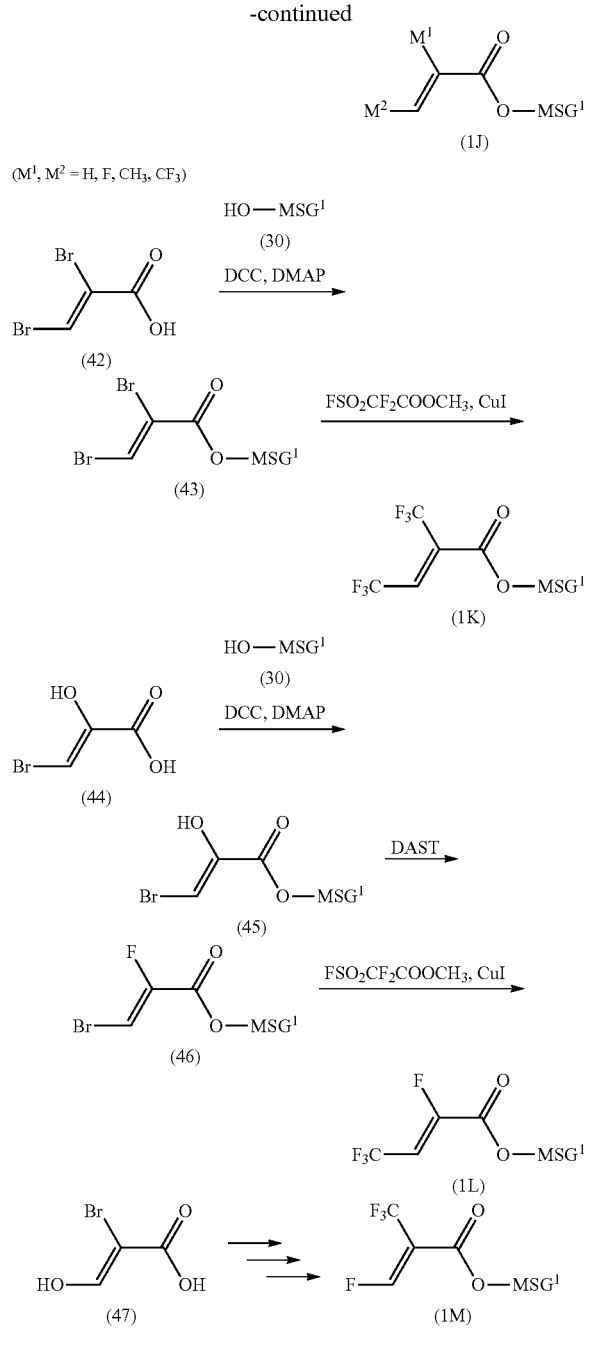

(44) and compound (30) in the presence of DDC and DMAP. Compound (46) is obtained by fluorinating compound (45) with fluorinating agents such as DST. Compound (1L) is prepared by allowing compound (46) to react with 2,2-difluoro-2-(fluorosulfonyl)methylacetate in the presence of the catalyst of copper iodide.

In the case where $M^1$ is —$CF_3$ and $M^2$ is fluorine, carboxylic acid (47) is used as a starting material, and compound (1M) is prepared according to the above method.

An example of a method of preparing a connecting group (S is not equal to a single bond) in compound (1) is as described in a scheme below. In the scheme, $MSG^1$ is a monovalent organic group having at least one ring. Compounds (1N) to (1Q) correspond to compound (1).

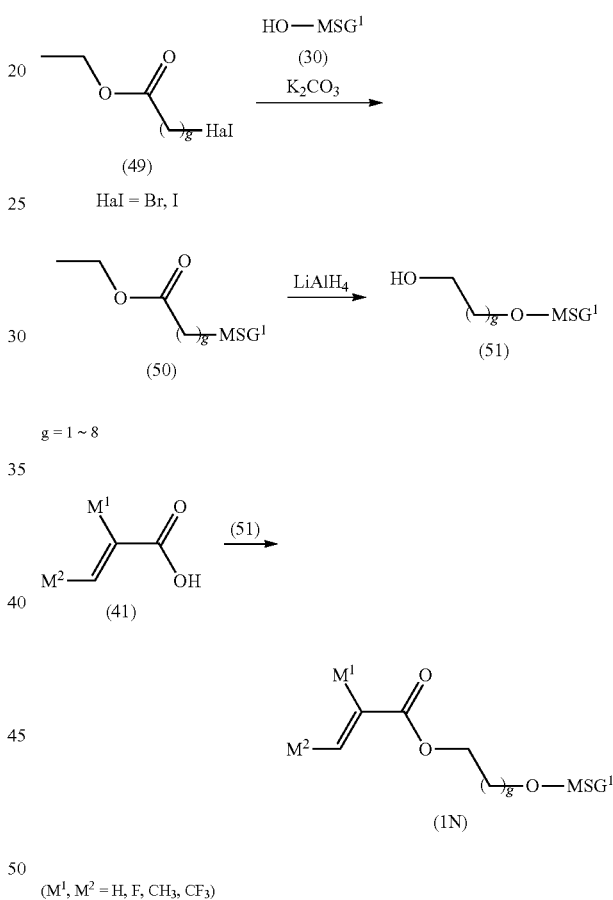

In the case where neither $M^1$ nor $M^2$ is —$CF_3$, in the case where $M^1$ is fluorine and $M^2$ is not —$CF_3$, or in the case where $M^1$ is —$CF_3$ and $M^2$ is not fluorine, carboxylic acid (41) described in the above scheme is commercially available. Compound (1J) is prepared by dehydrating carboxylic acid (41) and compound (30) in the presence of DDC and DMAP.

In the case where both $M^1$ and $M^2$ are —$CF_3$, compound (43) is obtained by dehydrating carboxylic acid (42) and compound (30) in the presence of DDC and DMAP. Compound (1K) is prepared by allowing compound (43) to react with 2,2-difluoro-2-(fluorosulfonyl)methylacetate in the presence of a catalyst of copper iodide.

In the case where $M^1$ is fluorine and $M^2$ is —$CF_3$, compound (45) is obtained by dehydrating carboxylic acid

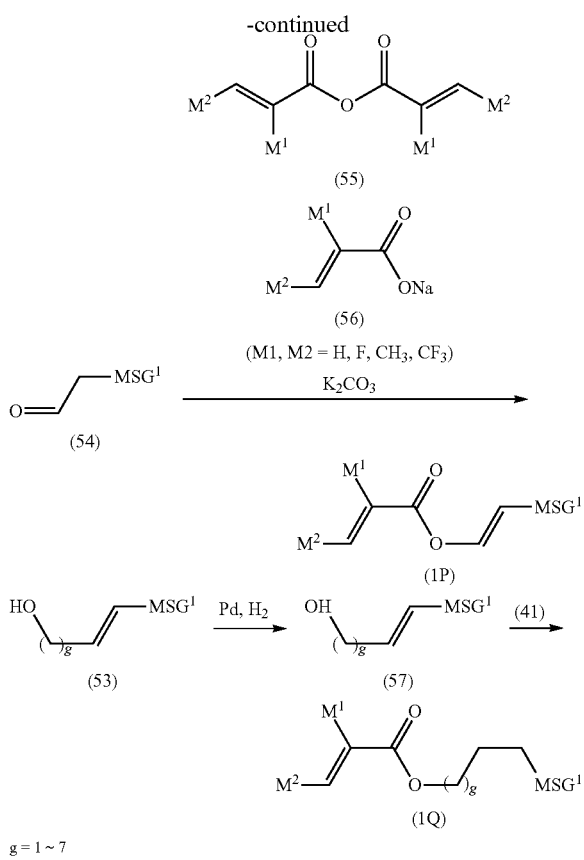

(2) Formation of —(CH$_2$)$_g$—O—

Compound (50) is obtained by allowing compound (49) prepared according to a known method to react with compound (30) in the presence of potassium carbonate or the like. Compound (51) is obtained by reducing compound (50) with a reducing agent such as lithium hydride aluminum. Compound (1N) is prepared by dehydrating compound (51) and carboxylic acid (41).

(3) Formation of —(CH$_2$)$_g$—CH=CH—

Phosphorus ylide is prepared by treating phosphonium salt (52) prepared according to a known method with a base such as potassium t-butoxide, and compound (53) is obtained by allowing the phosphorus ylide to react with aldehyde (32). Compound (10) is prepared by dehydrating compound (53) and carboxylic acid (41).

(4) Formation of —CH=CH—

Compound (1P) is prepared by allowing aldehyde (54) prepared according to a known method to react with acid anhydride (55) and sodium carboxylate (56) in the presence of potassium carbonate or the like.

(5) Formation of —(CH$_2$)$_g$—CH$_2$CH$_2$—

Alcohol (57) is prepared by hydrogenating compound (53) in the presence of a catalyst of palladium on carbon or the like. Compound (1Q) is obtained by dehydrating the alcohol and carboxylic acid (41).

(6) Groups (P-2) and (P-3)

In a compound in which the polymerizable group is vinyloxy (P-2) subjected to replacement, a single bond is formed as described below. A compound having vinyloxy subjected to replacement is obtained by allowing HO-MGS$^1$ (30) to react with vinyl bromide subjected to replacement in the presence of potassium carbonate. In a compound in which the polymerizable group is allyloxy (P-3) subjected to replacement, a single bond is formed according to Williamson synthesis. More specifically, a compound having allyloxy subjected to replacement is obtained by allowing a sodium salt of HO-MGS$^1$ (30) to react with allyl bromide subjected to replacement.

3. Polymerizable Composition

A polymerizable composition contains at least one compound (1) as a first component. A component of the composition may be only the first component. The composition may contain a second component, a third component or the like. A kind of the second component or the like depends on a kind of an objective polymer or application. The polymerizable composition may further contain any other polymerizable compound different from compound (1) as the second component. Preferred examples of any other polymerizable compound include acrylate, methacrylate, a vinyl compound, a vinyloxy compound, propenyl ether, ethylene oxide (oxirane, oxetane) and vinyl ketone. Further preferred example include a compound having at least one of acryloyloxy and a compound having at least one of methacryloyloxy. A most preferred example includes a compound having acryloyloxy and methacryloyloxy.

Additional examples of any other polymerizable compound include compounds (M-1) to (M-12). In compounds (M-1) to (M-12), R$^{25}$, R$^{26}$ and R$^{27}$ are independently hydrogen or methyl; u, x and y are independently 0 or 1; v and w are independently an integer from 1 to 10; and L$^{21}$, L$^{22}$, L$^{23}$, L$^{24}$, L$^{25}$ and L$^{26}$ are independently hydrogen or fluorine.

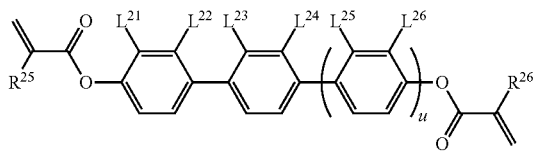

(M-1)

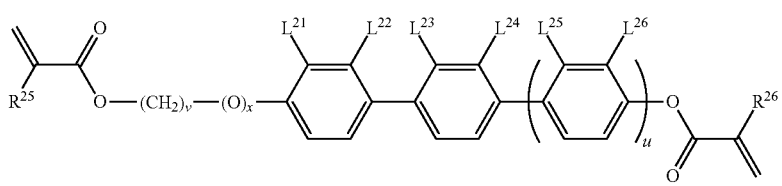

(M-2)

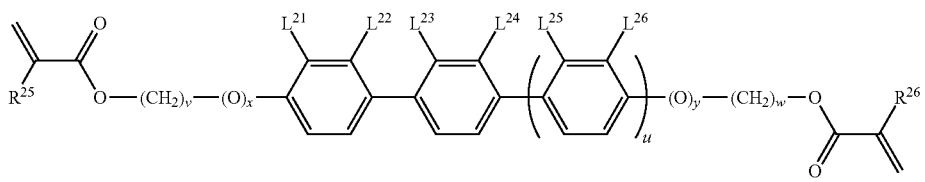
(M-3)
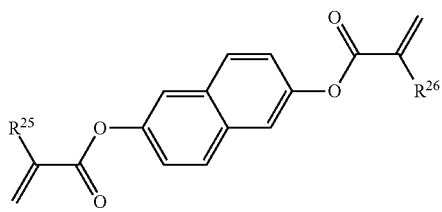
(M-4)
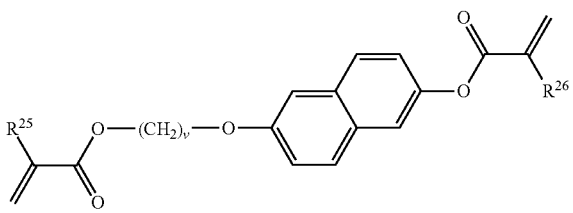
(M-5)
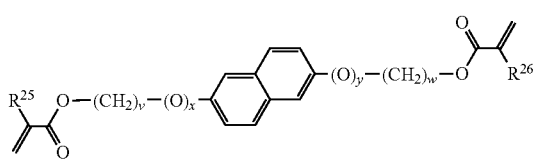
(M-6)
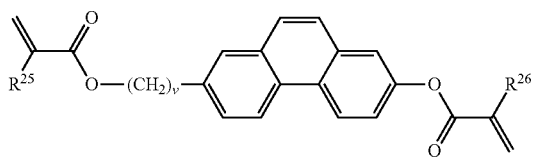
(M-7)
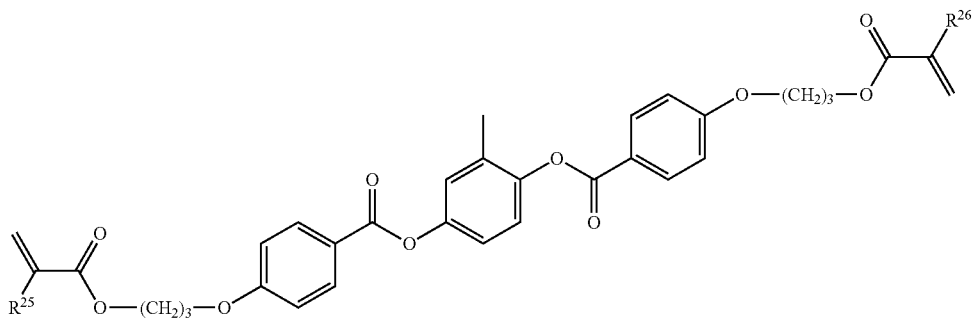
(M-8)
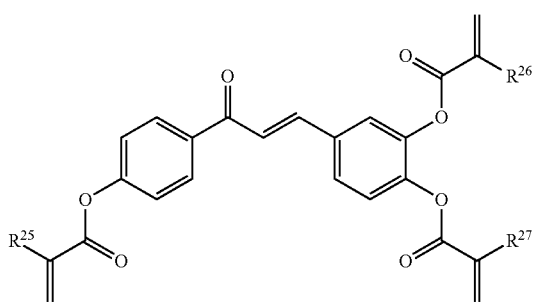
(M-9)
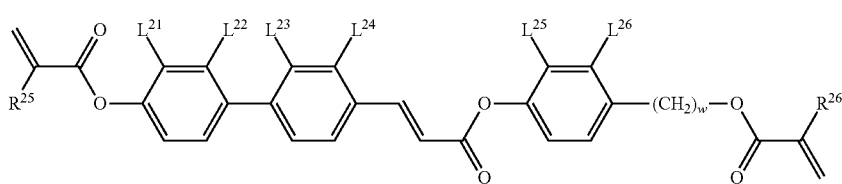
(M-10)
(M-11)

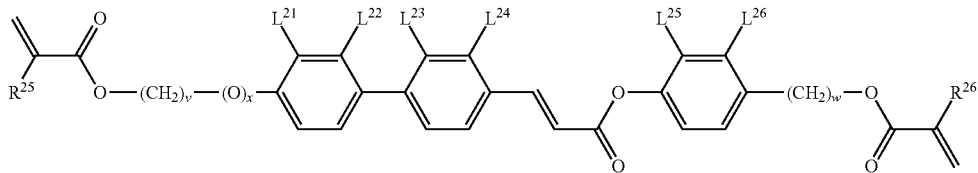

(M-12)

In the case where the second component of the polymerizable composition is a polymerizable compound having the liquid crystal phase, an optically anisotropic body is formed by polymerizing the polymerizable compound while controlling alignment of liquid crystal molecules. The optically anisotropic body can be used for a phase difference membrane, a polarizing element, a circular polarizing element, an elliptic polarizing element, antireflection film, selective reflection film, color compensation film, viewing angle compensation film or the like. An additive such as the polymerization initiator may be added to the polymerizable composition for the purpose of adjusting the physical properties of the optically anisotropic body.

The polymerizable composition may also contain the liquid crystal composition as the second component. In the case of aiming at the liquid crystal display device having a mode such as the PS-TN mode, the PS-IPS mode, the PS-FFS mode, the PSA-VA mode and the PSA-OCB mode, the composition preferably contains compound (1) as component A, and further preferably contains a compound selected from components B, C and D described below. Component B includes compounds (2) to (4). Component C includes compounds (5) to (7). Component D includes compound (8). In the case of preparing such a composition, in consideration of a value of dielectric anisotropy or the like, components B, C and D are preferably selected. The composition may contain any other liquid crystal compound different from components B, C and D. A composition in which the component is suitably selected has a high maximum temperature, a low minimum temperature, a small viscosity, a suitable optical anisotropy (more specifically, a large or small optical anisotropy), a large dielectric anisotropy and a suitable elastic constant (more specifically, a large or small elastic constant).

The polymerizable composition is prepared by adding compound (1) to the liquid crystal composition. In the composition, an amount of addition of compound (1), namely component A, is in the range of 0.05% to 20% by weight based on the weight of the liquid crystal composition. A further preferred amount of addition is in the range of 0.1% to 10% by weight based thereon. A most preferred amount of addition is in the range of 0.2% to 1% by weight based thereon. At least one of other polymerizable compounds different from compound (1) may be added thereto. In the above case, a total amount of addition of compound (1) and any other polymerizable compound is preferably within the range described above. Physical properties of a produced polymer can be adjusted by suitably selecting any other polymerizable compound. Examples of any other polymerizable compound include acrylate and methacrylate, as previously described. The examples include compounds (M-1) to (M-12).

Component B is a compound in which two terminal groups are alkyl or the like. Preferred examples of component B include compounds (2-1) to (2-11), compounds (3-1) to (3-19) and compounds (4-1) to (4-7). In the compound of component B, $R^{11}$ and $R^{12}$ are defined in a manner identical with the definitions in formulas (2) to (4) described in item 12.

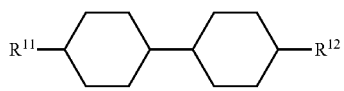

(2-1)

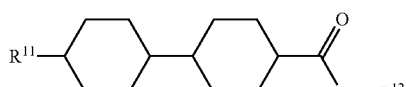

(2-2)

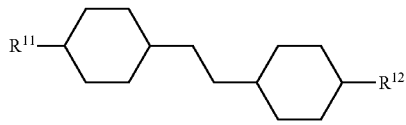

(2-3)

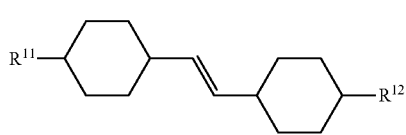

(2-4)

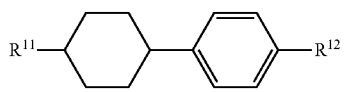

(2-5)

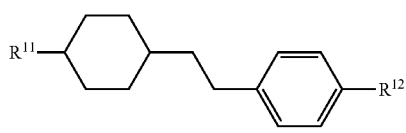

(2-6)

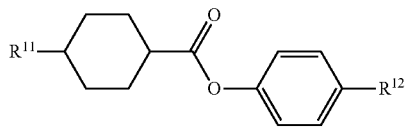

(2-7)

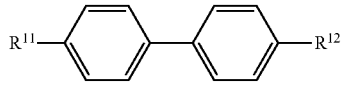

(2-8)

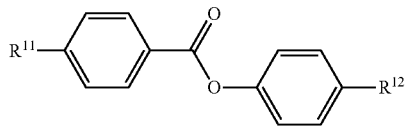

(2-9)

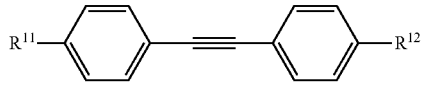

(2-10)

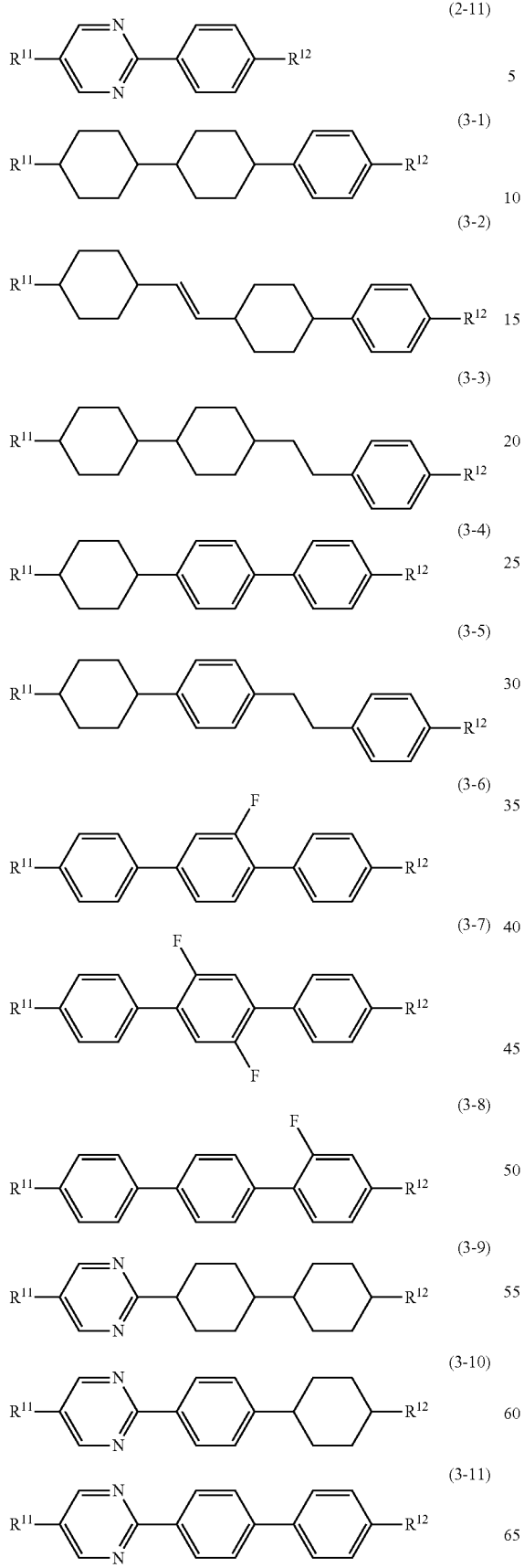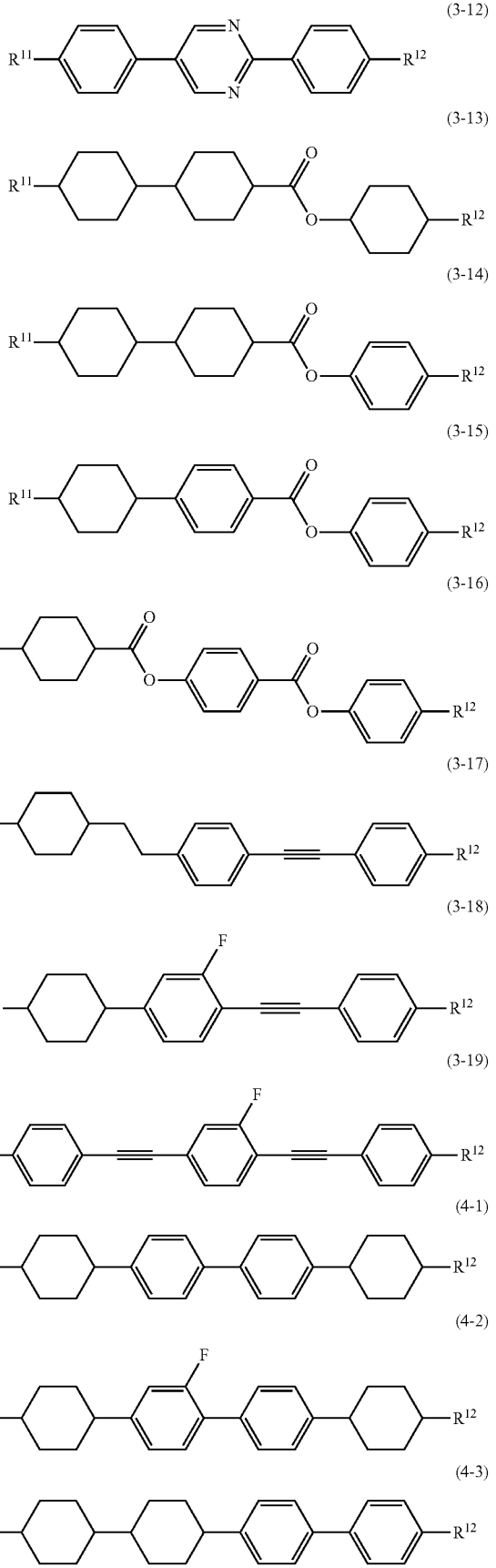

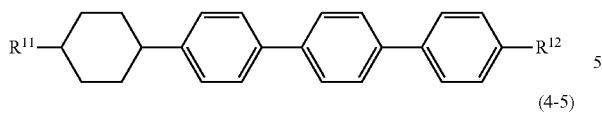
(4-4)

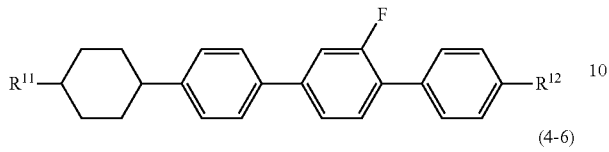
(4-5)

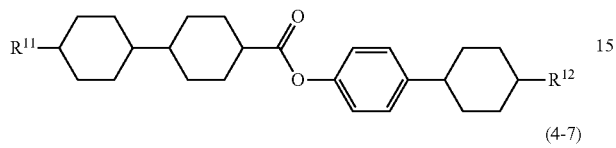
(4-6)

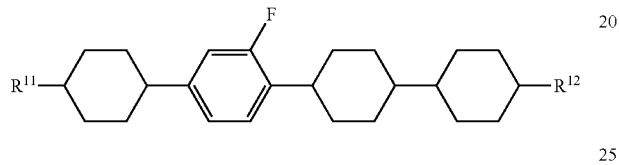
(4-7)

Component B has a small absolute value of dielectric anisotropy, and therefore is a compound close to neutrality. Compound (2) is effective mainly in adjusting the viscosity or the optical anisotropy. Compounds (3) and (4) are effective in extending a temperature range of the nematic phase by increasing the maximum temperature, or in adjusting the optical anisotropy.

If a content of component B is increased, the viscosity of the composition decreases, but the dielectric anisotropy thereof decreases. Thus, as long as a desired value of threshold voltage of the device is met, the content is preferably as large as possible. Therefore, when a composition for the PS-IPS mode, the PS-VA mode or the like is prepared, the content of component B is preferably about 30% by weight or more, and further preferably about 40% by weight or more, based on the weight of the liquid crystal composition.

Component C is a compound having a halogen-containing or fluorine-containing group at a right terminal. Preferred examples of component C include compounds (5-1) to (5-16), compounds (6-1) to (6-113) and compounds (7-1) to (7-57). In the compound of component C, $R^{13}$ and $X^{11}$ are defined in a manner identical with the definitions in formulas (5) to (7) described in item 13.

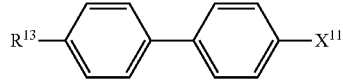
(5-1)

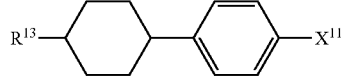
(5-2)

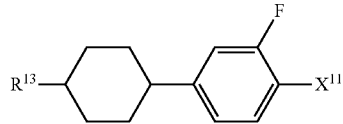
(5-3)

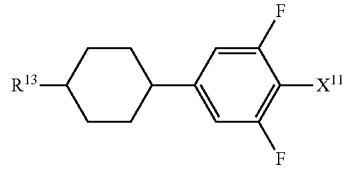
(5-4)

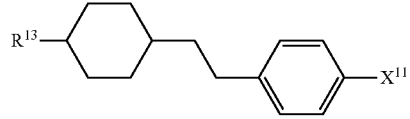
(5-5)

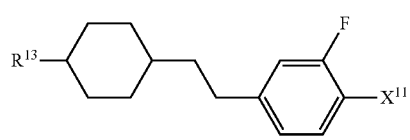
(5-6)

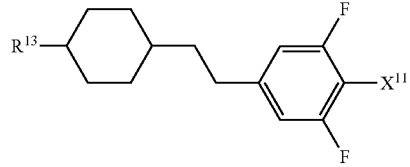
(5-7)

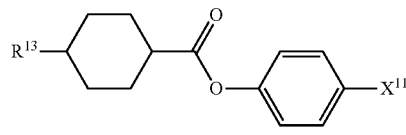
(5-8)

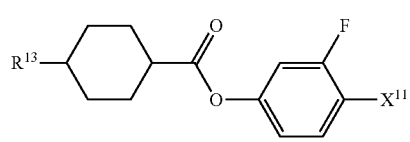
(5-9)

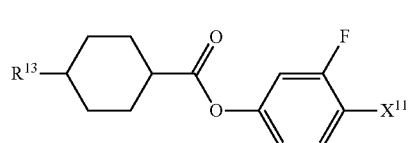
(5-10)

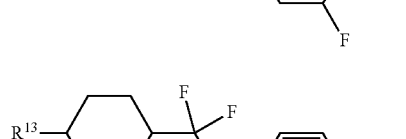
(5-11)

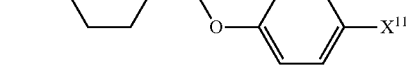
(5-12)

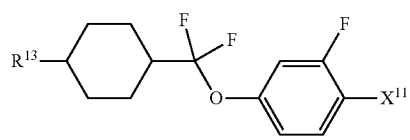
(5-13)

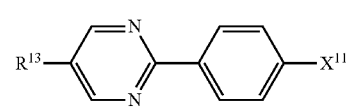 (5-14)
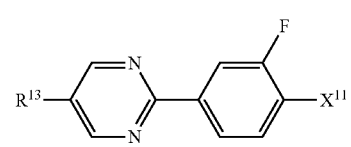 (5-15)
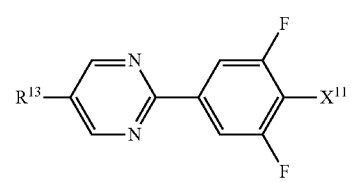 (5-16)
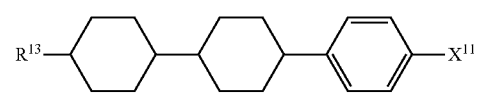 (6-1)
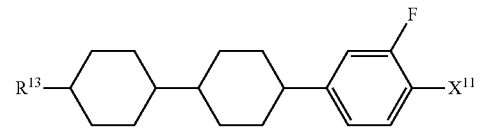 (6-2)
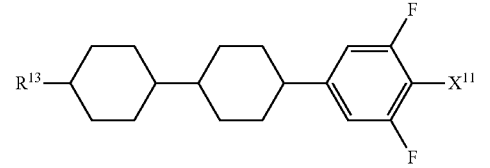 (6-3)
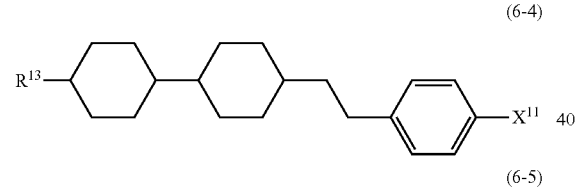 (6-4)
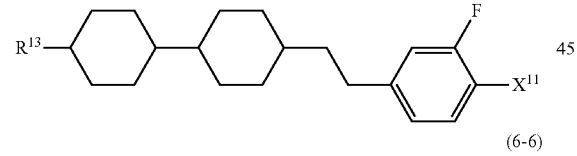 (6-5)
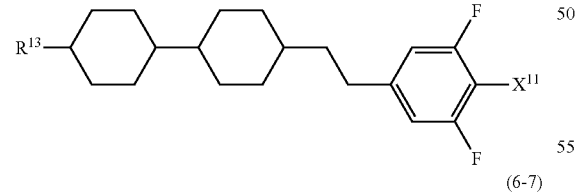 (6-6)
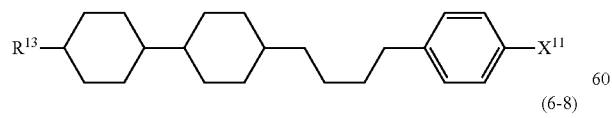 (6-7)
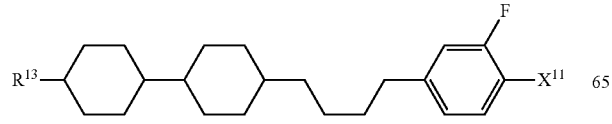 (6-8)
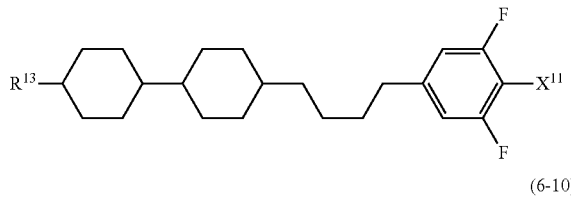 (6-9)
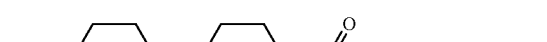 (6-10)
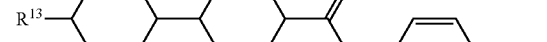 (6-11)
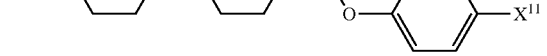 (6-12)
 (6-13)
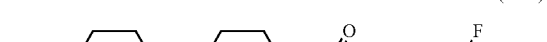 (6-14)
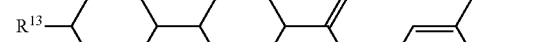 (6-15)
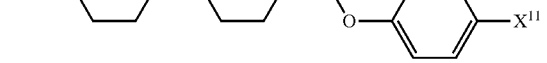 (6-16)
 (6-17)

(6-18) 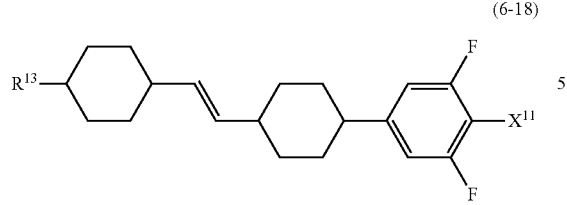
(6-19) 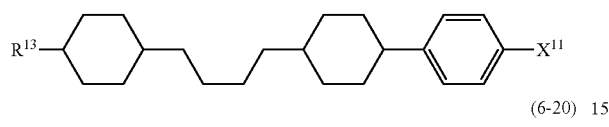
(6-20) 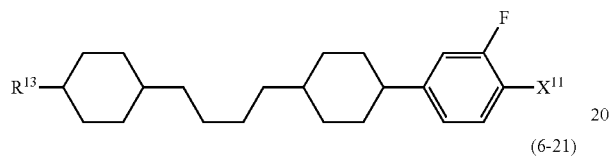
(6-21) 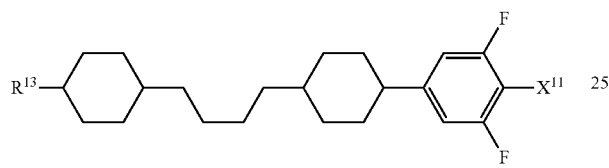
(6-22) 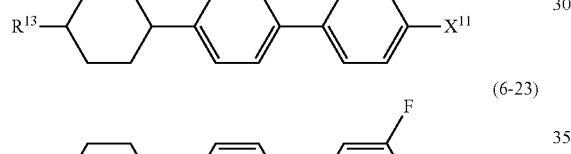
(6-23) 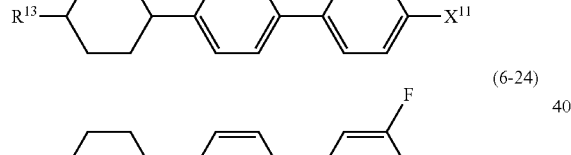
(6-24) 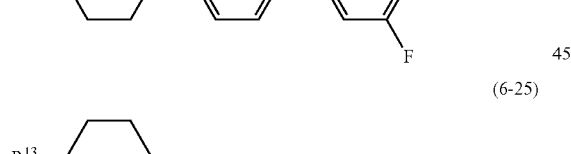
(6-25) 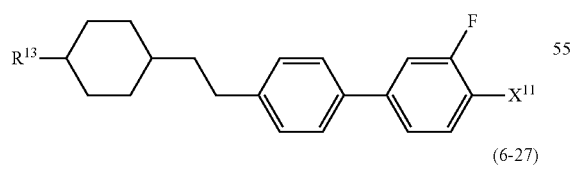
(6-26) 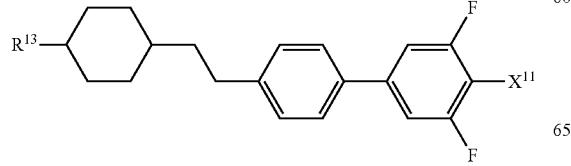
(6-27)
(6-28) 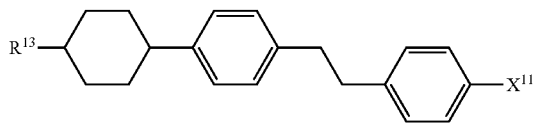
(6-29) 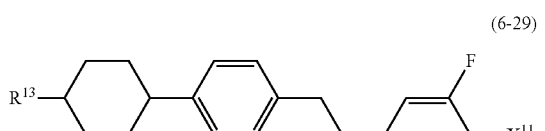
(6-30) 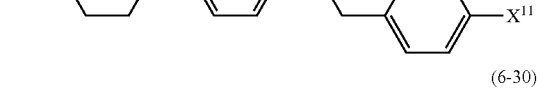
(6-31) 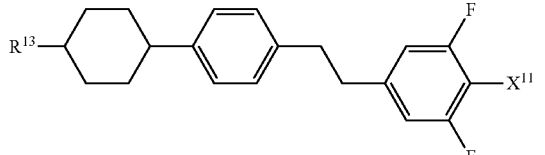
(6-32) 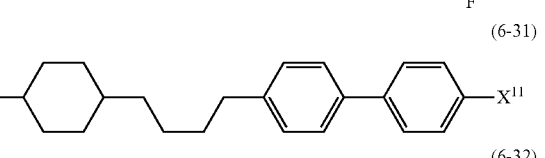
(6-33) 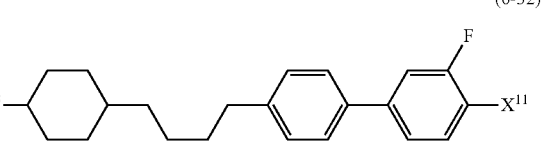
(6-34) 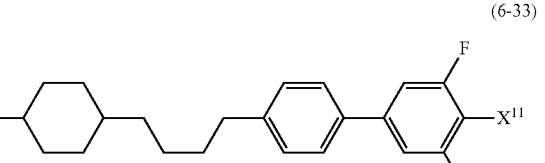
(6-35) 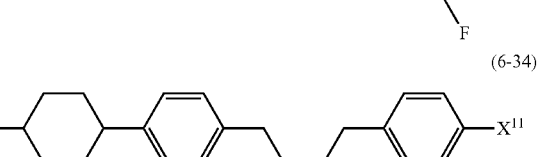
(6-36) 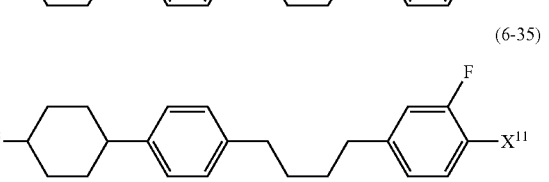
(6-37) 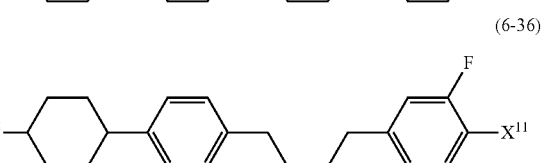

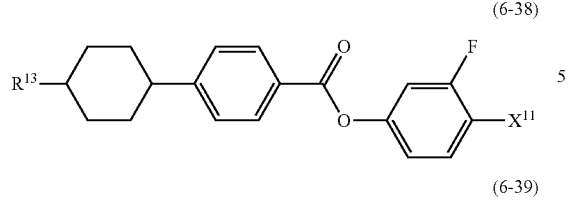 (6-38)
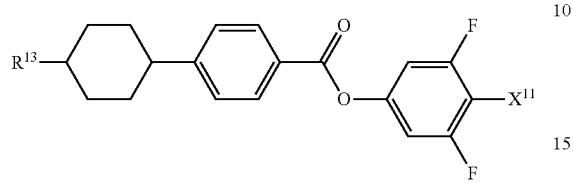 (6-39)
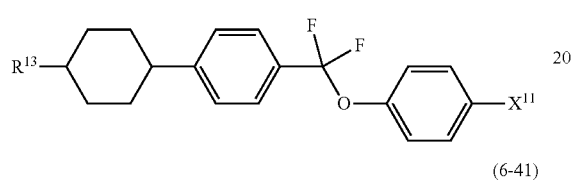 (6-40)
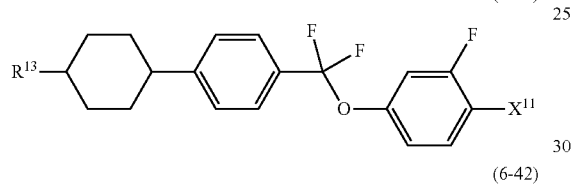 (6-41)
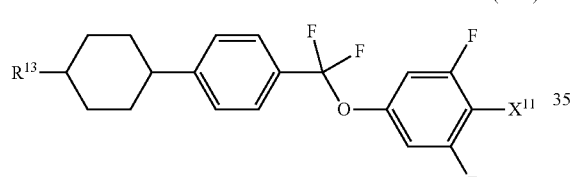 (6-42)
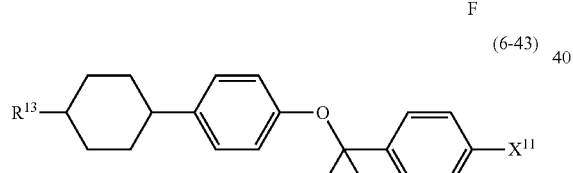 (6-43)
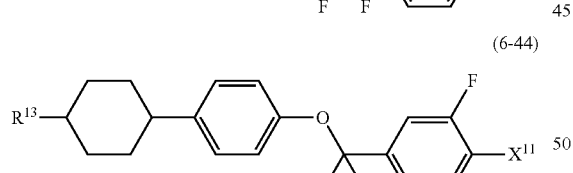 (6-44)
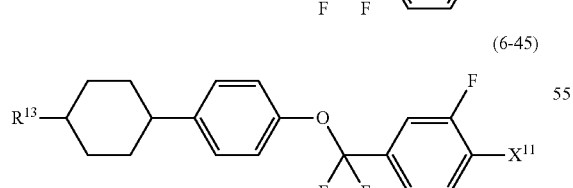 (6-45)
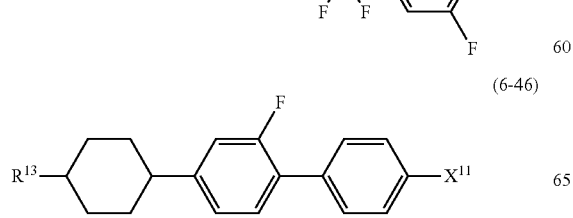 (6-46)
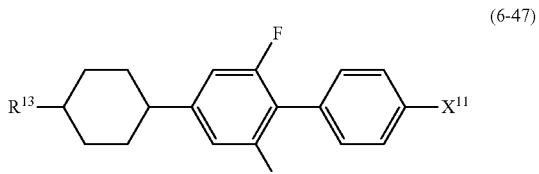 (6-47)
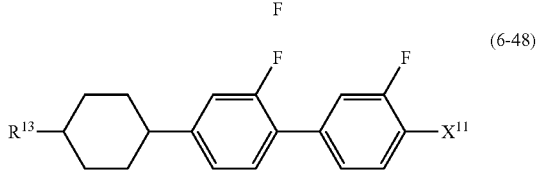 (6-48)
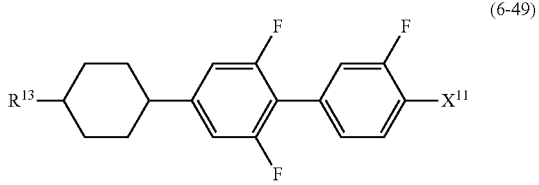 (6-49)
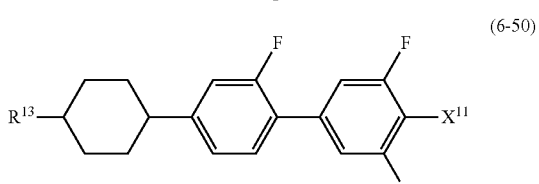 (6-50)
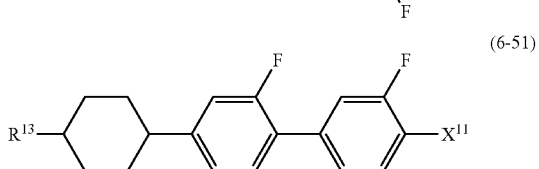 (6-51)
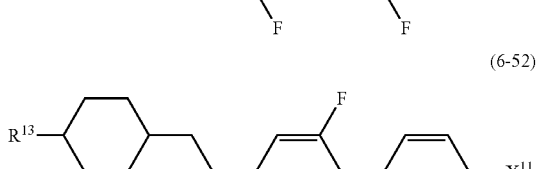 (6-52)
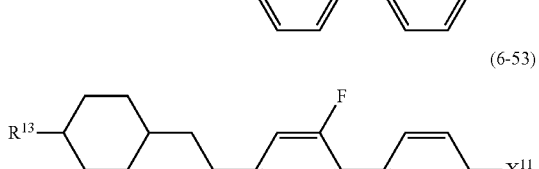 (6-53)
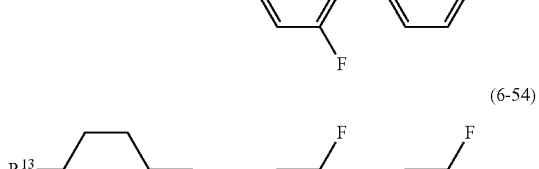 (6-54)
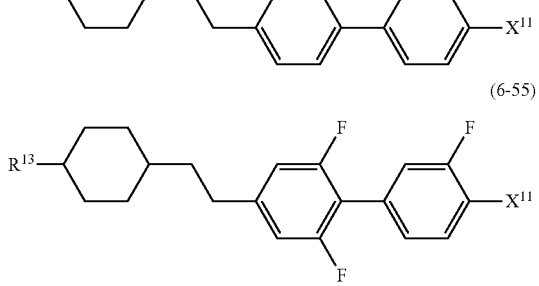 (6-55)

(6-56) 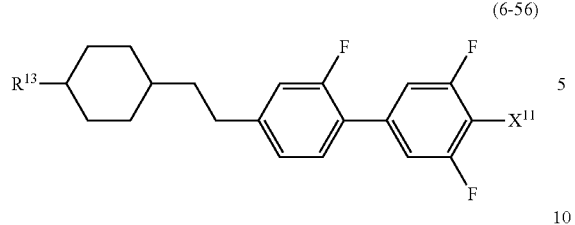
(6-57) 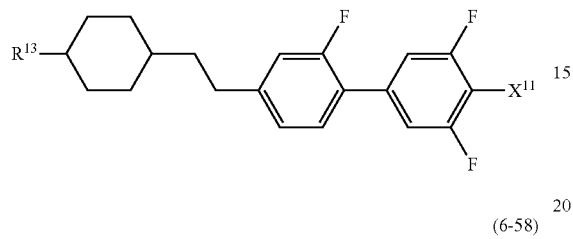
(6-58) 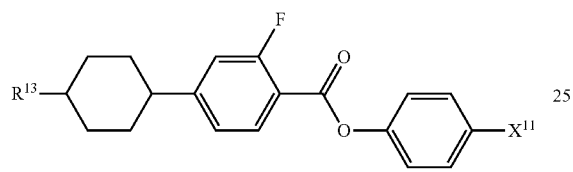
(6-59) 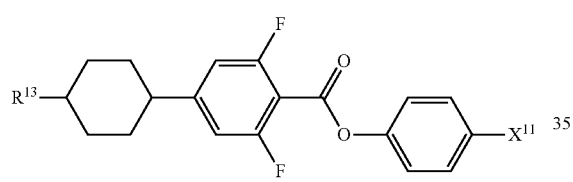
(6-60) 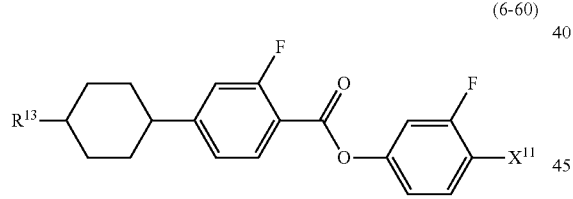
(6-61) 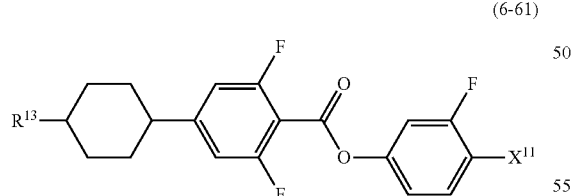
(6-62) 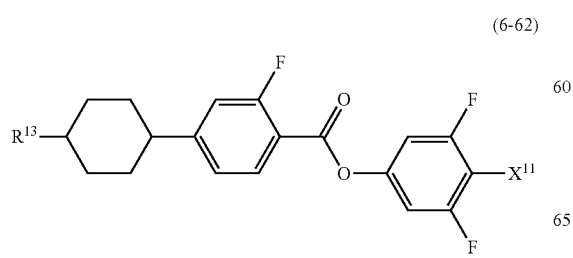
(6-63) 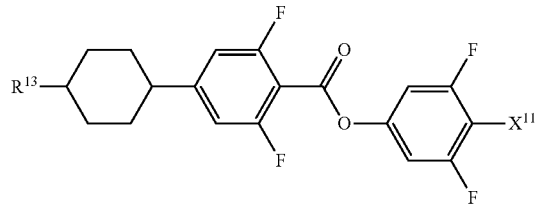
(6-64) 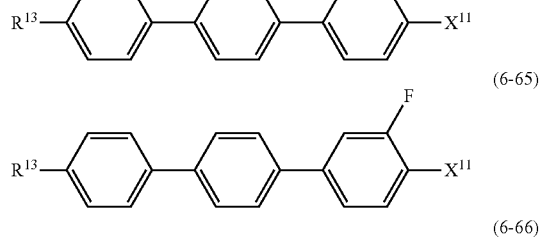
(6-65) 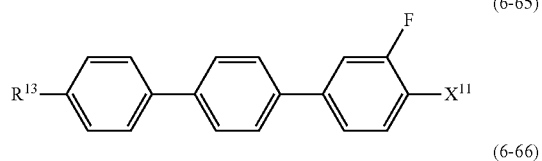
(6-66) 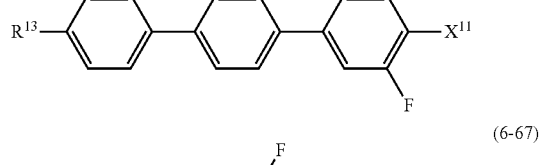
(6-67) 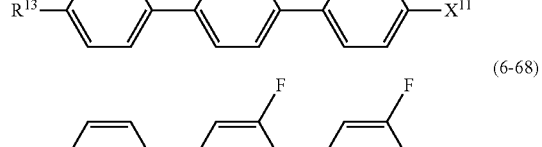
(6-68) 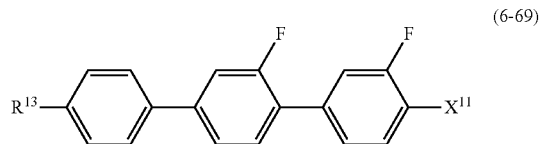
(6-69) 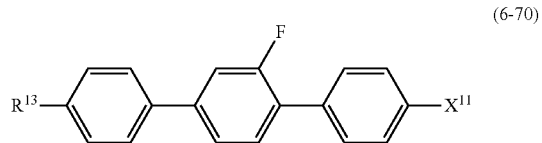
(6-70) 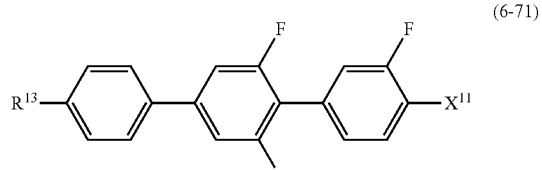
(6-71) 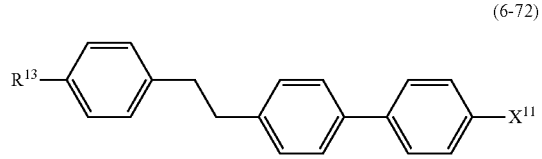
(6-72) 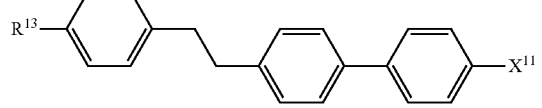

-continued
(6-73)
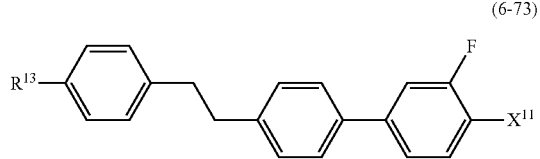
(6-74)
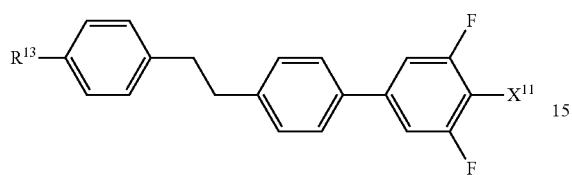
(6-75)
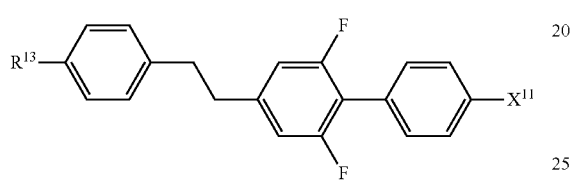
(6-76)
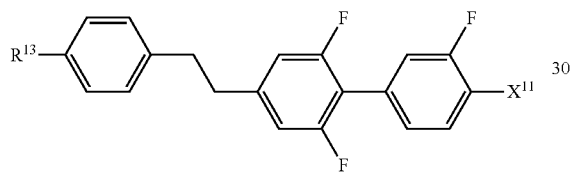
(6-77)
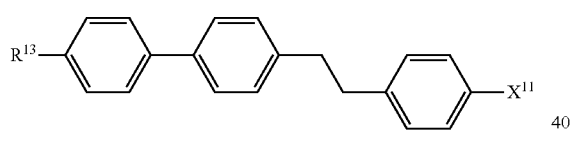
(6-78)
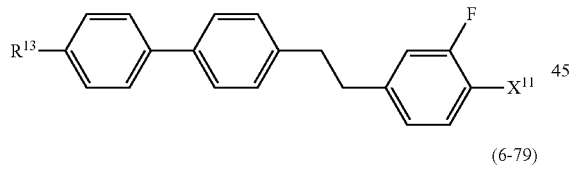
(6-79)
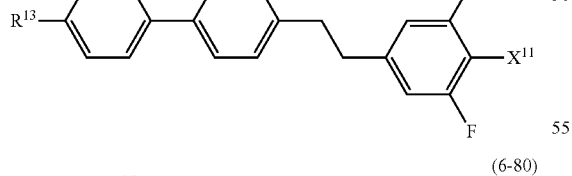
(6-80)
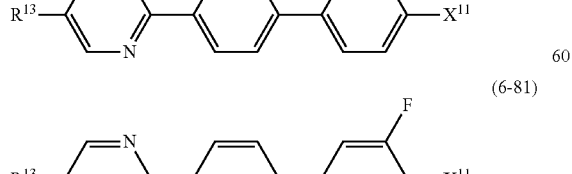
(6-81)
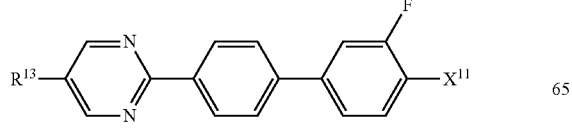
-continued
(6-82)
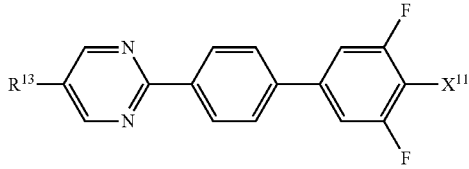
(6-83)
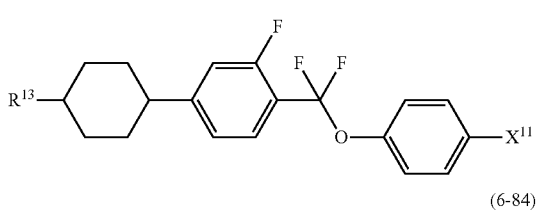
(6-84)
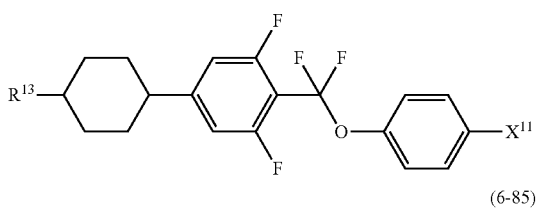
(6-85)
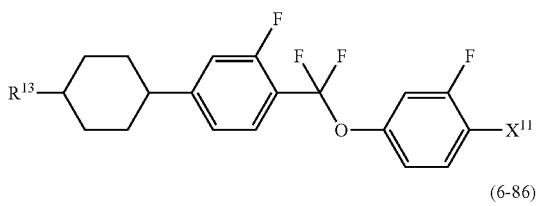
(6-86)
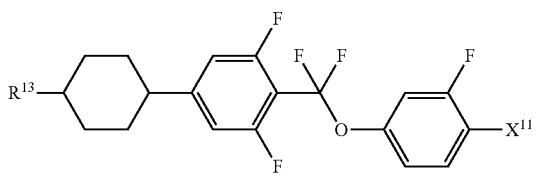
(6-87)
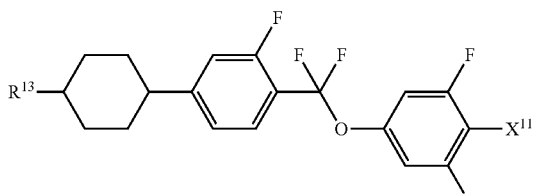
(6-88)
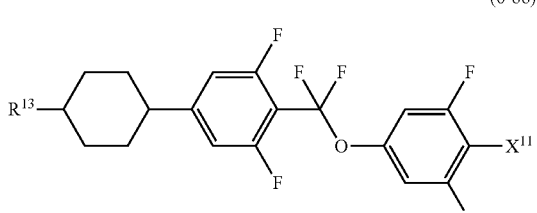
(6-89)
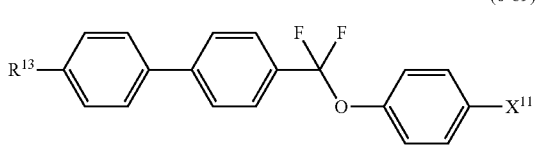

(6-90)
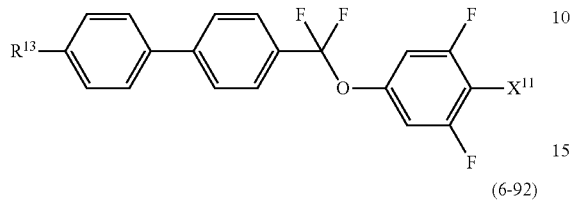
(6-91)
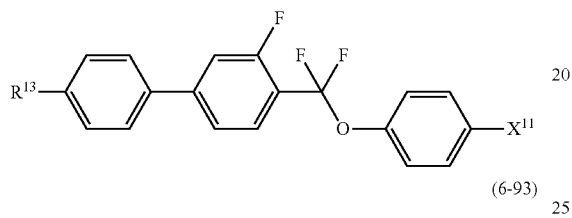
(6-92)
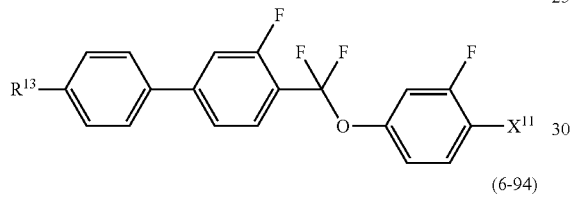
(6-93)
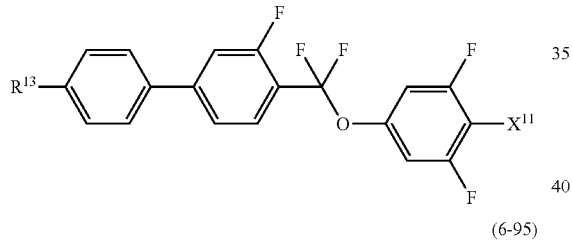
(6-94)
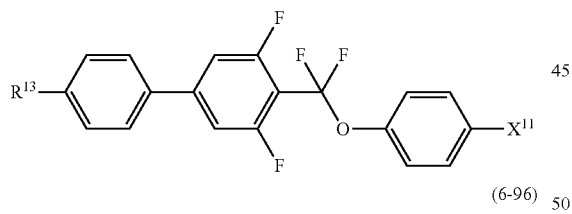
(6-95)
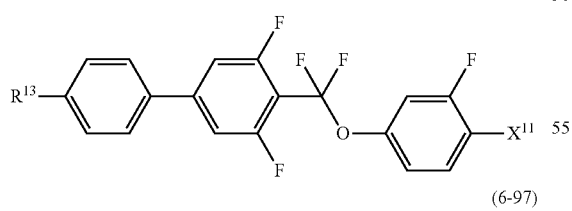
(6-96)
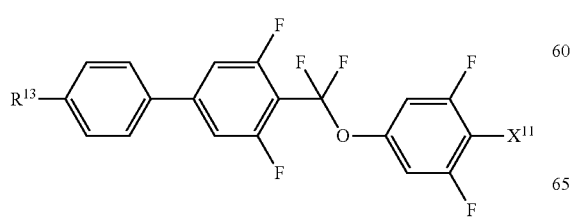
(6-97)
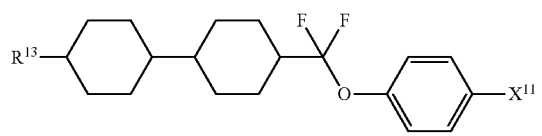
(6-98)
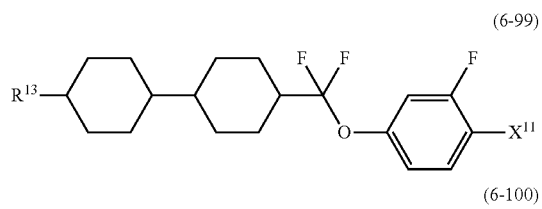
(6-99)
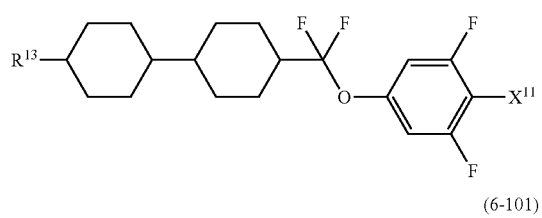
(6-100)
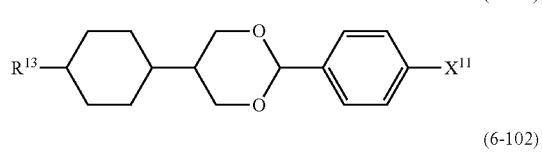
(6-101)
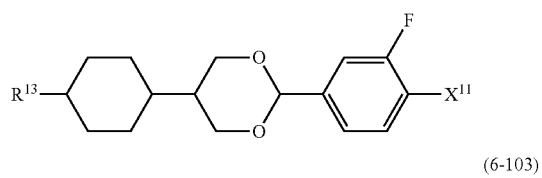
(6-102)
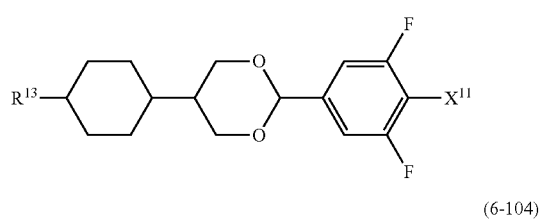
(6-103)
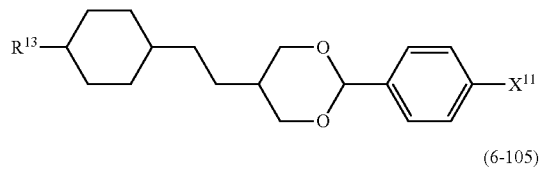
(6-104)
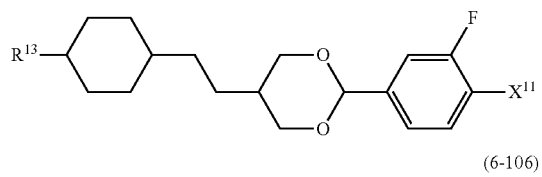
(6-105)
(6-106)

(6-107) 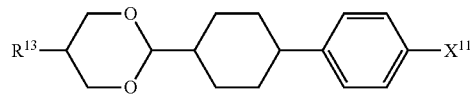
(6-108) 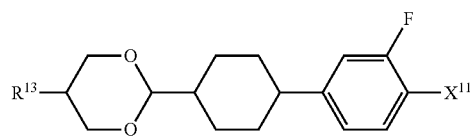
(6-109) 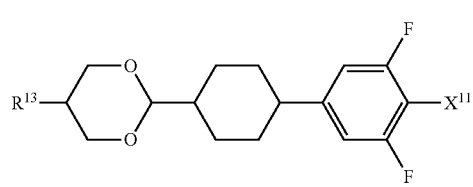
(6-110) 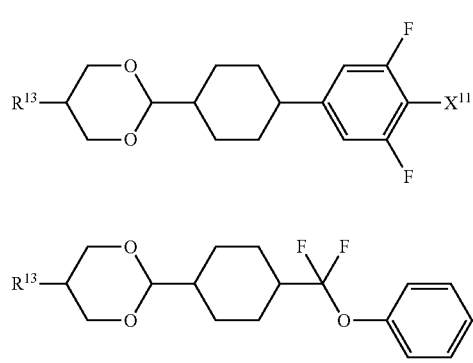
(6-111) 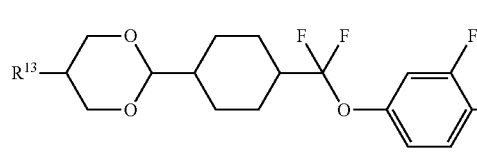
(6-112) 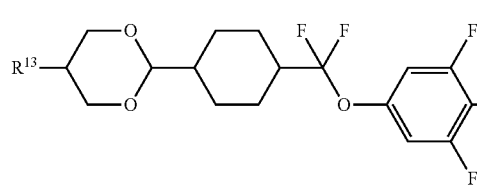
(6-113) 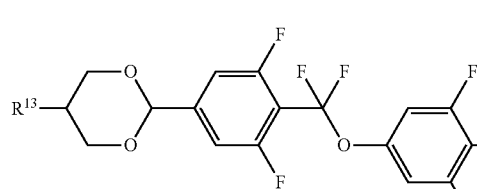
(7-1) 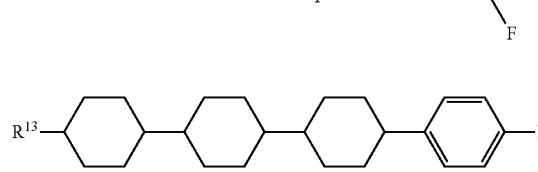
(7-2) 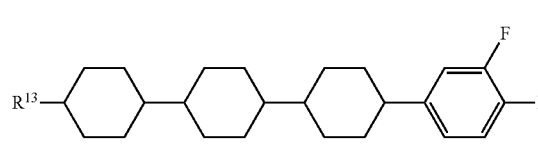
(7-3) 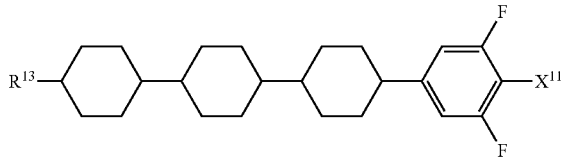
(7-4) 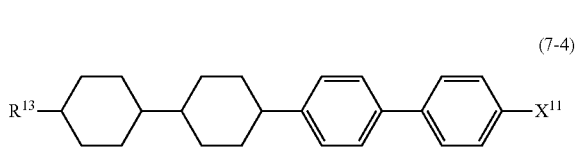
(7-5) 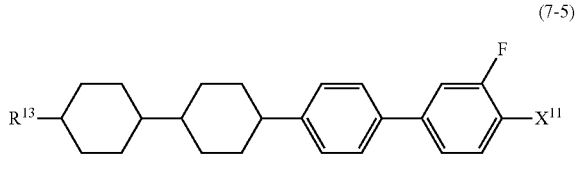
(7-6) 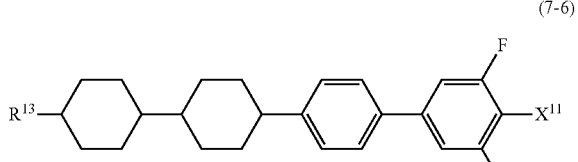
(7-7) 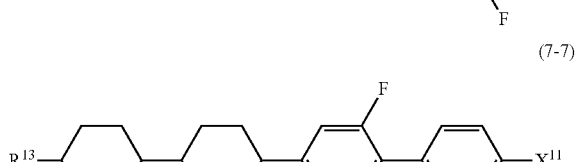
(7-8) 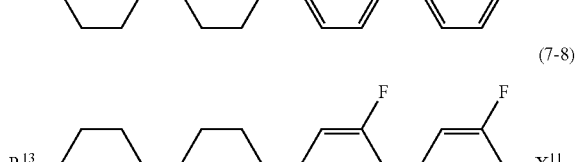
(7-9) 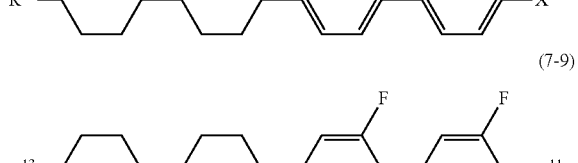
(7-10) 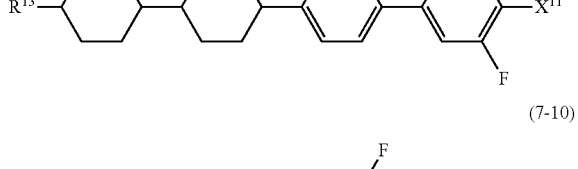
(7-11) 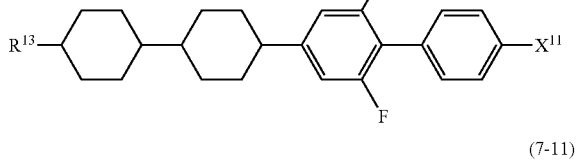
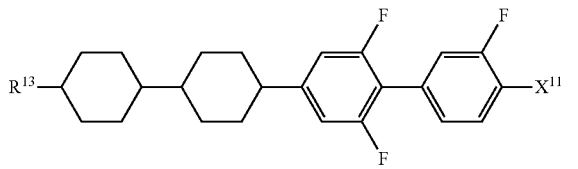

(7-12) 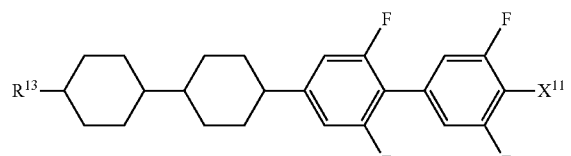
(7-13) 
(7-14) 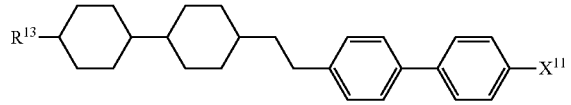
(7-15) 
(7-16) 
(7-17) 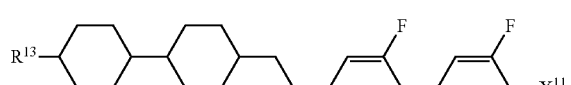
(7-18) 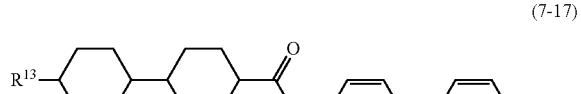
(7-19) 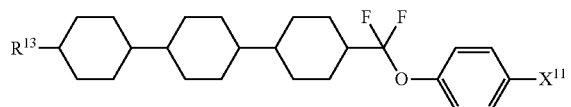
(7-20) 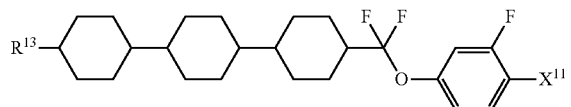
(7-21) 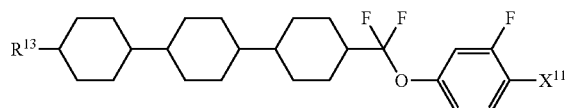
(7-22) 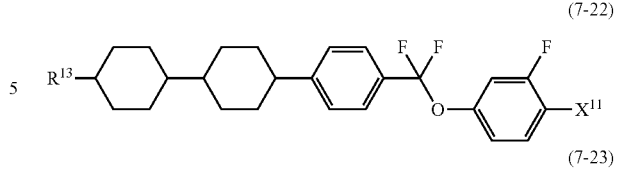
(7-23) 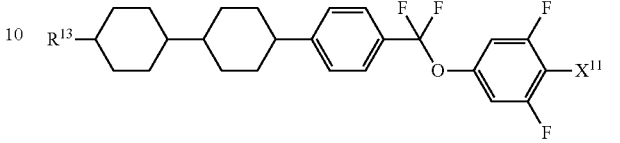
(7-24) 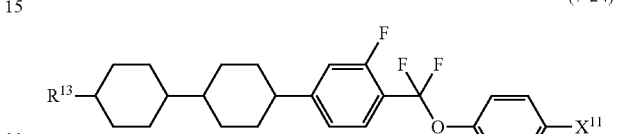
(7-25) 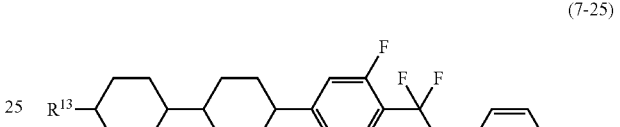
(7-26) 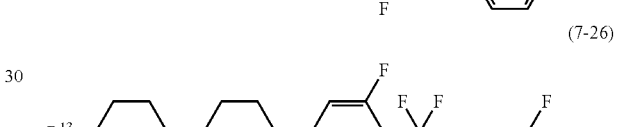
(7-27) 
(7-28) 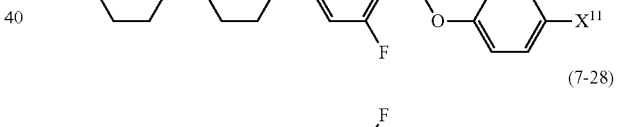
(7-29) 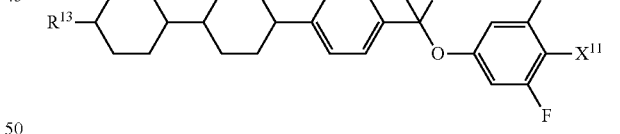
(7-29) 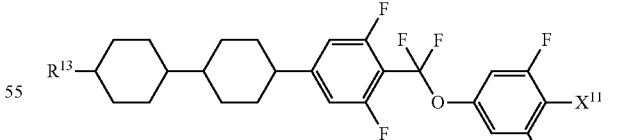
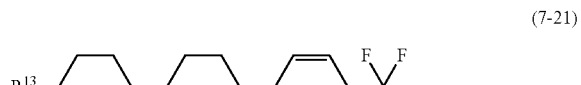
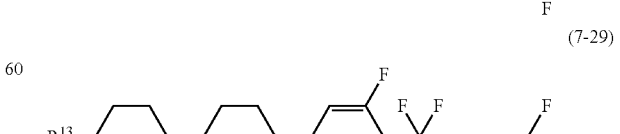

(7-30)
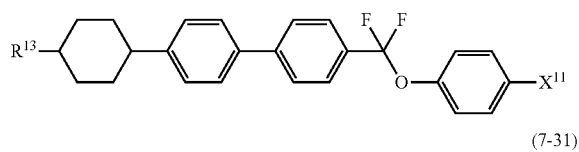
(7-31)
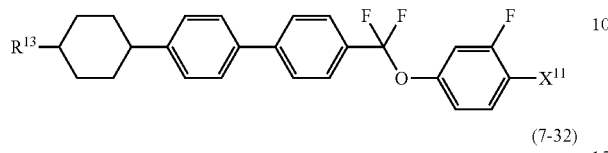
(7-32)
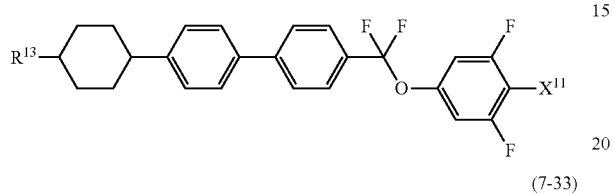
(7-33)
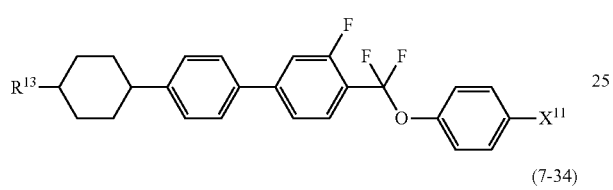
(7-34)
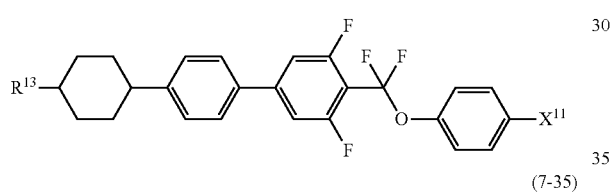
(7-35)
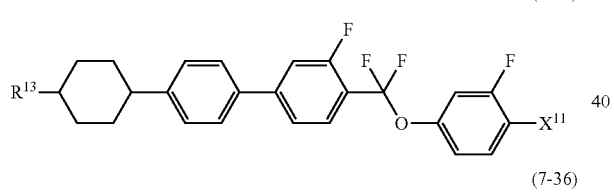
(7-36)
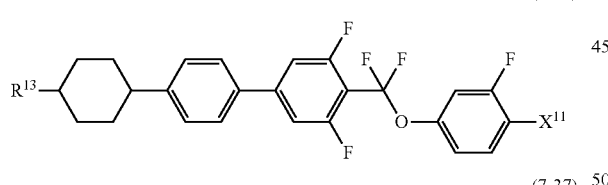
(7-37)
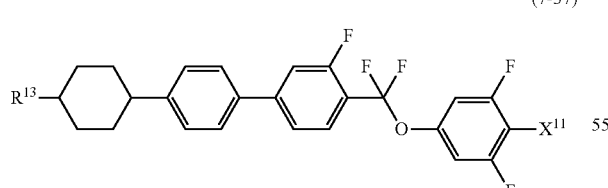
(7-38)
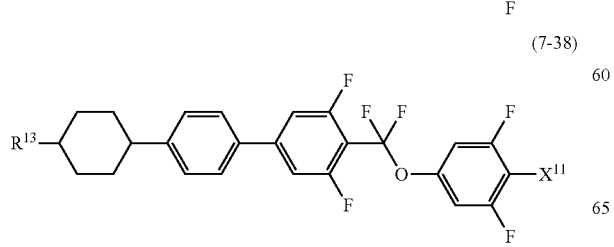
(7-39)
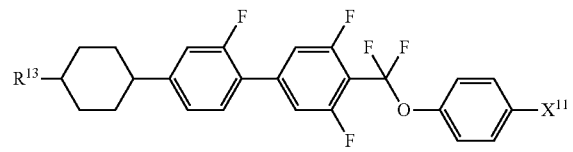
(7-40)
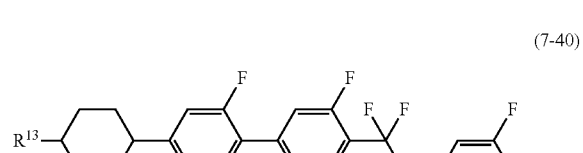
(7-41)
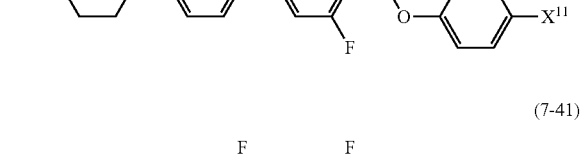
(7-42)
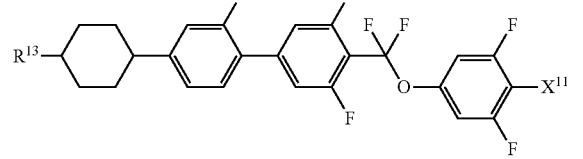
(7-43)
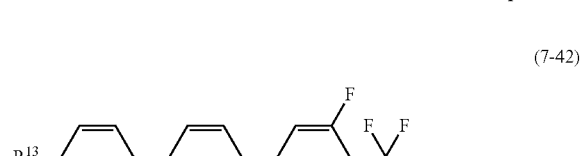
(7-44)
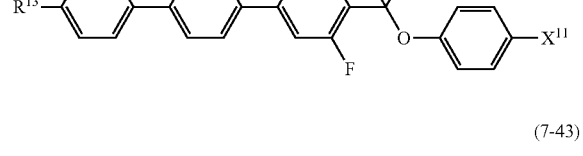
(7-45)
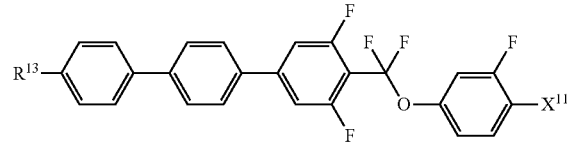
(7-46)
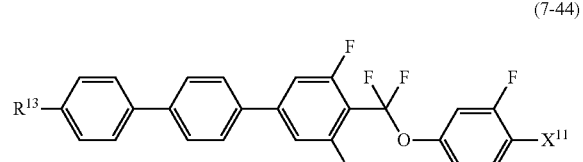

(7-47)
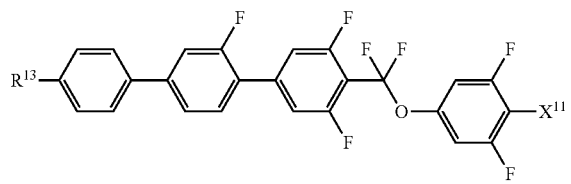

(7-48)
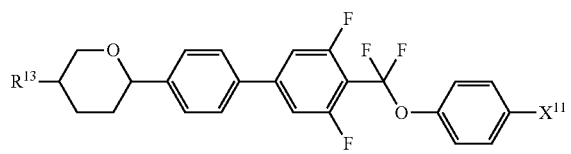

(7-49)
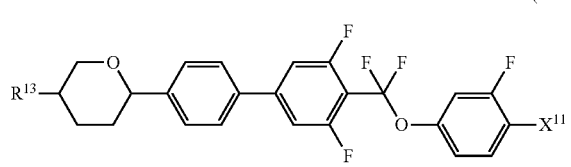

(7-50)
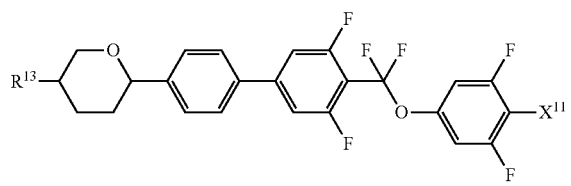

(7-51)
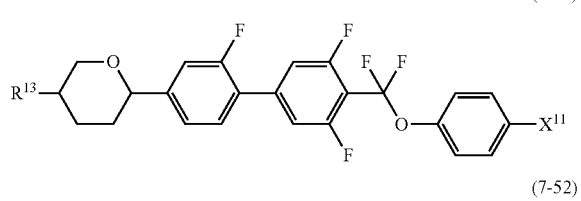

(7-52)
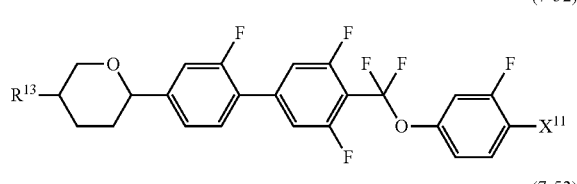

(7-53)
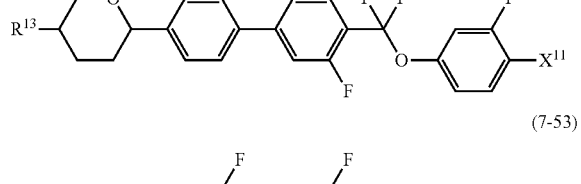

(7-54)
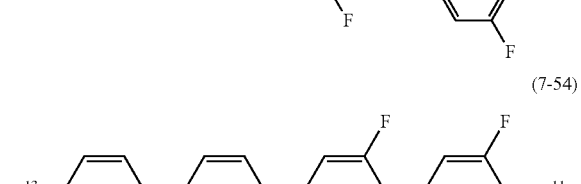

(7-55)
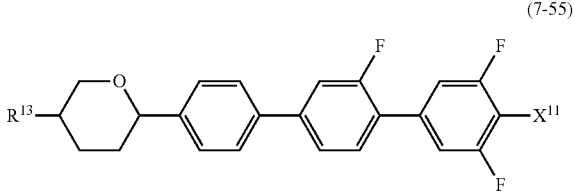

(7-55)
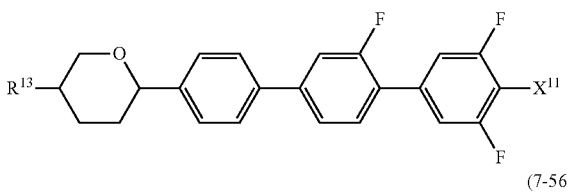

(7-56)
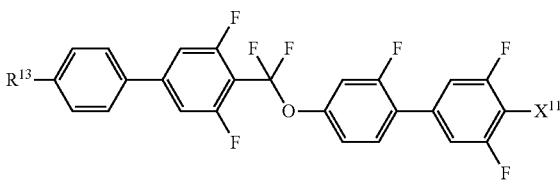

(7-57)
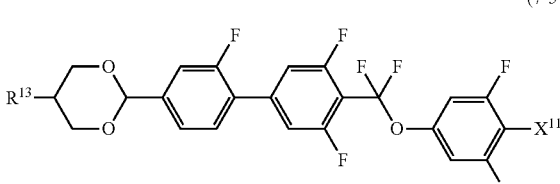

Component C has the positive dielectric anisotropy and a superb stability to heat, light and so forth, and therefore is used when a composition for the mode such as PS-IPS, PS-FFS, and PSA-OCB is prepared. A content of Compound C is suitably in the range of 1 to 99% by weight, preferably 10 to 97% by weight, and further preferably 40 to 95% by weight, based on the weight of the composition. When component C is added to a composition having the negative dielectric anisotropy, a preferred content of component C is 30% by weight or less based on the weight of the composition. An elastic constant of the composition and a voltage-transmittance curve of the device can be adjusted by adding component C.

Component D is compound (8) in which a right-terminal group is —C≡N or —C≡C—C≡N. Preferred examples of component D include compounds (8-1) to (8-64). In the compound of component D, $R^{14}$ and $X^{12}$ are defined in a manner identical with the definitions in formula (8) described in item 14.

(8-1)
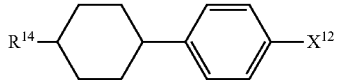

(8-2)
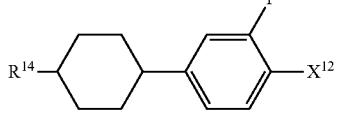

-continued
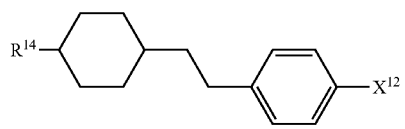 (8-3)
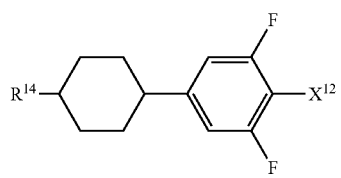 (8-4)
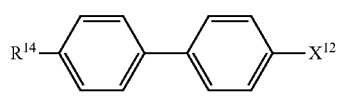 (8-5)
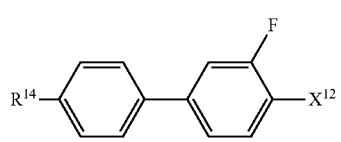 (8-6)
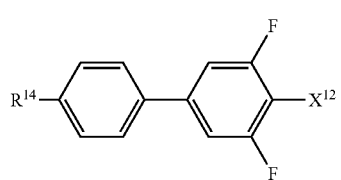 (8-7)
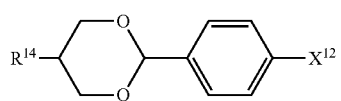 (8-8)
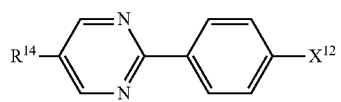 (8-9)
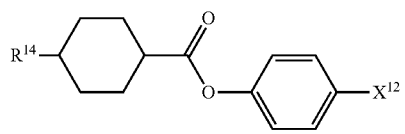 (8-10)
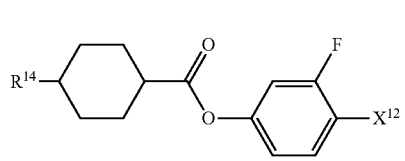 (8-11)
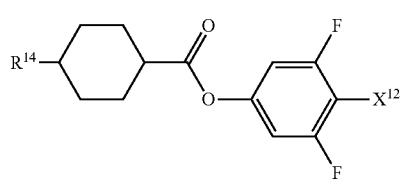 (8-12)
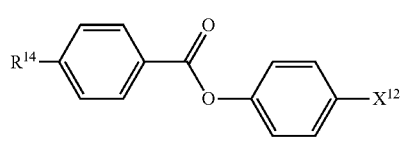 (8-13)
-continued
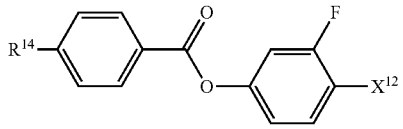 (8-14)
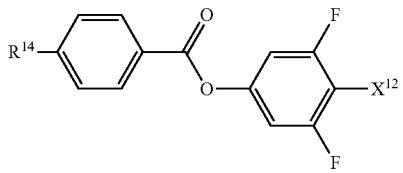 (8-15)
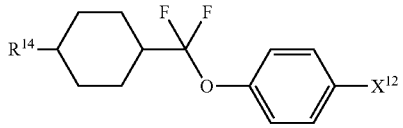 (8-16)
 (8-17)
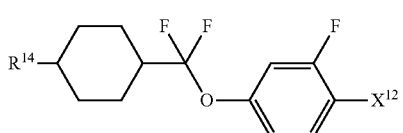 (8-18)
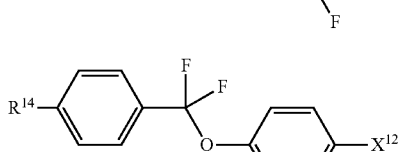 (8-19)
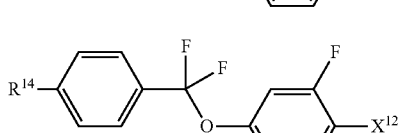 (8-20)
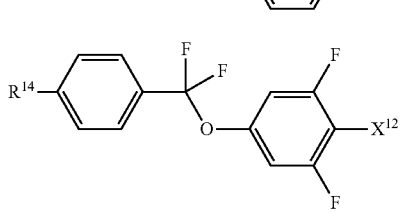 (8-21)
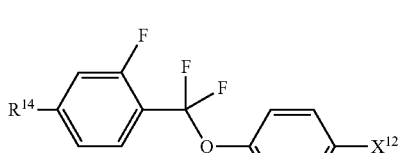 (8-22)
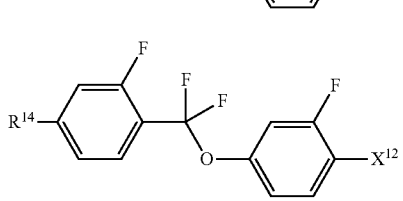 (8-23)

(8-24) 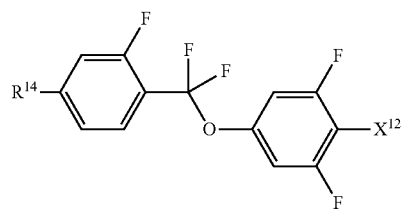
(8-25) 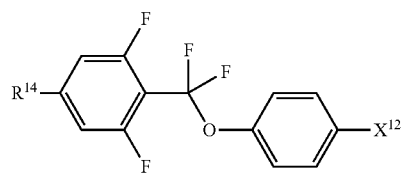
(8-26) 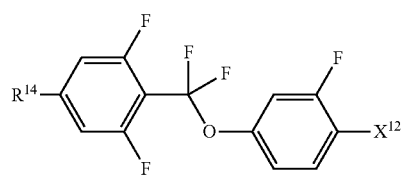
(8-27) 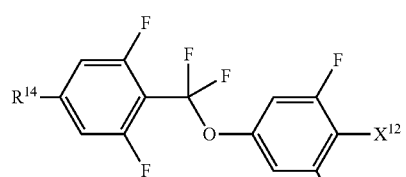
(8-28) 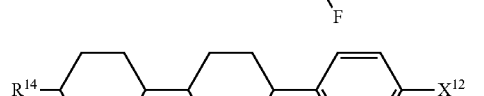
(8-29) 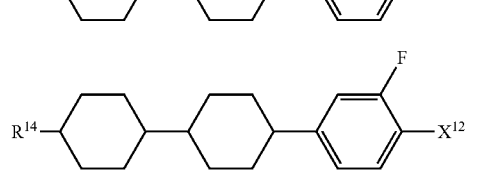
(8-30) 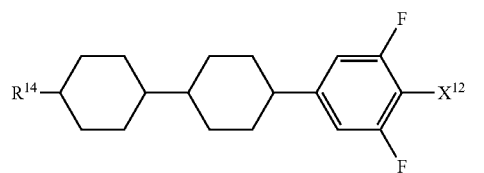
(8-31) 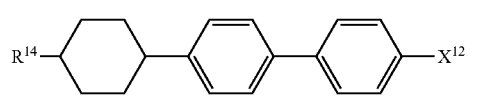
(8-32) 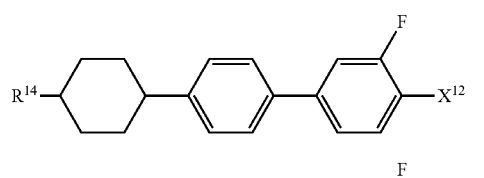
(8-33) 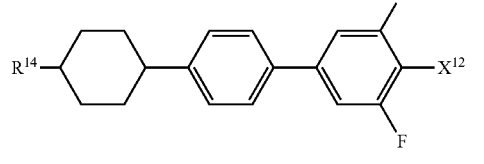
(8-34) 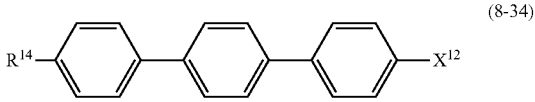
(8-35) 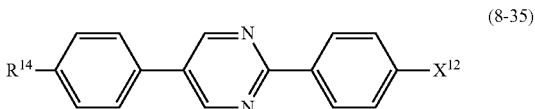
(8-36) 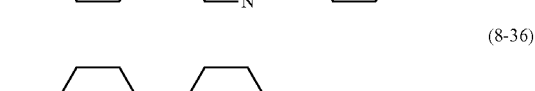
(8-37) 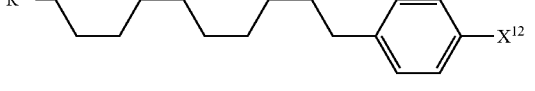
(8-38) 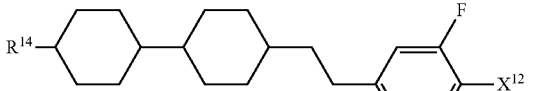
(8-39) 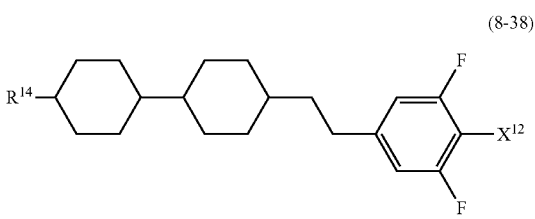
(8-40) 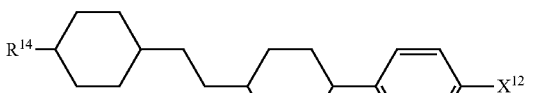
(8-41) 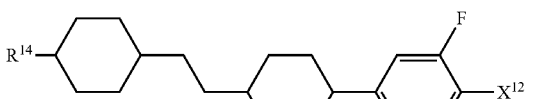
(8-42) 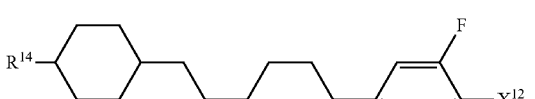
(8-43) 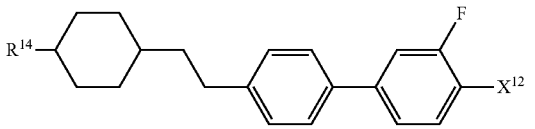

-continued
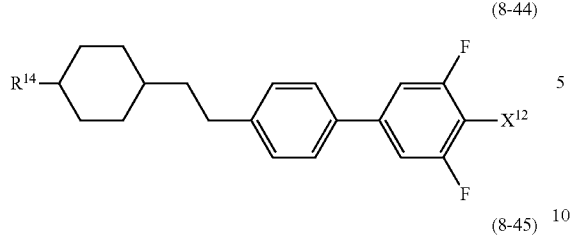
(8-44)
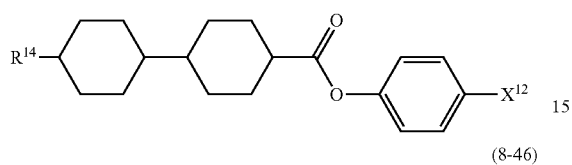
(8-45)
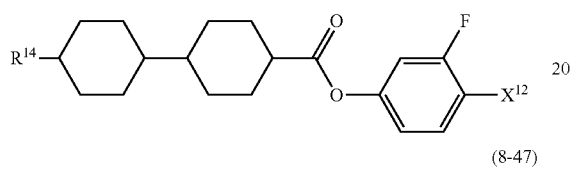
(8-46)
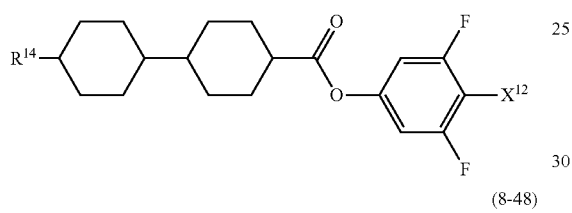
(8-47)
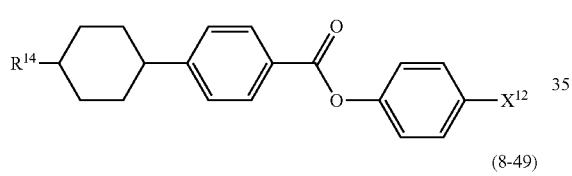
(8-48)
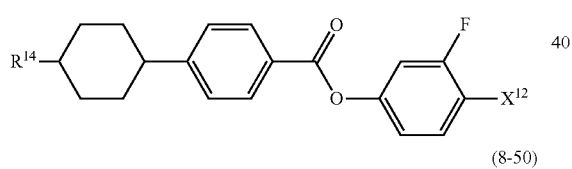
(8-49)
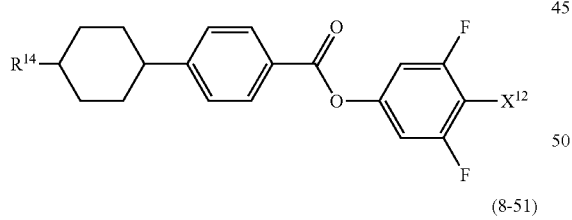
(8-50)
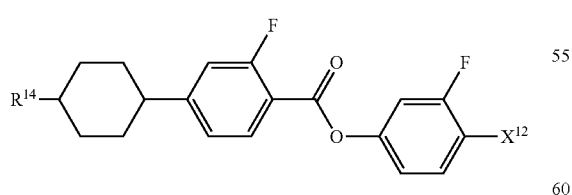
(8-51)
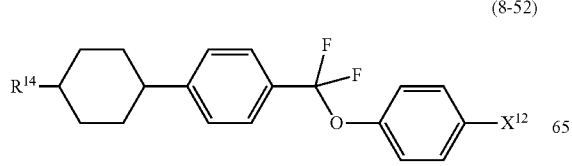
(8-52)
-continued
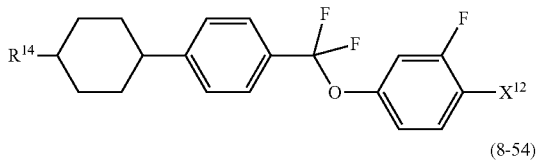
(8-53)
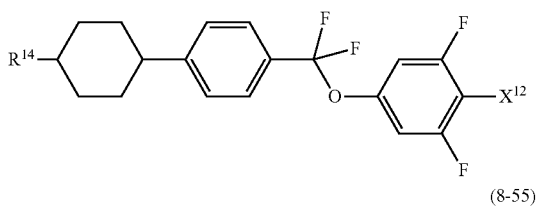
(8-54)
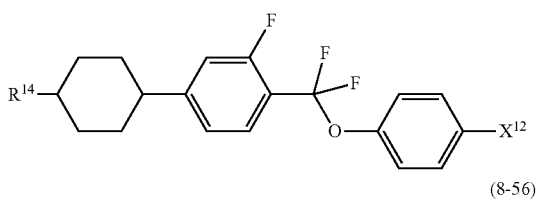
(8-55)
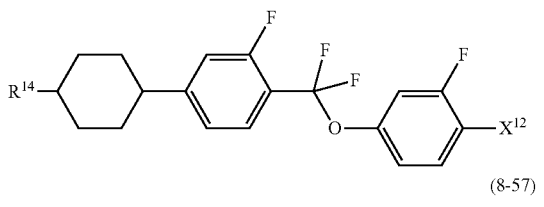
(8-56)
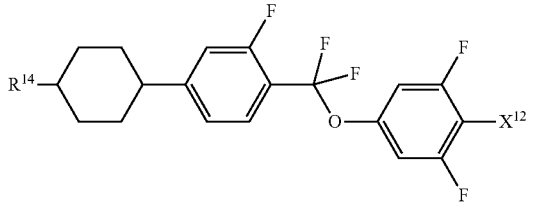
(8-57)
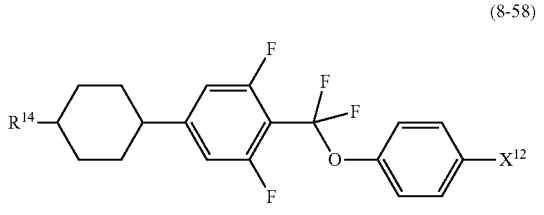
(8-58)
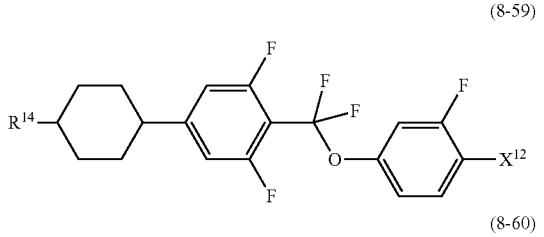
(8-59)
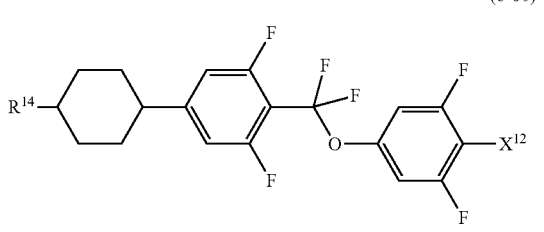
(8-60)

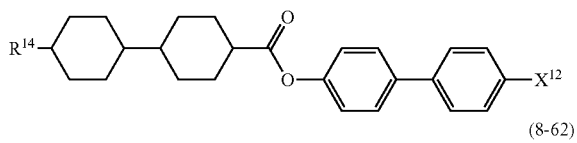
(8-61)

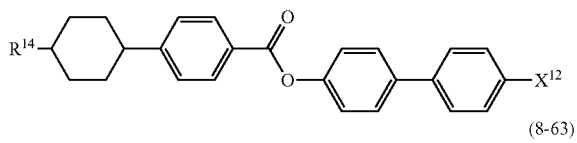
(8-62)

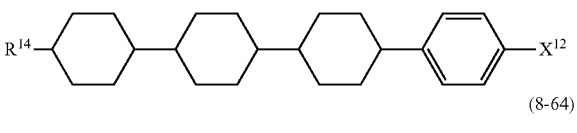
(8-63)

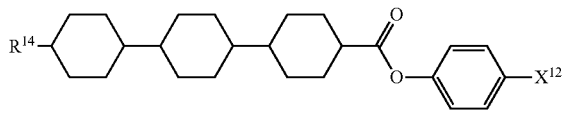
(8-64)

Component D has a large positive dielectric anisotropy, and therefore is mainly used for preparing a composition for the mode such as PS-TN. The dielectric anisotropy of the composition can be increased by adding component D. Component D is effective in extending the temperature range of the liquid crystal phase, adjusting the viscosity or the optical anisotropy. Component D is useful also in adjusting the voltage-transmittance curve of the device.

When a composition for the PS-TN mode or the like is prepared, a content of component D is suitably in the range of 1% to 99% by weight, preferably 10% to 97% by weight, and further preferably 40% to 95% by weight, based on the weight of the composition. When component D is added to the composition having the negative dielectric anisotropy, the content of component D is preferably 30% by weight or less based on the weight of the composition. The elastic constant of the composition and the voltage-transmittance curve of the device can be adjusted by adding component D.

The polymerizable composition is prepared by a method for dissolving necessary components at a temperature higher than room temperature, or the like. According to the application, the additive may be added to the composition. Specific examples of the additive include an optically active compound, an antioxidant, an ultraviolet light absorber, a light stabilizer, a heat stabilizer, an antifoaming agent, a polymerization initiator and a polymerization inhibitor. Such additives are well known to those skilled in the art, and described in literature.

The optically active compound is effective in inducing a helical structure in liquid crystal molecules to give a required twist angle, thereby being effective in preventing a reverse twist. A helical pitch can be adjusted by adding the optically active compound thereto. Two or more optically active compounds may be added for the purpose of adjusting temperature dependence of the helical pitch. Specific preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

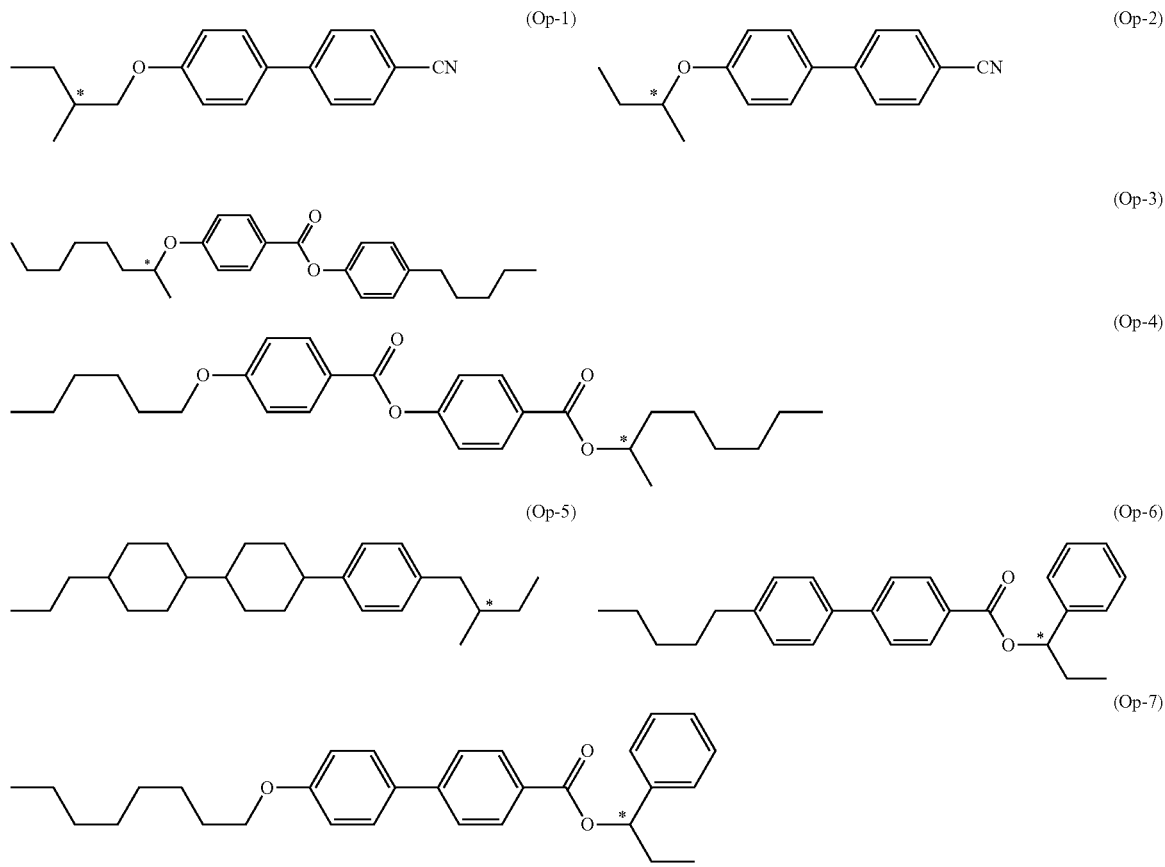

-continued
(Op-8)
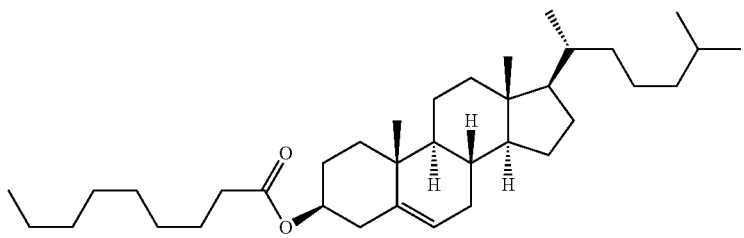
(Op-9)
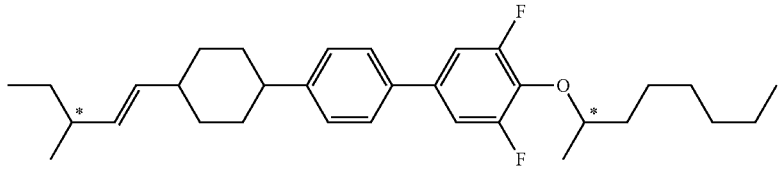
(Op-10)
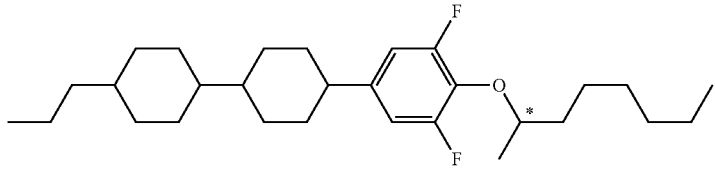
(Op-11)
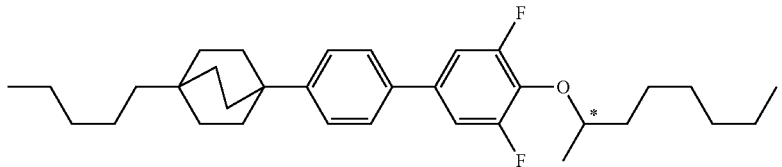
(Op-12)
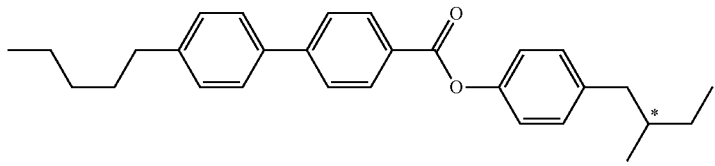
(Op-13)
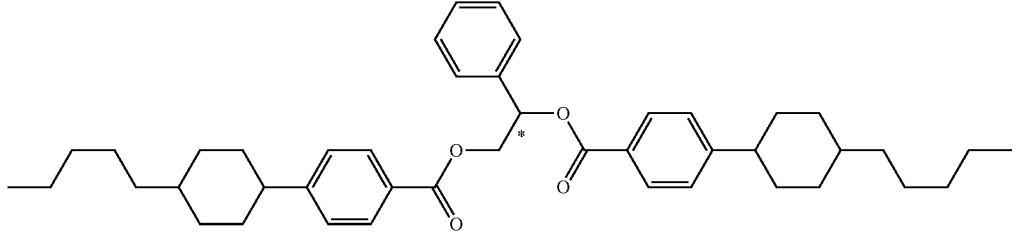
(Op-14)
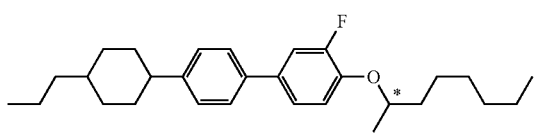
(Op-15)
(Op-16)
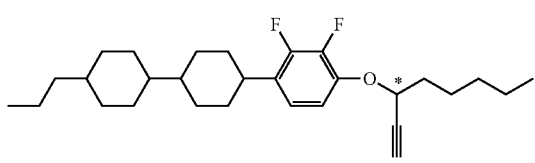
(Op-17)
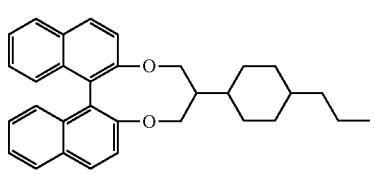

(Op-18)

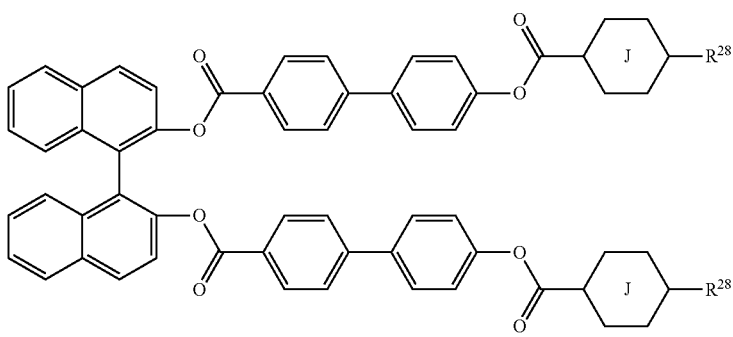

The antioxidant is effective for maintaining a large voltage holding ratio. Specific preferred examples of the antioxidant include compounds (AO-1) and (AO-2) described below, and IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease of the maximum temperature. Preferred examples of the ultraviolet light absorber include a benzophenone derivative, a benzoate derivative and a triazole derivative. Specific examples include (AO-3) and (AO-4) described below, TINUVIN 329, TINUVIN P, TINUVIN 326, TINUVIN 234, TINUVIN 213, TINUVIN 400, TINUVIN 328, TINUVIN 99-2 (trade name: BASF SE) and 1,4-diazabicyclo[2.2.2]octane (DABCO). The light stabilizer such as amine having steric hindrance is preferred for maintaining the large voltage holding ratio. Specific preferred examples of the light stabilizer include (AO-5) and (AO-6) described below, and TINUVIN 144, TINUVIN 765 and TINUVIN 770DF (trade name: BASF SE). Moreover, the heat stabilizer is also effective for maintaining the large voltage holding ratio, and preferred examples include IRGAFOS 168 (trade name: BASF SE). The defoaming agent is effective for preventing foam formation. Specific examples of the preferred defoaming agent include dimethyl silicone oil and methylphenyl silicone oil.

(AO-1)

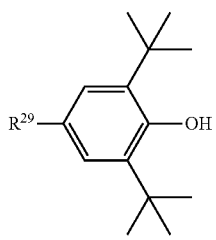

(AO-2)

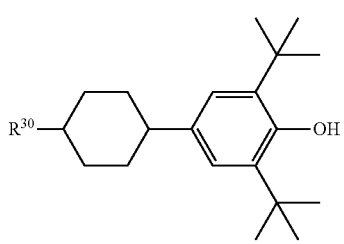

(AO-3)

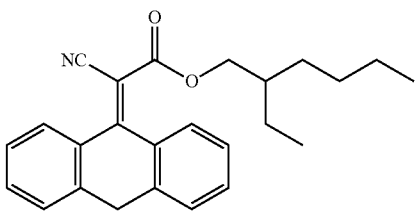

(AO-4)

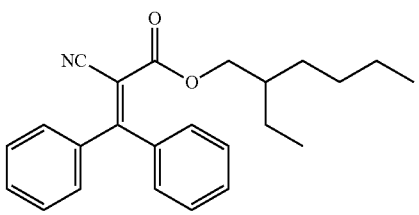

(AO-5)

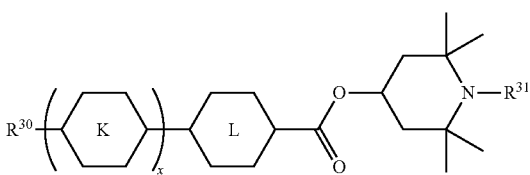

(AO-6)

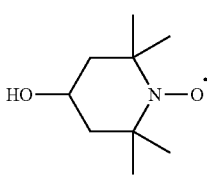

In compound (AO-1), $R^{29}$ is alkyl having 1 to 20 carbons, alkoxy having 1 to 20 carbons, —$COOR^{32}$ or —$CH_2CH_2COOR^{32}$, and $R^{32}$ is alkyl having 1 to 20 carbons. In compound (AO-2) and (AO-5), $R^{30}$ is alkyl having 1 to 20 carbons. In compound (AO-5), $R^{31}$ is hydrogen, methyl or $O^-$ (oxygen radical), ring K and ring L are 1,4-cyclohexylene or 1,4-phenylene, and x is 0, 1 or 2.

4. Liquid Crystal Composite

Compound (1) has a high polymerizability, a high conversion ratio and the high solubility in the liquid crystal composition. The liquid crystal composite is formed by polymerizing the polymerizable composition containing compound (1) and the liquid crystal composition. Compound (1) produces the polymer in the liquid crystal composition by polymerization. The polymer is effective in producing a pretilt in the liquid crystal molecules. The polymerization is preferably carried out at a temperature at which the polymerizable composition shows the liquid crystal phase. The polymerization progresses by heat, light or the like. A preferred reaction method is photopolymerization. The photopolymerization is preferably carried out at 100° C. or less in order to prevent thermopolymerization from occurring simultaneously. The polymerization may be carried out in a state in which an electric field or a magnetic field is applied.

The polymerizability and the conversion ratio of compound (1) can be adjusted. Compound (1) is suitable for radical polymerization. An amount of remaining compound (1) can be decreased by optimizing a reaction temperature. Compound (1) can be rapidly polymerized by adding the polymerization initiator. Specific examples of a photoradical polymerization initiator include TPO, 1173 and 4265 from DAROCUR series, and 184, 369, 500, 651, 784, 819, 907, 1300, 1700, 1800, 1850 and 2959 from IRGACURE series, each being supplied from Ciba Specialty Chemicals Inc.

Additional specific examples of the photoradical polymerization initiator include 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyldimethylketal, 2-methyl-1-[4-(methylthio)phenyl]-2-morpholinopropane-1-one, a 2,4-diethylxanthone-methylp-dimethylaminobenzoate mixture and a benzophenone-methyltriethanolamine mixture.

The polymerization can be carried out by adding a photoradical polymerization initiator to the polymerizable composition, and then irradiating the composition with ultraviolet light in a state in which the electric field is applied thereto. However, an unreacted polymerization initiator or a decomposed product of the polymerization initiator may possibly cause poor display such as image persistence to the device. Photopolymerization may be carried out without the polymerization initiator in order to prevent the poor display. Preferred wavelength of light for irradiation is in the range of 150 to 500 nanometers. Further preferred wavelength is in the range of 250 to 450 nanometers, and a most preferred wavelength is in the range of 300 to 400 nanometers.

Upon storing the polymerizable compound, the polymerization inhibitor may be added thereto. The polymerizable compound is ordinarily added to the composition without removing the polymerization inhibitor. Specific examples of the polymerization inhibitor include hydroquinone, a hydroquinone derivative such as methylhydroquinone, 4-tert-butylcatechol, 4-methoxyphenol or phenothiazine.

5. Liquid Crystal Display Device

An effect of the polymer in the liquid crystal display device is understood as described below. The polymerizable composition is the mixture of the liquid crystal compound, the polymerizable compound and so forth. The liquid crystal molecules align in a direction of the electric field by applying the electric field to the composition. The polymerizable compound also aligns according to the alignment. The composition is irradiated with ultraviolet light to polymerize the polymerizable compound with maintaining the alignment to form three-dimensional network structure. Alignment of the polymer is maintained even when the electric field is eliminated. The liquid crystal molecules are stabilized due to the effect of the polymer in a state in which the liquid crystal molecules align in the direction of the electric field. Accordingly, a response time of the device is to be shortened.

The polymerizable composition is preferably polymerized in the display device. One example is described below. A display device having two glass substrates equipped with transparent electrodes and an alignment film is arranged. A polymerizable composition containing as components compound (1), a liquid crystal composition and an additive is prepared. The composition is injected into the display device. The display device is irradiated with ultraviolet light while an electric field is applied to polymerize compound (1). A liquid crystal composite is formed by the polymerization. A liquid crystal display device having the liquid crystal composite can be easily produced by the method. In the method, rubbing treatment on the alignment film may be omitted. In addition, a method of stabilizing the liquid crystal molecules in a state without the electric field can be adopted.

When an amount of addition of the polymer is in the range 0.1% to 2% by weight based on the weight of the liquid crystal composition, a liquid crystal display device having the PSA mode can be produced. The device having the PSA mode can be driven in a driving mode such as an active matrix (AM) or passive matrix (PM) mode. Such a device can applies to any of a reflective type, a transmissive type and transflective type. A device having a polymer dispersed mode can also be produced by increasing the amount of addition of the polymer.

EXAMPLES

The invention will be described in greater detail by way of Examples. However, the invention is not limited by the Examples.

6. Example of Compound (1)

Compound (1) was prepared by the method described in Example 1 or the like. The prepared compound was identified by methods such as an NMR analysis. Physical properties of the compound were measured by methods described below.

NMR Analysis

As a measuring apparatus, DRX-500 (made by Bruker BioSpin Corporation) was used. In $^1$H-NMR measurement, a sample was dissolved in a deuterated solvent such as $CDCl_3$, and measurement was carried out under conditions of room temperature, 500 MHZ and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra, s, d, t, q, quin, sex, m stand for a singlet, a doublet, a triplet, a quartet, a quintet, a sextet, a multiplet, and br being broad, respectively.

HPLC Analysis

As a measuring apparatus, Prominence (LC-20AD; SPD-20A), made by Shimadzu Corporation was used. As a column, YMC-Pack ODS-A (length 150 mm, bore 4.6 mm, particle diameter 5 μm) made by YMC Co., Ltd. was used. As an elution liquid, acetonitrile and water were appropriately mixed and used. As a detector, a UV detector, an RI detector, a CORONA detector or the like was appropriately used. When the UV detector was used, a detection wavelength was adjusted to 254 nm. A sample was dissolved in acetonitrile and prepared to be a 1% solution, and 1 microliter of the solution obtained was injected into a sample injector. As a recorder, C-R7Aplus made by Shimadzu Corporation was used.

Ultraviolet-Visible Spectroscopy

As a measuring apparatus, PharmaSpec UV-1700 made by Shimadzu Corporation was used. A detection wavelength was adjusted to 190 to 700 nm. A sample was dissolved in acetonitrile, and prepared to be a solution of 0.01 mmol/L, and put in a quartz cell (optical path length: 1 cm).

Sample for Measurement

In measuring a phase structure and a transition temperature (clearing point, melting temperature, polymerization start temperature, or the like), a compound itself was used as a sample. In measuring physical properties such as a maximum temperature of a nematic phase, viscosity, optical anisotropy and dielectric anisotropy, a mixture of the compound and a base liquid crystal was used as a sample.

Measuring Methods

Physical properties were measured according to the methods described below. Most of the methods were applied as described in the Standard of the Japan Electronics and Information Technology Industries Association (JEITA EIAJ ED-2521B) to be discussed and established by JEITA, or modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

Measurement was carried out by using Diamond DSC System, differential scanning calorimeter made by PerkinElmer, Inc. or a high sensitivity differential scanning calorimeter, X-DSC7000, made by SII NanoTechnology, Inc. A sample was heated and then cooled at a rate of 3° C. per minute, a starting point of an endothermic peak or an exothermic peak caused by a phase change of the sample was determined by extrapolation, and thus a transition temperature was determined. A melting point and a polymerization start temperature of a compound were also measured using the apparatus. Temperature at which the compound undergoes transition from a solid to a liquid crystal phase such as a smectic phase and a nematic phase may be occasionally abbreviated as "minimum temperature of the liquid crystal phase." Temperature at which a compound undergoes transition from the liquid crystal phase to a liquid may be occasionally abbreviated as "clearing point."

Crystals were expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. The liquid (isotropic) was expressed as I. The transition temperature was expressed as "C 50.0 N 100.0 I," for example. The expression indicates that the transition temperature from the crystal to the nematic phase is 50.0° C., and the transition temperature from the nematic phase to the liquid is 100.0° C.

(3) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when a part of the sample began to change from a nematic phase to an isotropic liquid was measured. A maximum temperature of the nematic phase may be occasionally abbreviated as "maximum temperature." When the sample was a mixture of a compound and the base liquid crystal, the maximum temperature was expressed in terms of a symbol $T_{NI}$. When the sample was a mixture of a compound, component B, C, D or E, the maximum temperature was expressed in terms of a symbol NI.

(4) Minimum Temperature of Nematic Phase ($T_c$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c \leq -20°$ C. A minimum temperature of the nematic phase may be occasionally abbreviated as "minimum temperature."

(5) Viscosity (Bulk Viscosity; η; Measured at 20° C.; mPa·s)

A cone-plate (E type) rotational viscometer made by Tokyo Keiki, Inc. was used for measurement.

(6) Optical Anisotropy (Refractive Index Anisotropy; Measured at 25 C; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(7) Specific Resistance (ρ; Measured at 25° C.; Ωcm)

Into a vessel equipped with electrodes, 1.0 mL of sample was injected. A direct current voltage (10 V) was applied to the vessel, and a direct current after 10 seconds was measured. Specific resistance was calculated from the following equation: (specific resistance)={(voltage)×(electric capacity of the vessel)}/{(direct current)×(dielectric constant of vacuum)}.

(8) Voltage Holding Ratio (VHR-1; Measured at 25° C.; %)

A TN device used for measurement had a polyimide alignment film, and a distance (cell gap) between two glass substrates was 5 micrometers. A sample was put in a device, and a device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(9) Voltage Holding Ratio (VHR-2; Measured at 80° C.; %)

A voltage holding ratio was measured according to procedures identical with the procedures described above except that measurement was carried out at 80° C. in place of 25° C. The thus obtained results were expressed in terms of VHR-2.

Methods of measuring physical properties may be different between a sample having positive dielectric anisotropy and a sample having negative dielectric anisotropy in several cases. Measuring methods when dielectric anisotropy was positive were described in sections (10) to (14).

(10) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. A voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device by which the rotational viscosity was measured and by a method described below.

(11) Dielectric Anisotropy ($\Delta\varepsilon$; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (Eli) in the major axis direction of liquid crystal molecules was measured. Sine waves (0.5 V, 1 kHz) were applied to the device, and after 2 seconds, a dielectric constant ($\varepsilon\perp$) in the minor axis direction of the liquid crystal molecules was measured. A value of dielectric anisotropy was calculated from an equation: $\Delta\varepsilon=\varepsilon\|-\varepsilon\perp$.

(12) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and the values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K is a mean value of the thus determined $K_{11}$, $K_{22}$ and $K_{33}$.

(13) Threshold Voltage ($V_{th}$; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 90% transmittance.

(14) Response Time (τ; Measured at 25° C.; Ms)

An LCD-5100 luminance meter made by Otsuka Electronics Co., Ltd. was used for measurement. A light source was a halogen lamp. A low-pass filter was set at 5 kHz. A sample was put in a normally white mode TN device in which a distance (cell gap) between two glass substrates was 5.0 micrometers and a twist angle was 80 degrees. Rectangular waves (60 Hz, 5 V, 0.5 sec) was applied to the device. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. Arise time (τr; millisecond) is a time taken for transmittance to change from 90% to 10%. A fall time (if: millisecond) is a time taken for transmittance to change from 10% to 90%. Response time was expressed in terms of a sum of the thus determined rise time and fall time.

Example 1

Synthesis of Compound (1-3-89)

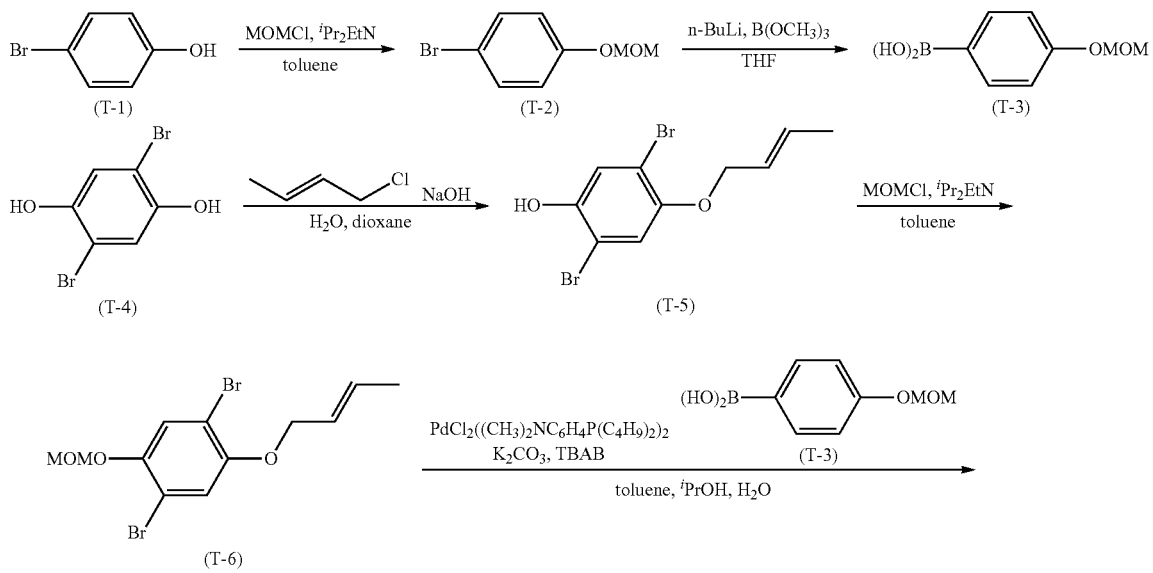

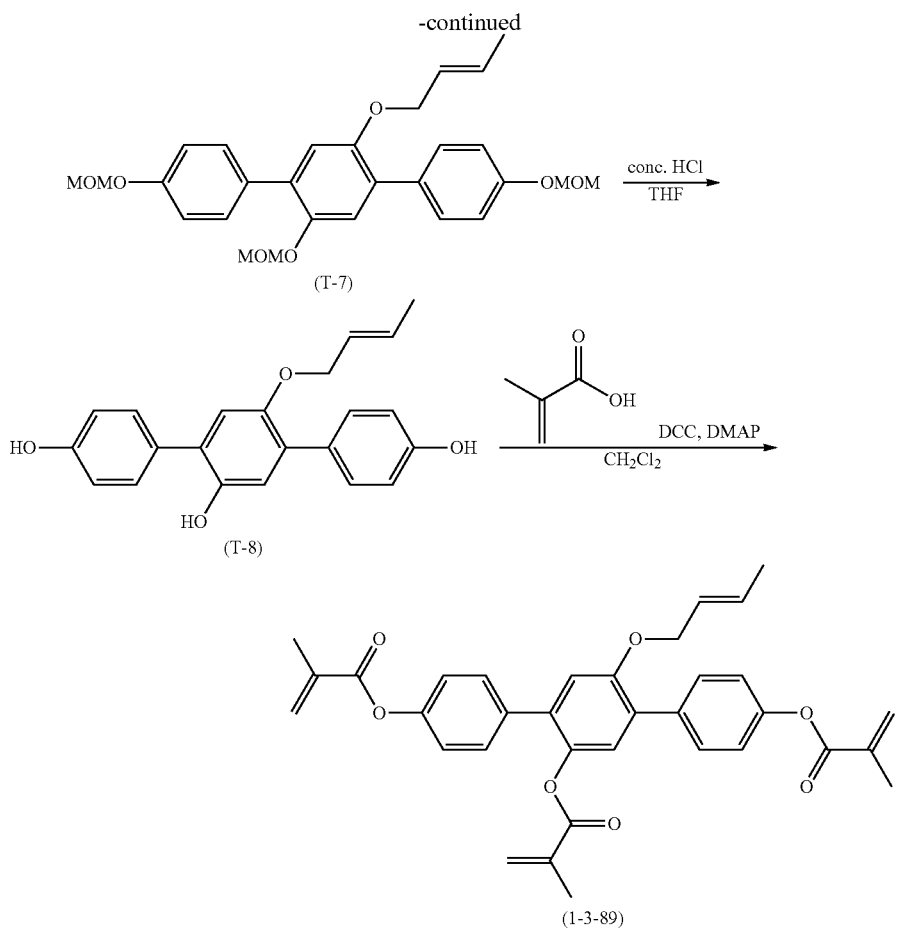

First Step:

A toluene (250 mL) solution of 4-bromophenol (T-1) (50.0 g, 289.01 mmol; Tokyo Chemical Industry Co., Ltd.) and diisopropylethylamine (56.03 g, 433.5 mmol) was ice-cooled, and chloromethyl methyl ether (34.9 g, 433.51 mmol) was added dropwise thereto. The resulting mixture was stirred for 3 hours, and then the reaction mixture was poured into a saturated aqueous solution of ammonium chloride (200 mL), and subjected to extraction with ethyl acetate. The extracted liquid was washed with water (300 mL) and saturated brine (200 mL), dried over anhydrous magnesium sulfate, and concentrated under reduced pressure. The residue was purified by column chromatography (eluent:toluene:heptane=2:1 (volume ratio)) to obtain compound (T-2) (57.6 g, 265.1 mol, 91.7%).

Second Step:

A THF (290 mL) solution of compound (T-2) (57.6 g, 265.1) obtained in the first step was cooled to −40° C., and n-BuLi (1.59 M, 200.3 mL, 318.4 mmol) was added dropwise thereto. The resulting mixture was stirred at −40° C. for 2 hours, and then trimethoxyboron (35.85 g, 344.97 mmol) was added dropwise thereto. The resulting mixture was stirred at room temperature for 8 hours, and then the reaction mixture was poured into a saturated aqueous solution of ammonium chloride (300 mL), and subjected to extraction with ethyl acetate. Then, the extracted liquid was washed with water (300 mL) and saturated brine (200 mL), dried over anhydrous magnesium sulfate, and concentrated under reduced pressure to obtain compound (T-3) (32.7 g, 179.69 mol, 67.7%).

Third Step:

Then, 2,5-dibromohydroquinone (T-4) (25.0 g, 93.32 mmol; Wako Pure Chemical Industries, Ltd.) and sodium hydroxide (8.21 g, 205.3 mmol) were dissolved into a mixed solvent of 1,3-dioxane (250 mL) and water (250 mL), and ice-cooled. Into the solution, crotyl chloride (8.45 g, 93.3 mmol) was added dropwise. The resulting mixture was stirred under ice-cooling for 1 hour, and then the reaction mixture was poured into a saturated aqueous solution of ammonium chloride (300 mL), and subjected to extraction with ethyl acetate. The extracted liquid was washed with water (300 mL) and saturated brine (200 mL), dried over anhydrous magnesium sulfate, and concentrated under reduced pressure. The residue was purified by column chromatography (eluent:toluene:ethyl acetate=10:1 (volume ratio)) to obtain compound (T-5) (12.1 g, 37.6 mmol, 40.3%).

Fourth Step:

Operation similar to the operation in the first step was performed by using compound (T-5) (12.1 g, 37.6 mmol) obtained in the third step, diisopropylethylamine (7.28 g, 56.37 mmol), toluene (60 mL) and chloromethyl methyl ether (4.54 g, 56.37 mmol) to obtain compound (T-6) (7.8 g, 21.3 mmol, 56.7%).

Fifth Step:

Compound (T-3) (9.3 g, 51.1 mmol) obtained in the second step, compound (T-6) (7.8 g, 21.3 mmol) obtained in the fourth step, bis(di-tert-butyl-(4-dimethylaminophenyl)phosphine dichloropalladium(II) (0.0754 g, 0.11 mmol), potassium carbonate (8.83 g, 63.93 mmol), tetrabutylammonium bromide (TBAB) (1.37 g, 4.26 mmol), toluene (78 mL), isopropanol (78 mL) and water (78 mL) were mixed, and heated under reflux for 8 hours. The reaction mixture was allowed to cool to room temperature, and then filtrated. The filtrate was washed with water (100 mL) and saturated brine (50 mL), dried over anhydrous magnesium sulfate, and concentrated under reduced pressure. The residue was purified by column chromatography (eluent:toluene:ethyl acetate=9:1 (volume ratio)) to obtain compound (T-7) (4.2 g, 8.74 mmol, 41.0%).

Sixth Step:

To a THF (21 mL) solution of compound (T-7) (4.2 g, 8.74 mmol) obtained in the fifth step, concentrated hydrochloric acid (13.11 mL, 157.3=1) was added, and the resulting mixture was stirred at 70° C. for 3 hours. The reaction mixture was allowed to cool to room temperature, and then poured into water (100 mL), and subjected to extraction with ethyl acetate (50 mL). The extracted liquid was washed with water (100 mL), a saturated aqueous solution of sodium hydrogencarbonate (50 mL), water (100 mL) and saturated brine (50 mL), dried over anhydrous magnesium sulfate, and concentrated under reduced pressure to obtain compound (T-8) (3.0 g, 8.61 mmol, 98.5%).

Seventh Step:

Compound (T-8) (3.0 g, 8.61 mmol) obtained in the sixth step, methacrylic acid (2.44 g, 28.4 mmol) and N,N-dimethyl-4-aminopyridine (DMAP; 0.79 g, 6.46 mmol) were dissolved into dichloromethane (30 mL) and ice-cooled. Dicyclohexylcarbodiimide (DCC; 6.22 g, 30.14 mmol) was added little by little thereto with keeping a solid, and the resulting mixture was stirred at room temperature for 8 hours. The reaction mixture was filtrated through Cerite, and the residue was purified by column chromatography (eluent: toluene:heptane=2:1 (volume ratio)), and recrystallized (toluene:ethyl acetate=10:1 (volume ratio)) to obtain compound (1-3-89) (0.2 g, 0.36 mmol, 4.2%).

Melting point: 114.1° C.

$^1$H-NMR (CDCl$_3$; δ ppm): 7.63 (d, 2H), 7.47 (d, 2H), 7.16 (dd, 5H), 6.99 (s, 1H), 6.37 (s, 2H), 6.17 (s, 1H), 5.80-5.62 (m, 5H), 4.63-4.48 (m, 2H), 2.08 (s, 6H), 1.92 (s, 3H), 1.71 (d, 3H).

Example 2

Synthesis of Compound (1-3-58)

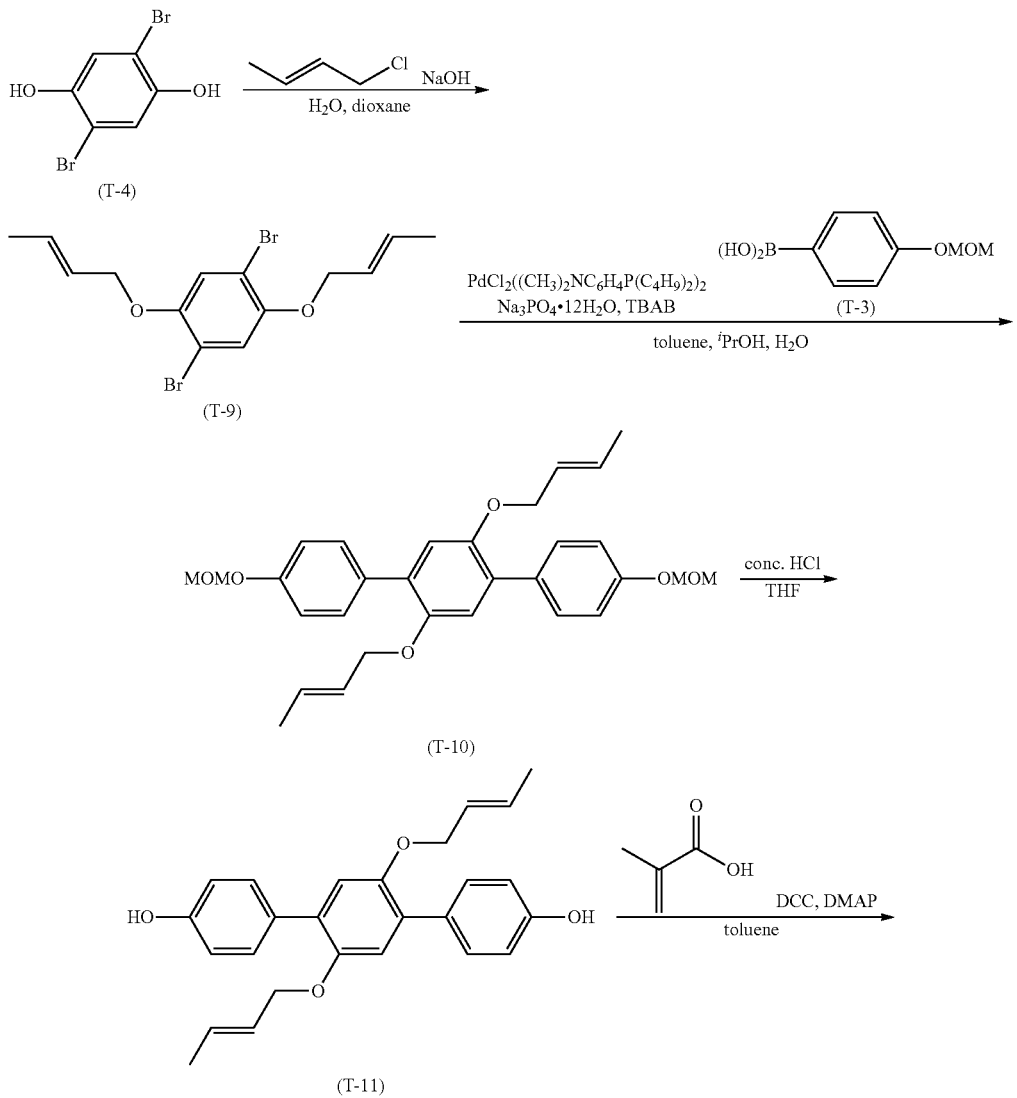

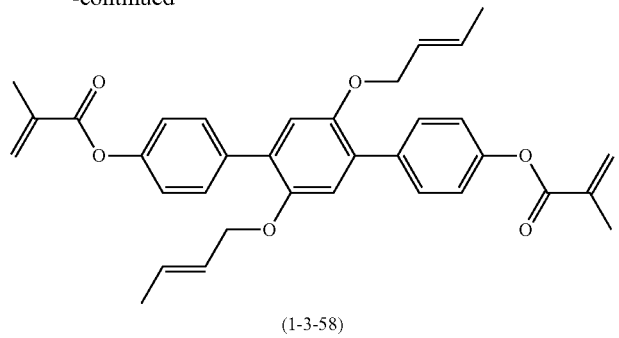

(1-3-58)

First Step:

Operation similar to the operation in the third step in Example 1 was performed by using 2,5-dibromohydroquinone (T-4) (9.55 g, 35.66 mmol), sodium hydroxide (7.1 g, 78.45 mmol), 1,3-dioxane (100 mL), water (100 mL) and crotyl chloride (3.14 g, 78.45 mmol) to obtain compound (T-9) (12.1 g, 32.17 mmol, 90.2%).

Second Step:

Operation similar to the operation in the fifth step in Example 1 was performed by using compound (T-3) (12.88 g, 70.78 mmol) obtained in the second step in Example 1, compound (T-9) (12.1 g, 32.17 mmol) obtained in the first step, bis(di-tert-butyl-(4-dimethylaminophenyl)phosphine) dichloro palladium(II) (0.11 g, 0.16 mmol), trisodium monophosphate 12 hydrate (39.69 g, 96.52 mmol), tetrabutylammonium bromide (TBAB) (2.07 g, 6.43 mmol), toluene (120 mL), isopropanol (120 mL) and water (120 mL) to obtain compound (T-10) (9.1 g, 18.55 mmol, 57.7%).

Third Step:

Operation similar to the operation in the sixth step in Example 1 was performed by using compound (T-10) (4.1 g, 8.36 mmol) obtained in the second step, THF (20 mL) and concentrated hydrochloric acid (9.19 mL, 110.3 mmol) to obtain compound (T-11) (3.2 g, 7.95 mmol, 95.1%).

Fourth Step:

Operation similar to the operation in the seventh step in Example 1 was performed by using compound (T-11) (3.2 g, 7.95 mmol) obtained in the third step, methacrylic acid (1.37 g, 15.9 mmol), N,N-dimethyl-4-aminopyridine (DMAP; 0.19 g, 15.9 mmol), toluene (30 mL) and dicyclohexylcarbodiimide (DCC; 3.44 g, 16.7 mmol) to obtain compound (1-3-58) (2.9 g, 5.38 mmol, 67.7%).

Melting point: 122.7° C.

$^1$H-NMR (CDCl$_3$; δ ppm): 7.61 (d, 4H), 7.17 (d, 4H), 6.98 (s, 2H), 6.38 (s, 2H), 5.78-5.60 (m, 6H), 4.40 (d, 4H), 2.09 (s, 6H), 1.70 (d, 6H).

Example 3

Synthesis of Compound (1-3-21)

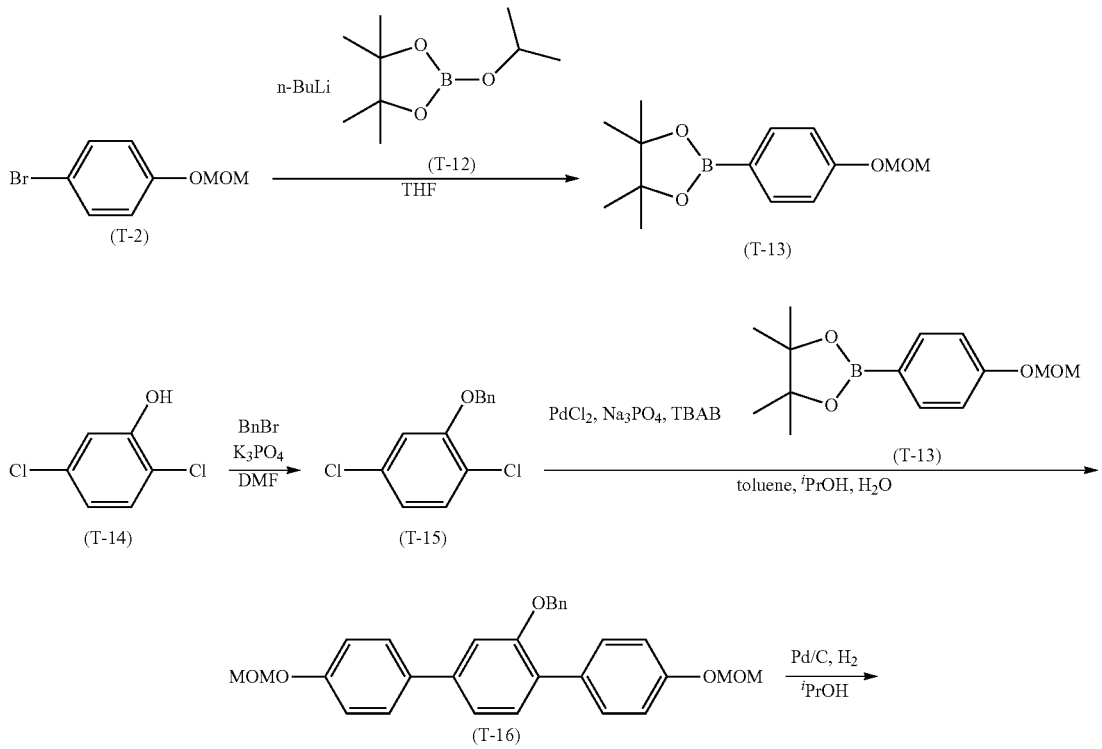

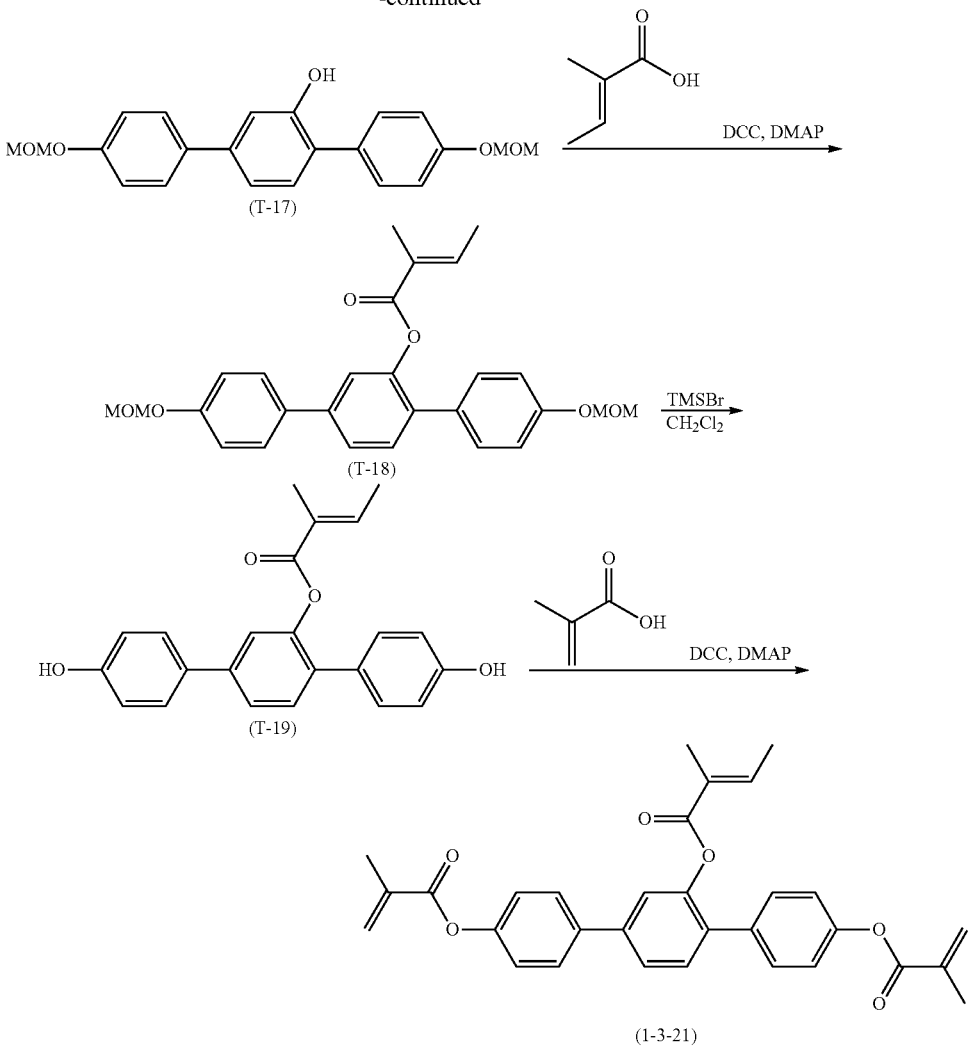

First Step:

Operation similar to the operation in the second step in Example 1 was performed by using compound (T-2) (50 g, 230 mmol) obtained in the first step in Example 1, THF (250 mL), n-BuLi (1.59 M, 173.8 mL, 276.4 mmol) and 2-isopropoxy-4,4,5,5-tetramethyl-1,3,2-dioxaborolane (T-12) (51.4 g, 276.4 mmol) to obtain compound (T-13) (50.3 g, 182.9 mmol, 79.5%).

Second Step:

Then, 2,5-dichlorophenol (T-14) (25.0 g, 153.37 mmol; Tokyo Chemical Industry Co., Ltd.), benzyl bromide (28.85 g, 168.71 mmol), potassium phosphate (48.83 g, 230.06 mmol) and DMF (125 mL) were mixed, and the resulting mixture was stirred at 50° C. for 8 hours. The reaction mixture was allowed to cool to room temperature, and then filtrated. The filtrate was poured into water, and subjected to extraction with toluene (100 mL). The extracted layer was washed with water (100 mL) and saturated brine (50 mL), dried over anhydrous magnesium sulfate, and concentrated under reduced pressure. The residue was purified by column chromatography (eluent:toluene:heptane=2:1 (volume ratio)) to obtain compound (T-15) (36.2 g, 142.87 mmol, 93.1%).

Third Step:

Operation similar to the operation in the fifth step in Example 1 was performed by using compound (T-13) (22.96 g, 86.91 mmol) obtained in the first step, compound (T-15) (10.0 g, 39.51 mmol) obtained in the second step, bis(di-tert-butyl-(4-dimethylaminophenyl)phosphine dichloropalladium(II) (0.14 g, 0.20 mmol), trisodium monophosphate 12 hydrate (45.05 g, 118.52 mmol), tetrabutylammonium bromide (TBAB) (5.09 g, 15.80 mmol), toluene (50 mL), isopropanol (50 mL) and water (50 mL) to obtain compound (T-16) (10.2 g, 22.32 mmol, 56.5%).

Fourth Step:

Compound (T-16) (10.2 g, 22.32 mmol) obtained in the third step was dissolved into isopropanol (100 mL), and then 5% palladium/carbon (0.51 g) was added thereto, and the resulting mixture was stirred under a hydrogen atmosphere for 24 hours. The reaction mixture was filtrated, the filtrate was concentrated, and then the residue was purified by column chromatography (eluent:toluene:ethyl acetate=5:1 (volume ratio)) to obtain compound (T-17) (7.2 g, 19.63 mmol, 87.9%).

Fifth Step:

Operation similar to the operation in the seventh step in Example 1 was performed by using compound (T-17) (2.2 g, 6.00 mmol) obtained in the fourth step, tiglic acid (0.66 g, 6.60 mmol), N,N-dimethyl-4-aminopyridine (DMAP) (0.15 g, 1.23 mmol), dichloromethane (20 mL) and dicyclohexylcarbodiimide (DCC) (1.36 g, 6.59 mmol) to obtain compound (T-18) (2.65 g, 5.91 mmol, 98.4%).

Sixth Step:

Compound (T-18) (2.60 g, 5.80 mmol) obtained in the fifth step was dissolved into dichloromethane (25 mL) and ice-cooled. Into the solution, trimethylsilyl bromide (8.87 g, 57.97 mmol) was added dropwise, and then the resulting mixture was stirred at room temperature 5 hours. The reaction mixture was poured in water (20 mL), and subjected to extraction with ethyl acetate (40 mL). The extracted liquid was washed with water (50 mL) and saturated brine (20 mL), dried over anhydrous magnesium sulfate, and concentrated under reduced pressure to obtain compound (T-19) (1.8 g, 4.99 mmol, 86.2%).

Seventh Step:

Operation similar to the operation in the seventh step in Example 1 was performed by using compound (T-19) (1.8 g, 4.99 mmol) obtained in the sixth step, methacrylic acid (0.94 g, 10.92 mmol), N,N-dimethyl-4-aminopyridine (DMAP) (0.24 g, 1.96 mmol), dichloromethane (18 mL) and dicyclohexylcarbodiimide (DCC; 2.37 g, 11.49 mmol) to obtain compound (1-3-21) (1.4 g, 2.81 mmol, 56.2%).

Melting point: 119.4° C.

$^{1}$H-NMR (CDCl$_{3}$; δ ppm): 7.63 (d, 2H), 7.53-7.47 (m, 4H), 7.38 (s, 1H), 7.20 (d, 2H), 7.15 (d, 2H), 6.96 (q, 1H), 6.37 (d, 2H), 5.78 (s, 2H), 2.08 (s, 6H), 1.82 (d, 6H).

Example 4

Compound (1-3-15)

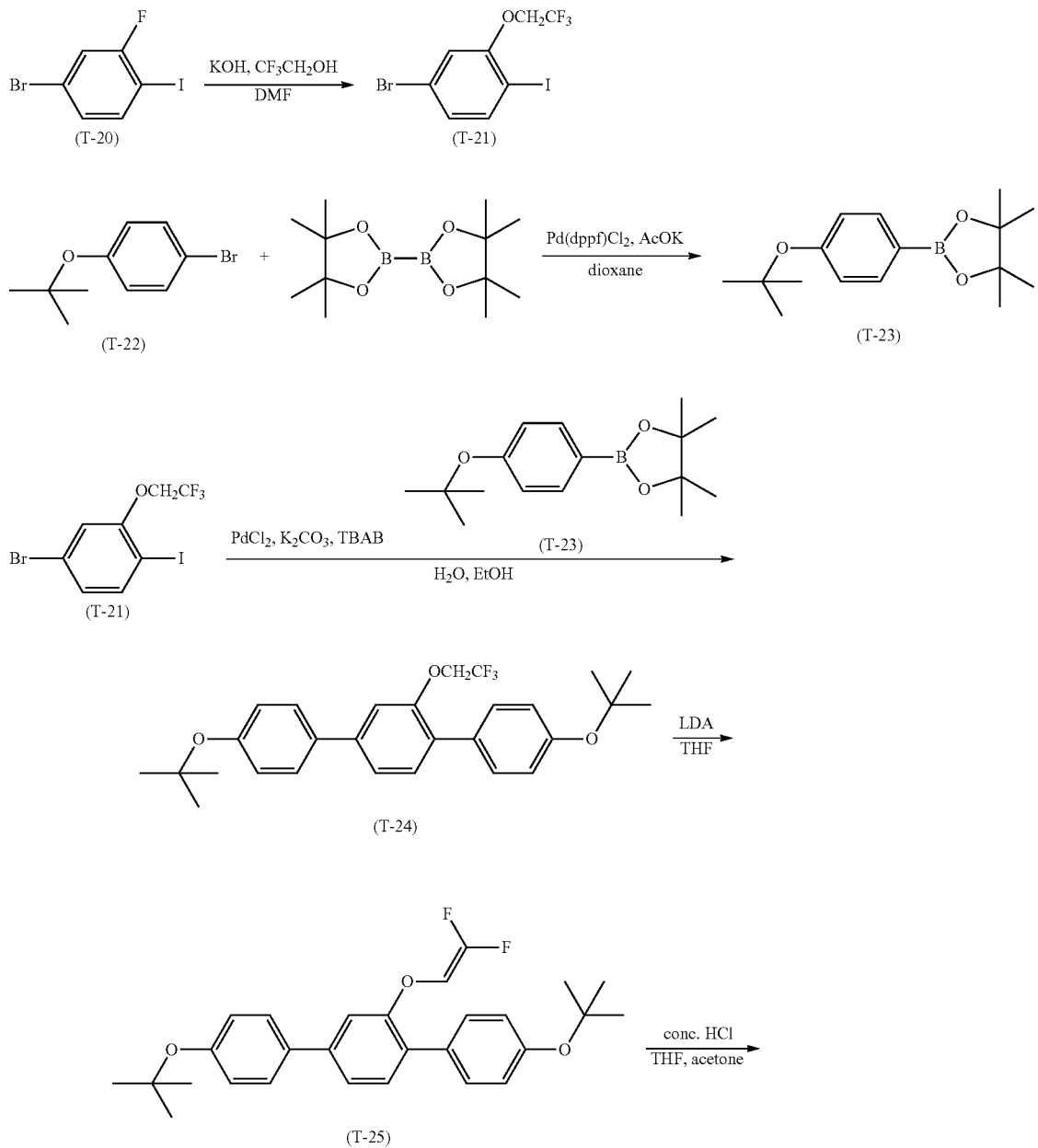

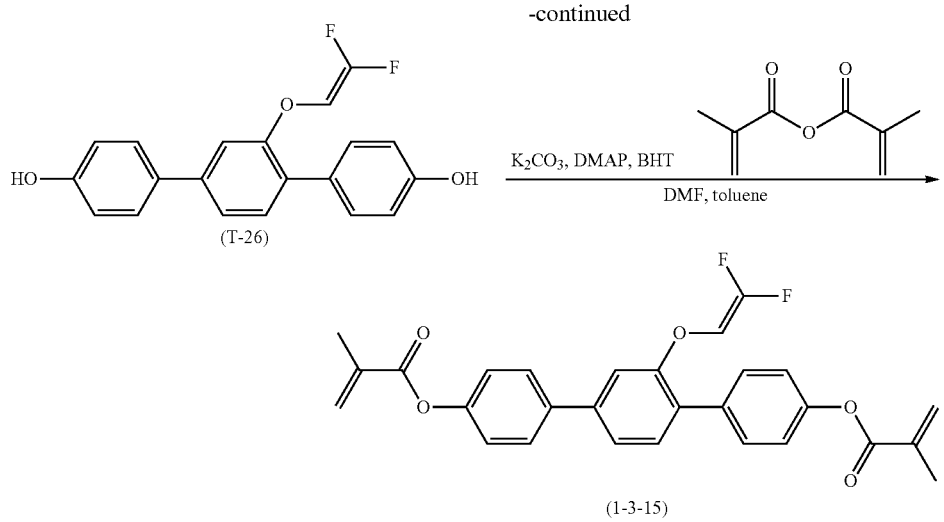

First Step:

Then, 3-fluoro-4-iodo-bromobenzene (T-20) (300 g, 997 mmol; Tokyo Chemical Industry Co., Ltd), potassium hydroxide (112 g, 1.996 mol) and DMF (800 mL) were mixed, and the resulting mixture was ice-cooled. Into the solution, 2,2,2-trifluoroethanol (200 g, 1.992 mmol) was added dropwise under ice-cooling, and then the reaction mixture was slowly heated, and stirred at 60° C. for 5 hours. The reaction mixture was allowed to cool to room temperature, and then poured into water (800 mL), and subjected to extraction with heptane (500 mL). The extracted layer was washed with water (500 mL) and saturated brine (300 mL), dried over anhydrous magnesium sulfate, and concentrated under reduced pressure to obtain compound (T-21) (270 g, 708.8 mmol, 71.1%).

Second Step:

Compound (T-22) (179.7 g, 784.5 mmol), bispinacolato diborane (239.0 g, 941.4 mmol), potassium acetate (92.4 g, 941.4 mmol), bis(diphenylphosphino ferrocene dichloropalladium(II) (10.0 g, 13.7 mmol) and 1,3-dioxane (1,000 mL) were mixed, and the resulting mixture was stirred at 90° C. for 4 hours. The reaction mixture was allowed to cool to room temperature, and then poured into water, and subjected to extraction with heptane (800 mL). The extracted layer was washed with water (1,000 mL) and saturated brine (500 mL), dried over anhydrous magnesium sulfate, and concentrated under reduced pressure. The residue was purified by column chromatography (eluent:heptane) to obtain compound (T-23) (182 g, 659 mmol, 84.10).

Third Step:

Compound (T-21) (104.6 g, 274.6 mmol) obtained in the first step, compound (T-23) (182 g, 659 mmol) obtained in the second step, potassium carbonate (141.0 g, 1.02 mol), tetrabutylammonium bromide (TBAB) (27.0 g, 83.7 mmol), bis(diphenylphosphino ferrocene dichloropalladium(II) (10.0 g, 13.7 mmol), water (1,000 mL) and ethanol (100 mL) were mixed, and the resulting mixture was stirred at 85° C. for 4 hours. The reaction mixture was allowed to cool to room temperature, and then poured into water, and subjected to extraction with toluene (800 mL). The extracted layer was washed with water (1,000 mL) and saturated brine (500 mL), dried over anhydrous magnesium sulfate, and concentrated under reduced pressure. The residue was purified by heptane to obtain compound (T-24) (97.1 g, 205.5 mmol, 74.8%).

Fourth Step:

Compound (T-24) (30.0 g, 63.5 mmol) obtained in the third step was dissolved into THF (200 mL), and the resulting mixture was cooled to −70° C. or less. Into the solution, lithium diisopropylamide (2 M, 34.9 mL, 69.8 mmol) was added dropwise, and the resulting mixture was stirred at −70° C. or less for 2 hours. The reaction mixture was poured into water, and subjected to extraction with toluene (200 mL). The extracted layer was washed with water (200 mL) and saturated brine (100 mL), dried over anhydrous magnesium sulfate, and concentrated under reduced pressure. The residue was purified by heptane to obtain compound (T-25) (23.5 g, 51.9 mmol, 81.7%).

Fifth Step:

Compound (T-25) (5.0 g, 11.0 mmol) obtained in the fourth step, concentrated hydrochloric acid (8 mL, 96 mmol), THF (50 mL) and acetone (20 mL) were mixed, and the resulting mixture was stirred at 60° C. for 2 hours. The reaction mixture was allowed to cool to room temperature, and water (300 mL) was added thereto. A precipitated deposit was obtained by filtration, and washed with water to obtain compound (T-26) (3.74 g, 10.9 mmol, 99.1%).

Sixth Step:

Toluene (50 mL) was added to compound (T-26) (3.74 g, 10.9 mmol) obtained in the fifth step, and the resulting mixture was heated under reflux, and then allowed to cool to room temperature. Into the solution, 2,6-di-tert-butyl-4-methylphenol (BHT) (50 mg), methacrylic anhydride (4.1 g, 26.6 mmol) and DMF (50 mL) were added. The resulting solution was added dropwise into a mixture of N,N-dimethyl-4-aminopyridine (DMAP) (0.24 g, 2.2 mmol), potassium carbonate (5.46 g, 39.5 mmol) and toluene (50 mL) while keeping 90° C., and heated under reflux for 3 hours. The reaction mixture was allowed to cool to room temperature and filtrated, and the filtrate was concentrated under reduced pressure. The residue was purified by column chromatography (eluent:dichloromethane:heptane=1:3 (volume ratio)) and recrystallized (heptane) to obtain compound (1-3-15) (4.1 g, 86 mmol, 78.9%).

Melting point: 141.0° C.

$^1$H-NMR (CDCl$_3$; δ ppm): 7.64-7.58 (m, 4H), 7.45 (d, 1H), 7.36 (dd, 1H), 7.26-7.19 (m, 5H), 6.38 (d, 2H), 6.06 (dd, 1H), 5.79-5.78 (m, 2H), 2.09 (d, 6H).

Example 5

Compound (1-3-26)

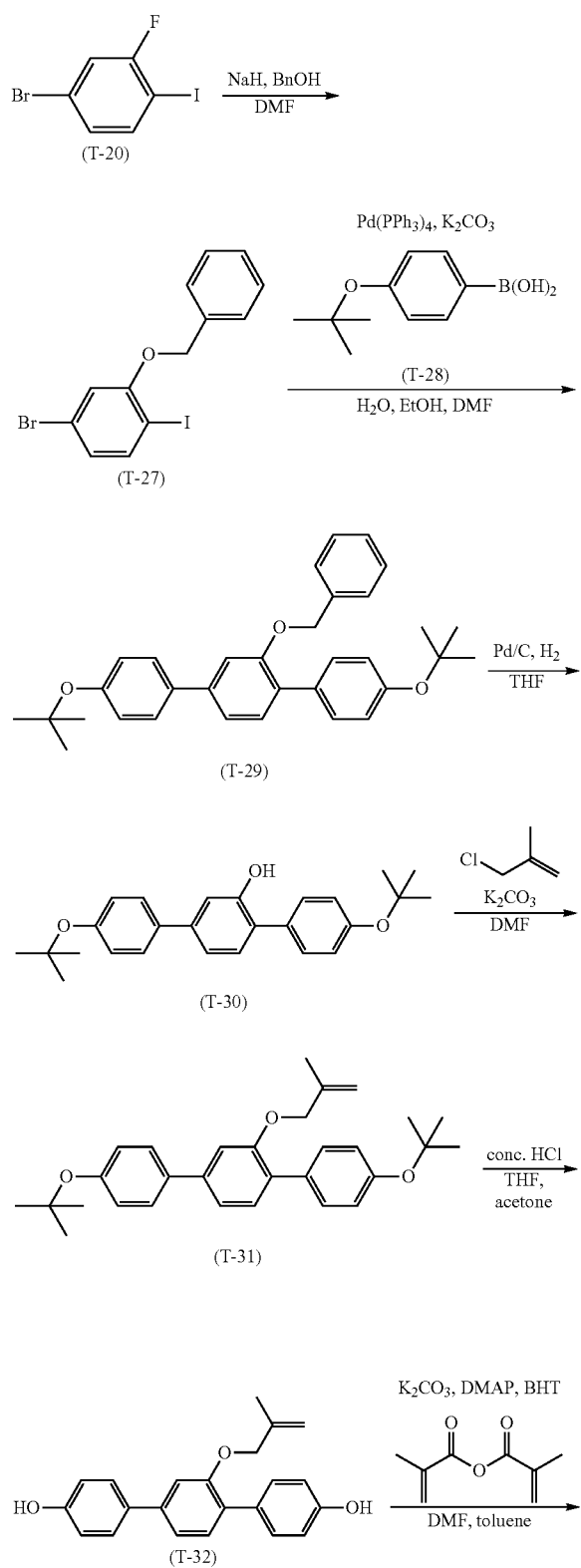

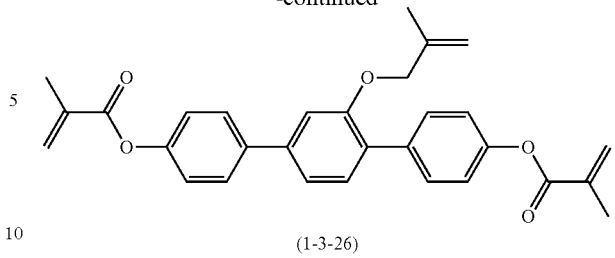

(1-3-26)

First Step:

Sodium hydride (60%, 21.9 g, 547 mmol) was added to DMF (800 mL), and then benzyl alcohol (59.3 g, 548.4 mmol) was added thereto, and the resulting mixture was stirred at 90° C. for 30 minutes. Into the reaction mixture that was allowed to cool to room temperature, 3-fluoro-4-iodo-bromobenzene (T-20) (150.0 g, 498.5 mmol; Tokyo Chemical Industry Co., Ltd) was added dropwise, and the resulting mixture was stirred at 90° C. for 10 hours. The reaction mixture was allowed to cool to room temperature, and concentrated under reduced pressure. Water (800 mL) was added dropwise to the residue at 80° C., and then the resulting mixture was cooled to 0° C. The precipitated solid was obtained by filtration, and then washed with water, and recrystallized from isopropanol (450 mL) and toluene (25 mL) to obtain compound (T-27) (125 g, 321.3 mmol, 64.4%).

Second Step:

Compound (T-27) (15.0 g, 99.2 mmol) obtained in the first step, compound (T-28) (15.0 g, 77.3 mmol), tetrakis(triphenylphosphine)palladium(0) (1.5 g, 1.3 mmol), potassium carbonate (16.0 g, 115.7 mmol), DMF (300 mL), ethanol (200 mL) and water (100 mL) were mixed, and the resulting mixture was stirred at 90° C. for 12 hours. Water (400 mL) was added to the reaction mixture, and the resulting mixture was allowed to cool to room temperature, and then the precipitated solid was washed with water. Toluene (300 mL) was added to the obtained solid, and the resulting mixture was heated under reflux for 1 hour, and then allowed to cool to room temperature. Silica gel (20 g) was added thereto, and the resulting mixture was stirred for 10 minutes. The mixture was filtrated through silica gel (100 g), and the filtrate was concentrated under reduced pressure, and when the mixture was concentrated to about 100 mL, heptane (100 mL) was added thereto. The precipitated solid was washed with heptane to obtain compound (T-29) (15.1 g, 31.2 mmol, 40.4%).

Third Step:

Compound (T-29) (15.1 g, 31.2 mmol) obtained in the second step was dissolved into THF (150 mL), and then 5% palladium/carbon (0.5 g) was added thereto, and the resulting mixture was stirred under a hydrogen atmosphere for 12 hours. The reaction mixture was filtrated, and then the filtrate was concentrated, and then toluene (100 mL) and heptane (300 mL) were added to the residue. The precipitated solid was washed with heptane to obtain compound (T-30) (12.1 g, 30.7 mmol, 98.4%).

Fourth Step:

Compound (T-30) (3.5 g, 9 mmol) obtained in the third step, 2-methyl-2-propenylchloride (0.98 g, 10.8 mmol), potassium carbonate (1.85 g, 13.4 mmol) and DMF (25 mL) were mixed, and the resulting mixture was stirred at 75° C. for 12 hours. To the reaction mixture that was allowed to cool to room temperature, toluene (50 mL) was added, and then filtrated. The filtrate was concentrated under reduced pressure, and the residue was recrystallized from methanol (60 mL) and water (100 mL) to obtain compound (T-27) (125 g, 321.3 mmol, 64.4%).

Fifth Step:

Operation similar to the operation in the fifth step in Example 4 was performed by using compound (T-31) (3.9 g, 8.8 mmol) obtained in the fourth step, concentrated hydrochloric acid (10 mL, 120 mmol), THF (150 mL) and acetone (30 mL) to obtain compound (T-32) (2.9 g, 8.8 mmol, 100%).

Sixth Step:

Operation similar to the operation in the sixth step in Example 4 was performed by using compound (T-32) (2.9 g, 8.8 mmol) obtained in the fifth step, dibutylhydroxytoluene (BHT) (50 mg), methacrylic anhydride (3.33 g, 21.6 mmol), N,N-dimethyl-4-aminopyridine (DMAP) (0.24 g, 1.96 mmol), potassium carbonate (7.45 g, 54.0 mmol), DMF (50 mL) and toluene (100 mL) to obtain compound (1-3-26) (3.3 g, 7.1 mmol, 80.6%).

Melting point: 116.1° C.

$^1$H-NMR (CDCl$_3$; δ ppm): 7.64-7.61 (m, 4H), 7.41 (d, 1H), 7.25-7.15 (m, 6H), 6.38 (d, 2H), 5.79-5.77 (m, 2H), 5.04 (s, 1H), 4.95 (s, 1H), 4.50 (s, 2H), 2.10 (s, 6H), 1.78 (s, 3H).

Example 6

Various kinds of compounds were prepared by using corresponding starting materials according to methods described in Examples 1 to 5, and the products obtained were confirmed to be the objective compounds.

Compound (1-3-25)

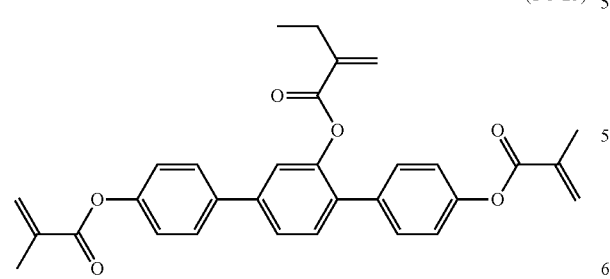

Melting point: 93.04° C.

$^1$H-NMR (CDCl$_3$; δ ppm): 7.64 (d, 2H), 7.56-7.44 (m, 4H), 7.40 (s, 1H), 7.21 (d, 2H), 7.16 (d, 2H), 6.37 (d, 2H), 6.24 (s, 1H), 5.78 (d, 2H), 5.64 (s, 1H), 2.31 (q, 2H), 2.09 (s, 3H), 2.08 (s, 3H), 1.04 (s, 3H).

Compound (1-3-23)

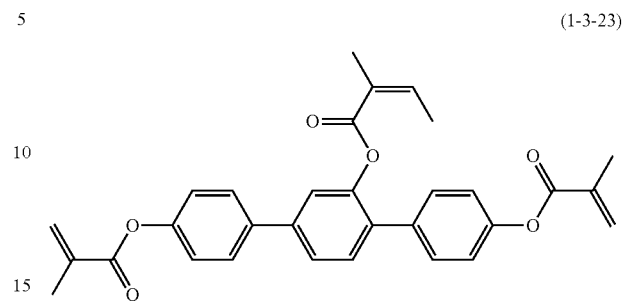

Melting point: 119.47° C.

$^1$H-NMR (CDCl$_3$; δ ppm): 7.63 (d, 2H), 7.53-7.47 (m, 4H), 7.38 (s, 1H), 7.20 (d, 2H), 7.15 (d, 2H), 6.38 (d, 2H), 6.15 (q, 1H), 5.78 (s, 2H), 2.08 (s, 6H), 1.92 (s, 3H), 1.90 (s, 3H).

Compound (1-3-19)

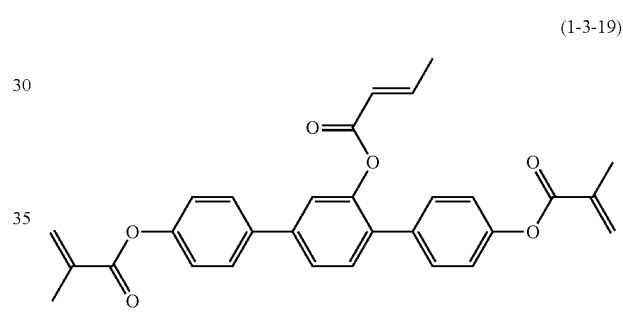

Melting point: 145.80° C.

$^1$H-NMR (CDCl$_3$; δ ppm): 7.63 (d, 2H), 7.53-7.47 (m, 4H), 7.38 (s, 1H), 7.20 (d, 2H), 7.16 (d, 2H), 7.07 (m, 1H), 6.37 (s, 2H), 5.93 (d, 1H), 5.78 (s, 2H), 2.17 (s, 6H), 2.05 (s, 6H), 1.91 (d, 3H).

Compound (1-3-18)

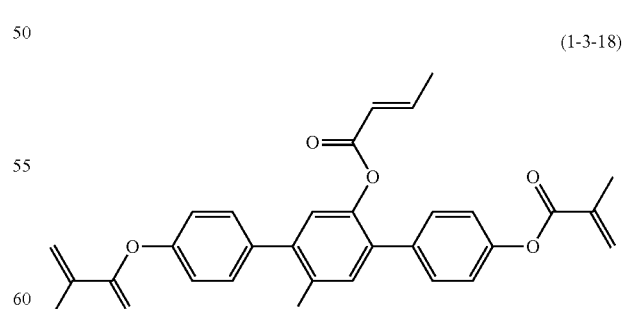

Melting point: 134.23° C.

$^1$H-NMR (CDCl$_3$; δ ppm): 7.63 (dd, 2H), 7.47 (d, 2H), 7.27 (d, 1H), 7.24 (d, 1H), 7.22 (d, 2H), 7.18 (d, 2H), 7.07 (m, 1H), 6.37 (s, 2H), 5.93 (d, 1H), 5.78 (s, 2H), 2.17 (s, 6H), 2.05 (s, 6H), 1.91 (d, 3H).

Compound (1-3-27)

(1-3-27)

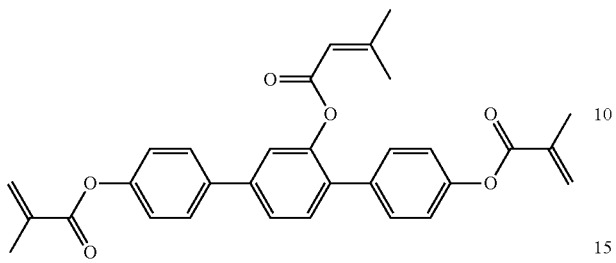

Melting point: 155.76° C.
¹H-NMR (CDCl₃; δ ppm): 7.63 (d, 2H), 7.53-7.47 (m, 4H), 7.36 (s, 1H), 7.20 (d, 2H), 7.17 (d, 2H), 6.37 (d, 2H), 5.80 (s, 1H), 5.77 (s, 2H), 2.24 (s, 3H), 2.21 (d, 6H), 1.98 (s, 3H).

Compound (1-3-28)

(1-3-28)

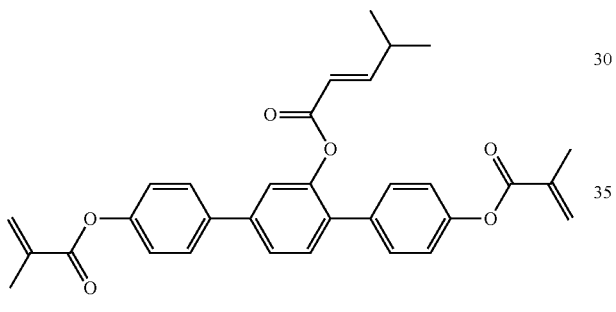

Melting point: 115.11° C.
¹H-NMR (CDCl₃; δ ppm): 7.63 (d, 2H), 7.53-7.47 (m, 4H), 7.36 (s, 1H), 7.20 (d, 2H), 7.17 (d, 2H), 7.03 (dd, 1H), 6.37 (d, 2H), 5.86 (d, 1H), 5.77 (s, 2H), 2.51 (q, 1H), 2.08 (d, 6H), 1.08 (d, 6H).

Compound (1-3-61)

(1-3-61)

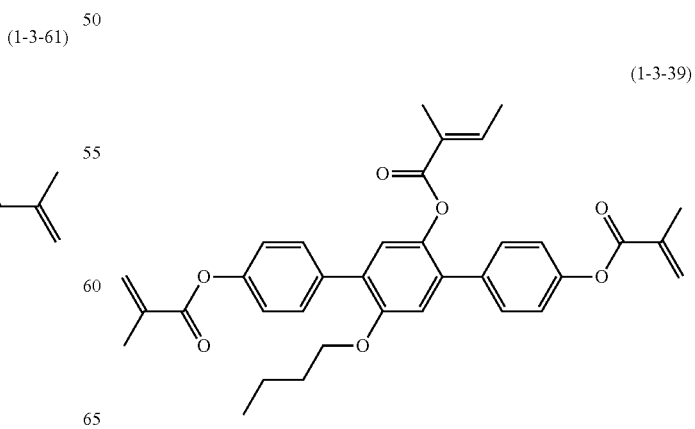

Melting point: 188.64° C.

¹H-NMR (CDCl₃; δ ppm): 7.48 (d, 4H), 7.25 (d, 2H), 7.15 (d, 4H), 6.95 (q, 2H), 6.36 (s, 2H), 5.77 (s, 2H), 2.06 (s, 6H), 1.81 (d, 12H).

Compound (1-3-29)

(1-3-29)

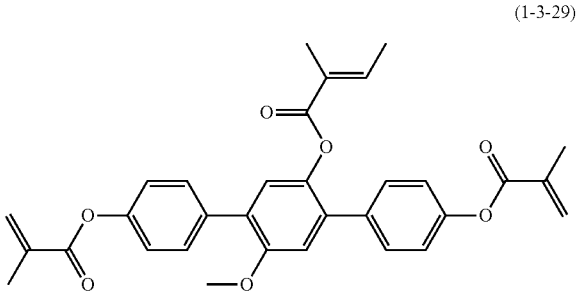 [SMILES: C=C(C)C(=O)Oc1ccc(-c2cc(OC(=O)/C(C)=C/C)c(-c3ccc(OC(=O)C(=C)C)cc3)cc2OC)cc1]

Melting point: 115.17° C.
¹H-NMR (CDCl₃; δ ppm): 7.63 (d, 2H), 7.50 (d, 2H), 7.16 (d, 4H), 7.05 (s, 1H), 6.98 (s, 1H), 6.93 (q, 1H), 6.37 (s, 2H), 5.77 (d, 2H), 3.84 (s, 3H), 2.08 (s, 6H), 1.81 (m, 6H).

Compound (1-3-30)

(1-3-30)

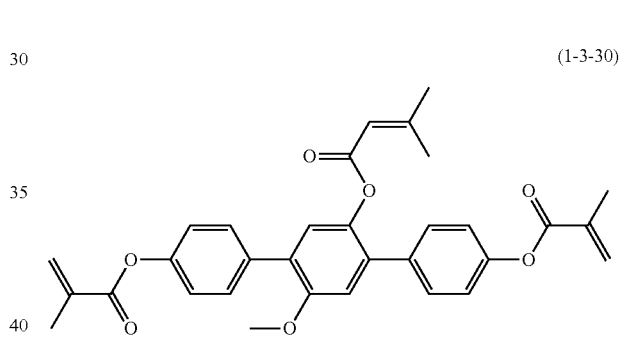

Melting point: 176.22° C.
¹H-NMR (CDCl₃; δ ppm): 7.63 (d, 2H), 7.50 (d, 2H), 7.16 (d, 4H), 7.05 (s, 1H), 6.98 (s, 1H), 6.93 (q, 1H), 6.37 (s, 2H), 5.78 (d, 3H), 3.83 (s, 3H), 2.10 (s, 3H), 2.08 (s, 6H), 1.91 (s, 3H).

Compound (1-3-39)

(1-3-39)

Melting point: 124.28° C.

¹H-NMR (CDCl₃; δ ppm): 7.62 (d, 2H), 7.48 (d, 2H), 7.16 (d, 4H), 7.13 (s, 1H), 6.97 (s, 1H), 6.93 (q, 1H), 6.37 (s, 2H), 5.77 (s, 2H), 3.98 (t, 2H), 2.08 (s, 6H), 1.82 (s, 3H), 1.80 (d, 3H), 1.72 (m, 2H), 1.42 (m, 2H), 0.92 (t, 3H).

Compound (1-3-40)

¹H-NMR (CDCl₃; δ ppm): 7.63 (d, 2H), 7.53-7.47 (m, 4H), 7.38 (s, 1H), 7.20 (d, 3H), 7.16 (d, 3H), 7.06 (m, 1H), 6.08 (d, 2H), 5.93 (d, 1H), 1.99 (d, 6H), 1.91 (d, 3H).

Compound (1-3-173)

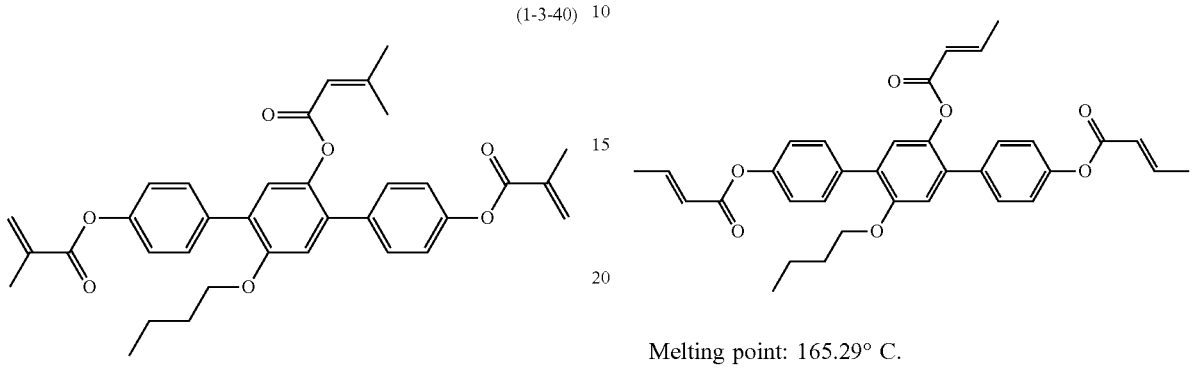

(1-3-40)

(1-3-173)

Melting point: 102.71° C.
¹H-NMR (CDCl₃; δ ppm): 7.62 (d, 2H), 7.49 (d, 2H), 7.17 (d, 2H), 7.16 (d, 2H), 7.12 (s, 1H), 6.97 (s, 1H), 6.37 (s, 2H), 5.77 (s, 3H), 3.98 (t, 2H), 2.10 (s, 3H), 2.08 (s, 6H), 1.91 (s, 3H), 1.72 (m, 2H), 1.42 (m, 2H), 0.92 (t, 3H).

Compound (1-3-169)

Melting point: 165.29° C.
¹H-NMR (CDCl₃; δ ppm): 7.63 (d, 2H), 7.47 (d, 2H), 7.22 (m, 3H), 7.16 (m, 4H), 7.03 (m, 1H), 6.96 (s, 1H), 6.07 (d, 2H), 5.90 (d, 1H), 3.96 (t, 2H), 1.98 (d, 6H), 1.90 (d, 3H), 1.72 (m, 2H), 1.43 (m, 2H), 0.92 (t, 3H).

Compound (1-3-170)

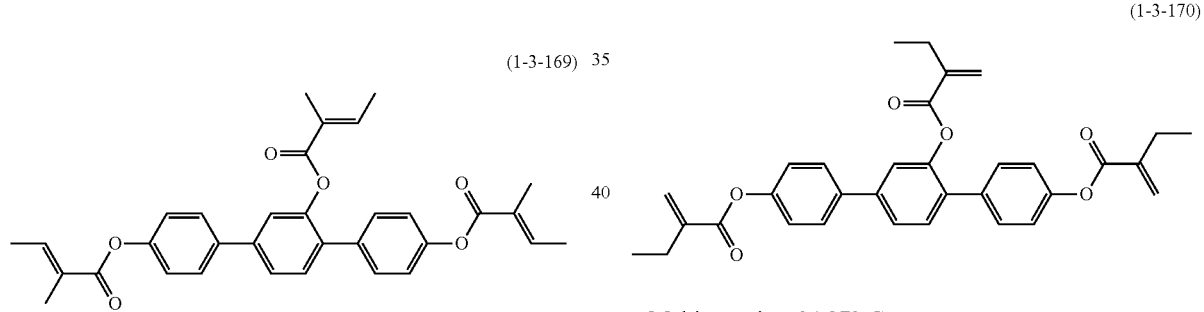

(1-3-169)

(1-3-170)

Melting point: 114.70° C.
¹H-NMR (CDCl₃; δ ppm): 7.63 (d, 2H), 7.53-7.47 (m, 4H), 7.37 (s, 1H), 7.18 (d, 2H), 7.14 (d, 4H), 6.96 (q, 1H), 1.97 (s, 6H), 1.90 (d, 6H), and 1.83 (m, 6H).

Compound (1-3-172)

Melting point: 94.27° C.
¹H-NMR (CDCl₃; δ ppm): 7.64 (d, 2H), 7.56-7.44 (m, 4H), 7.40 (s, 1H), 7.21 (d, 2H), 7.16 (d, 2H), 6.40 (d, 2H), 6.24 (s, 1H), 5.75 (d, 2H), 5.64 (s, 1H), 2.47 (m, 4H), 2.31 (q, 2H), 1.18 (s, 6H), 1.04 (t, 3H).

Compound (1-3-174)

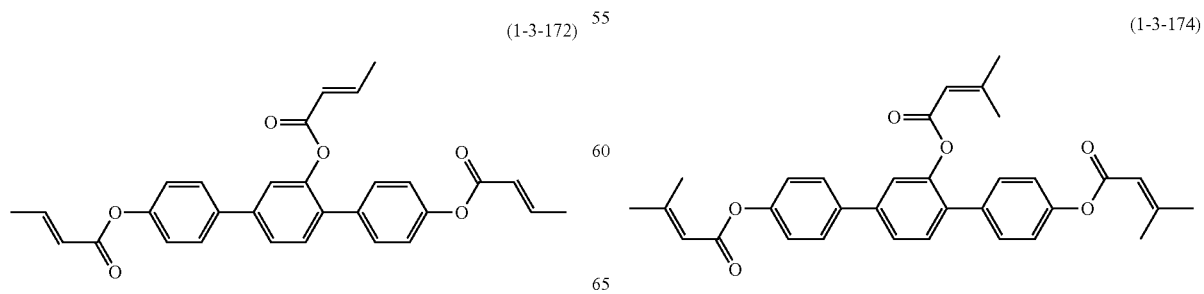

(1-3-172)

(1-3-174)

Melting point: 124.23° C.

Melting point: 161.38° C.

¹H-NMR (CDCl₃; δ ppm): 7.63 (d, 2H), 7.53-7.47 (m, 4H), 7.35 (s, 1H), 7.18 (d, 2H), 7.14 (d, 2H), 5.94 (s, 2H), 5.80 (s, 1H), 2.25 (s, 6H), 2.11 (s, 3H), 2.00 (s, 6H), 1.92 (s, 3H).

Compound (1-3-175)

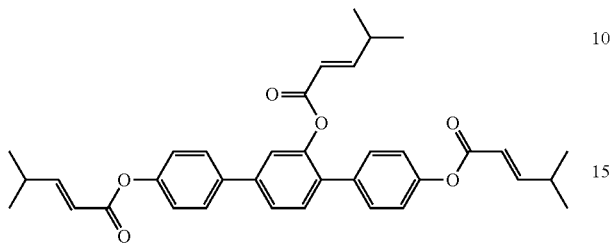
(1-3-175)

Melting point: 141.55° C.

¹H-NMR (CDCl₃; δ ppm): 7.63 (d, 2H), 7.53-7.47 (m, 4H), 7.38 (s, 1H), 7.20 (d, 2H), 7.17 (d, 2H), 7.04 (dd, 1H), 6.01 (d, 2H), 5.85 (d, 1H), 2.56 (m, 2H), 2.47 (m, 1H), 1.14 (d, 12H), 1.08 (d, 6H).

Compound (1-3-171)

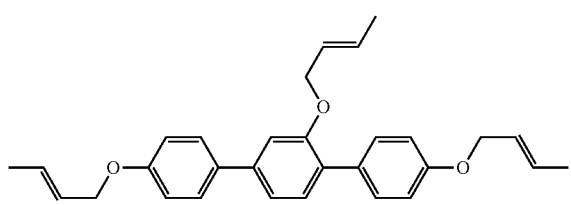
(1-3-171)

Melting point: 93.77° C.

¹H-NMR (CDCl₃; δ ppm): 7.53 (m, 4H), 7.36 (d, 1H), 7.19 (d, 1H), 7.13 (s, 1H), 6.97 (m, 4H), 5.94-5.62 (m, 6H), 4.51 (s, 6H), 1.78 (d, 6H), 1.72 (d, 3H).

Compound (1-4-11)

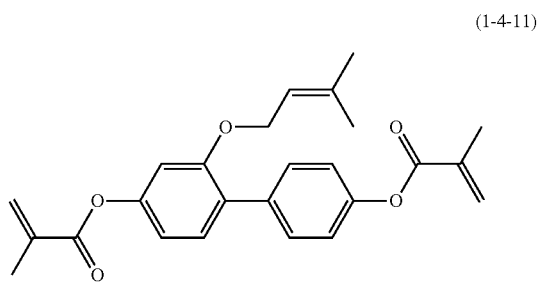 [SMILES: C=C(C)C(=O)Oc1ccc(-c2ccc(OC(=O)C(=C)C)cc2OCC=C(C)C)cc1]
(1-4-11)

Melting point: 103.41° C.

¹H-NMR (CDCl₃; δ ppm): 7.54 (d, 2H), 7.32 (d, 1H), 7.16 (d, 2H), 6.79 (d, 1H), 6.76 (d, 1H), 6.37 (td, 2H), 5.77 (td, 2H), 5.39 (tt, 1H), 4.50 (d, 2H), 2.08 (m, 6H), 1.74 (s, 3H), 1.67 (s, 3H).

With referring to experimental operation described in Examples 1 to 6 and "2. Synthetic method," compounds (1-2-1) to compound (1-2-49), compounds (1-3-1) to compound (1-3-182), compounds (1-4-1) to compound (1-4-37) and compounds (1-7-1) to compound (1-7-14) as shown below can be prepared.

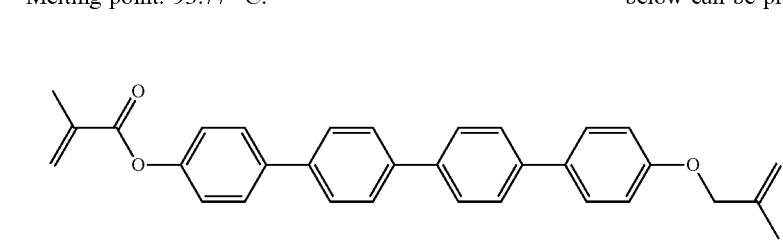
(1-2-1)

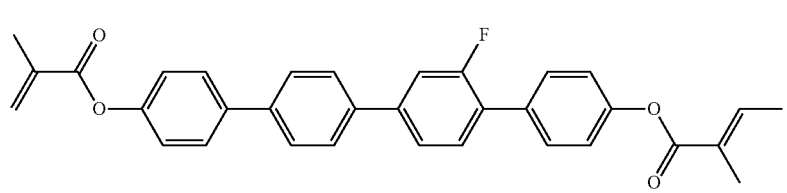
(1-2-2)

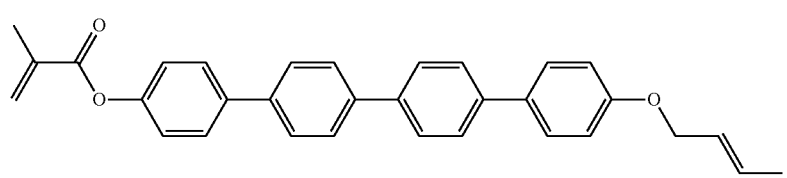
(1-2-3)

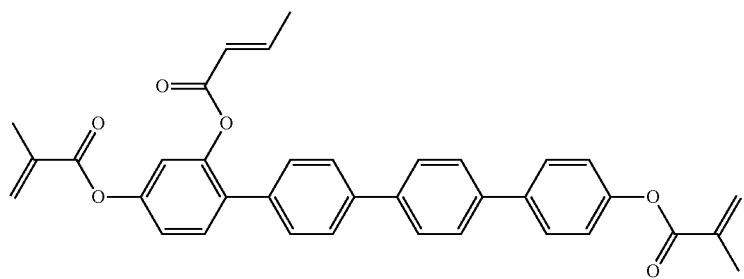
(1-2-4)
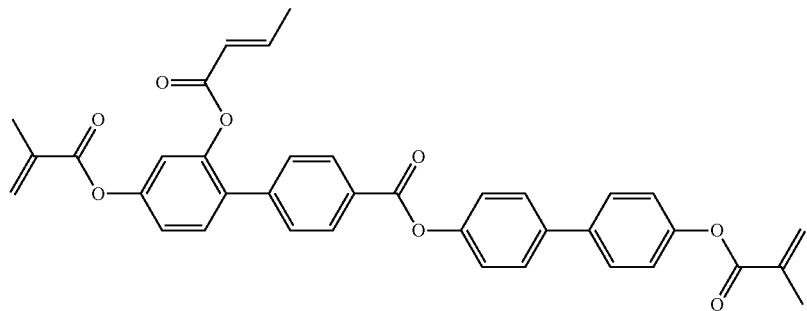
(1-2-5)
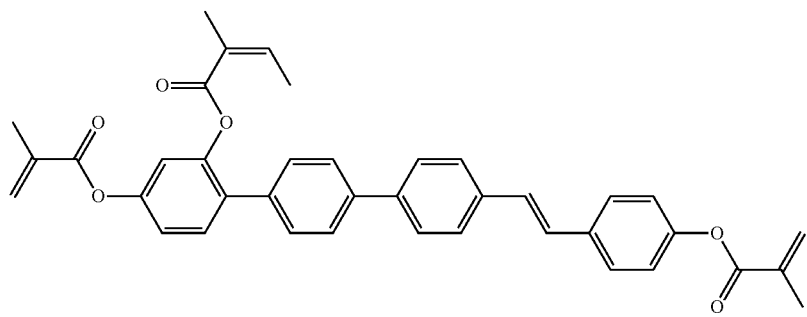
(1-2-6)
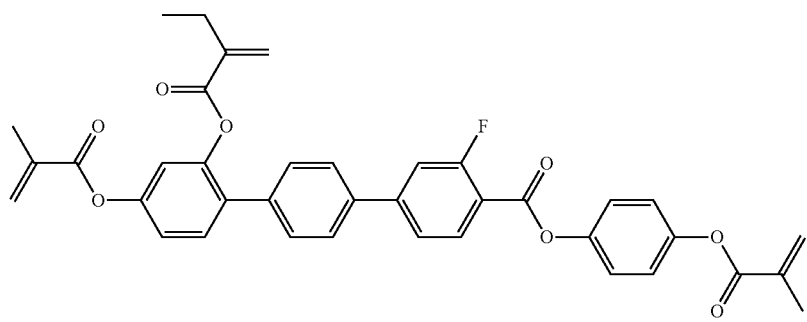
(1-2-7)
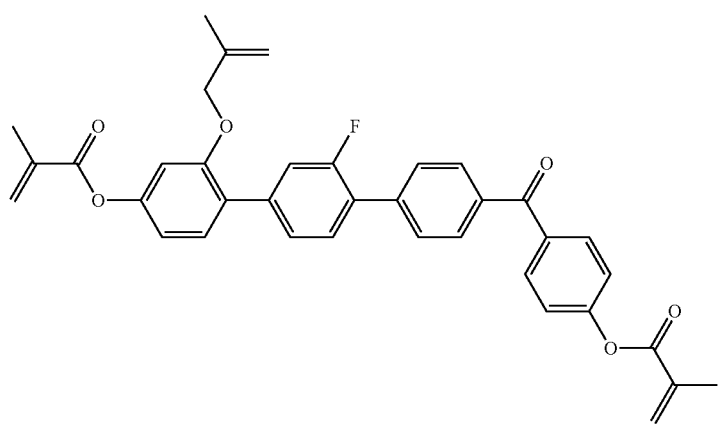
(1-2-10)

-continued
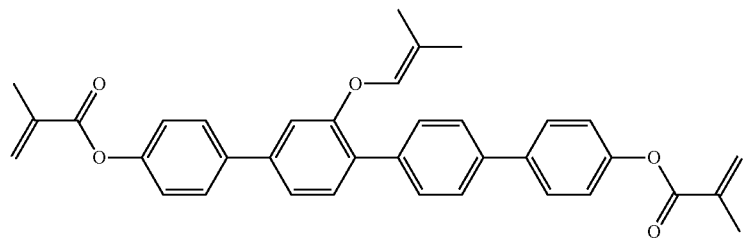
(1-2-11)
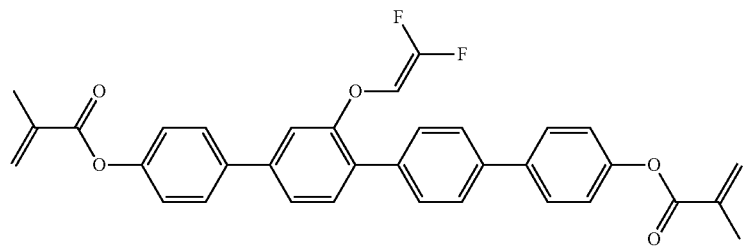
(1-2-12)
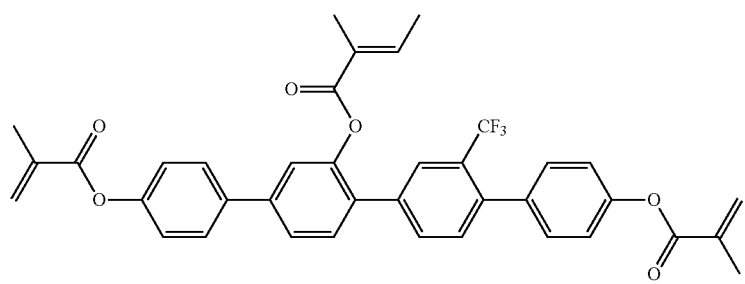
(1-2-13)
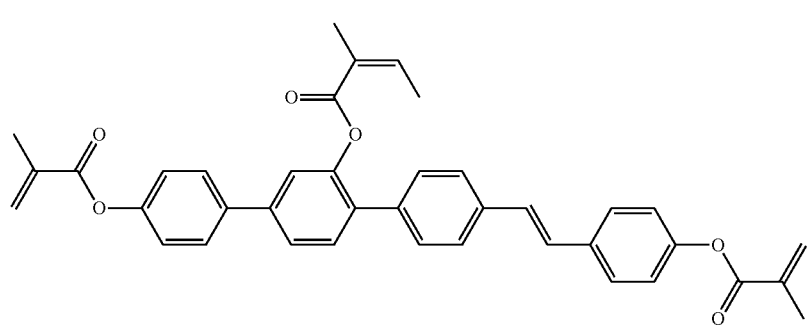
(1-2-14)
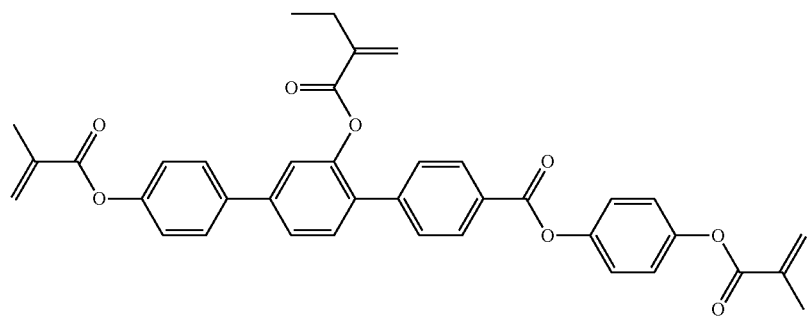
(1-2-15)

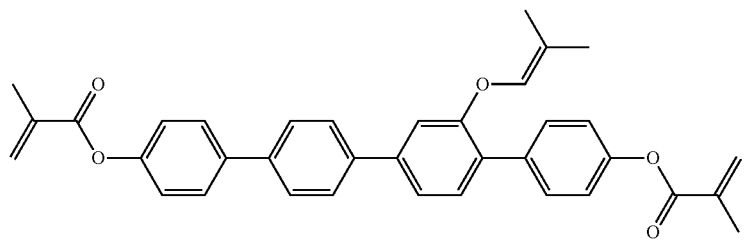
(1-2-16)
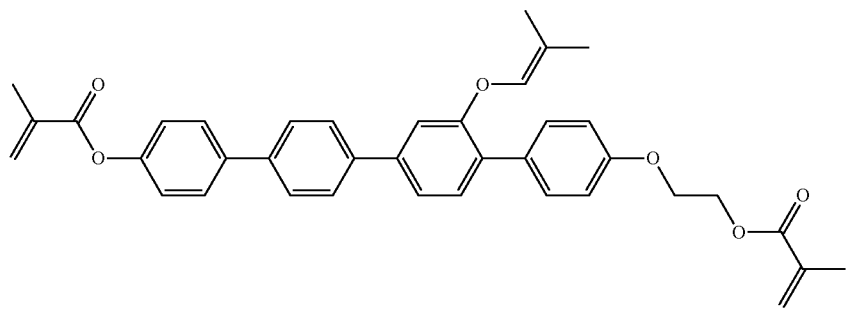
(1-2-17)
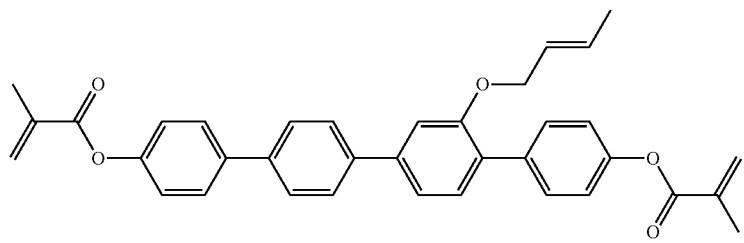
(1-2-18)
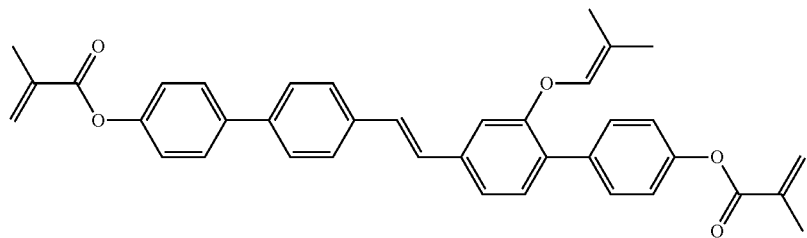
(1-2-19)
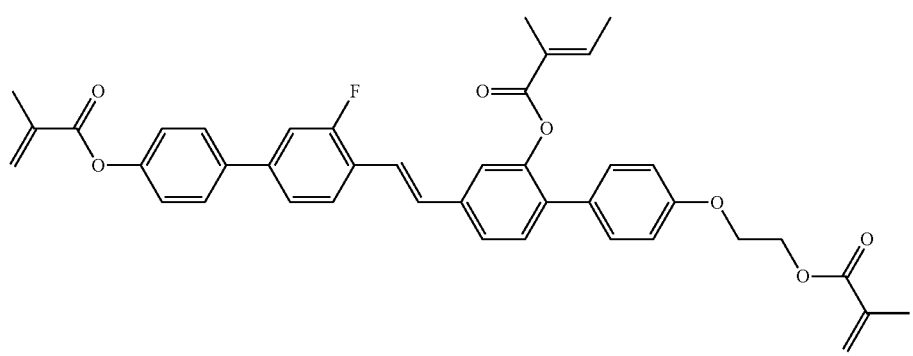
(1-2-20)

(1-2-21)
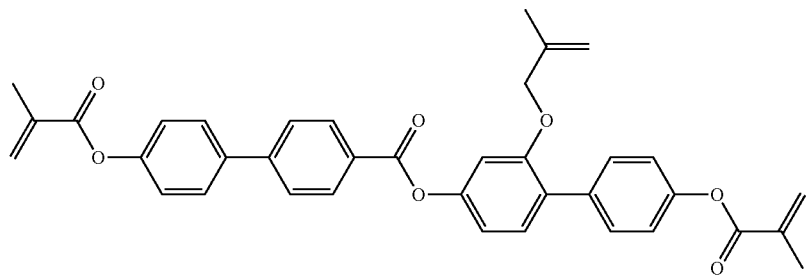
(1-2-22)
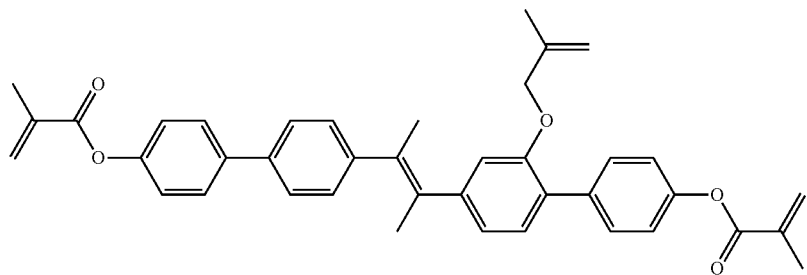
(1-2-23)
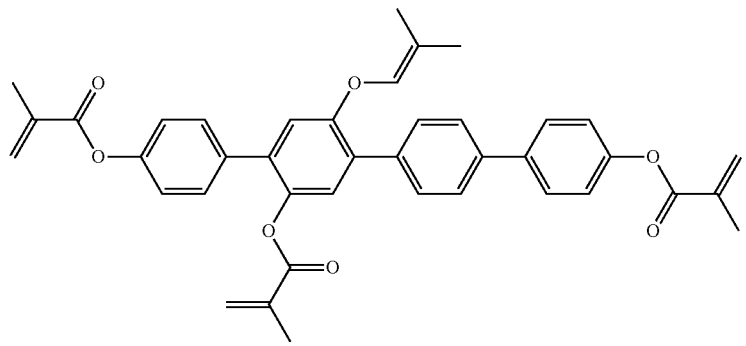
(1-2-24)
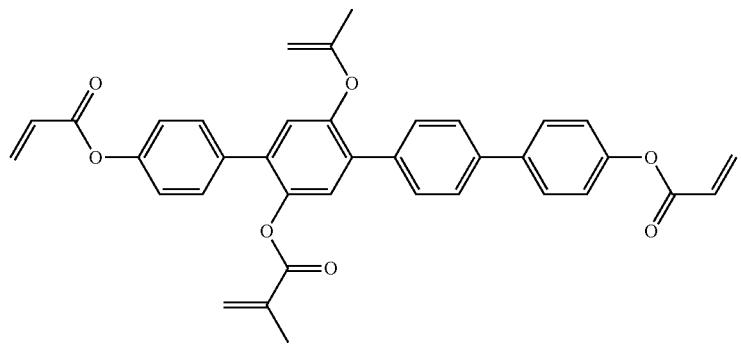
(1-2-25)
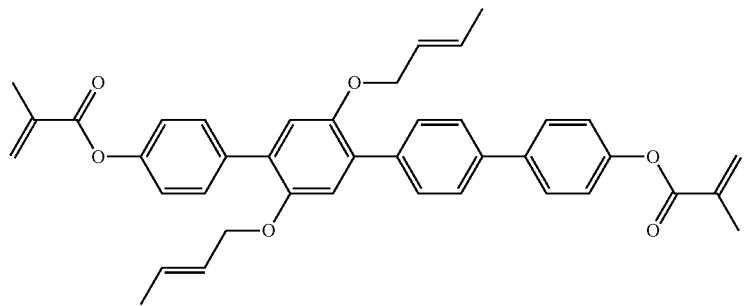

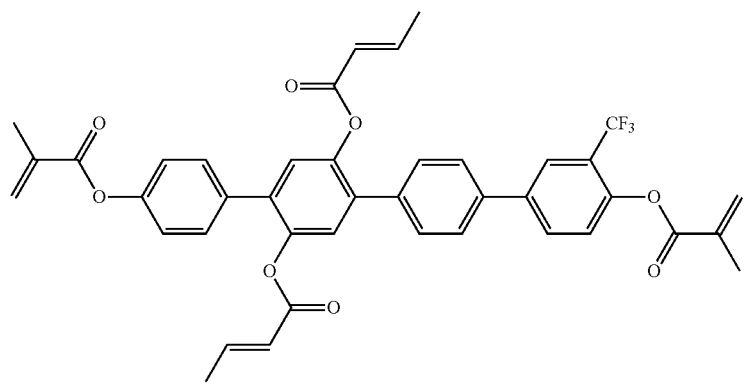
(1-2-26)
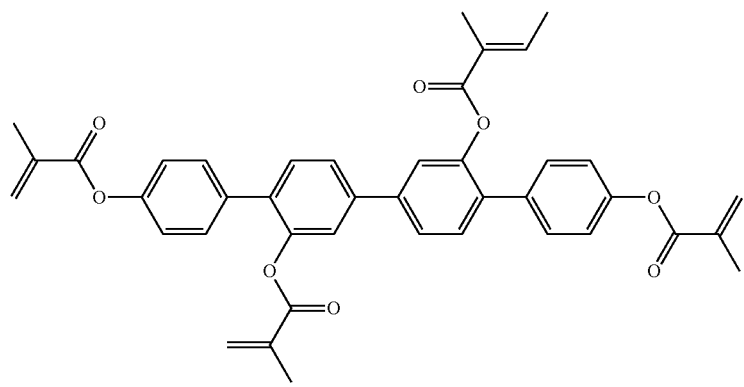
(1-2-27)
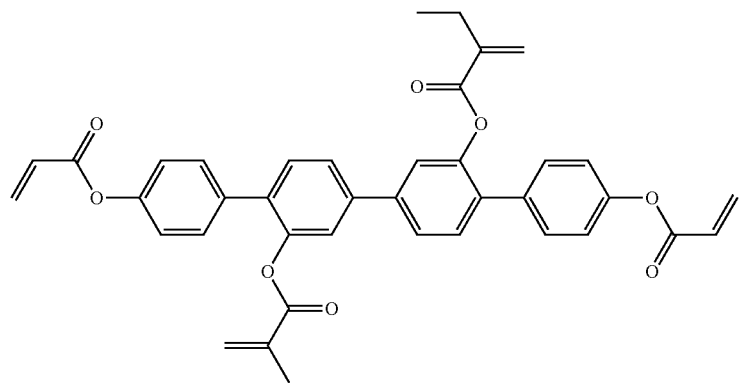
(1-2-28)
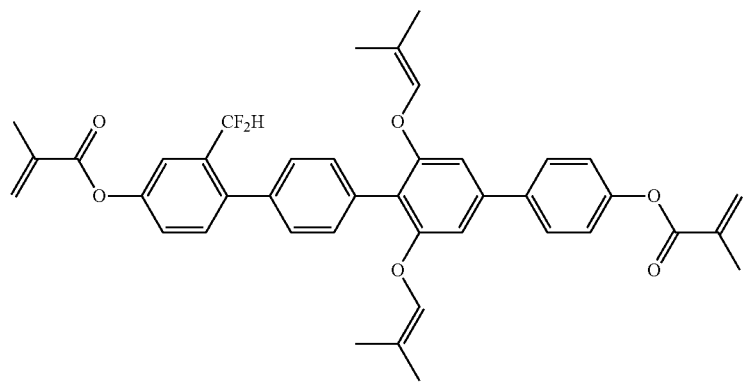
(1-2-29)

(1-2-30)
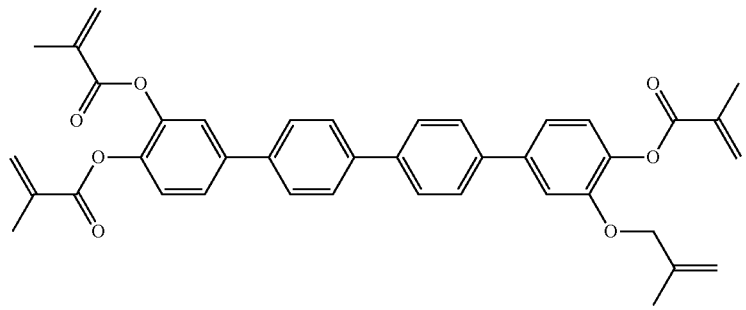
(1-2-31)
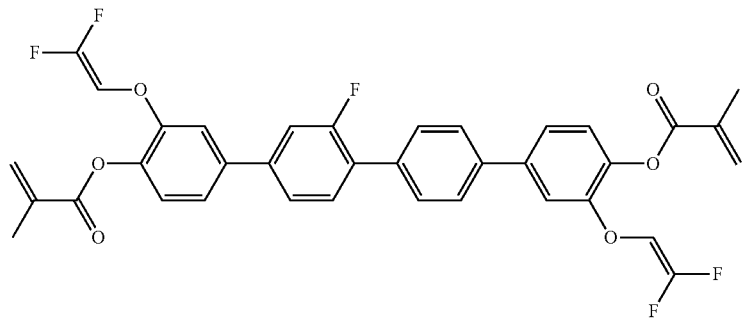
(1-2-32)
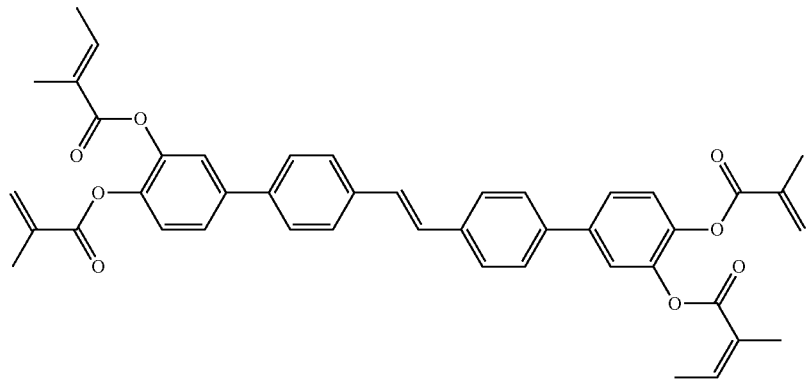
(1-2-33)
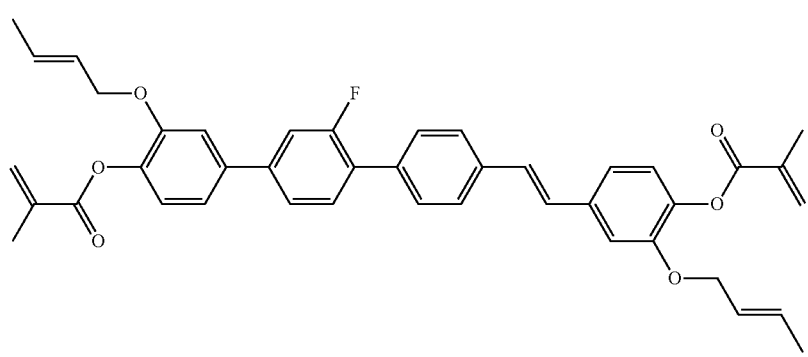

(1-2-34)
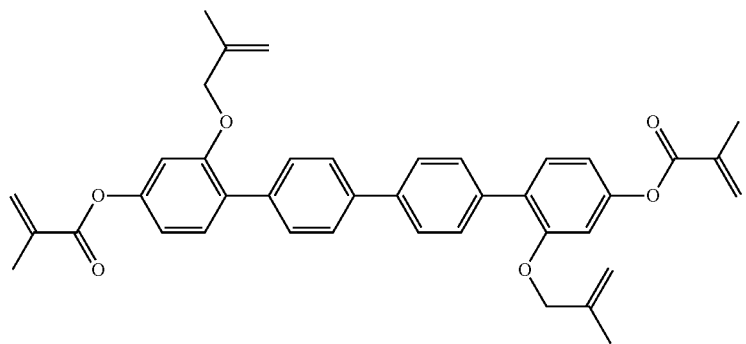
(1-2-35)
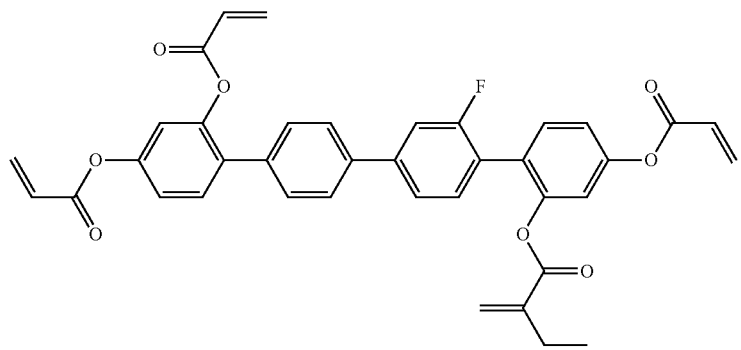
(1-2-36)
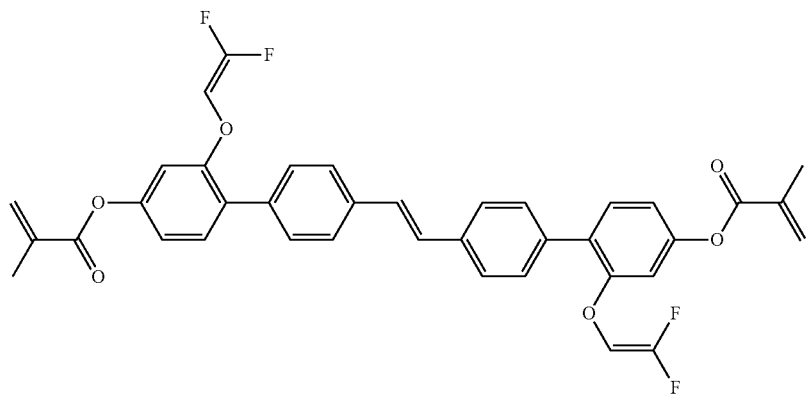
(1-2-37)
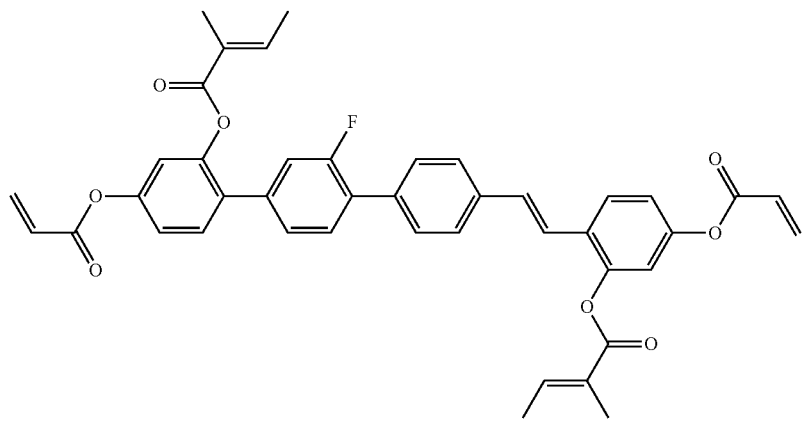

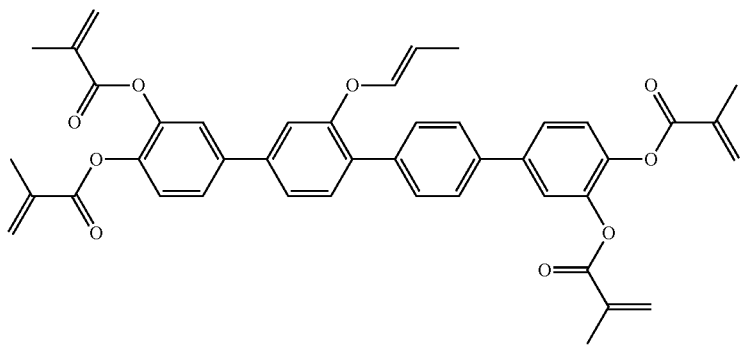
(1-2-38)
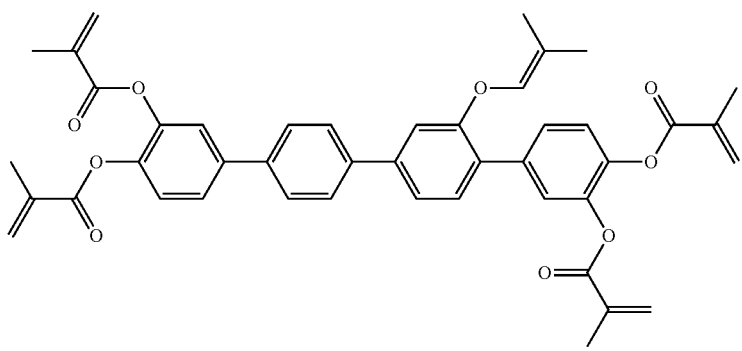
(1-2-39)
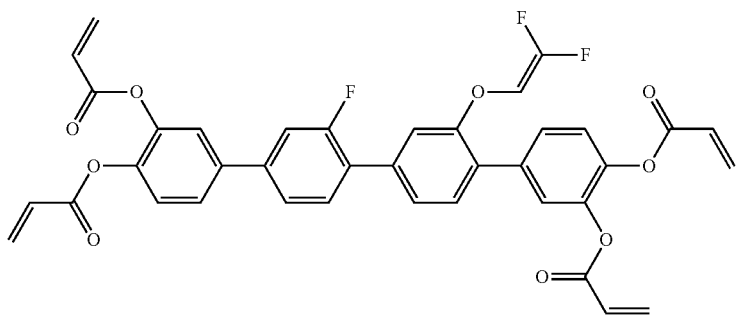
(1-2-40)
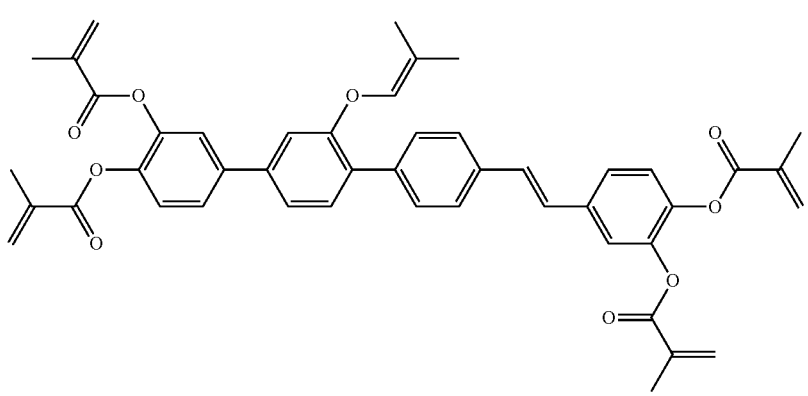
(1-2-41)

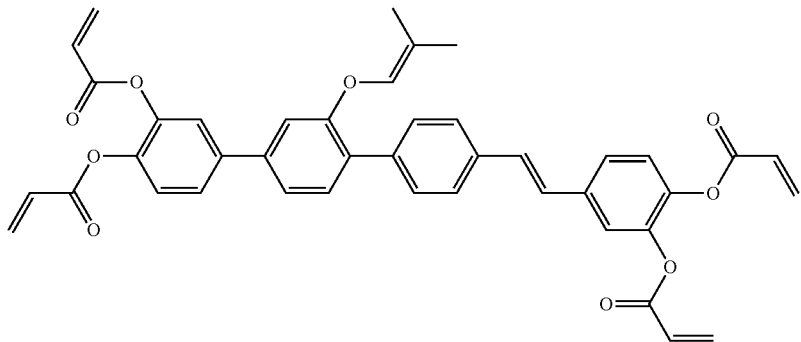
(1-2-41)
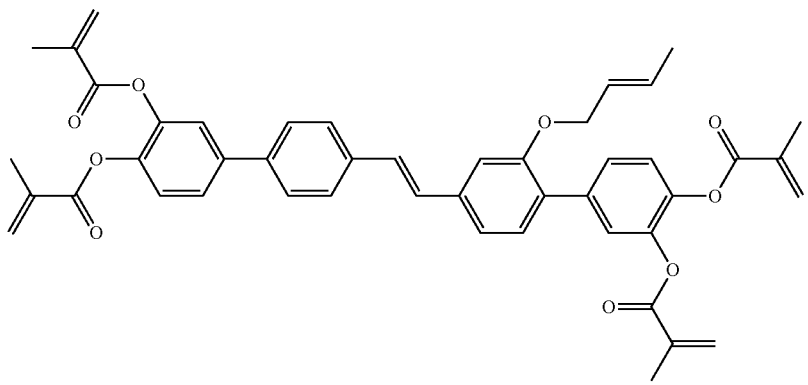
(1-2-42)
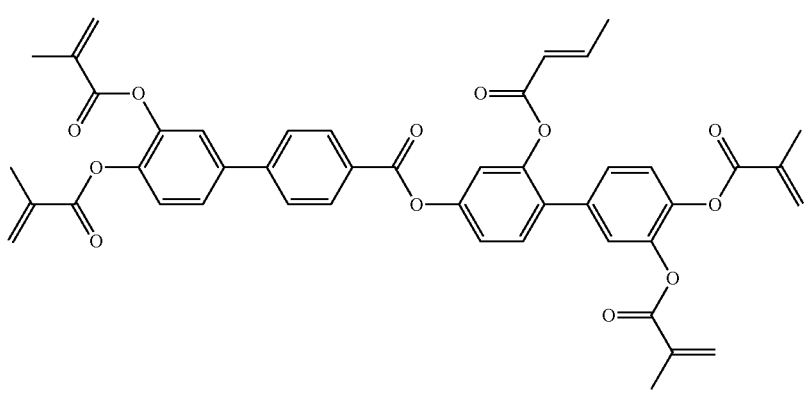
(1-2-43)
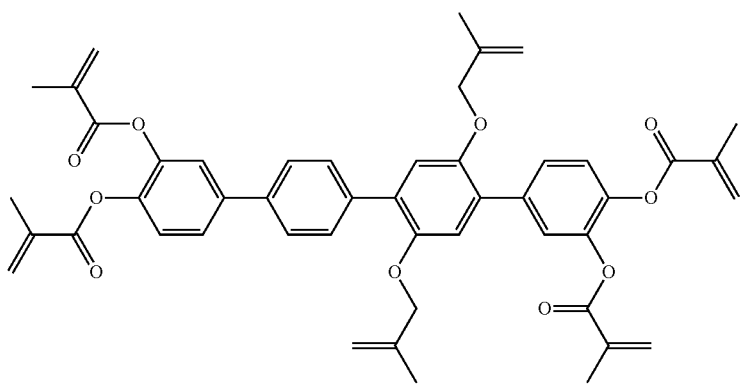
(1-2-44)

(1-2-45)
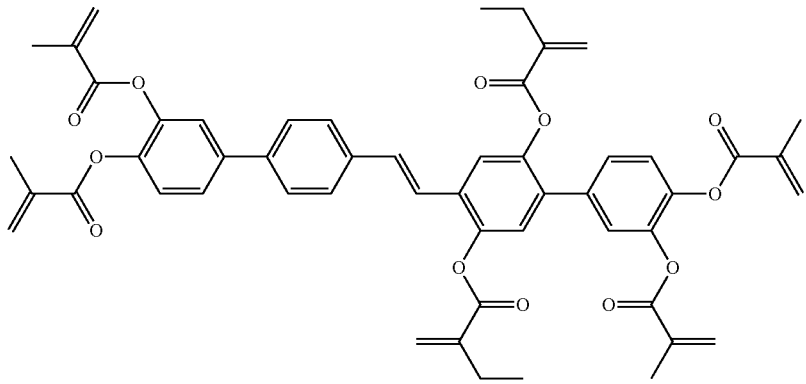
(1-2-46)
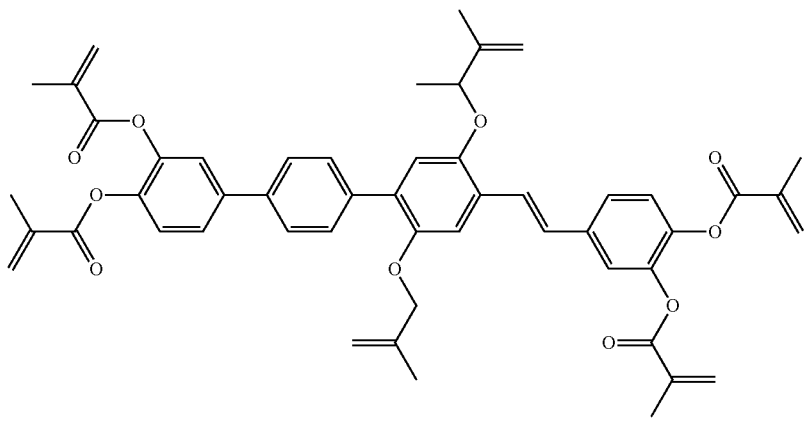
(1-2-47)
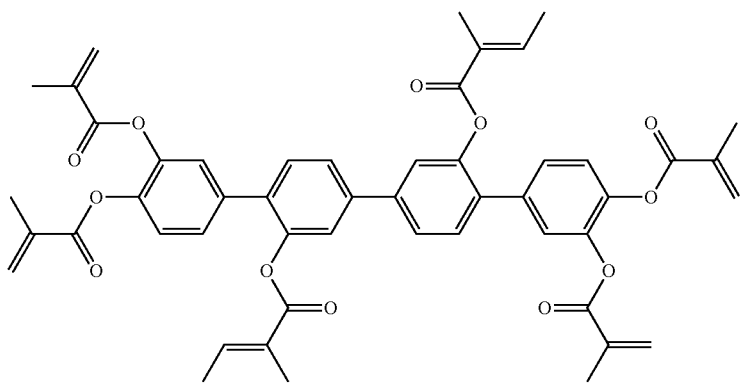
(1-2-48)
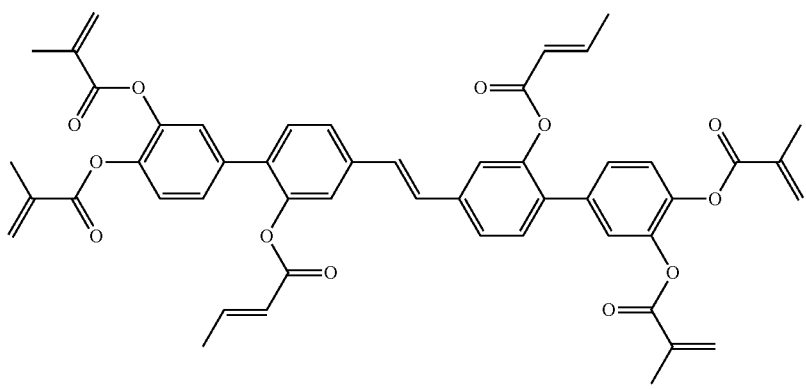

(1-2-49)
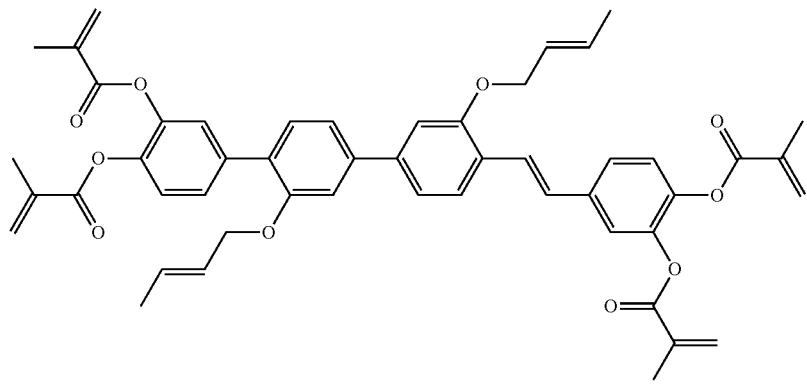
(1-3-1)
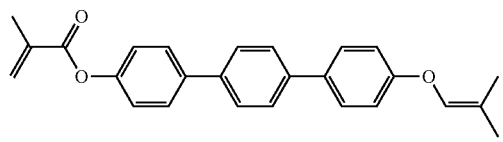
(1-3-2)
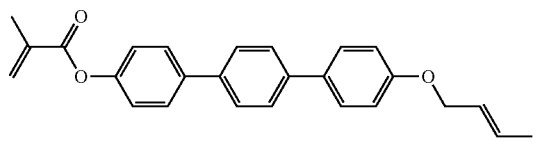
(1-3-3)
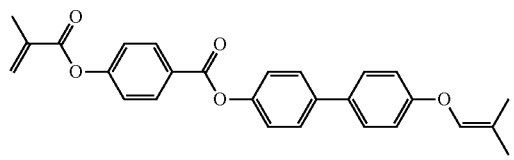
(1-3-4)
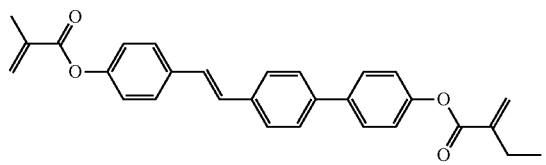
(1-3-5)
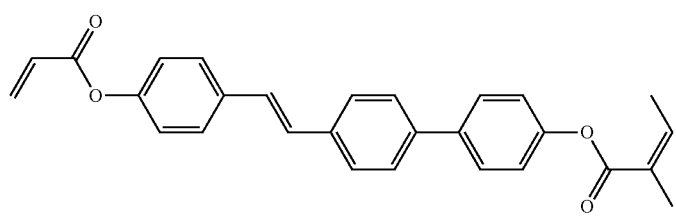
(1-3-6)
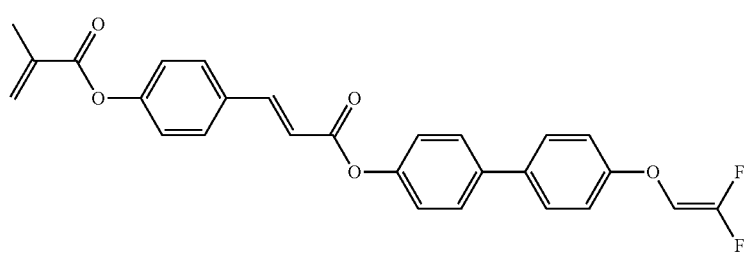
(1-3-7)
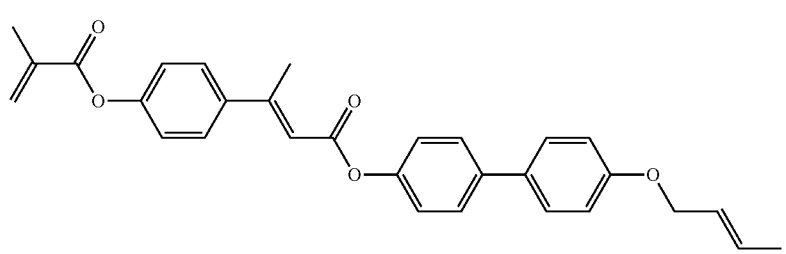

(1-3-8)
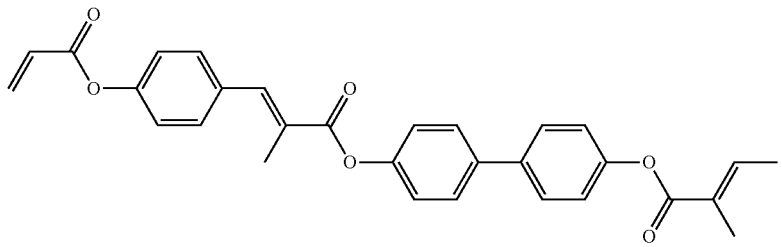
(1-3-9)
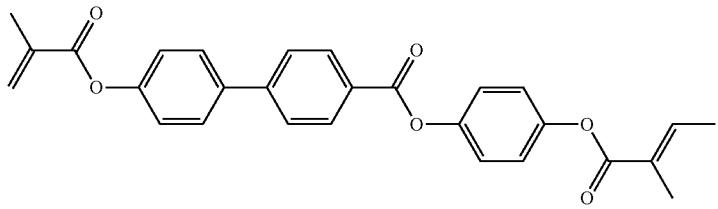
(1-3-10)
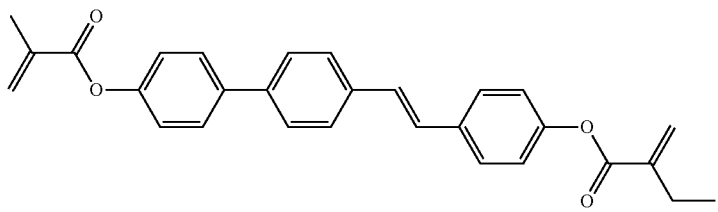
(1-3-11)
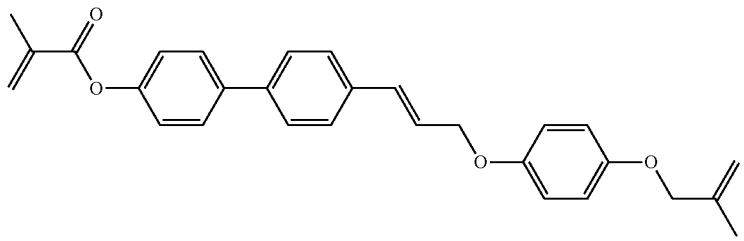
(1-3-12)
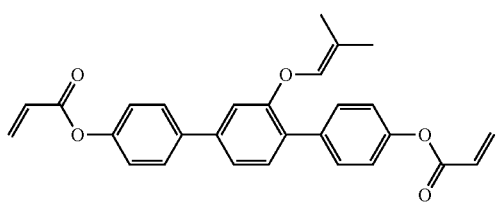
(1-3-13)
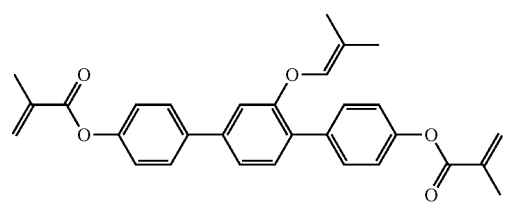
(1-3-14)
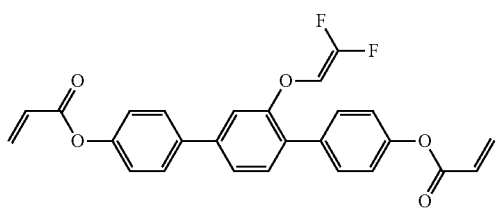
(1-3-15)
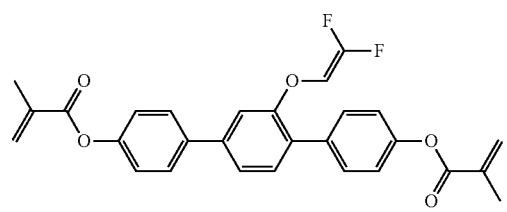
(1-3-16)
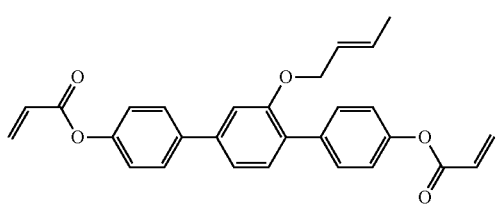
(1-3-17)
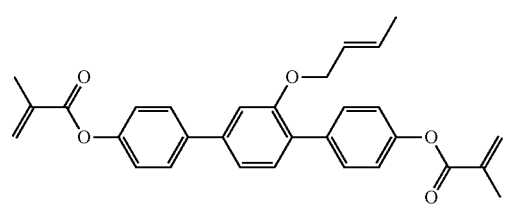

-continued
(1-3-18)
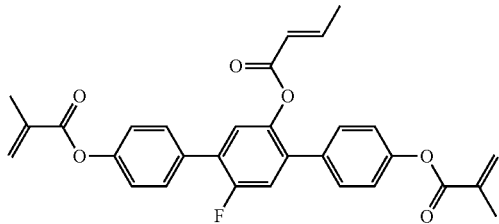
(1-3-19)
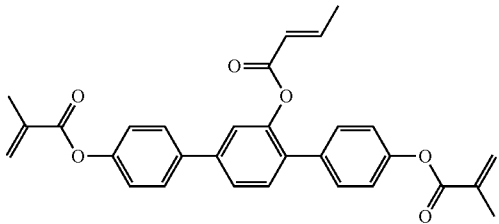
(1-3-20)
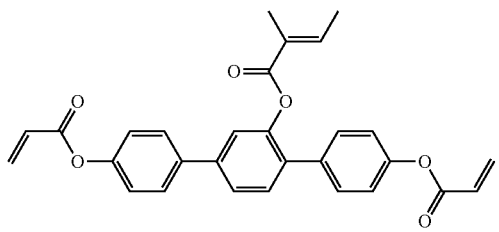
(1-3-21)
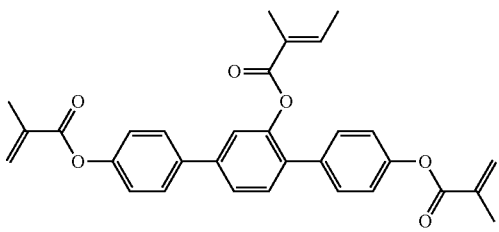
(1-3-22)
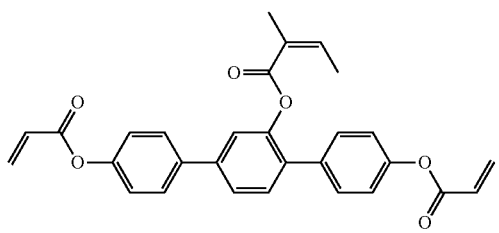
(1-3-23)
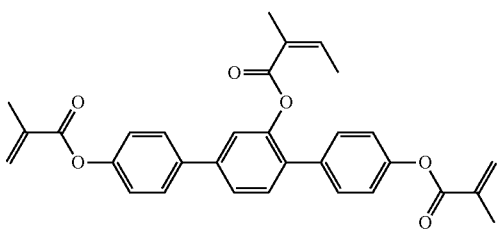
(1-3-24)
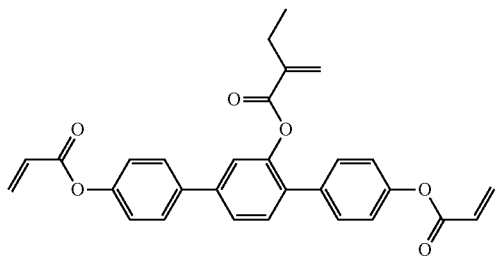
(1-3-25)
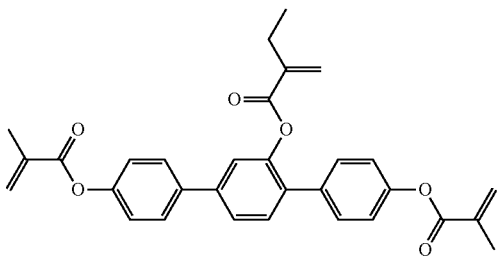
(1-3-26)
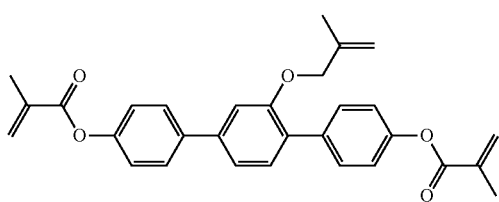
(1-3-27)
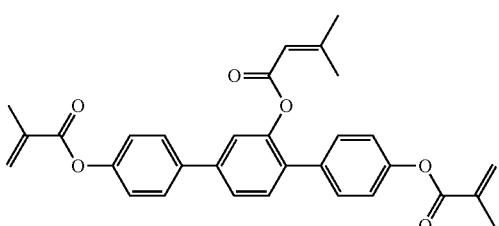
(1-3-28)
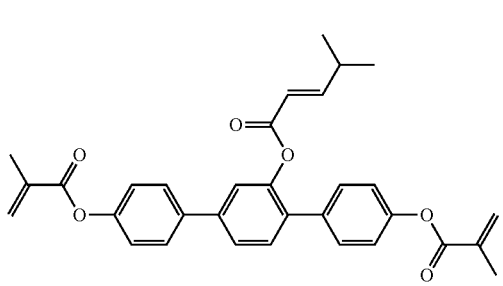
(1-3-29)
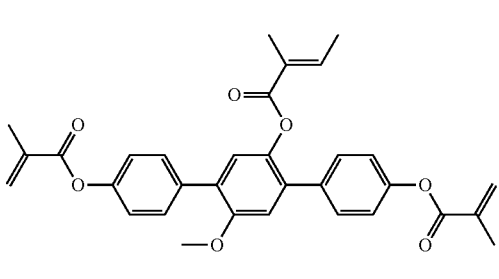

-continued
(1-3-30)
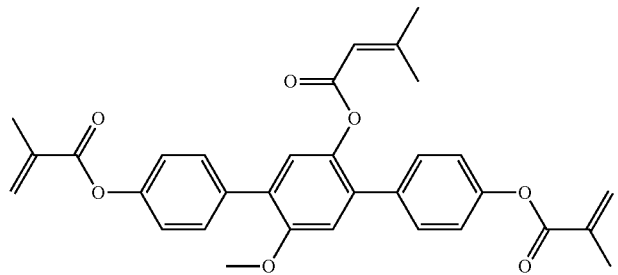
(1-3-31)
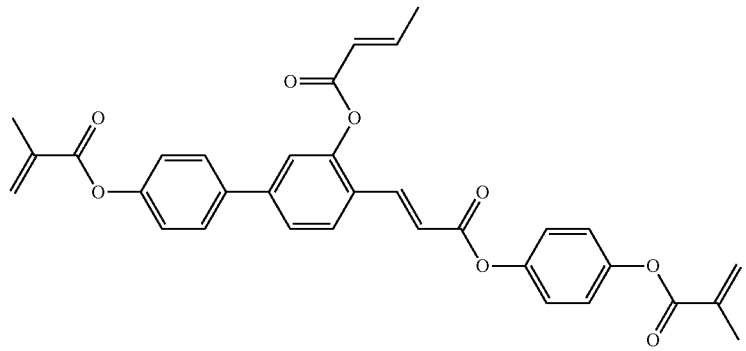
(1-3-32)
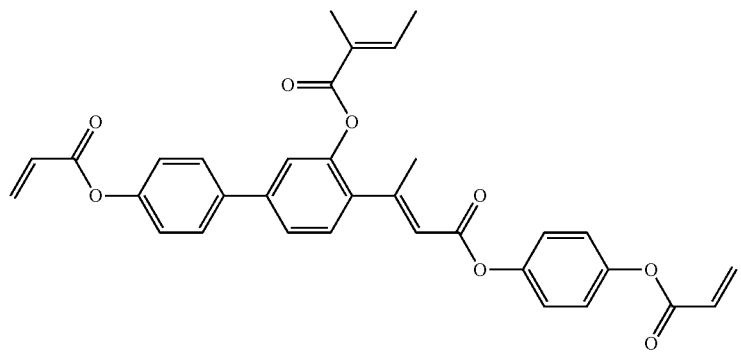
(1-3-33)
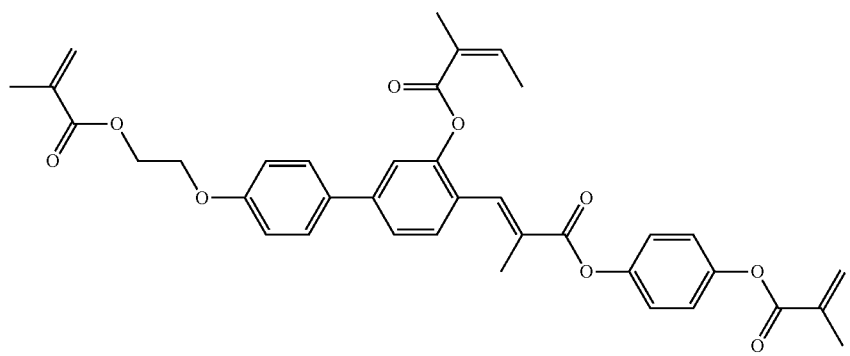
(1-3-34)
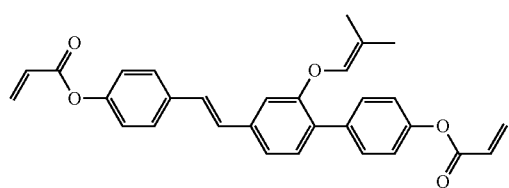
(1-3-35)
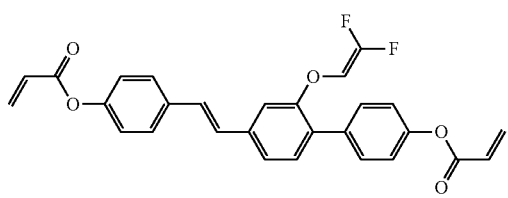

-continued
(1-3-36)
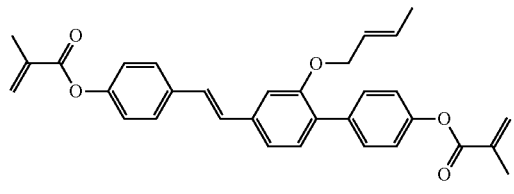
(1-3-37)
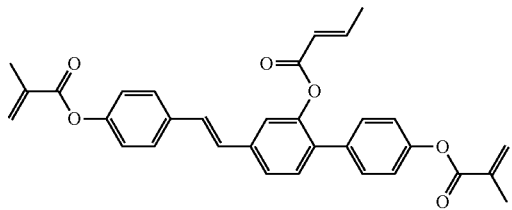
(1-3-38)
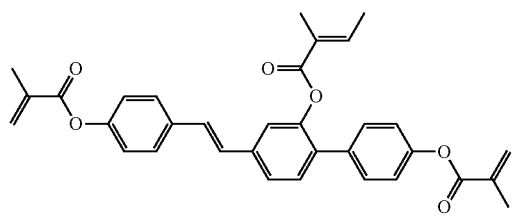
(1-3-39)
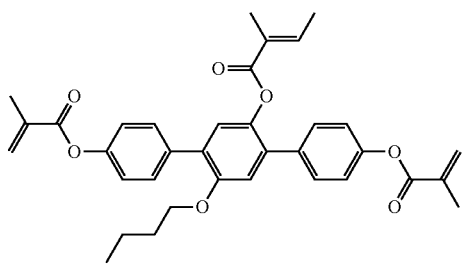
(1-3-40)
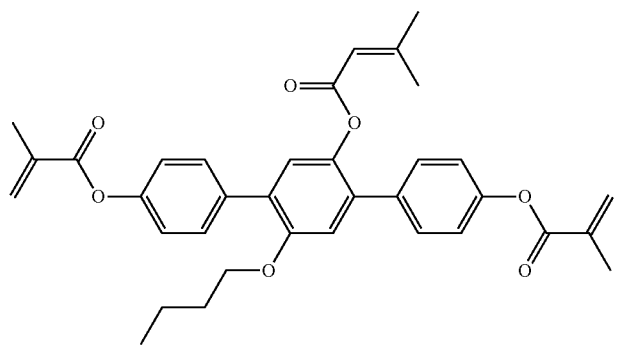
(1-3-41)
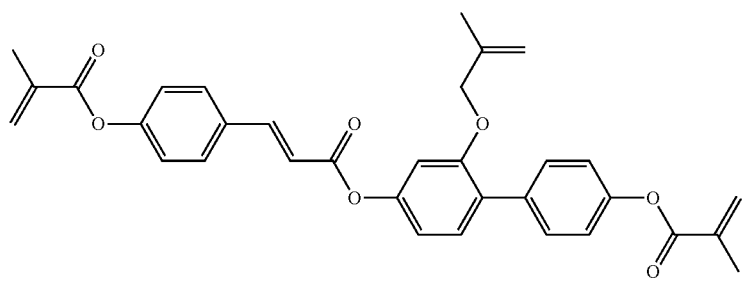
(1-3-42)
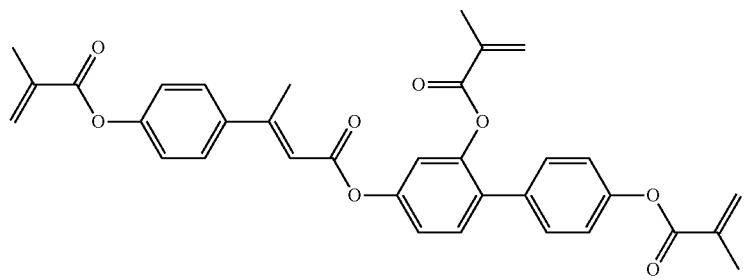

-continued
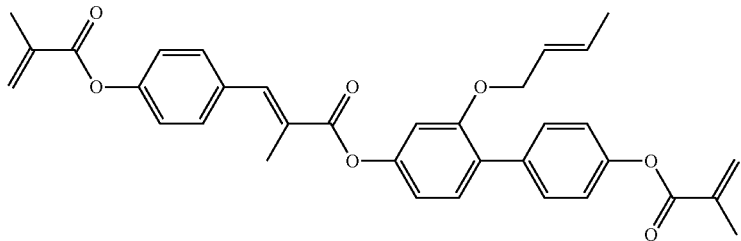
(1-3-43)
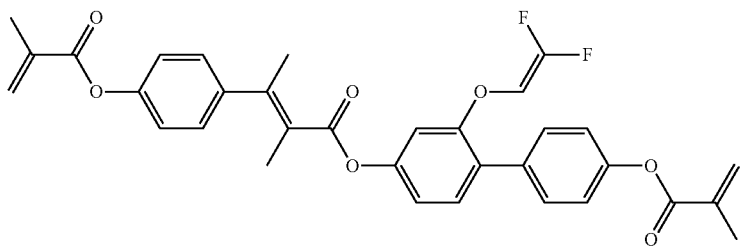
(1-3-44)
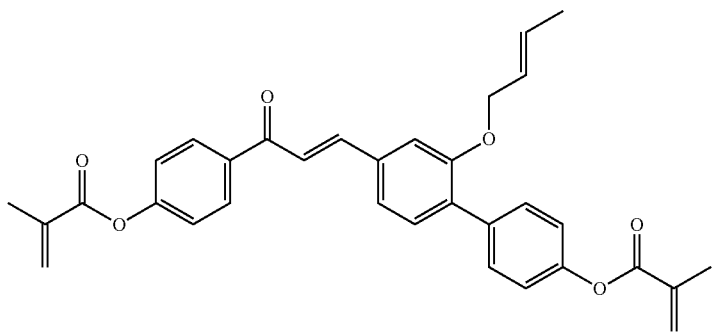
(1-3-45)
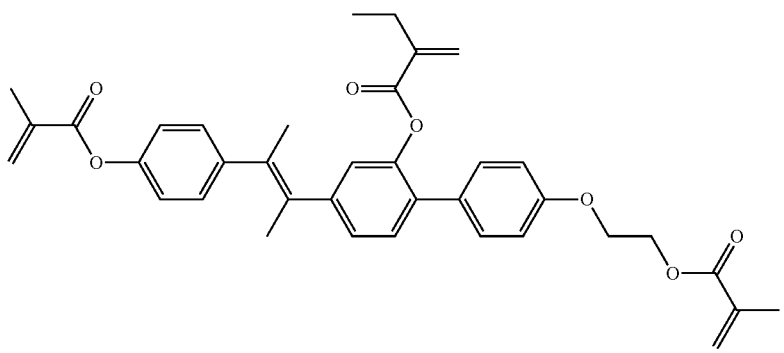
(1-3-46)
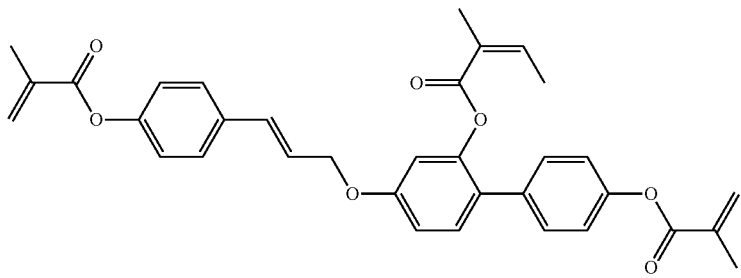
(1-3-47)

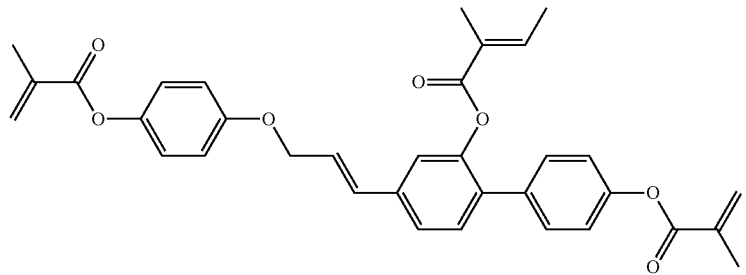
(1-3-48)
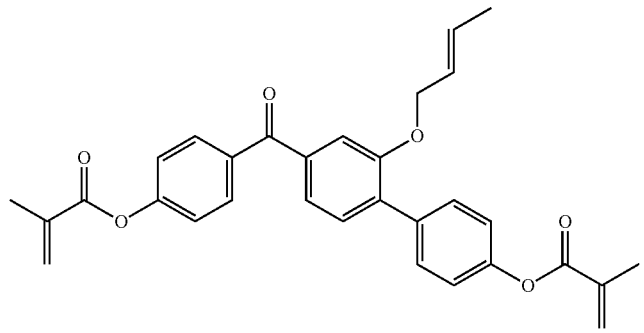
(1-3-49)
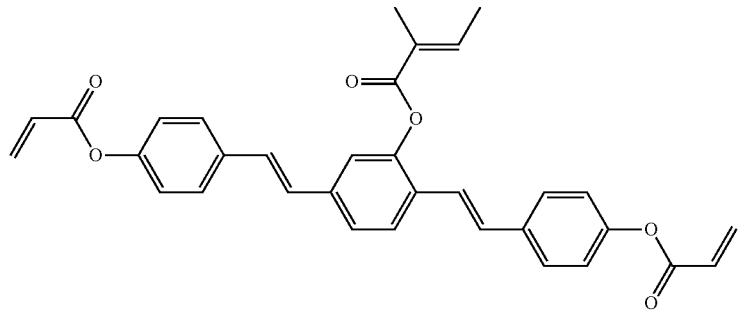
(1-3-50)
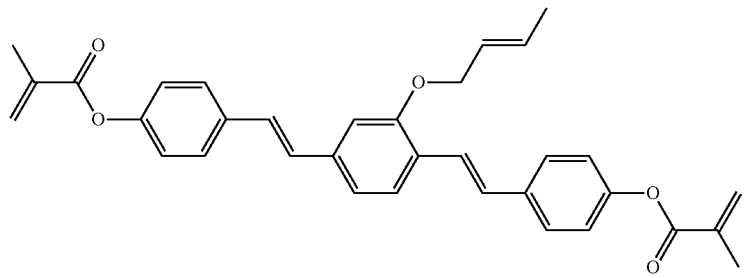
(1-3-51)
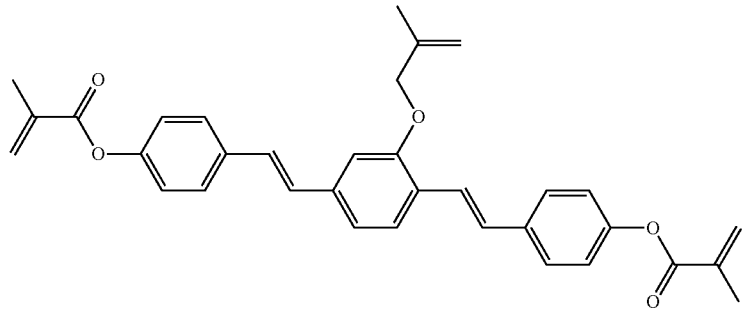
(1-3-52)

-continued
(1-3-53)
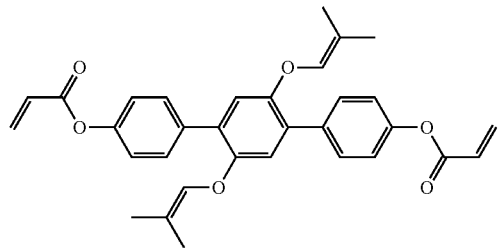
(1-3-54)
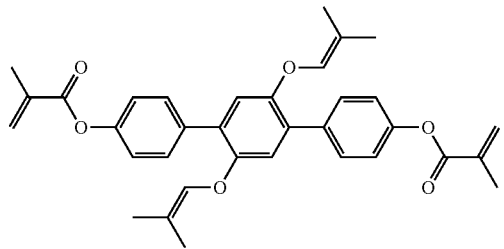
(1-3-55)
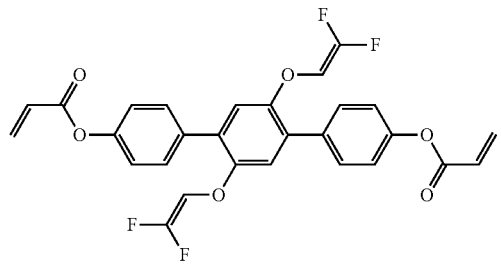
(1-3-56)
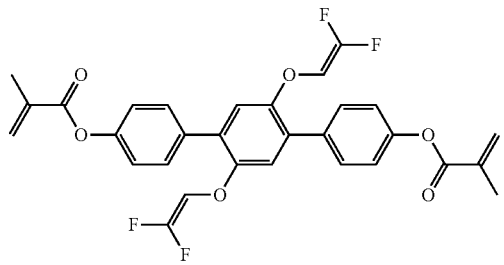
(1-3-57)
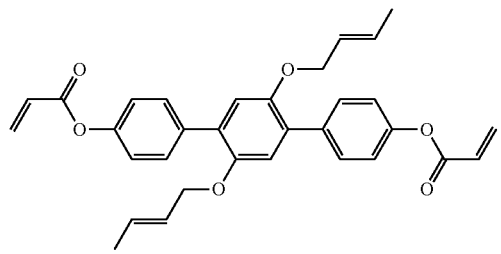
(1-3-58)
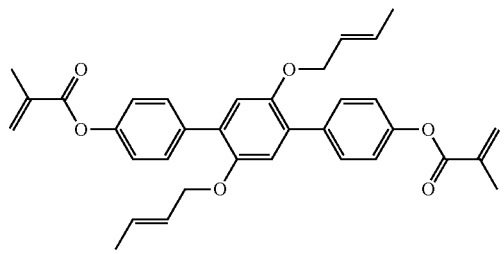
(1-3-59)
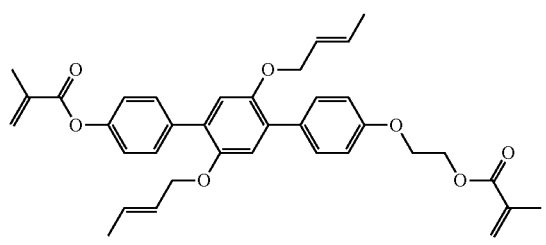
(1-3-60)
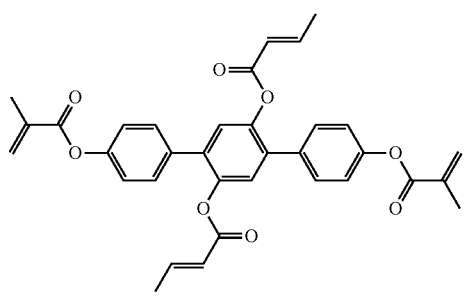
(1-3-61)
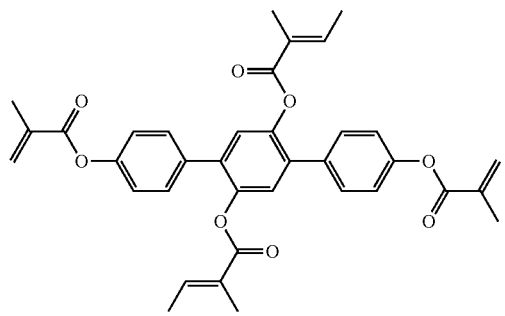
(1-3-62)
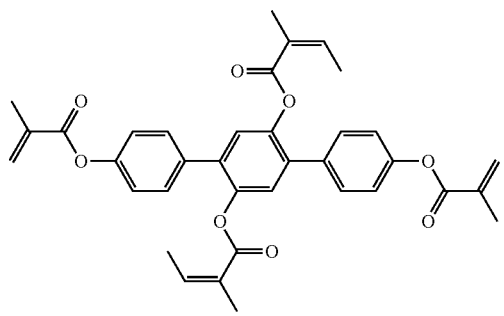

-continued
(1-3-63)
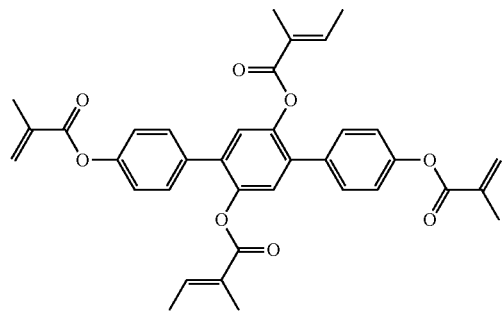
(1-3-64)
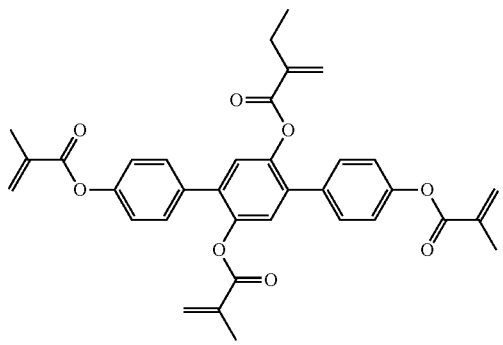
(1-3-65)
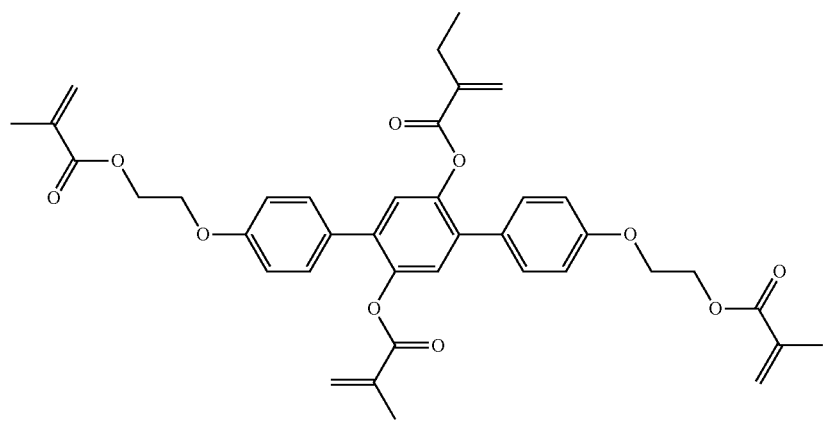
(1-3-66)
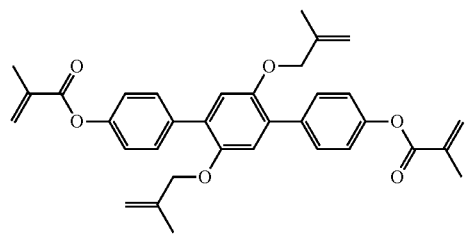
(1-3-67)
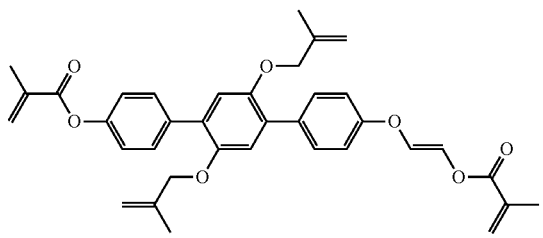
(1-3-68)
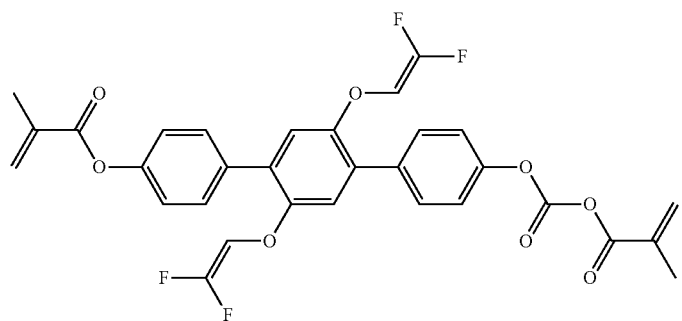

-continued
(1-3-69)
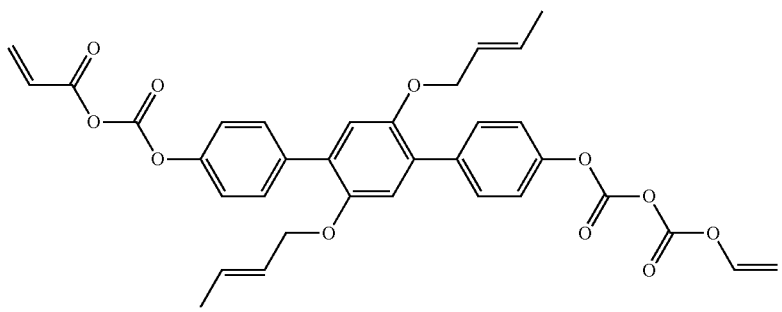
(1-3-70)
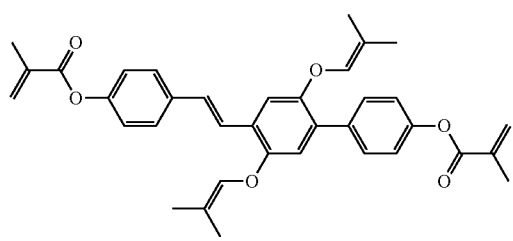
(1-3-71)
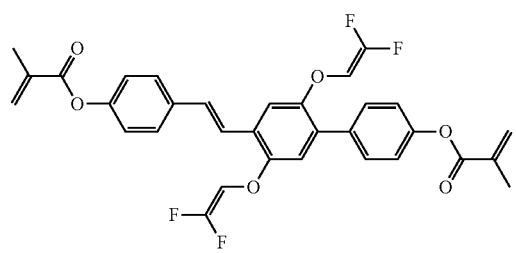
(1-3-72)
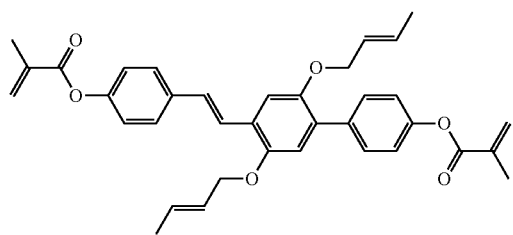
(1-3-73)
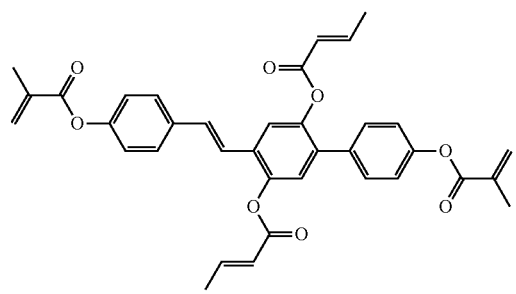
(1-3-74)
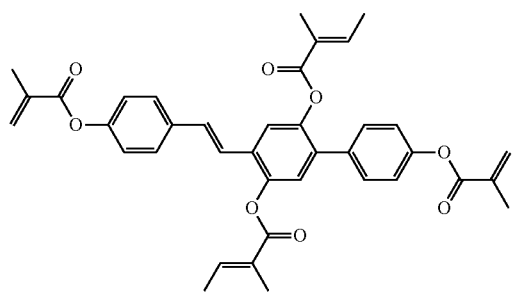
(1-3-75)
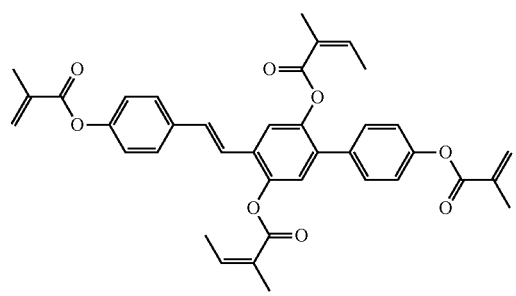
(1-3-76)
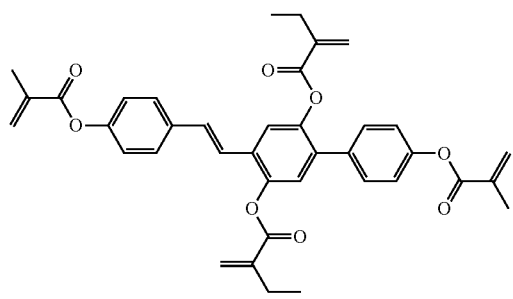
(1-3-77)
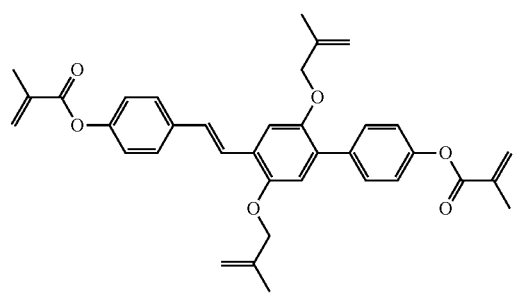

-continued
(1-3-78)
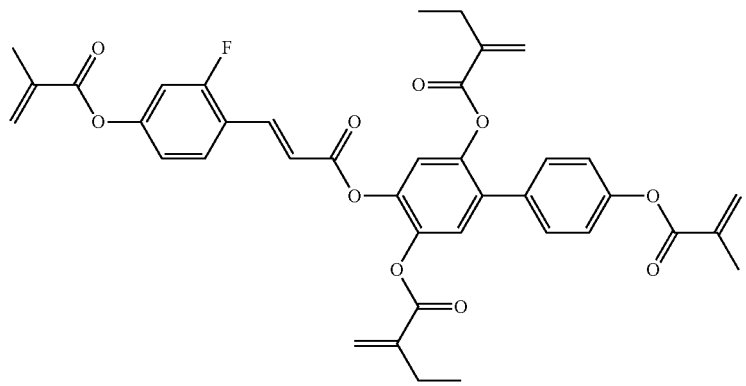
(1-3-79)
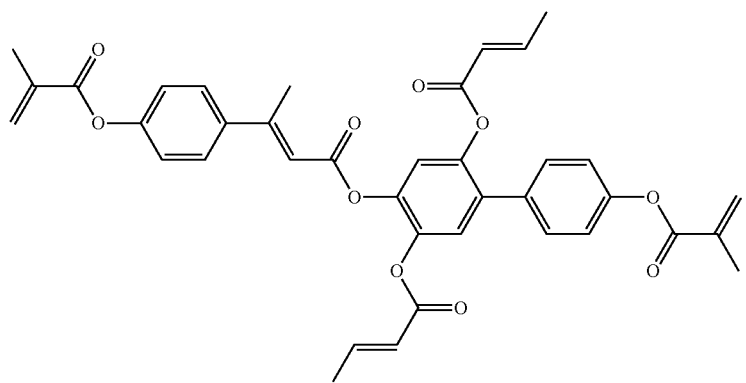
(1-3-80)
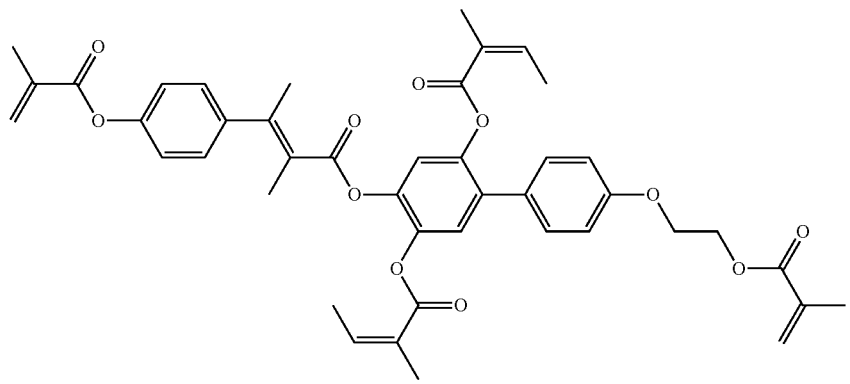
(1-3-81)
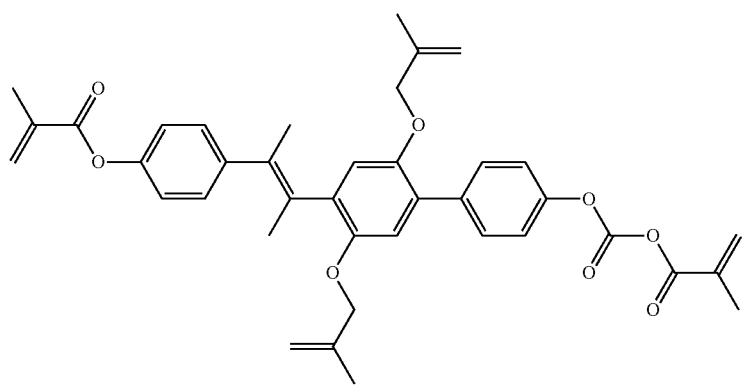

(1-3-82)
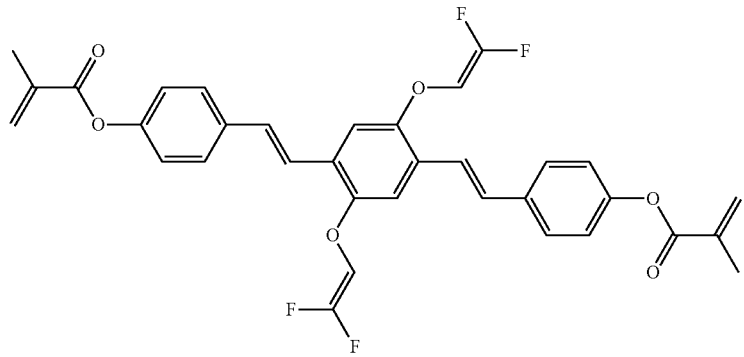
(1-3-83)
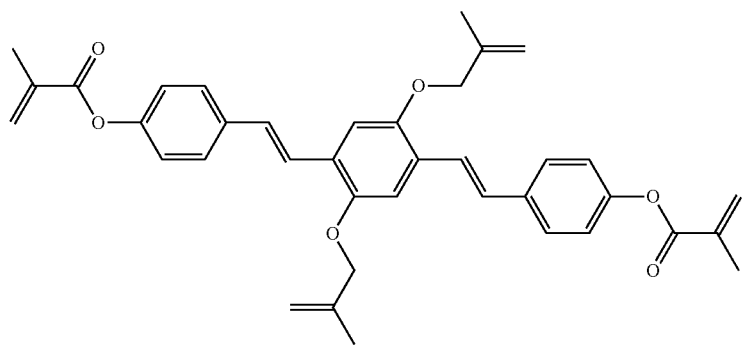
(1-3-84)
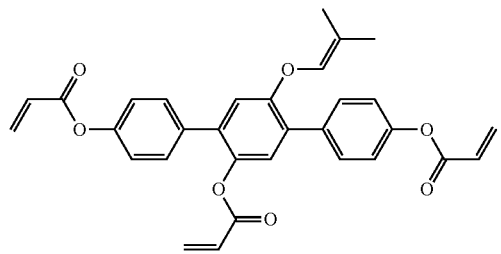
(1-3-85)
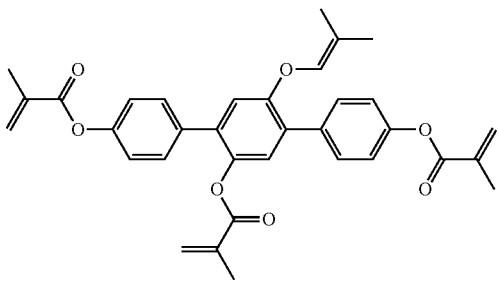
(1-3-86)
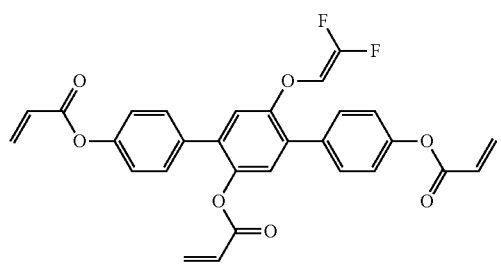
(1-3-87)
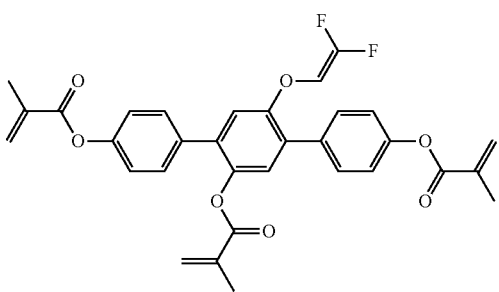
(1-3-88)
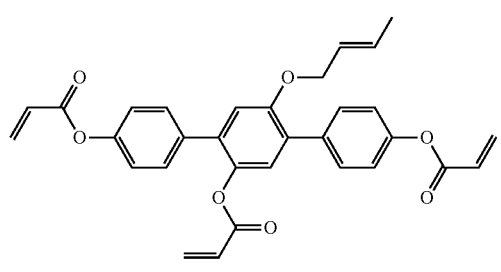
(1-3-89)
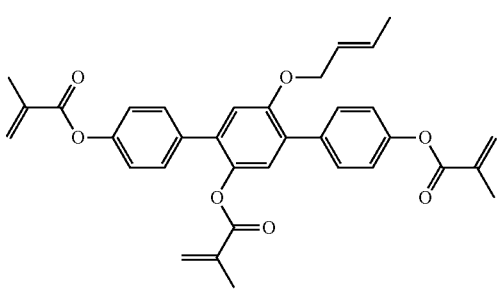

-continued
(1-3-90)
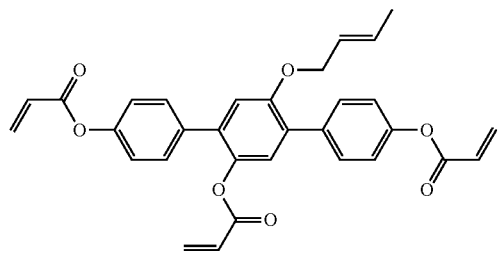
(1-3-91)
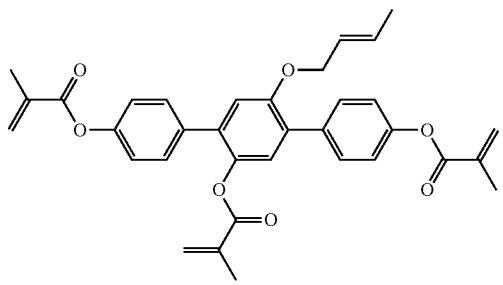
(1-3-92)
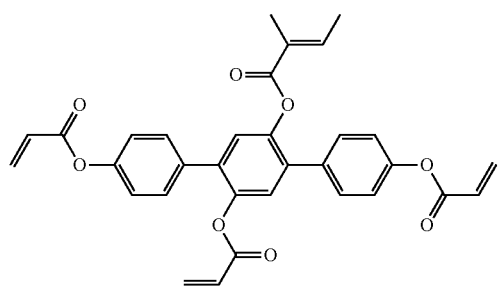
(1-3-93)
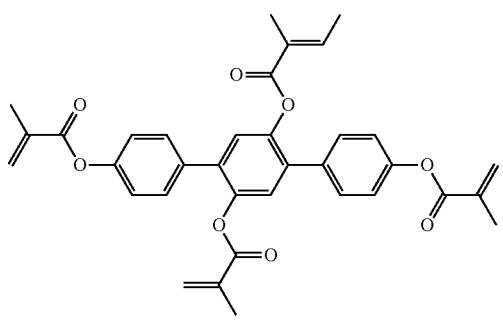
(1-3-94)
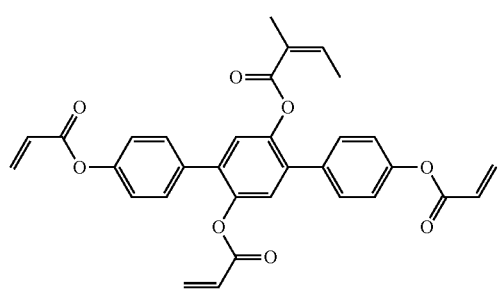
(1-3-96)
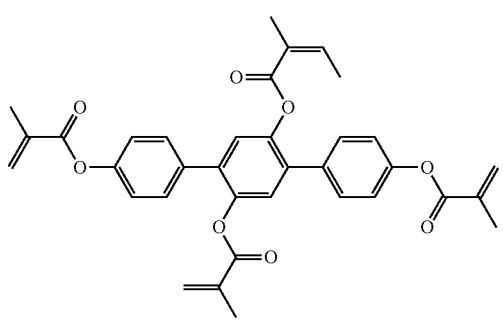
(1-3-97)
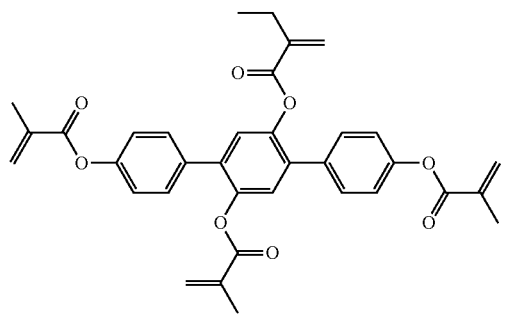
(1-3-98)
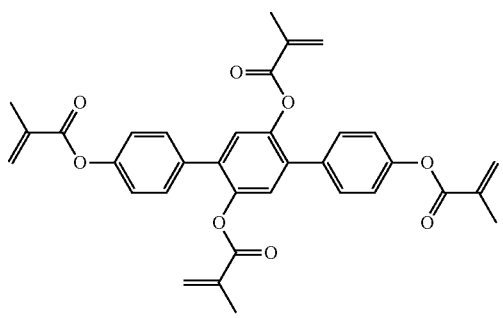
(1-3-99)
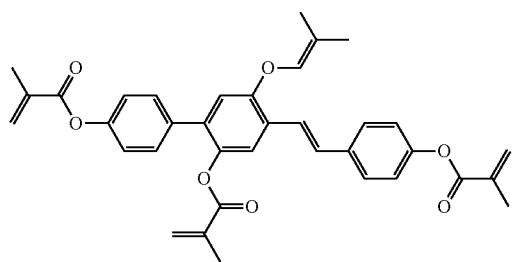
(1-3-100)
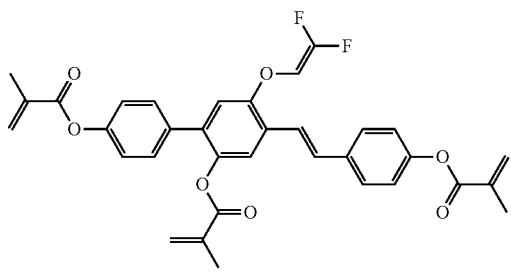

-continued
(1-3-101)
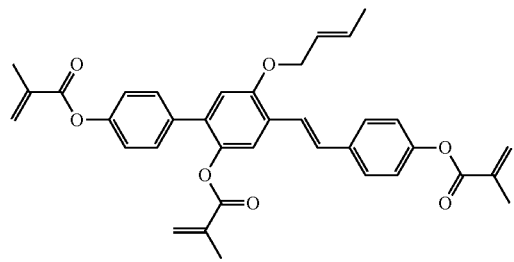
(1-3-102)
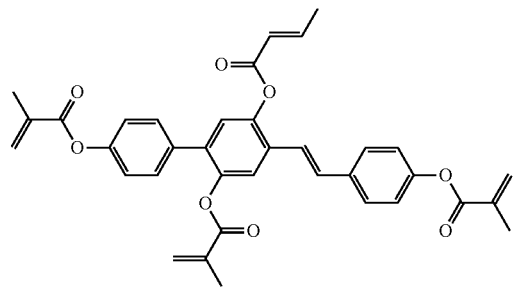
(1-3-103)
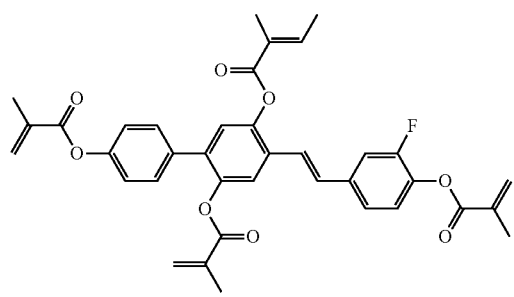
(1-3-104)
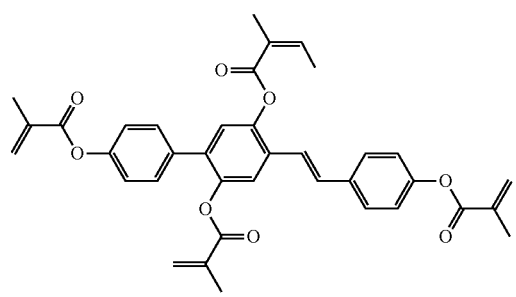
(1-3-105)
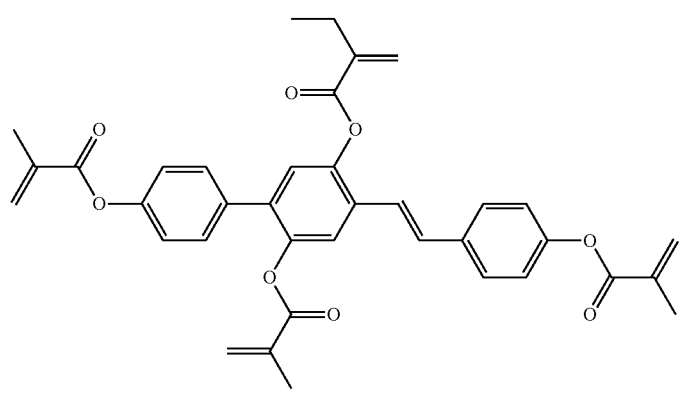
(1-3-106)
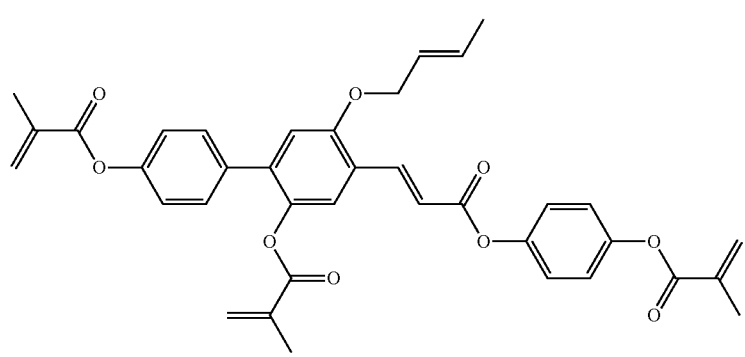

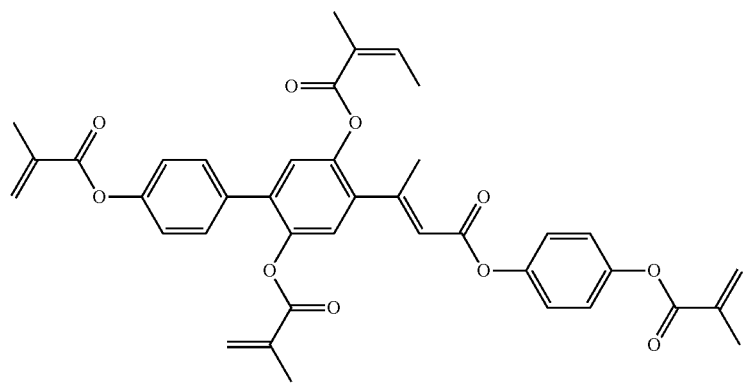
(1-3-107)
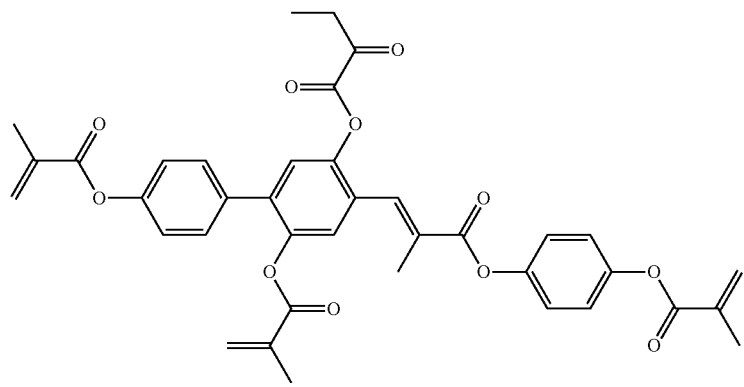
(1-3-108)
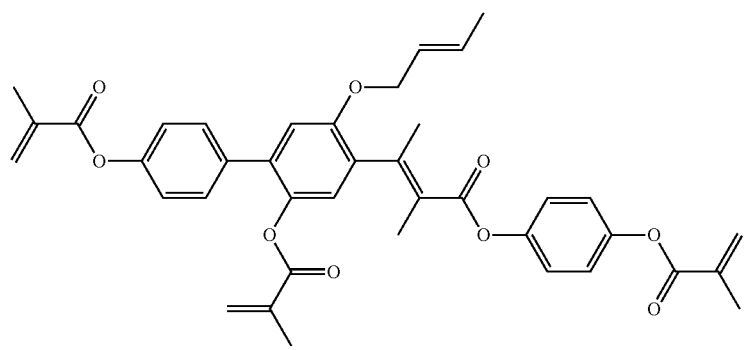
(1-3-109)
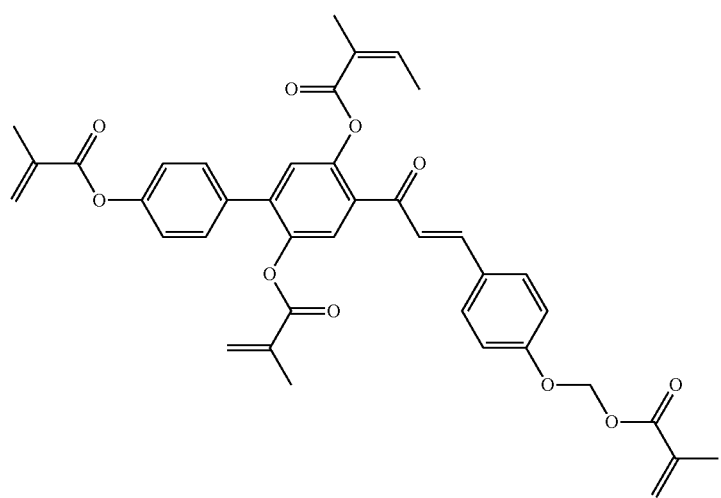
(1-3-110)

(1-3-111)
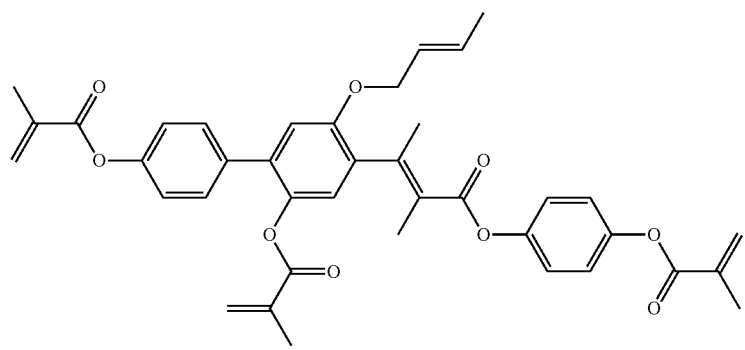
(1-3-112)
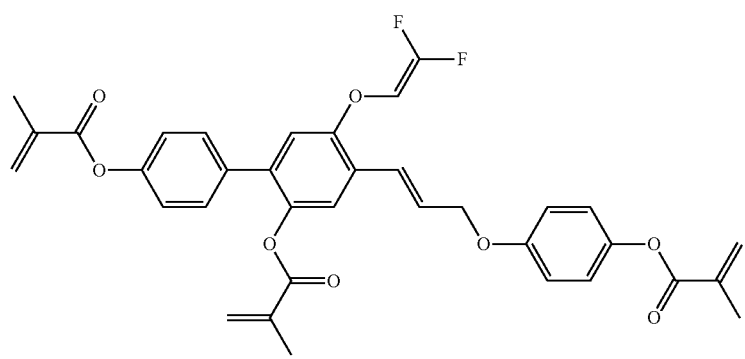
(1-3-113)
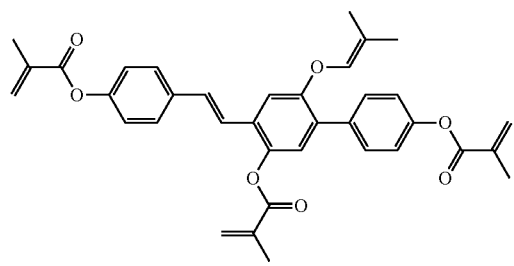
(1-3-114)
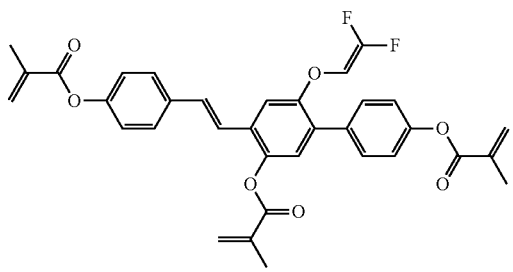
(1-3-115)
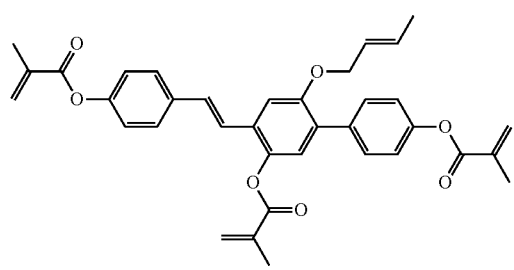
(1-3-116)
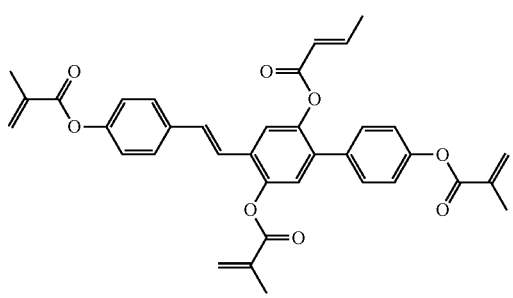
(1-3-117)
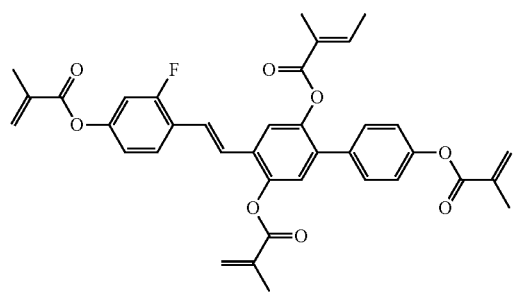
(1-3-118)
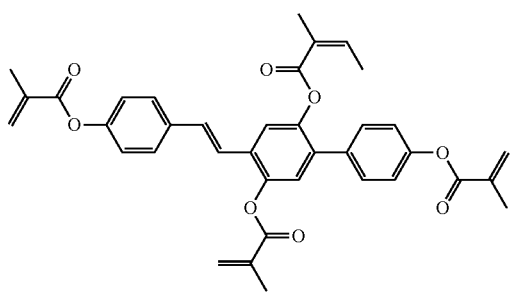

-continued
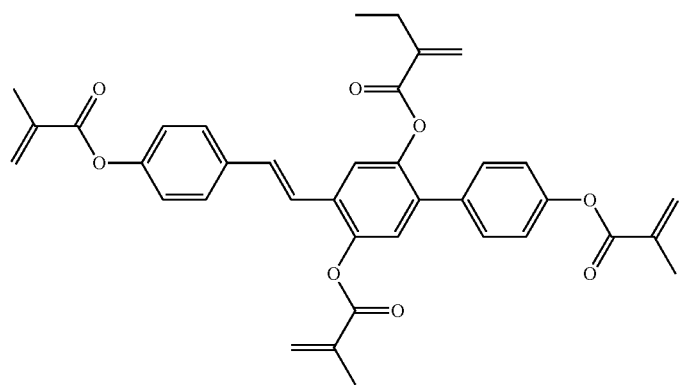
(1-3-119)
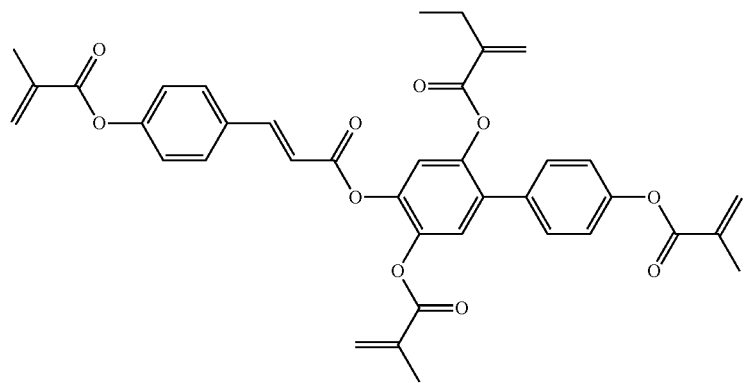
(1-3-120)
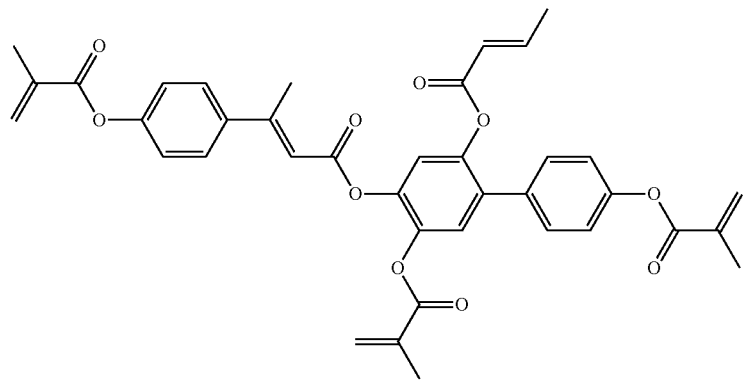
(1-3-121)
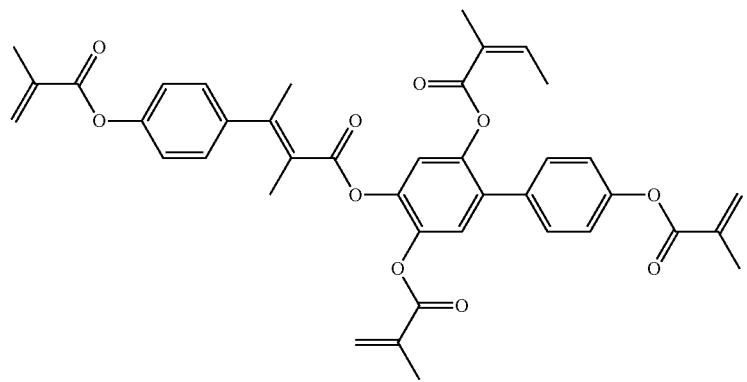
(1-3-122)

(1-3-123)
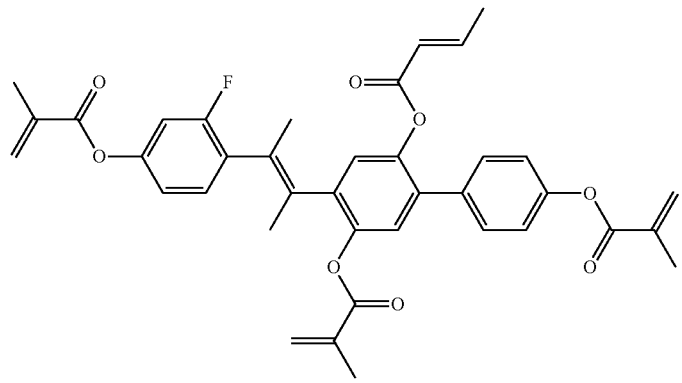
(1-3-124)
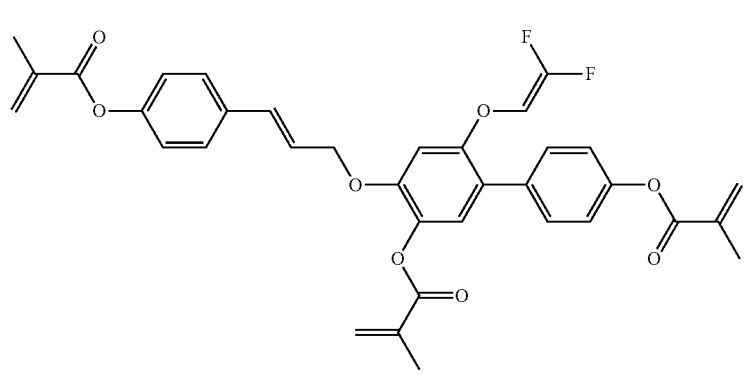
(1-3-125)
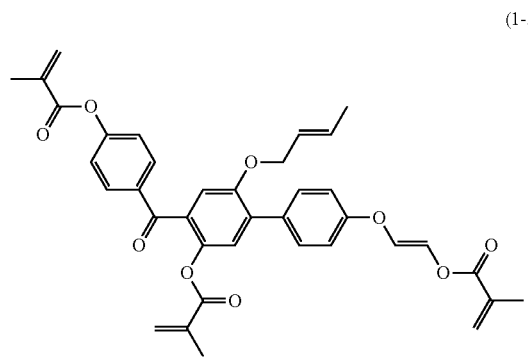
(1-3-126)
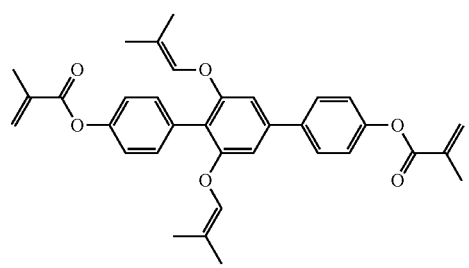
(1-3-127)
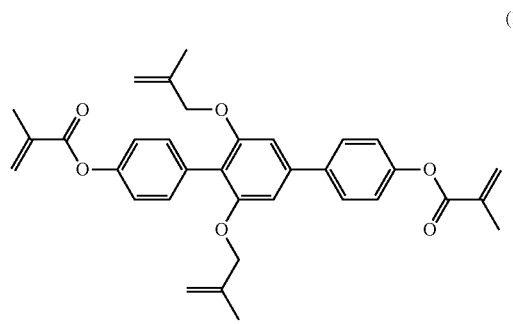
(1-3-128)
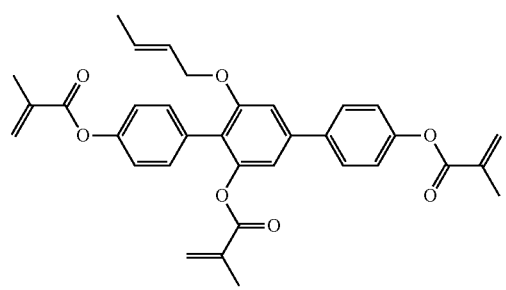

-continued
(1-3-129)
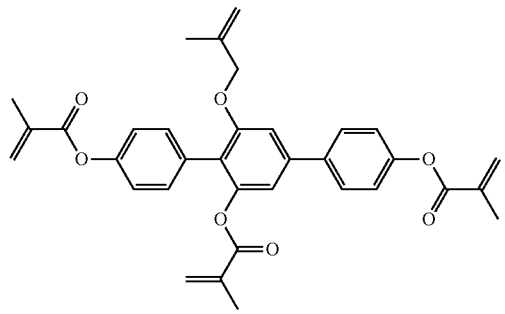
(1-3-130)
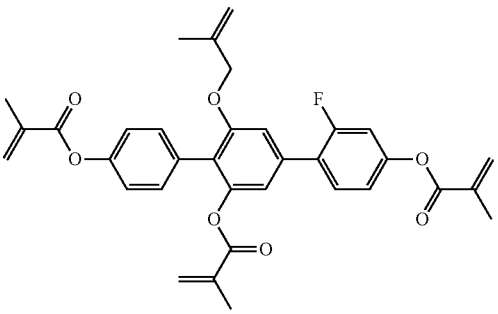
(1-3-131)
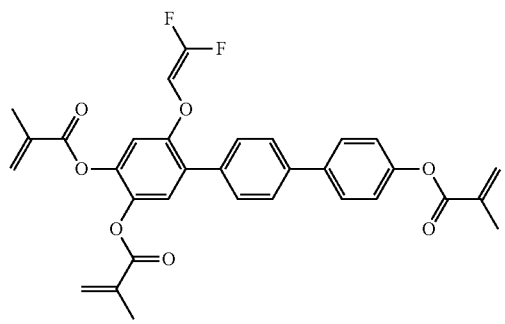
(1-3-132)
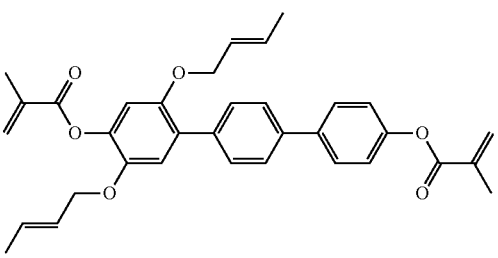
(1-3-133)
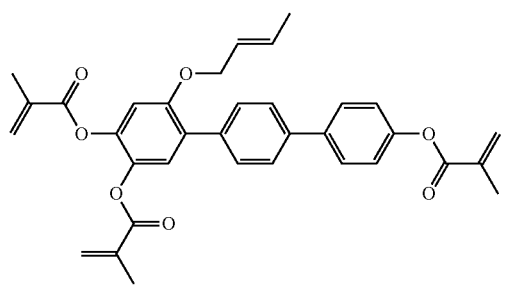
(1-3-134)
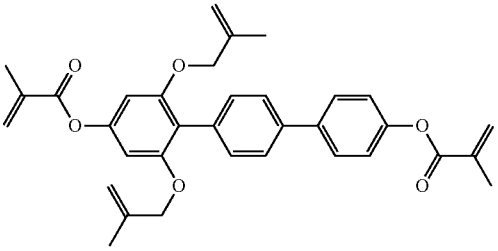
(1-3-135)
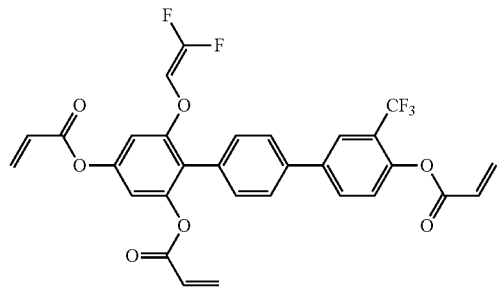
(1-3-136)
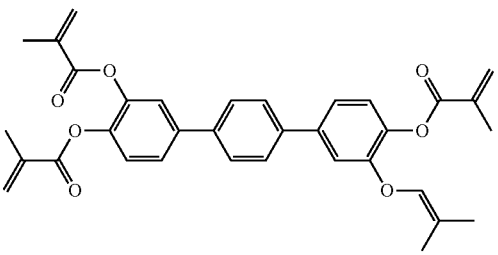
(1-3-137)
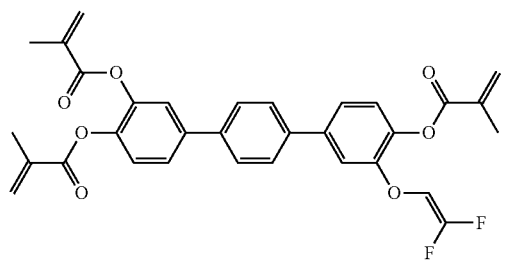
(1-3-138)
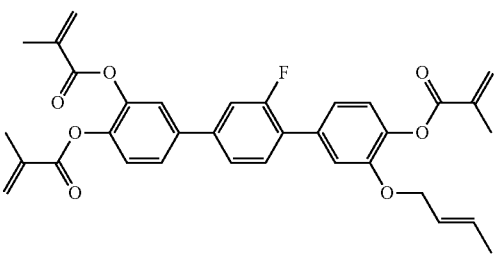

(1-3-139)
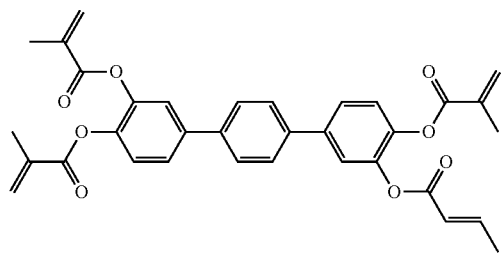
(1-3-140)
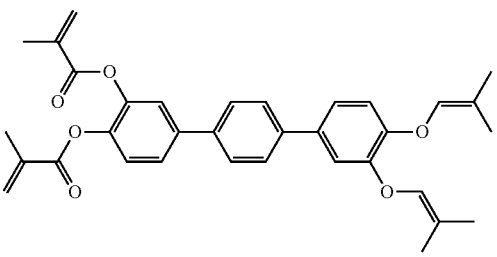
(1-3-141)
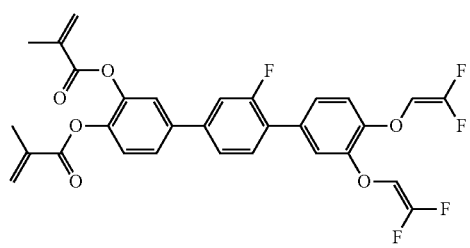
(1-3-142)
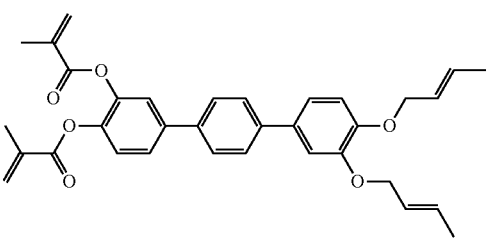
(1-3-143)
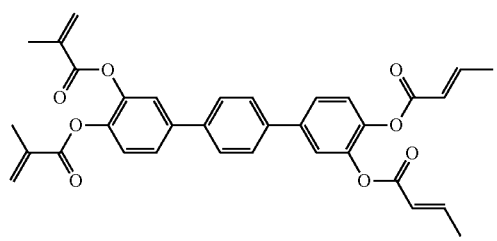
(1-3-144)
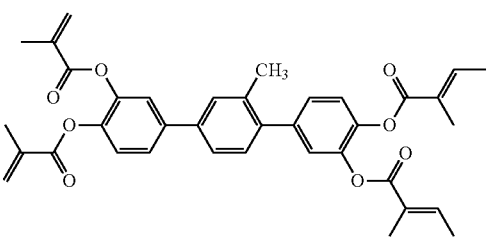
(1-3-145)
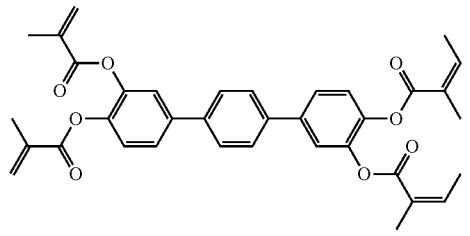
(1-3-146)
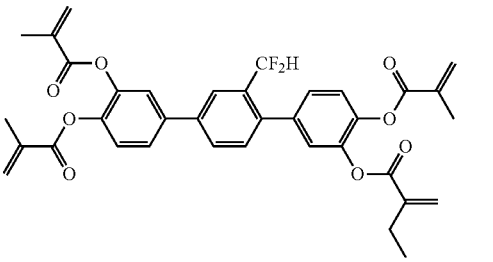
(1-3-147)
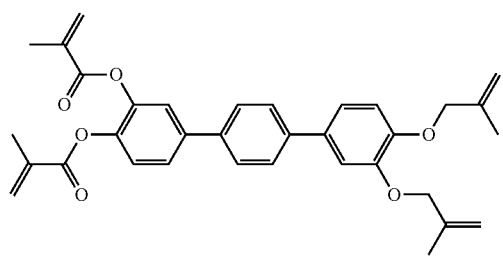
(1-3-148)
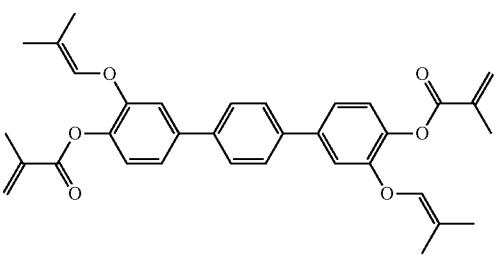
(1-3-149)
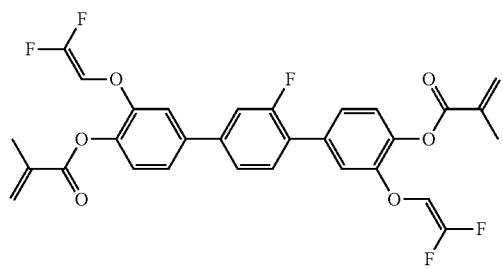
(1-3-150)
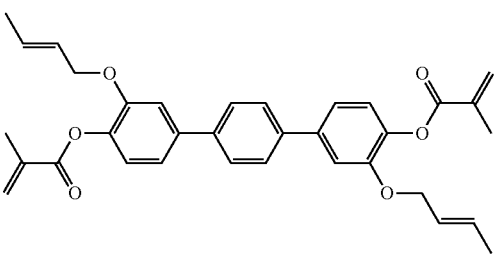

-continued
(1-3-151)
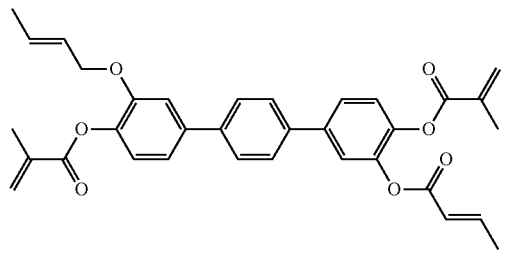
(1-3-152)
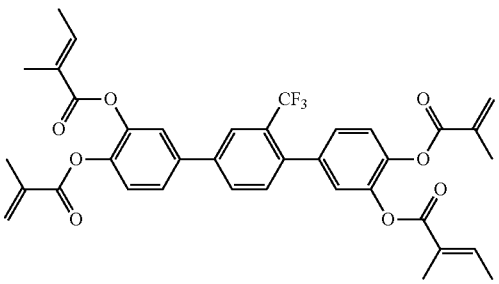
(1-3-153)
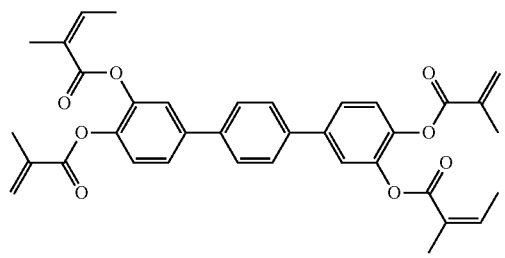
(1-3-154)
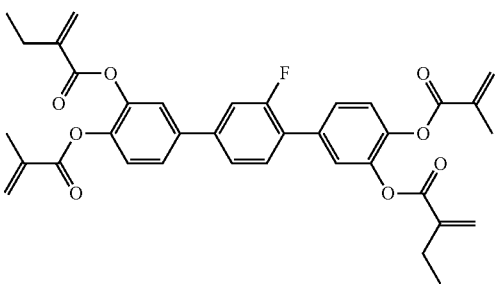
(1-3-155)
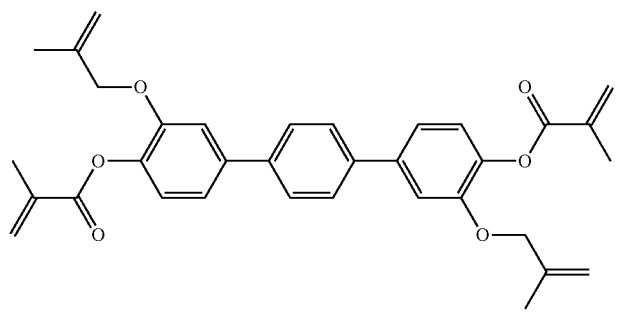
(1-3-156)
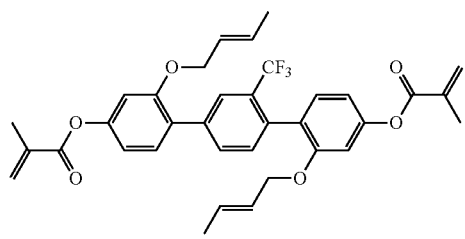
(1-3-157)
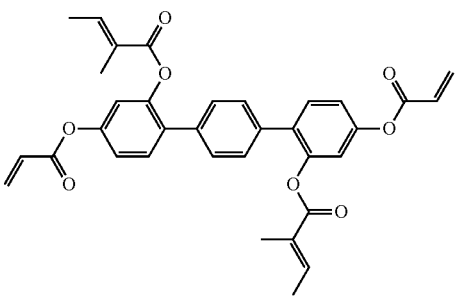
(1-3-158)
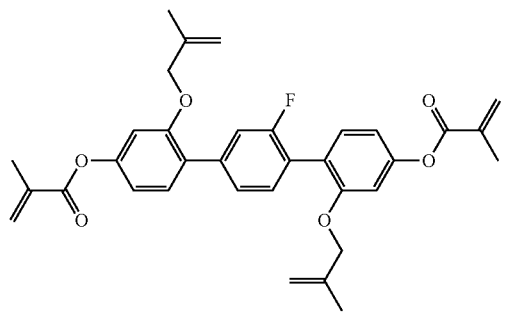
(1-3-159)
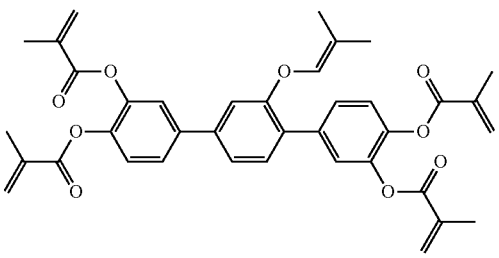

-continued
(1-3-160)
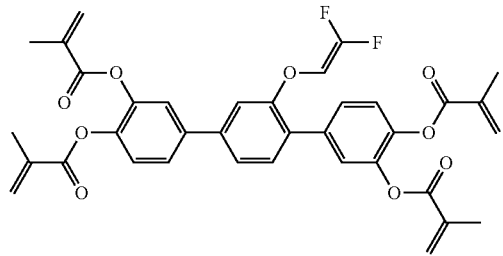
(1-3-161)
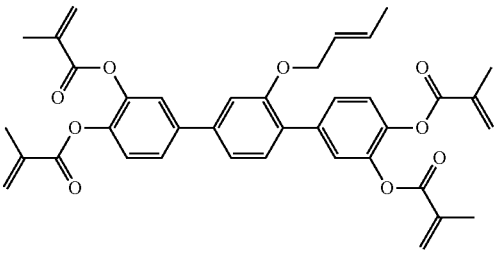
(1-3-162)
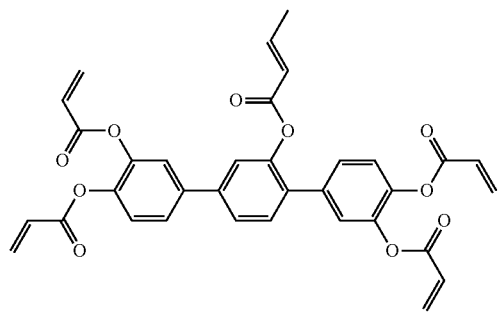
(1-3-163)
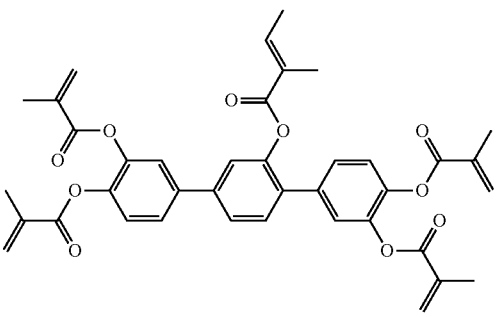
(1-3-164)
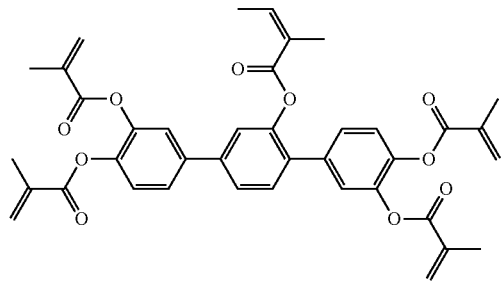
(1-3-165)
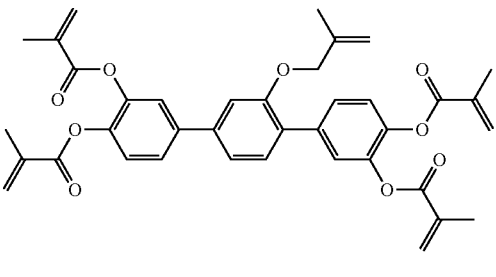
(1-3-166)
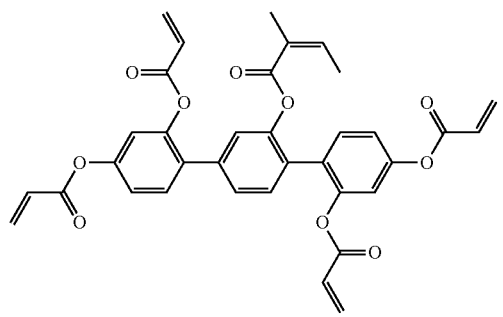
(1-3-167)
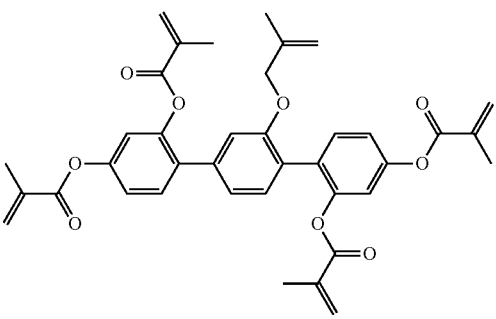
(1-3-168)
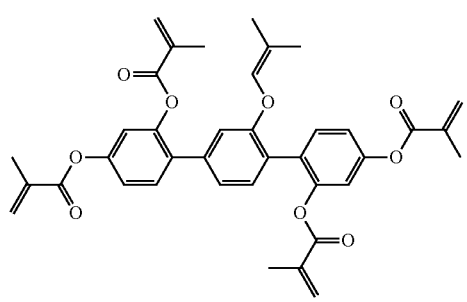
(1-3-169)
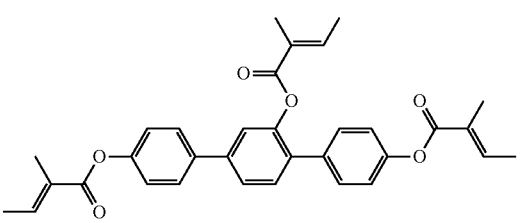

-continued
(1-3-170)
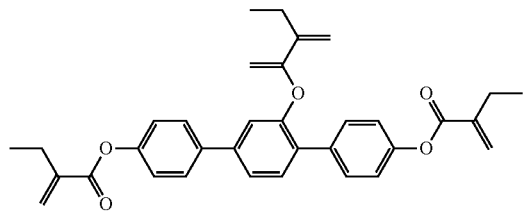
(1-3-171)
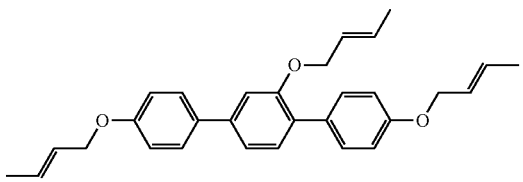
(1-3-172)
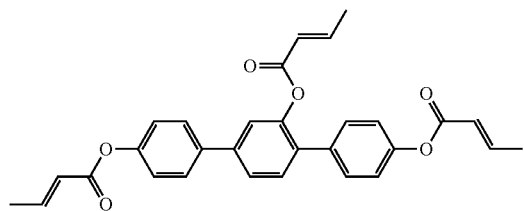
(1-3-173)
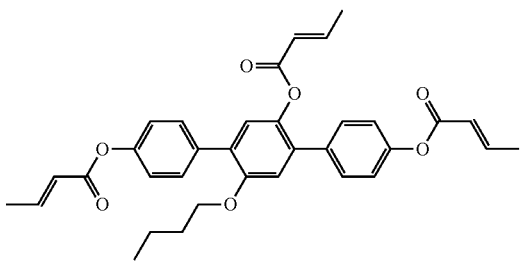
(1-3-174)
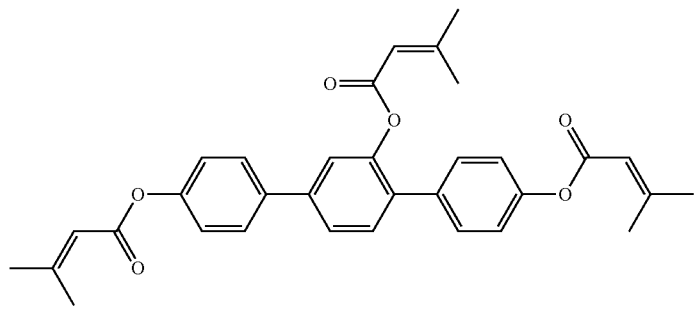
(1-3-175)
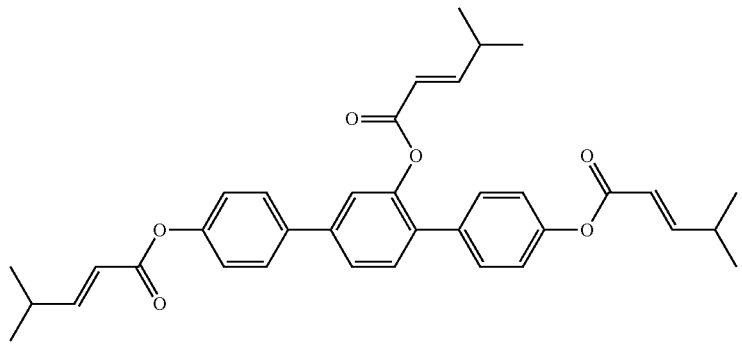
(1-3-176)
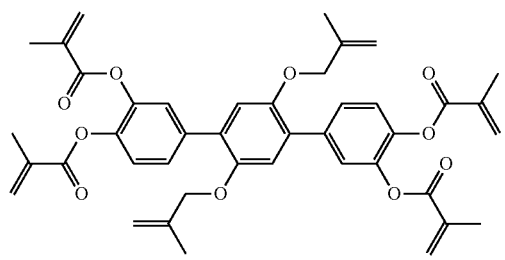
(1-3-177)
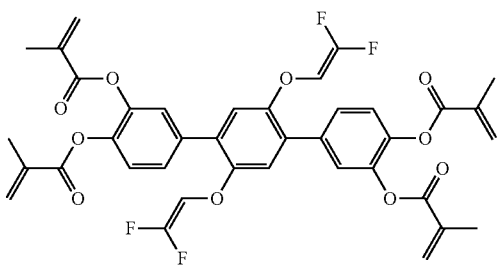

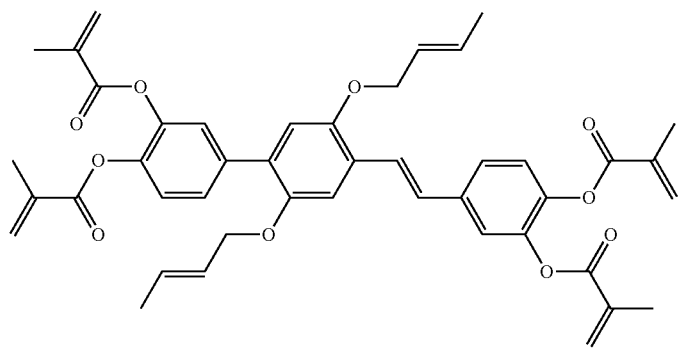
(1-3-178)
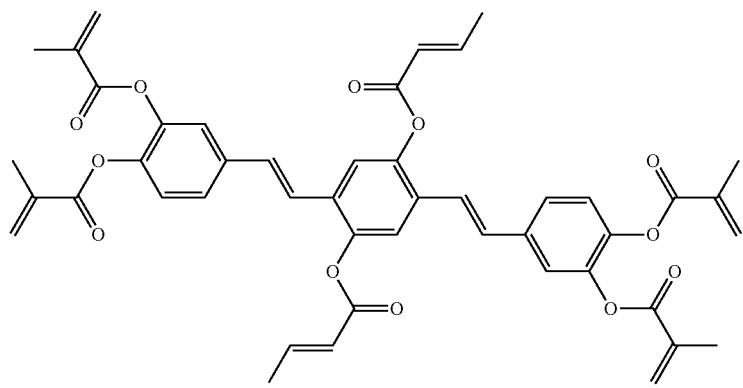
(1-3-179)
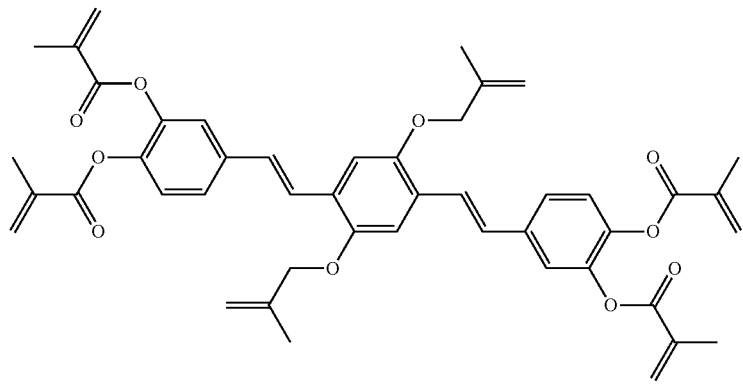
(1-3-180)
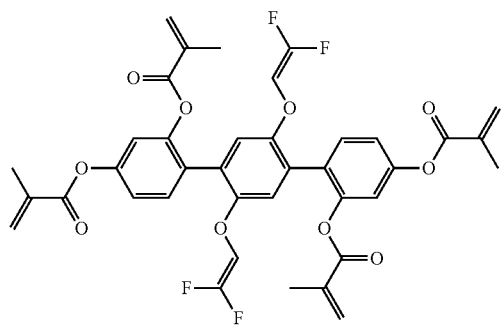
(1-3-181)
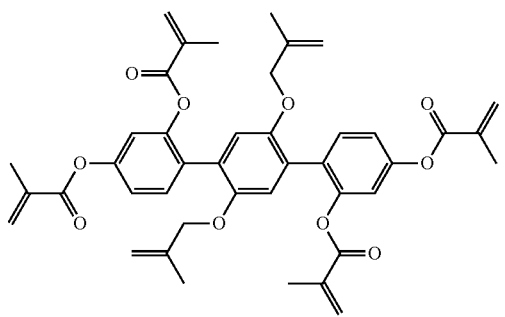
(1-3-182)

-continued
(1-4-1)
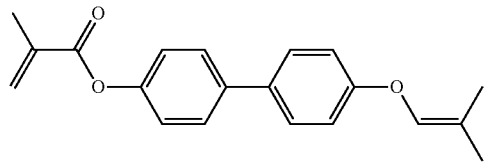
(1-4-2)
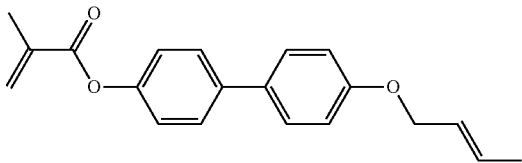
(1-4-3)
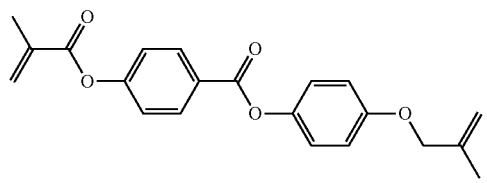
(1-4-4)
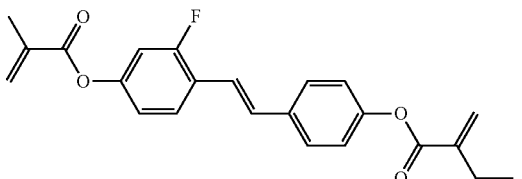
(1-4-5)
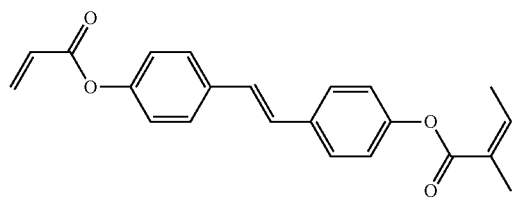
(1-4-6)
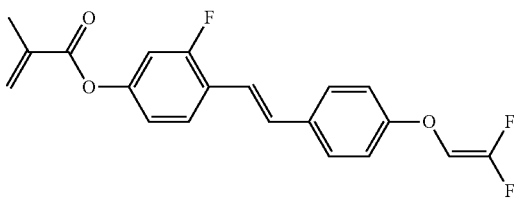
(1-4-7)
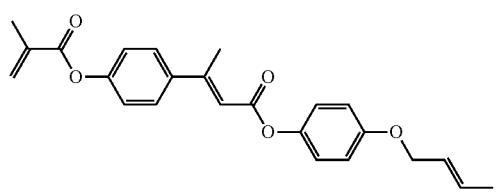
(1-4-8)
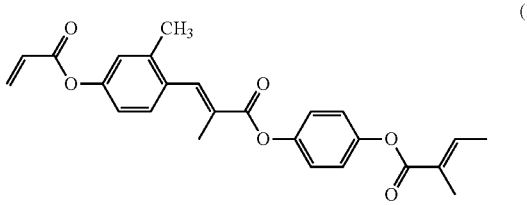
(1-4-9)
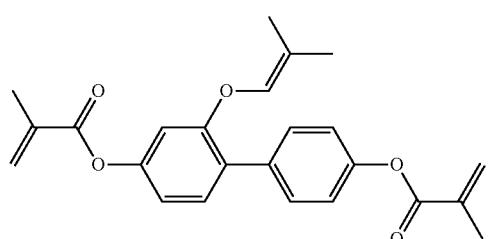
(1-4-10)
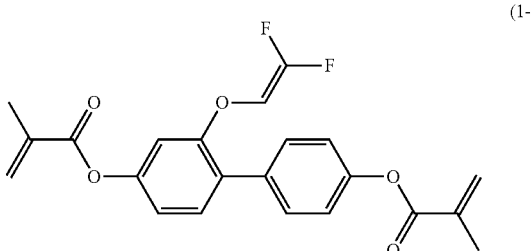
(1-4-11)
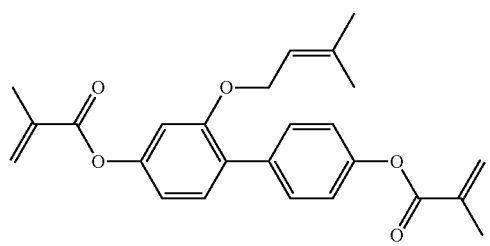
(1-4-12)
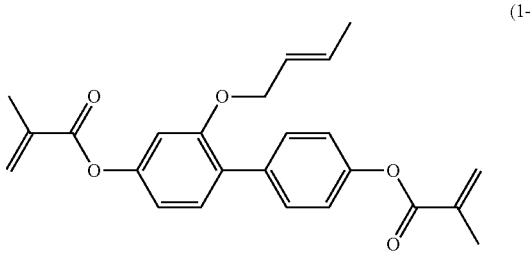
(1-4-13)
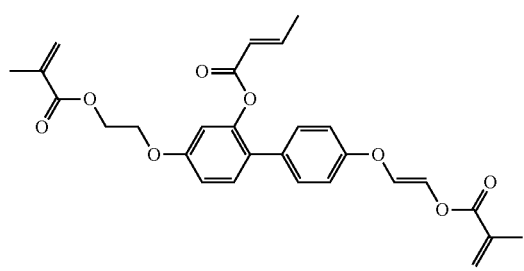
(1-4-14)
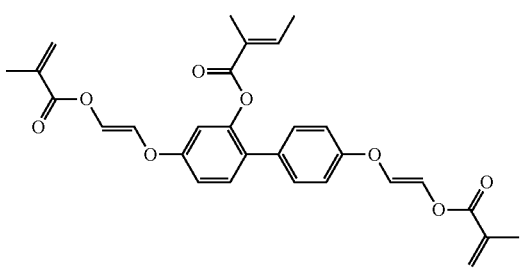

-continued
(1-4-15)
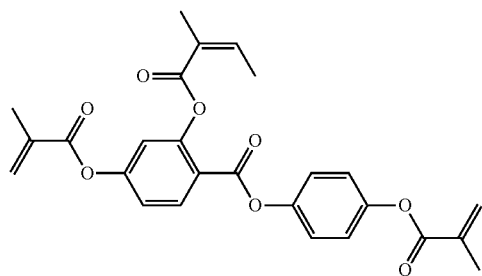
(1-4-16)
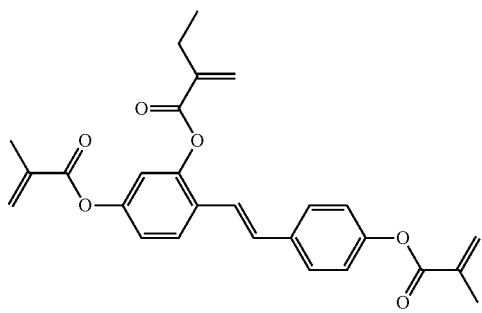
(1-4-17)
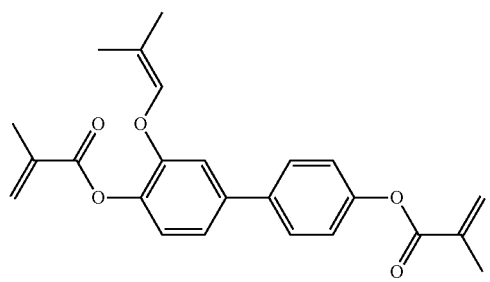
(1-4-18)
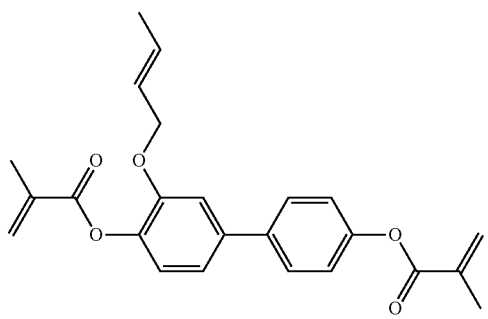
(1-4-19)
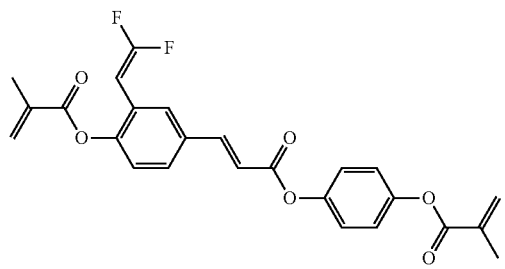
(1-4-20)
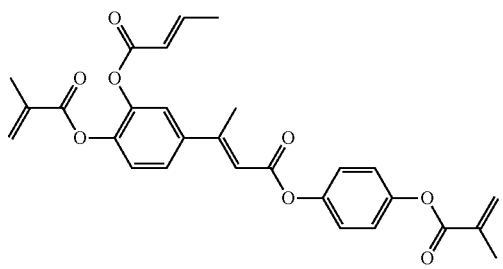
(1-4-21)
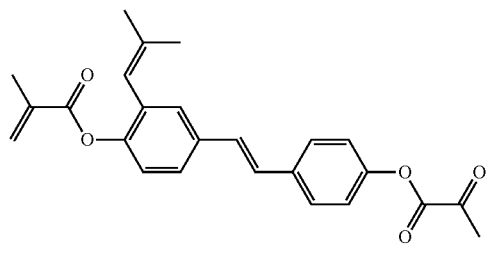
(1-4-22)
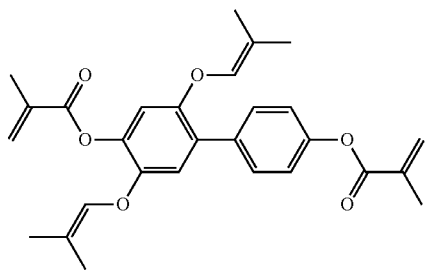
(1-4-23)
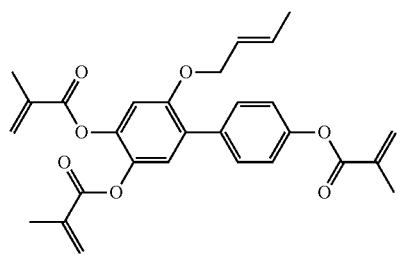
(1-4-24)
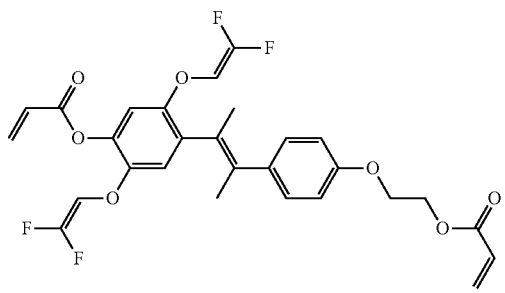

(1-4-25)
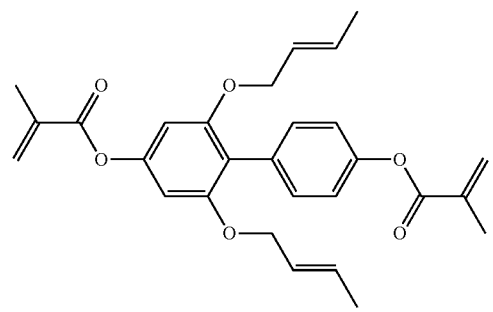
(1-4-26)
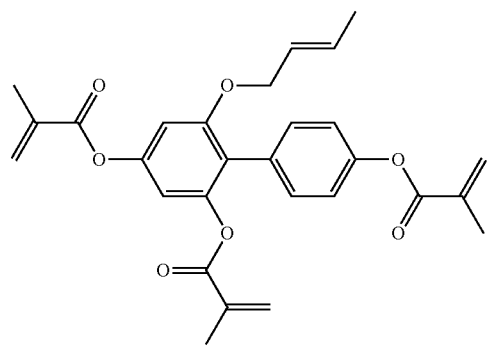
(1-4-27)
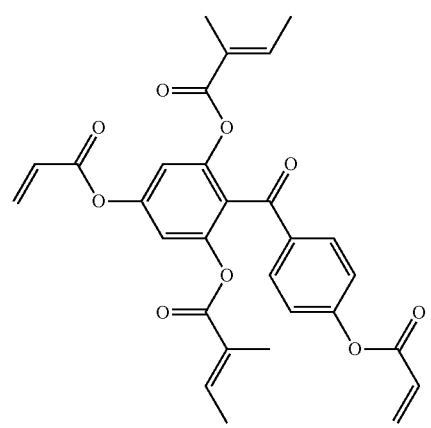
(1-4-28)
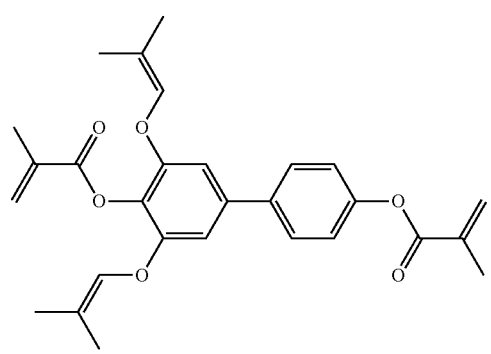
(1-4-29)
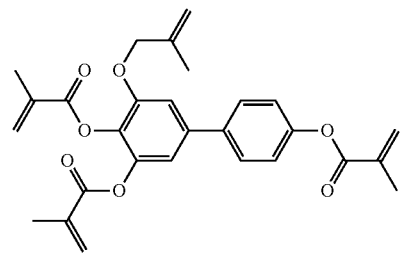
(1-4-30)
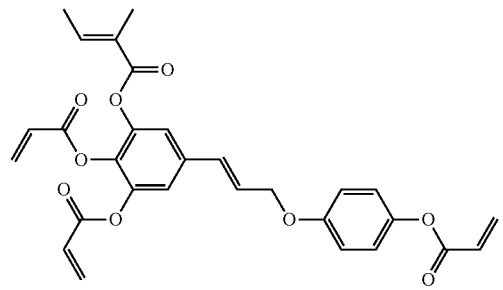
(1-4-31)
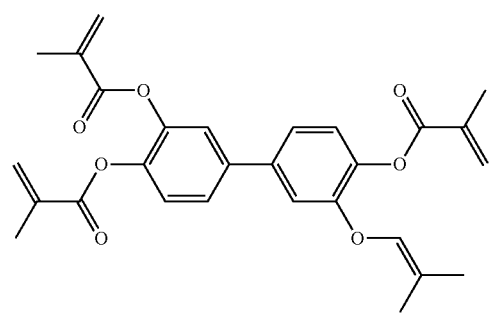
(1-4-32)
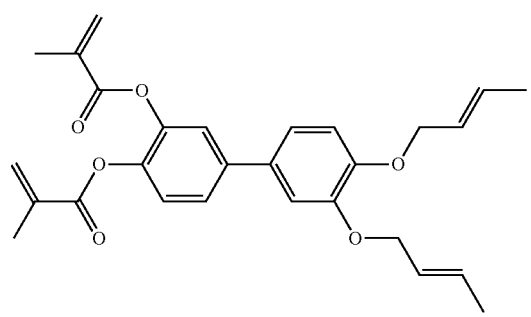

-continued
(1-4-33)
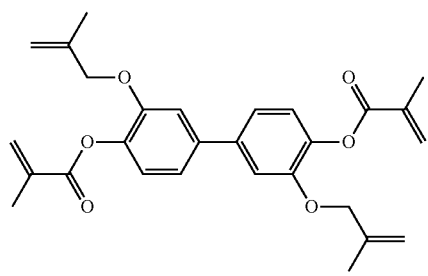
(1-4-34)
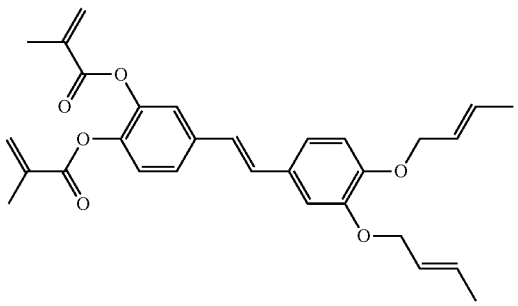
(1-4-35)
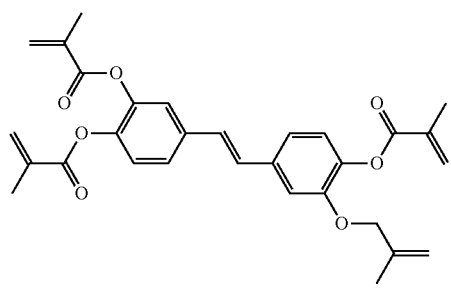
(1-4-36)
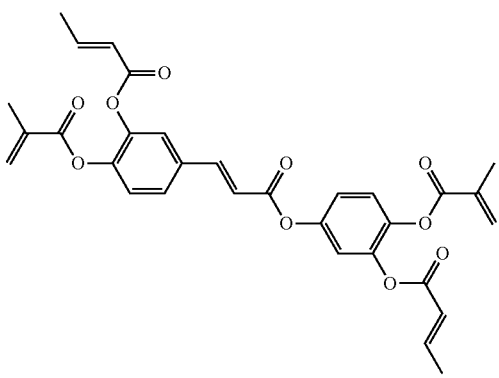
(1-4-37)
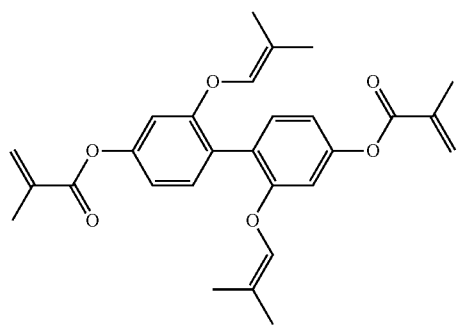
(1-7-1)
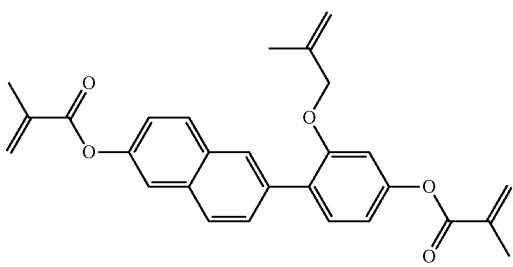
(1-7-2)
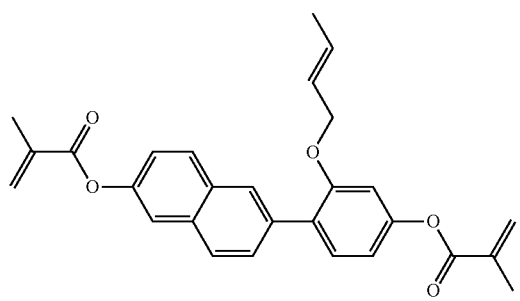
(1-7-3)
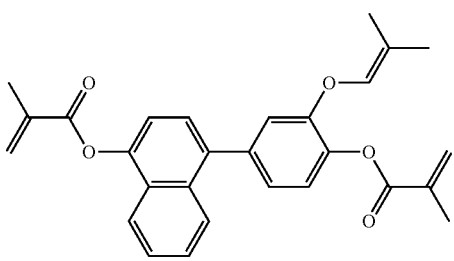

-continued
(1-7-4)
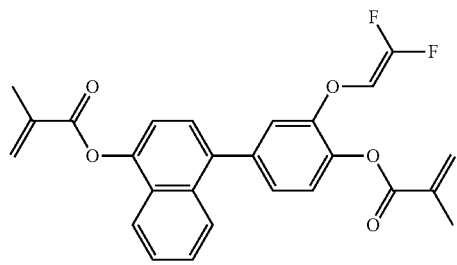
(1-7-5)
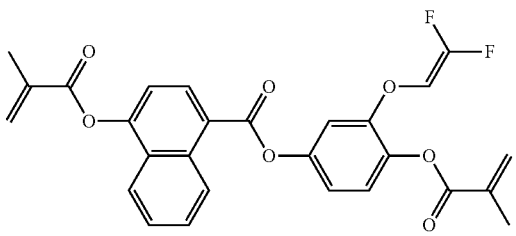
(1-7-6)
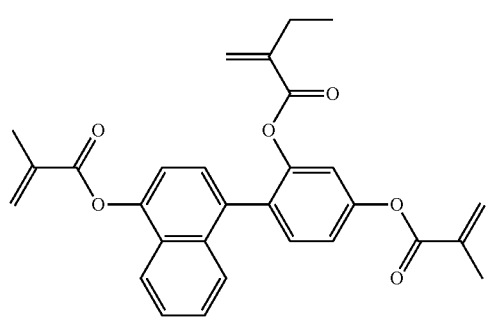
(1-7-7)
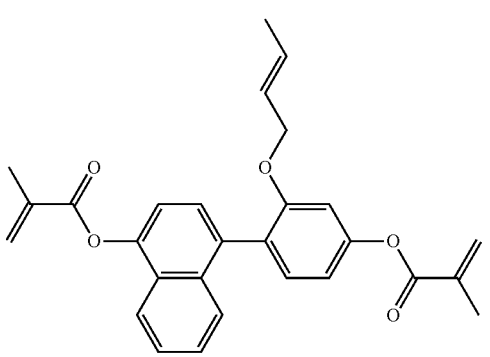
(1-7-8)
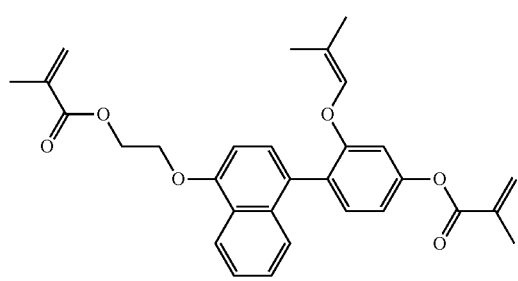
(1-7-9)
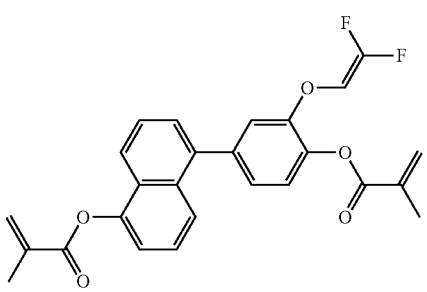
(1-7-10)
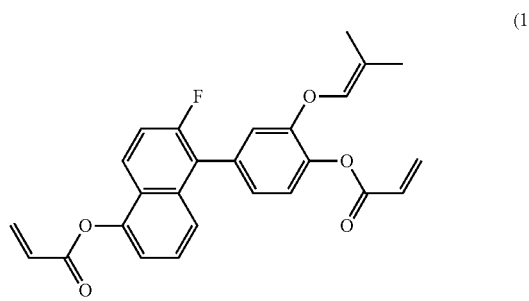
(1-7-11)
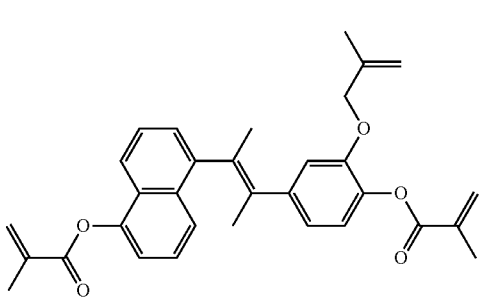
(1-7-12)
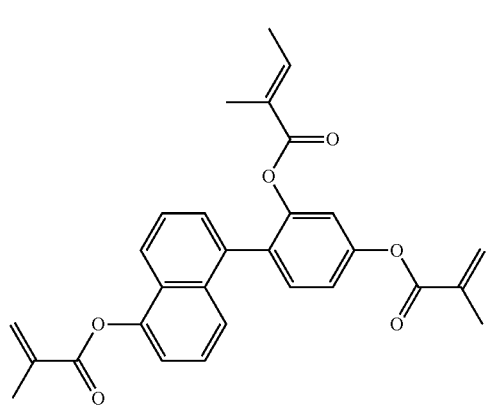
(1-7-13)
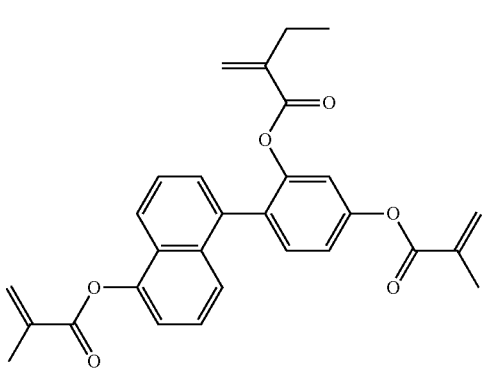

(1-7-14)

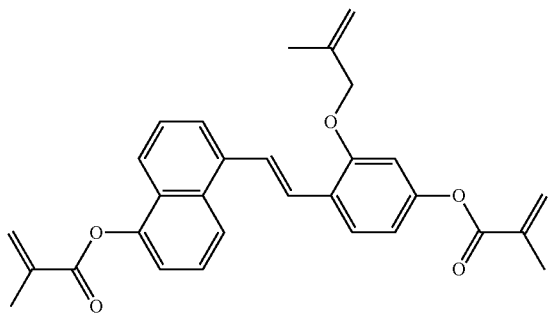

Synthesis of Comparative Compound

Comparative compound (R-1): [1,1'-biphenyl]-4,4'-diyl-bis(2-methacrylate) was prepared according to a reaction formula described below to obtain a colorless crystal of comparative compound (R-1).

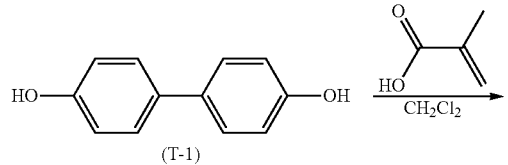
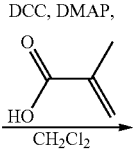

(T-1)

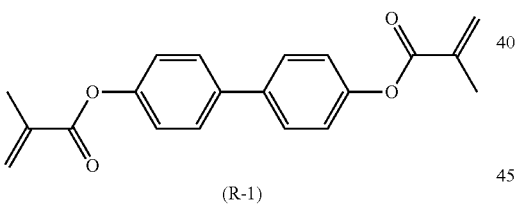

(R-1)

$^1$H-NMR (DMSO-d; δ ppm): 7.24 (d, 4H), 6.96 (d, 4H), 6.41 (d, 2H), 6.26 (d, 2H), 1.98 (s, 6H).

Physical properties of comparative compound (R-1) were as described below. Melting point: 150.0° C.

Comparative Example 1

Comparison of Solubility in Liquid Crystal Composition

Compound (1-3-89) was added to liquid crystal composition A at a rate of 0.3% by weight, and the resulting mixture was heated at 50° C. for 30 minutes. The obtained solution was left to stand at room temperature for two days. Then, whether or not any crystal precipitated was visually observed. Meanwhile, comparative compound (R-1) was also observed in a similar manner. The results are shown in Table 1. In symbols in Table 2, "○" stands for no precipitation of any crystal, and "x" stands for occurrence of precipitation of any crystal. Table 2 shows that the polymerizable compound of the invention has a good solubility in liquid crystal composition A. In addition, components in liquid crystal composition A and ratios thereof were as described below.

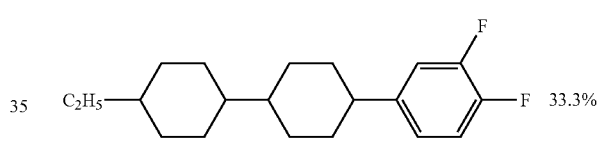 33.3%

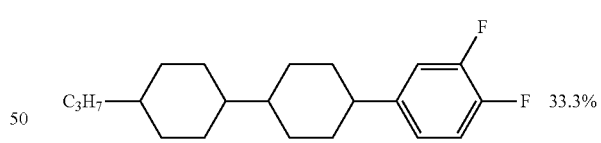 33.3%

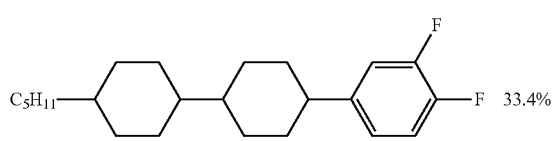 33.4%

TABLE 1

| Compound | Structural formula | Solubility (for 2 days at room temperature) |
|---|---|---|
| Compound (1-3-89) | 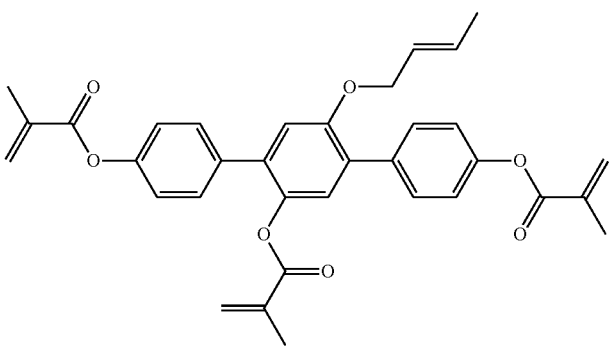 [SMILES: C=C(C)C(=O)Oc1ccc(-c2cc(OC(=O)C(=C)C)c(-c3ccc(OC(=O)C(=C)C)cc3)cc2OC/C=C/C)cc1] | ○ |
| Comparative compound (R-1) | 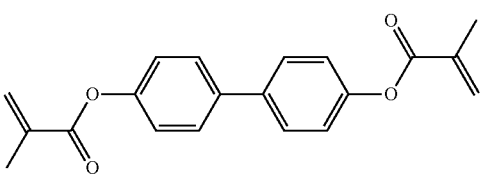 [SMILES: C=C(C)C(=O)Oc1ccc(-c2ccc(OC(=O)C(=C)C)cc2)cc1] | X |

7. Example of Polymerizable Composition

Compounds in Examples were described using symbols according to definitions in Table 2 below. In Table 2, a configuration of 1,4-cyclohexylene is trans. A parenthesized number next to a symbolized compound in Examples corresponds to the number of a compound. A symbol (-) represents any other liquid crystal compound. A ratio (percentage) of a liquid crystal compound is expressed in terms of weight percent (% by weight) based on the weight of the liquid crystal composition. Finally, values of physical properties of the polymerizable composition were summarized. The physical properties were measured according to the methods described above, the measured values were directly described (without extrapolation).

TABLE 2

| Method of Description of Compound using Symbols R—($A_1$)—$Z_1$— ... —$Z_n$—($A_n$)—R' | |
|---|---|
| 1) Left-terminal Group R— | Symbol |
| $C_nH_{2n+1}$— | n- |
| $C_nH_{2n+1}O$— | nO— |
| $C_mH_{2m+1}OC_nH_{2n}$— | mOn- |
| $CH_2$=CH— | V— |
| $C_nH_{2n+1}$—CH=CH— | nV— |
| $CH_2$=CH—$C_nH_{2n}$— | Vn- |
| $C_mH_{2m+1}$—CH=CH—$C_nH_{2n}$— | mVn- |
| $CF_2$=CH— | VFF— |
| $CF_2$=CH—$C_nH_{2n}$— | VFFn- |
| 2) Right-terminal Group —R' | Symbol |
| —$C_nH_{2n+1}$ | -n |
| —$OC_nH_{2n+1}$ | —On |
| —COOCH$_3$ | —EMe |
| —CH=CH$_2$ | —V |
| —CH=CH—$C_nH_{2n+1}$ | —Vn |
| —$C_nH_{2n}$—CH=CH$_2$ | -nV |
| —$C_mH_{2m}$—CH=CH—$C_nH_{2n+1}$ | -mVn |

TABLE 2-continued

| | |
|---|---|
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —CF=CH—CF$_3$ | —FVCF3 |
| —C≡N | —C |
| 3) Bonding Group —$Z_n$— | Symbol |
| —$C_nH_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —$A_n$— | Symbol |
| 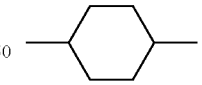 | H |
| 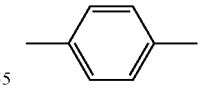 | B |
| 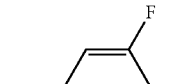 | B(F) |
| 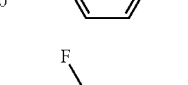 | B(2F) |

TABLE 2-continued

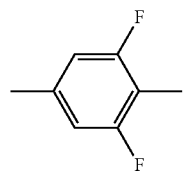 B(F,F)

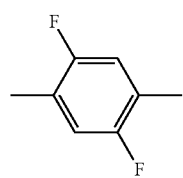 B(2F,5F)

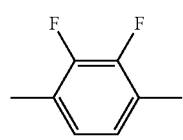 B(2F,3F)

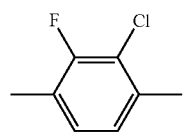 B(2F,3CL)

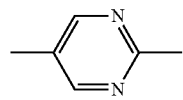 Py

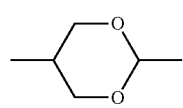 G

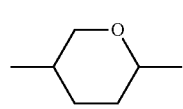 dh

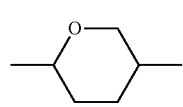 Dh

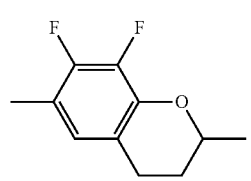 Cro(7F,8F)

5) Examples of Description

Example 1. 3-BB(F,F)XB(F,F)—F

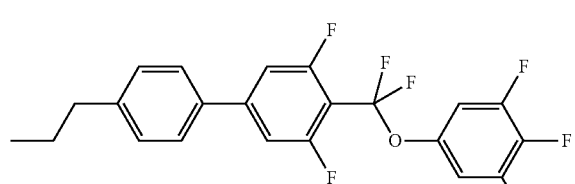

TABLE 2-continued

Example 2. 3HBB(2F,3F)—O2

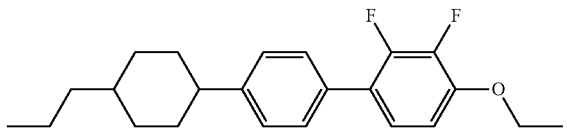 [SMILES: CCCC1CCC(c2ccc(-c3ccc(OCC)c(F)c3F)cc2)CC1]

Example 3. 3-HH-4

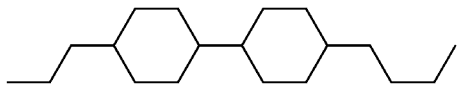 [SMILES: CCCCC1CCC(C2CCC(CCC)CC2)CC1]

Example 4. 3HBB(F,F)—F

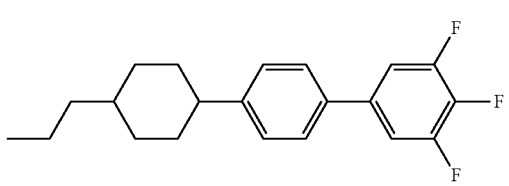 [SMILES: CCCC1CCC(c2ccc(-c3cc(F)c(F)c(F)c3)cc2)CC1]

Example 7

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 8% |
| 5-PyBB-F | (6-80) | 10% |
| 5-HBB(F)B-2 | (4-5) | 10% |
| 5-HBB(F)B-3 | (4-5) | 12% |

Based on the composition, compound (1-3-58) described below was added at a ratio of 0.15% by weight.

(1-3-58)

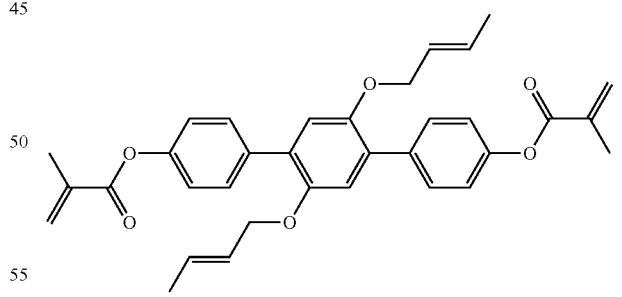

NI=101.2° C.; Δn=0.191; Δε=7.8; η=39.8 mPa·s.

Example 8

| | | |
|---|---|---|
| 2-HB-C | (8-1) | 5% |
| 3-HB-C | (8-1) | 12% |
| 3-HB-O2 | (2-5) | 13% |
| 2-BTB-1 | (2-10) | 3% |

-continued

| | | |
|---|---|---|
| 3-HHB-F | (6-1) | 4% |
| 3-HHB-1 | (3-1) | 10% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

Based on the composition, compound (1-3-89) described below was added at a ratio of 0.3% by weight.

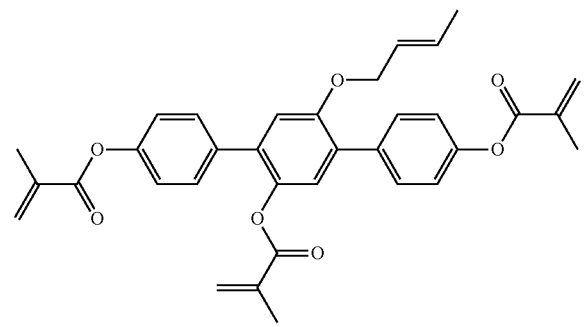

(1-3-89)

NI=103.3° C.; Δn=0.101; Δε=4.6; η=18.5 mPa·s.

Example 9

| | | |
|---|---|---|
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 7% |
| 3-HBB(F)-F | (6-23) | 9% |
| 5-HBB(F)-F | (6-23) | 16% |
| 2-HBB-F | (6-22) | 4% |
| 3-HBB-F | (6-22) | 4% |
| 5-HBB-F | (6-22) | 5% |
| 3-HBB(F,F)-F | (6-24) | 5% |
| 5-HBB(F,F)-F | (6-24) | 10% |

Based on the composition, compound (1-3-13) described below was added at a ratio of 0.2% by weight.

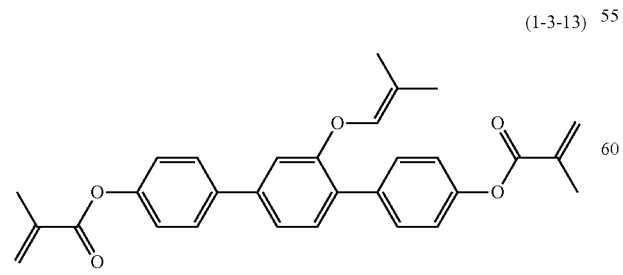

(1-3-13)

NI=86.7° C.; Δn=0.115; Δε=5.7; η=24.7 mPa·s.

Example 10

| | | |
|---|---|---|
| 5-HB-CL | (5-2) | 16% |
| 3-HH-4 | (2-1) | 10% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 11% |
| 5-HHB(F)-F | (6-2) | 9% |
| 7-HHB(F)-F | (6-2) | 8% |
| 5-HBB(F)-F | (6-23) | 4% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

Based on the composition, compound (1-3-15) described below was added at a ratio of 0.3% by weight.

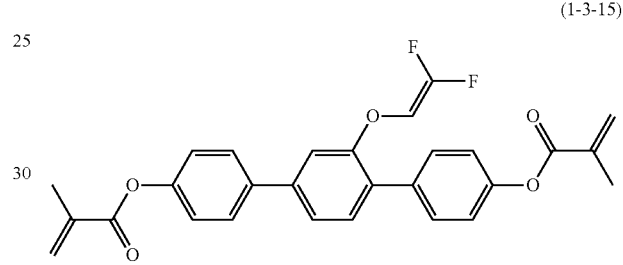

(1-3-15)

NI=115.7° C.; Δn=0.092; Δε=3.9; η=20.1 mPa·s.

Example 11

| | | |
|---|---|---|
| 3-HHB(F,F)-F | (6-3) | 11% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 21% |
| 5-HBB(F,F)-F | (6-24) | 20% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 2% |
| 1O1-HBBH-5 | (4-1) | 4% |

Based on the composition, compound (1-3-17) described below was added at a ratio of 0.3% by weight.

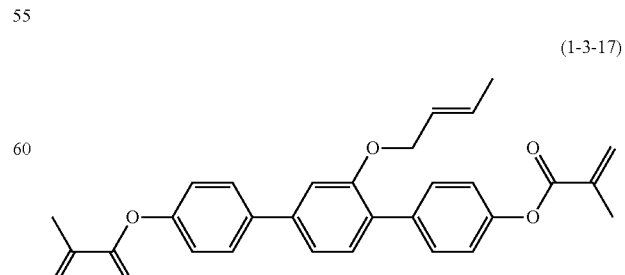

(1-3-17)

NI=94.5° C.; Δn=0.114; Δε=9.1; η=34.3 mPa·s.

Example 12

| | | |
|---|---|---|
| 5-HB-CL | (5-2) | 9% |
| 3-HH-4 | (2-1) | 8% |
| 3-HHB-1 | (3-1) | 7% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

Based on the composition, compound (1-3-19) described below was added at a ratio of 0.3% by weight.

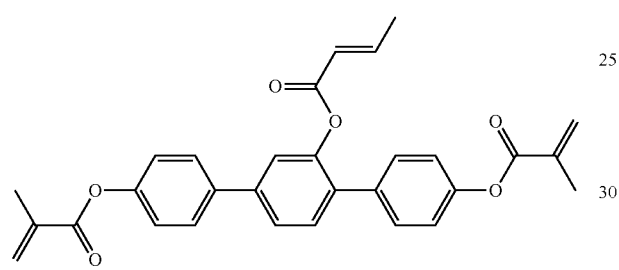

(1-3-19)

NI=83.4° C.; Δn=0.104; Δε=8.6; η=22.9 mPa·s.

Example 13

| | | |
|---|---|---|
| 3-HH-4 | (2-1) | 4% |
| 3-HHB-1 | (3-1) | 2% |
| 3-HBB(F,F)-F | (6-24) | 33% |
| 5-HBB(F,F)-F | (6-24) | 30% |
| 3-H2HB(F,F)-F | (6-15) | 10% |
| 4-H2HB(F,F)-F | (6-15) | 10% |
| 5-H2HB(F,F)-F | (6-15) | 8% |
| 3-HHBB(F,F)-F | (7-6) | 3% |

Based on the composition, compound (1-3-21) described below was added at a ratio of 0.2% by weight.

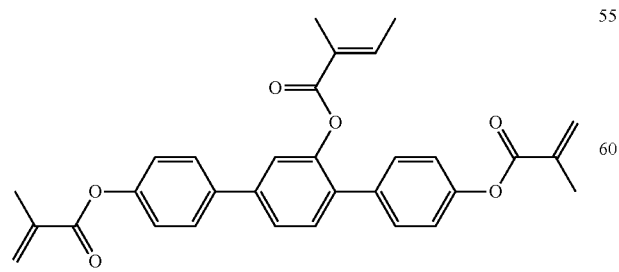

(1-3-21)

NI=66.7° C.; Δn=0.105; Δε=8.5; η=29.6 mPa·s.

Example 14

| | | |
|---|---|---|
| 5-HB-CL | (5-2) | 3% |
| 7-HB(F)-F | (5-3) | 7% |
| 3-HH-4 | (2-1) | 9% |
| 3-HH-EMe | (2-2) | 23% |
| 3-HHEB-F | (6-10) | 10% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 5% |

Based on the composition, compound (1-3-61) described below was added at a ratio of 0.2% by weight.

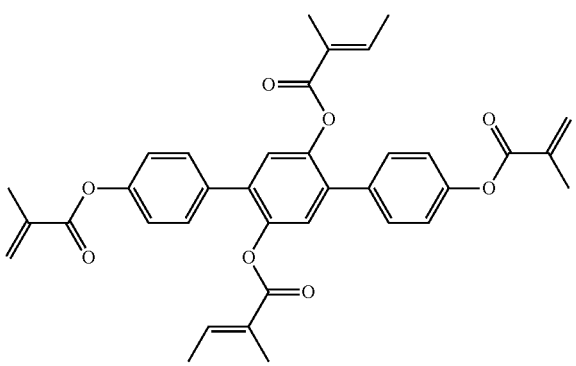

(1-3-61)

NI=81.7° C.; Δn=0.065; Δε=5.4; η=19.1 mPa·s.

Example 15

| | | |
|---|---|---|
| 1V2-BEB(F,F)-C | (8-15) | 6% |
| 3-HB-C | (8-1) | 18% |
| 2-BTB-1 | (2-10) | 10% |
| 5-HH-VFF | (2-1) | 30% |
| 3-HHB-1 | (3-1) | 6% |
| VFF-HHB-1 | (3-1) | 8% |
| VFF2-HHB-1 | (3-1) | 9% |
| 3-H2BTB-2 | (3-17) | 5% |
| 3-H2BTB-3 | (3-17) | 4% |
| 3-H2BTB-4 | (3-17) | 4% |

Based on the composition, compound (1-3-23) described below was added at a ratio of 0.2% by weight.

(1-3-23)

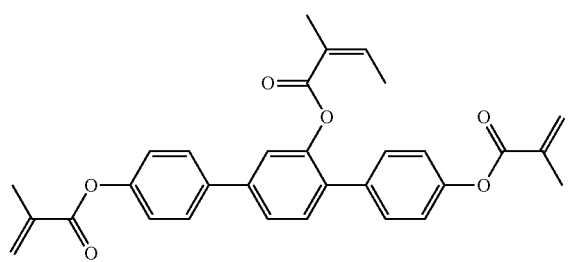

NI=81.7° C.; Δn=0.130; Δε=6.4; η=11.8 mPa·s.

Example 16

| | | |
|---|---|---|
| 3-GB(F)B(F,F)XB(F,F)-F | (7-57) | 5% |
| 3-BB(F)B(F,F)XB(F,F)-F | (7-47) | 1% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 5% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

Based on the composition, compound (1-3-25) described below was added at a ratio of 0.2% by weight.

(1-3-25)

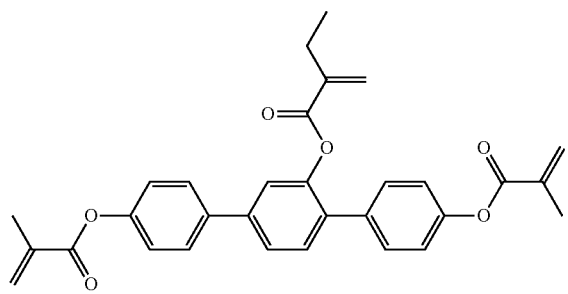

NI=82.5° C.; Δn=0.100; Δε=6.7; η=12.4 mPa·s.

Example 17

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 38% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |

-continued

| | | |
|---|---|---|
| 3-BB(F,F)XB(F,F)-F | (6-97) | 14% |
| 3-HHBB(F,F)-F | (7-6) | 3% |

Based on the composition, compound (1-3-89) described below was added at a ratio of 0.1% by weight.

(1-3-89)

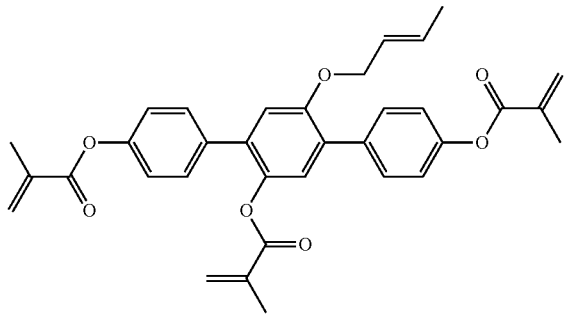

In addition, based on the composition, compound (S-1) described below was added at a ratio of 0.3% by weight.

(S-1)

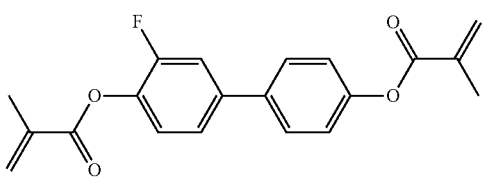

NI=80.3° C.; Δn=0.107; Δε=7.2; η=14.0 mPa·s.

Example 18

| | | |
|---|---|---|
| 1V2-BEB(F,F)-C | (8-15) | 6% |
| 3-HB-C | (8-1) | 18% |
| 2-BTB-1 | (2-10) | 10% |
| 5-HH-VFF | (2-1) | 30% |
| 3-HHB-1 | (3-1) | 6% |
| VFF-HHB-1 | (3-1) | 8% |
| VFF2-HHB-1 | (3-1) | 9% |
| 3-H2BTB-2 | (3-17) | 5% |
| 3-H2BTB-3 | (3-17) | 4% |
| 3-H2BTB-4 | (3-17) | 4% |

Based on the composition, compound (1-3-15) described below was added at a ratio of 0.2% by weight.

(1-3-15)

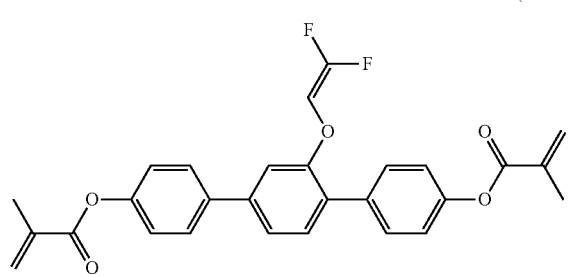

NI=81.9° C.; Δn=0.130; Δε=6.3; η=11.7 mPa·s.

Example 19

| | | |
|---|---|---|
| 3-GB(F)B(F,F)XB(F,F)-F | (7-57) | 5% |
| 3-BB(F)B(F,F)XB(F,F)-F | (7-47) | 1% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 5% |
| 3-HHB-1 | (3-1) | 4% |
| V-HHB-1 | (3-1) | 5% |
| V2-BB(F)B-1 | (3-6) | 5% |
| 1V2-BB-F | (2-8) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

Based on the composition, compound (1-3-26) described below was added at a ratio of 0.2% by weight.

(1-3-26)

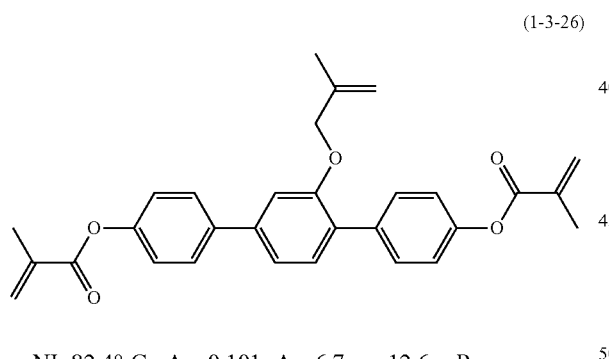

NI=82.4° C.; Δn=0.101; Δε=6.7; η=12.6 mPa·s.

Example 20

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 8% |
| 5-PyBB-F | (6-80) | 10% |
| 5-HBB(F)B-2 | (4-5) | 10% |
| 5-HBB(F)B-3 | (4-5) | 12% |

To the composition, compound (1-3-18) described below was added at a ratio of 0.15% by weight.

(1-3-18)

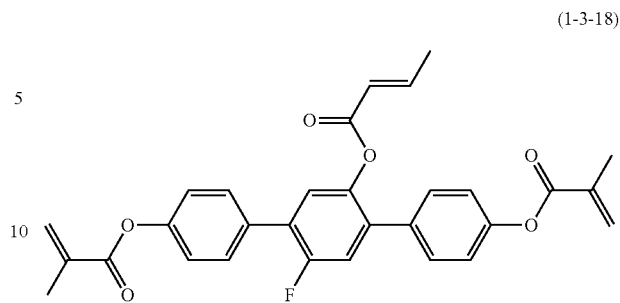

NI=101.2° C.; Δn=0.191; Δε=7.8; η=39.8 mPa·s.

Example 21

| | | |
|---|---|---|
| 2-HB-C | (8-1) | 5% |
| 3-HB-C | (8-1) | 12% |
| 3-HB-O2 | (2-5) | 13% |
| 2-BTB-1 | (2-10) | 3% |
| 3-HHB-F | (6-1) | 4% |
| 3-HHB-1 | (3-1) | 10% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

To the composition, compound (1-3-28) described below was added at a ratio of 0.3% by weight.

(1-3-28)

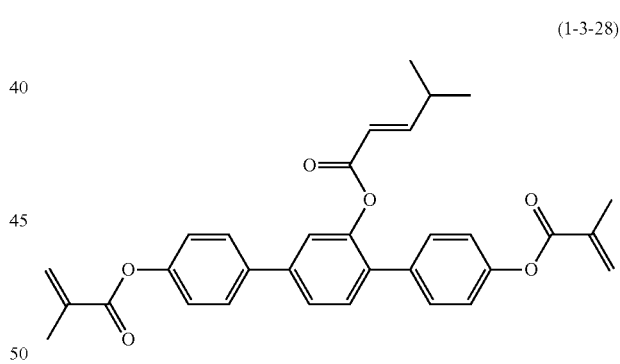

NI=103.3° C.; Δn=0.101; Δε=4.6; η=18.5 mPa·s.

Example 22

| | | |
|---|---|---|
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 7% |
| 3-HBB(F)-F | (6-23) | 9% |
| 5-HBB(F)-F | (6-23) | 16% |
| 2-HBB-F | (6-22) | 4% |
| 3-HBB-F | (6-22) | 4% |
| 5-HBB-F | (6-22) | 5% |

| | | |
|---|---|---|
| 3-HBB(F,F)-F | (6-24) | 5% |
| 5-HBB(F,F)-F | (6-24) | 10% |

To the composition, compound (1-4-11) described below was added at a ratio of 0.2% by weight.

(1-4-11)

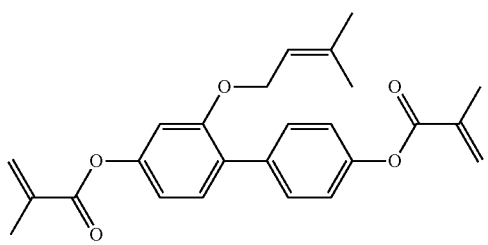

NI=86.7° C.; Δn=0.115; Δε=5.7; =24.7 mPa·s.

Example 23

| | | |
|---|---|---|
| 5-HB-CL | (5-2) | 16% |
| 3-HH-4 | (2-1) | 10% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 11% |
| 5-HHB(F)-F | (6-2) | 9% |
| 7-HHB(F)-F | (6-2) | 8% |
| 5-HBB(F)-F | (6-23) | 4% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

To the composition, compound (1-3-27) described below was added at a ratio of 0.3% by weight.

(1-3-27)

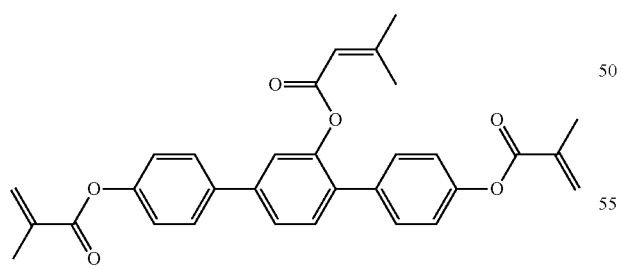

NI=115.7° C.; Δn=0.092; Δε=3.9; η=20.1 mPa·s.

Example 24

| | | |
|---|---|---|
| 3-HHB(F,F)-F | (6-3) | 11% |
| 3-H2HB(F,F)-F | (6-15) | 8% |
| 4-H2HB(F,F)-F | (6-15) | 8% |
| 5-H2HB(F,F)-F | (6-15) | 8% |
| 3-HBB(F,F)-F | (6-24) | 21% |
| 5-HBB(F,F)-F | (6-24) | 20% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 2% |
| 1O1-HBBH-5 | (4-1) | 4% |

To the composition, compound (1-3-30) described below was added at a ratio of 0.3% by weight.

(1-3-30)

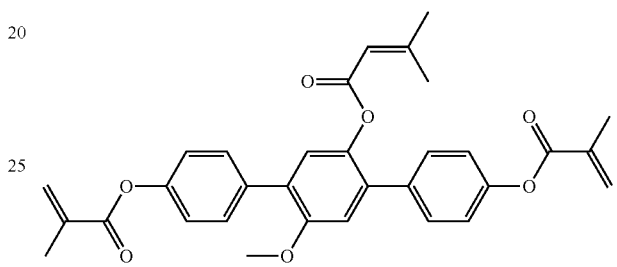

NI=94.5° C.; Δn=0.114; Δε=9.1; η=34.3 mPa·s.

Example 25

| | | |
|---|---|---|
| 5-HB-CL | (5-2) | 9% |
| 3-HH-4 | (2-1) | 8% |
| 3-HHB-1 | (3-1) | 7% |
| 3-HHB(F,F)-F | (6-3) | 8% |
| 3-HBB(F,F)-F | (6-24) | 20% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

To the composition, compound (1-3-29) described below was added at a ratio of 0.3% by weight.

(1-3-29)

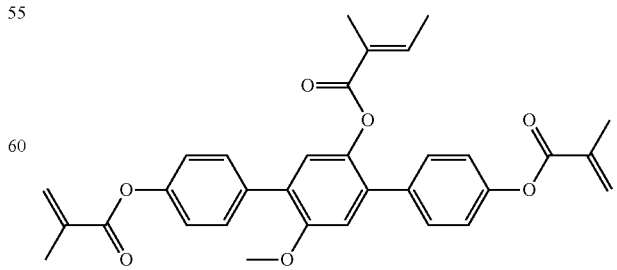

NI=83.4° C.; Δn=0.104; Δε=8.6; η=22.9 mPa·s.

Example 26

| | | |
|---|---|---|
| 3-HH-4 | (2-1) | 4% |
| 3-HHB-1 | (3-1) | 2% |
| 3-HBB(F,F)-F | (6-24) | 33% |
| 5-HBB(F,F)-F | (6-24) | 30% |
| 3-H2HB(F,F)-F | (6-15) | 10% |
| 4-H2HB(F,F)-F | (6-15) | 10% |
| 5-H2HB(F,F)-F | (6-15) | 8% |
| 3-HHBB(F,F)-F | (7-6) | 3% |

To the composition, compound (1-3-172) described below was added at a ratio of 0.2% by weight.

(1-3-172)

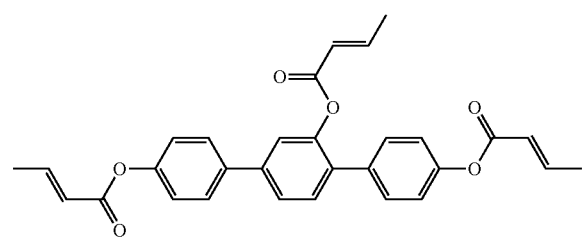

NI=66.7° C.; Δn=0.105; Δε=8.5; η=29.6 mPa·s.

Example 27

| | | |
|---|---|---|
| 5-HB-CL | (5-2) | 3% |
| 7-HB(F)-F | (5-3) | 7% |
| 3-HH-4 | (2-1) | 9% |
| 3-HH-EMe | (2-2) | 23% |
| 3-HHEB-F | (6-10) | 10% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 5% |

To the composition, compound (1-3-171) described below was added at a ratio of 0.2% by weight.

(1-3-171)

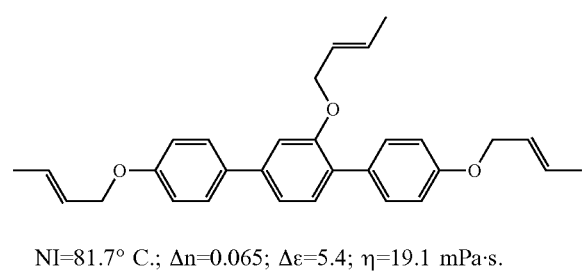

NI=81.7° C.; Δn=0.065; Δε=5.4; η=19.1 mPa·s.

Example 28

| | | |
|---|---|---|
| 1V2-BEB(F,F)-C | (8-15) | 6% |
| 3-HB-C | (8-1) | 18% |
| 2-BTB-1 | (2-10) | 10% |
| 5-HH-VFF | (2-1) | 30% |
| 3-HHB-1 | (3-1) | 6% |
| VFF-HHB-1 | (3-1) | 8% |
| VFF2-HHB-1 | (3-1) | 9% |
| 3-H2BTB-2 | (3-17) | 5% |
| 3-H2BTB-3 | (3-17) | 4% |
| 3-H2BTB-4 | (3-17) | 4% |

To the composition, compound (1-3-169) described below was added at a ratio of 0.2% by weight.

(1-3-169)

NI=81.7° C.; Δn=0.130; Δε=6.4; η=11.8 mPa·s.

Example 29

| | | |
|---|---|---|
| 3-GB(F)B(F,F)XB(F,F)-F | (7-57) | 5% |
| 3-BB(F)B(F,F)XB(F,F)-F | (7-47) | 1% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 41% |
| 3-HH-V1 | (2-1) | 7% |
| 3-HHEH-5 | (3-13) | 5% |
| 3-HHB-1 | (3-1) | 4% |
| V-HHB-1 | (3-1) | 5% |
| V2-BB(F)B-1 | (3-6) | 5% |
| 1V2-BB-F | (2-8) | 3% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

To the composition, compound (1-3-173) described below was added at a ratio of 0.2% by weight.

(1-3-173)

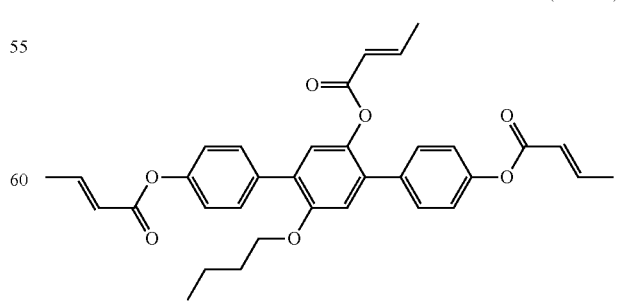

NI=82.5° C.; Δn=0.100; Δε=6.7; η=12.4 mPa·s.

Example 30

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 38% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 14% |
| 3-HHBB(F,F)-F | (7-6) | 3% |

To the composition, compound (1-3-170) described below was added at a ratio of 0.1% by weight.

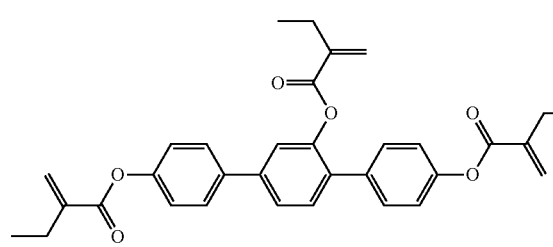

(1-3-170)

To the composition, a compound described below was added at a ratio of 0.3% by weight.

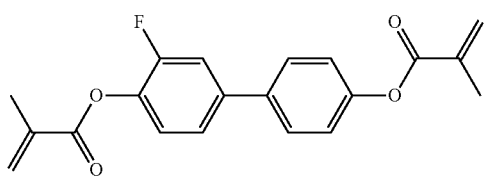 [SMILES: C=C(C)C(=O)Oc1ccc(-c2ccc(OC(=O)C(=C)C)c(F)c2)cc1]

NI=80.3° C.; Δn=0.107; Δε=7.2; η=14.0 mPa·s.

Example 31

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 8% |
| 5-PyBB-F | (6-80) | 10% |
| 5-HBB(F)B-2 | (4-5) | 10% |
| 5-HBB(F)B-3 | (4-5) | 12% |

To the composition, compound (1-3-174) described below was added at a ratio of 0.15% by weight.

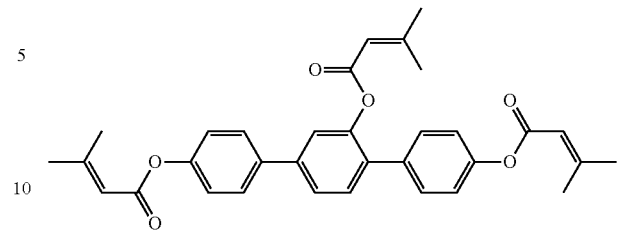

(1-3-174)

NI=101.2° C.; Δn=0.191; Δε=7.8; η=39.8 mPa·s.

Example 32

| | | |
|---|---|---|
| 2-HB-C | (8-1) | 5% |
| 3-HB-C | (8-1) | 12% |
| 3-HB-O2 | (2-5) | 13% |
| 2-BTB-1 | (2-10) | 3% |
| 3-HHB-F | (6-1) | 4% |
| 3-HHB-1 | (3-1) | 10% |
| 3-HHB-O1 | (3-1) | 5% |
| 3-HHB-3 | (3-1) | 14% |
| 3-HHEB-F | (6-10) | 4% |
| 5-HHEB-F | (6-10) | 4% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

To the composition, compound (A15) described below was added at a ratio of 0.3% by weight.

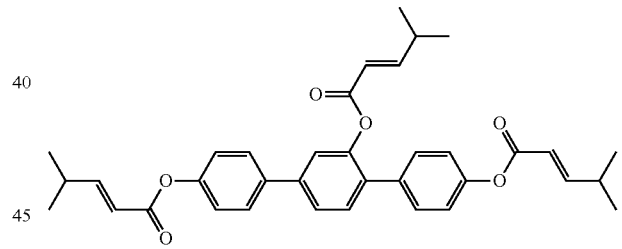

(1-3-175)

NI=103.3° C.; Δn=0.101; Δε=4.6; η=18.5 mPa·s.

Example 33

| | | |
|---|---|---|
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 10% |
| 2-HBB(F)-F | (6-23) | 7% |
| 3-HBB(F)-F | (6-23) | 9% |
| 5-HBB(F)-F | (6-23) | 16% |
| 2-HBB-F | (6-22) | 4% |
| 3-HBB-F | (6-22) | 4% |
| 5-HBB-F | (6-22) | 5% |
| 3-HBB(F,F)-F | (6-24) | 5% |
| 5-HBB(F,F)-F | (6-24) | 10% |

To the composition, compound (1-3-40) described below was added at a ratio of 0.2% by weight.

(1-3-40)

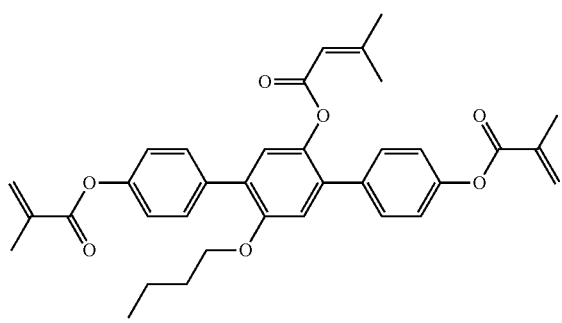

NI=86.7° C.; Δn=0.115; Δε=5.7; η=24.7 mPa·s.

Example 34

| | | |
|---|---|---|
| 5-HB-CL | (5-2) | 16% |
| 3-HH-4 | (2-1) | 10% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 11% |
| 5-HHB(F)-F | (6-2) | 9% |
| 7-HHB(F)-F | (6-2) | 8% |
| 5-HBB(F)-F | (6-23) | 4% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

To the composition, compound (1-3-39) described below was added at a ratio of 0.3% by weight.

(1-3-39)

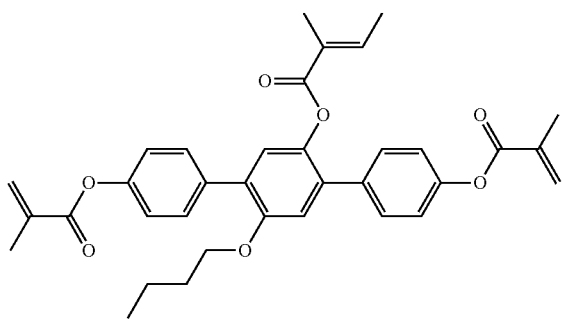

NI=115.7° C.; Δn=0.092; Δε=3.9; η=20.1 mPa·s.

INDUSTRIAL APPLICABILITY

A liquid crystal display device having a mode such as a PSA mode can be produced by polymerizing a polymerizable composition containing compound (1) and a liquid crystal composition. The polymerizable compound can also be used as a raw material of an optically anisotropic body.

What is claimed is:

1. A polymerizable compound represented by formula (1):

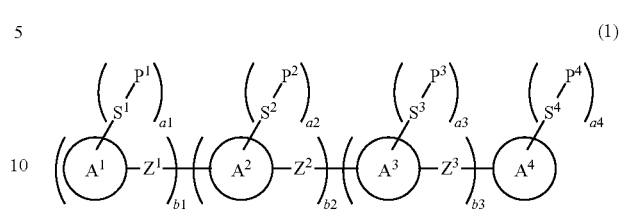

(1)

wherein, in formula (1),
at least one of $P^1$, $P^2$, $P^3$ and $P^4$ is acryloyloxy or methacryloyloxy, and at least one remainder is a polymerizable group selected from the group of groups represented by formulas (P-1), (P-2) and (P-3);

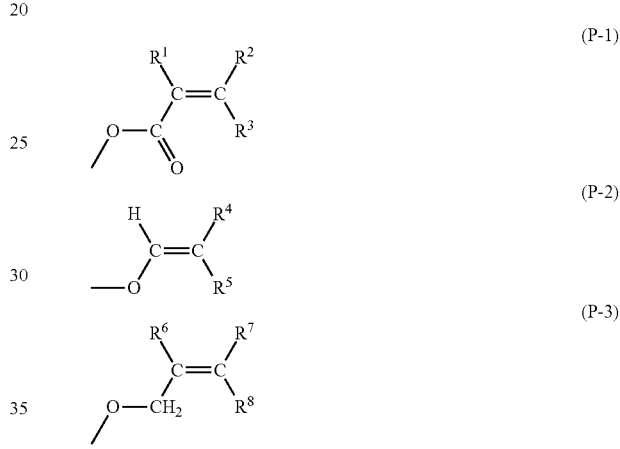

wherein, in formulas (P-1) to (P-3), $R^1$, $R^2$, $R^3$, $R^4$, $R^5$, $R^6$, $R^7$ and $R^8$ are independently hydrogen, fluorine, alkyl having 1 to 3 carbons, or alkyl having 1 to 3 carbons in which at least one of hydrogen is replaced by halogen;

in formula (P-1), when $R^1$ is hydrogen or methyl, at least one of $R^2$ and $R^3$ is fluorine, alkyl having 1 to 3 carbons, or alkyl having 1 to 3 carbons in which at least one of hydrogen is replaced by halogen;

in formula (P-2), at least one of $R^4$ and $R^5$ is fluorine, alkyl having 1 to 3 carbons, or alkyl having 1 to 3 carbons in which at least one of hydrogen is replaced by halogen; and in formula (P-3), at least one of $R^6$, $R^7$ and $R^8$ is fluorine, alkyl having 1 to 3 carbons, or alkyl having 1 to 3 carbons in which at least one of hydrogen is replaced by halogen;

in formula (1),
$S^1$, $S^2$, $S^3$ and $S^4$ are independently a single bond or alkylene having 1 to 10 carbons, and in the alkylene, at least one of —$CH_2$— may be replaced by —O—, —COO—, —OCO— or —OCOO—, at least one of —$CH_2$—$CH_2$— may be replaced by —CH═CH— or —C≡C—, and at least one of hydrogen may be replaced by fluorine or chlorine;

a1, a2, a3 and a4 are independently 0, 1, 2, 3 or 4, and a sum of a1, a2, a3 and a4 is an integer from 2 to 10;

ring $A^1$ and ring $A^4$ are independently phenyl, pyrimidyl, pyridyl, naphthyl, cyclohexyl, cyclohexenyl, tetrahydropyranyl or 1,3-dioxanyl, and in the rings, at least one of hydrogen may be replaced by halogen, alkyl having 1 to 12 carbons, or alkyl having 1 to 12 carbons in which at least one of hydrogen is replaced by halogen;

ring $A^2$ and ring $A^3$ are independently 1,4-phenylene, pyrimidine-2,5-diyl, pyridine-2,5-diyl, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, 1,4-cyclohexylene, 1,4-cyclohexenylene, tetrahydropyran-2,5-diyl or 1,3-dioxane-2,5-diyl, and in the rings, at least one of hydrogen may be replaced by halogen, alkyl having 1 to 12 carbons, or alkyl having 1 to 12 carbons in which at least one of hydrogen may be replaced by halogen;

1 to 5 carbons or alkoxy having 1 to 5 carbons in which at least one of hydrogen is replaced by halogen;

$Z^1$, $Z^2$ and $Z^3$ are independently a single bond, alkylene having 1 to 5 carbons, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CH=CH—CH$_2$O—, —OCH$_2$—CH=CH—, —CH=CH—OCH$_2$— or —CH$_2$O—CH=CH—; and b1, b2 and b3 are independently 0 or 1, and at least one of b1, b2, and b3 is 1.

3. The polymerizable compound according to claim 1, represented by formula (1-1):

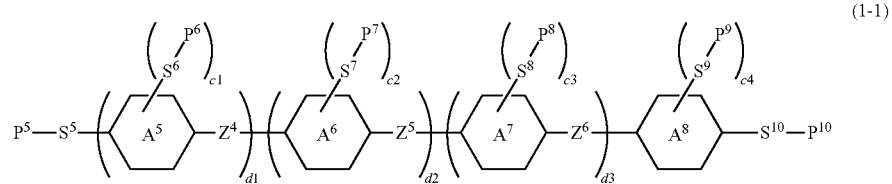

(1-1)

$Z^1$, $Z^2$ and $Z^3$ are independently a single bond, alkylene having 1 to 5 carbons, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CH=CH—CH$_2$O—, —OCH$_2$—CH=CH—, —CH=CH—OCH$_2$— or —CH$_2$O—CH=CH—; and b1, b2 and b3 are independently 0 or 1, and at least one of b1, b2, and b3 is 1.

2. The polymerizable compound according to claim 1, wherein, in formula (1) described in claim 1, at least one of $P^1$, $P^2$, $P^3$ and $P^4$ is acryloyloxy or methacryloyloxy, and at least one remainder is 2-butenoyloxy, 2-methyl-2-butenoyloxy, 2-methylenebutanoyloxy, 2-methyl-1-ropenyloxy, 2,2-difluorovinyloxy, 2-butenyloxy or 2-methyl-2-propenyloxy;

$S^1$, $S^2$, $S^3$ and $S^4$ are independently a single bond or alkylene having 1 to 10 carbons, and in the alkylene, at least one of —CH$_2$— may be replaced by —O—, —COO—, —OCO— or —OCOO—, at least one of —CH$_2$—CH$_2$— may be replaced by —CH=CH— or —C≡C—, and at least one of hydrogen may be replaced by fluorine or chlorine;

a1, a2, a3 and a4 are independently 0, 1, 2 or 3, and a sum of a1, a2, a3 and a4 is an integer from 2 to 6;

ring $A^1$ and ring $A^4$ are independently phenyl, pyrimidyl, pyridyl or naphthyl, and in the rings, at least one of hydrogen may be replaced by halogen, alkyl having 1 to 12 carbons, or alkyl having 1 to 12 carbons in which at least one of hydrogen is replaced by halogen;

ring $A^2$ and ring $A^3$ are independently 1,4-phenylene, pyrimidine-2,5-diyl, pyridine-2,5-diyl, naphthalene-1,4-diyl, naphthalene-1,5-diyl, naphthalene-2,6-diyl, 1,4-cyclohexylene, tetrahydropyran-2,5-diyl or 1,3-dioxane-2,5-diyl, and in the rings, at least one of hydrogen may be replaced by fluorine, chlorine, alkyl having 1 to 5 carbons, alkoxy having 1 to 5 carbons, or alkyl having wherein, in formula (1-1), at least one of $P^5$, $P^6$, $P^7$, $P^8$, $P^9$ and $P^{10}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

$S^5$, $S^6$, $S^7$, $S^8$, $S^9$ and $S^{10}$ are independently a single bond or alkylene having 1 to 5 carbons, and in the alkylene, at least one of —CH$_2$— may be replaced by —O—, —COO— or —OCO—, and at least one of —CH$_2$—CH$_2$— may be replaced by —CH=CH—;

c1, c2, c3 and c4 are independently 0, 1 or 2, and a sum of c1, c2, c3 and c4 is an integer from 0 to 5;

ring $A^5$, ring $A^6$, ring $A^7$ and ring $A^8$ are independently 1,4-phenylene, pyrimidine-2,5-diyl, pyridine-2,5-diyl, naphthalene-1,4-diyl, naphthalene-1,5-diyl, naphthalene-2,6-diyl, 1,4-cyclohexylene, tetrahydropyran-2,5-diyl or 1,3-dioxane-2,5-diyl, and in the rings, at least one of hydrogen may be replaced by fluorine, chlorine, alkyl having 1 to 5 carbons, alkoxy having 1 to 5 carbons, or alkyl having 1 to 5 carbons or alkoxy having 1 to 5 carbons in which at least one of hydrogen is replaced by halogen;

$Z^4$, $Z^5$ and $Z^6$ are independently a single bond, alkylene having 1 to 5 carbons, —CH=CH—, —CH=CH—COO—, —OCO—CH=CH—, —C(CH$_3$)=CH—COO—, —OCO—CH=C(CH$_3$)—, —CH=C(CH$_3$)—COO—, —OCO—(CH$_3$)C=CH—, —C(CH$_3$)=C(CH$_3$)—COO—, —OCO—C(CH$_3$)=C(CH$_3$)—, —CH=CH—CH$_2$O—, —OCH$_2$—CH=CH—, —CH=CH—OCH$_2$— or —CH$_2$O—CH=CH—; and d1, d2 and d3 are independently 0 or 1, and at least one of d1, d2, and d3 is 1.

4. The polymerizable compound according to claim 3, wherein, in formula (1-1) described in claim 3, $P^5$ and $P^0$ are independently acryloyloxy or methacryloyloxy, at least one of $P^6$, $P^7$, $P^8$ and $P^9$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy: $S^5$, $S^6$, $S^7$, $S^8$, $S^9$ and $S^{10}$ are a single bond; c1, c2, c3 and c4 are independently 0 or 1, and a sum of c1, c2, c3 and c4 is 1, 2 or 3; ring $A^5$, ring $A^6$, ring $A^7$ and ring $A^8$ are independently 1,4-phenylene, and at least one of hydrogen may be replaced by fluorine, chlorine, alkyl having 1 to 5 carbons, alkoxy having 1 to 5 carbons, or alkyl having 1 to 5 carbons or alkoxy having 1 to 5 carbons in which at least one of hydrogen is replaced by halogen; $Z^4$, $Z^5$ and $Z^6$ are a single bond; and d1, d2 and d3 are independently 0 or 1, and a sum of d1, d2 and d3 is 1, 2 or 3.

5. The polymerizable compound according to claim 1, represented by any one of formulas (1-1-1) to (1-1-3):

2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; and in formulas (1-1-1) to (1-1-3), $S^{11}$, $S^{12}$, $S^{13}$, $S^{14}$, $S^{15}$ and $S^{16}$ are independently a single bond, —$CH_2$—, —$CH_2O$—, —$OCH_2$—, —COO—, —OCO—, —CH=CH—, —C≡C—, —$CH_2CH_2O$—, —$OCH_2CH_2$—, —CH=CH—O— or —O—CH=CH—;

e1, e2, e3 and e4 are independently 0, 1 or 2;

$Z^7$, $Z^8$ and $Z^9$ are independently a single bond, —CH=CH—, —CH=CH—COO—, —C(CH$_3$)=CH—COO—, —CH=C(CH$_3$)—COO—,

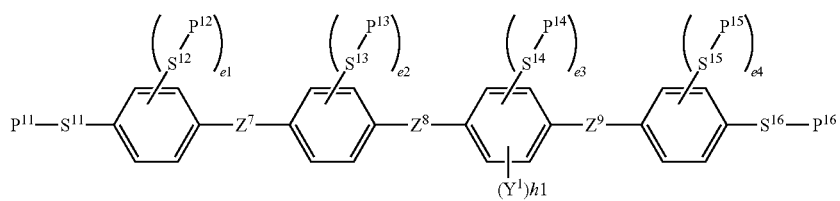

(1-1-1)

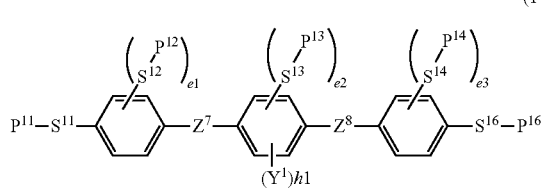

(1-1-2)

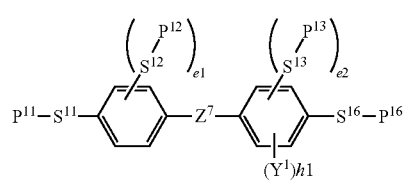

(1-1-3)

wherein, in formula (1-1-1), at least one of $P^{11}$, $P^{12}$, $P^{13}$, $P^{14}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-1-2), at least one of $P^{11}$, $P^{12}$, $P^{13}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-1-3), at least one of $P^{11}$, $P^{12}$, $P^{15}$ and $P^{16}$ is acryloyloxy or methacryloyloxy, and at least one remainder is —C(CH$_3$)=C(CH$_3$)—COO—, —COCH=CH—, —CH=CH—CH$_2$O— or —CH=CH—OCH$_2$—;

h1 is 0, 1 or 2; and $Y^1$ is halogen, alkyl having 1 to 5 carbons, alkoxy having 1 to 5 carbons, alkyl having 1 to 5 carbons in which at least one of hydrogen is replaced by halogen or alkoxy having 1 to 5 carbons in which at least one of hydrogen is replaced by halogen.

6. The polymerizable compound according to claim 1, represented by any one of formulas (1-2) to (1-4):

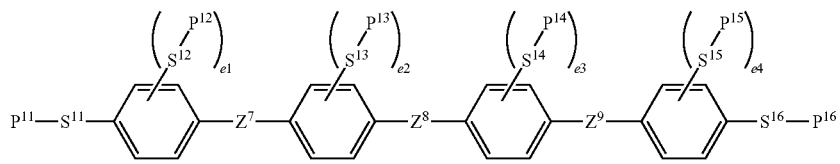

(1-2)

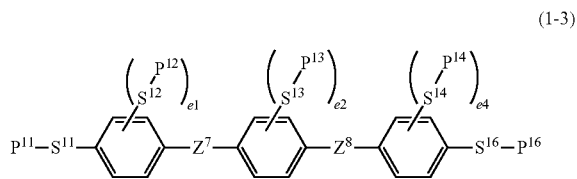

(1-3)

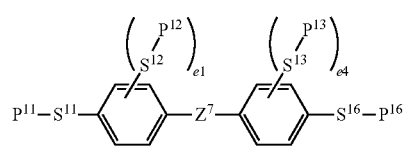

(1-4)

wherein, in formula (1-2),
at least one of $P^{11}$, $P^{12}$, $P^{13}$, $P^{14}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-3),
at least one of $P^{11}$, $P^{12}$, $P^{13}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy;

in formula (1-4),
at least one of $P^{11}$, $P^{12}$, $P^{15}$ and $P^{16}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; and in formulas (1-2) to (1-4),
$S^{11}$, $S^{12}$, $S^{13}$, $S^{14}$, $S^{15}$ and $S^{16}$ are independently a single bond, —CH$_2$—, —CH$_2$O—, —OCH$_2$—, —COO—, —OCO—, —CH=CH—, —C≡C—, —CH$_2$CH$_2$O—, —OCH$_2$CH$_2$—, —CH=CH—O— or —O—CH=CH—;
e1, e2, e3 and e4 are independently 0, 1 or 2; and
$Z^7$, $Z^8$ and $Z^9$ are independently a single bond, —CH=CH—, —CH=CH—COO—, —C(CH$_3$)=CH—COO—, —CH=C(CH$_3$)—COO—, —C(CH$_3$)=C(CH$_3$)—COO—, —COCH=CH—, —CH=CH—CH$_2$O— or —CH=CH—OCH$_2$—.

7. The polymerizable compound according to claim 6, wherein, in formulas (1-2) to (1-4) described in claim 6, $P^{11}$ and $P^{16}$ are independently acryloyloxy or methacryloyloxy, at least one of $P^{12}$, $P^{13}$, $P^{14}$ and $P^{15}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; $S^{11}$, $S^{12}$, $S^{13}$, $S^{14}$, $S^{15}$ and $S^{16}$ are a single bond; e1, e2, e3 and e4 are independently 0, 1 or 2, and a sum of e1, e2, e3 and e4 is 1, 2, 3 or 4; and $Z^7$, $Z^8$ and $Z^9$ are a single bond.

8. The polymerizable compound according to claim 1, represented by formula (1-1-4) or (1-1-5):

(1-1-4)

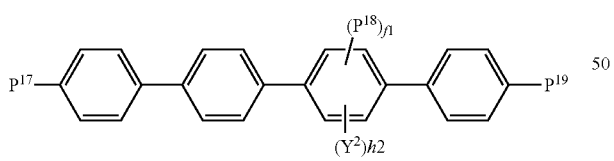

(1-1-5)

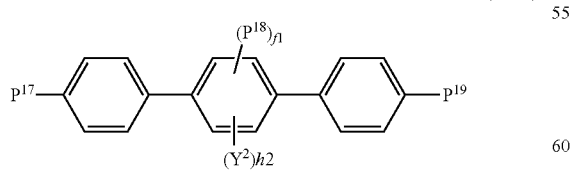

wherein, in formulas (1-1-4) and (1-1-5), at least one of $P^{17}$, $P^{18}$ and $P^{19}$ is acryloyloxy or methacryloyloxy, and at least one remainder is a polymerizable group selected from the group of groups represented by formulas (P-1), (P-2) and (P-3):

(P-1)

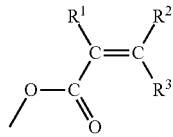

(P-2)

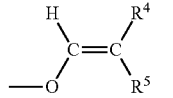

(P-3)

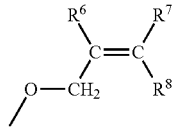

wherein, in formulas (P-1) to (P-3), $R^1$, $R^2$, $R^3$, $R^4$, $R^5$, $R^6$, $R^7$ and $R^8$ are independently hydrogen, fluorine, methyl, ethyl or trifluoromethyl;

in formula (P-1), when $R^1$ is hydrogen or methyl, at least one of $R^2$ and $R^3$ is fluorine, methyl, ethyl or trifluoromethyl;

in formula (P-2), at least one of $R^4$ and $R^5$ is fluorine, methyl, ethyl or trifluoromethyl; and in formula (P-3), at least one of $R^6$, $R^7$ and $R^8$ is fluorine, methyl, ethyl or trifluoromethyl;

f1 and h2 are independently 1 or 2; and $Y^2$ is halogen, alkyl having 1 to 5 carbons, alkoxy having 1 to 5 carbons, alkyl having 1 to 5 carbons in which at least one of hydrogen is replaced by halogen or alkoxy having 1 to 5 carbons in which at least one of hydrogen is replaced by halogen.

9. The polymerizable compound according to claim 1, represented by formula (1-5) or (1-6):

(1-5)

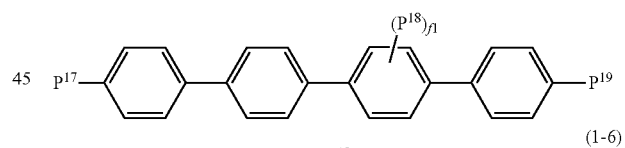

(1-6)

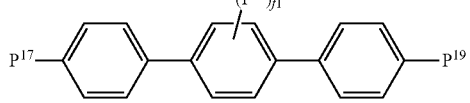

wherein, in formulas (1-5) and (1-6), at least one of $P^{17}$, $P^{18}$ and $P^{19}$ is acryloyloxy or methacryloyloxy, and at least one remainder is a polymerizable group selected from the group of groups represented by formulas (P-1), (P-2) and (P-3);

(P-1)

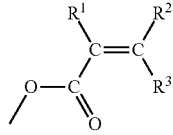

-continued (P-2)

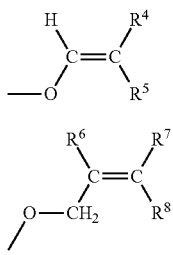

(P-3)

wherein, in formulas (P-1) to (P-3), $R^1$, $R^2$, $R^3$, $R^4$, $R^5$, $R^6$, $R^7$ and $R^8$ are independently hydrogen, fluorine, methyl, ethyl or trifluoromethyl;

in formula (P-1), when $R^1$ is hydrogen or methyl, at least one of $R^2$ and $R^3$ is fluorine, methyl, ethyl or trifluoromethyl;

in formula (P-2), at least one of $R^4$ and $R^5$ is fluorine, methyl, ethyl or trifluoromethyl; and in formula (P-3), at least one of $R^6$, $R^7$ and $R^8$ is fluorine, methyl, ethyl or trifluoromethyl; and f1 is 1 or 2.

10. The polymerizable compound according to claim 9, wherein, in formulas (1-5) and (1-6) described in claim 9, at least one of $P^{17}$, $P^{18}$ and $P^{19}$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy or 2-methyl-2-propenyloxy; and f1 is 1 or 2.

11. A polymerizable composition, containing at least one compound according to claim 1.

12. The polymerizable composition according to claim 11, further containing at least one compound selected from of the group of compounds represented by formulas (2) to (4):

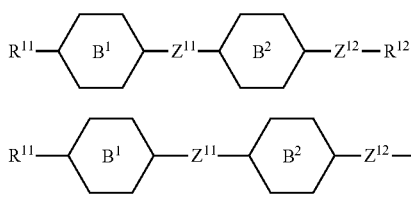
(2)

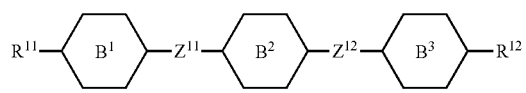
(3)

(4)

wherein, in formulas (2) to (4), $R^1$ and $R^{12}$ are independently alkyl having 1 to 10 carbons or alkenyl having 2 to 10 carbons, and in the alkyl or the alkenyl, at least one of —CH$_2$— may be replaced by —O—, and at least one of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —CH$_2$CH$_2$—, —CH=CH—, —C≡C— or —COO—.

13. The polymerizable composition according to claim 11, further containing at least one compound selected from the group of compounds represented by formulas (5) to (7):

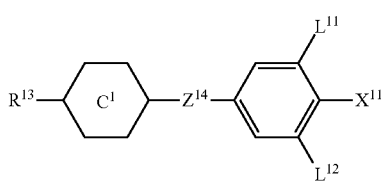
(5)

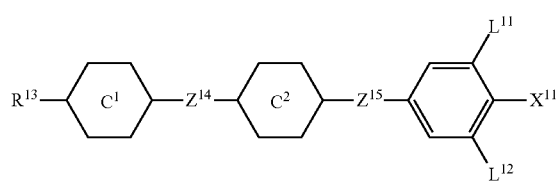
(6)

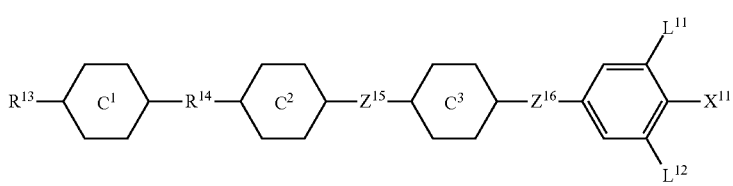
(7)

wherein, in formulas (5) to (7), $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

14. The polymerizable composition according to claim 11, further containing at least one compound selected from the group of compounds represented by formula (8):

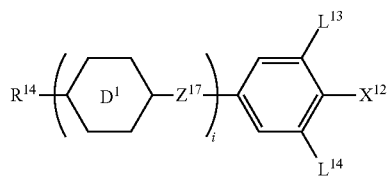

(8)

wherein, in formula (8), $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{12}$ is —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

15. A liquid crystal composite, produced by polymerization of the polymerizable composition according to claim 11.

16. An optical anisotropic body, produced by polymerization of the polymerizable composition according to claim 11.

17. A liquid crystal display device, including the polymerizable composition according to claim 11.

* * * * *